(12) United States Patent
Mogensen et al.

(10) Patent No.: US 6,867,218 B2
(45) Date of Patent: Mar. 15, 2005

(54) COMPOUNDS, THEIR PREPARATION AND USE

(75) Inventors: John Patrick Mogensen, Herlev (DK); Per Sauerberg, Farum (DK); Paul Stanley Bury, Kobenhavn (DK); Lone Jeppesen, Virum (DK); Ingrid Pettersson, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/370,856

(22) Filed: Feb. 20, 2003

(65) Prior Publication Data

US 2003/0195200 A1 Oct. 16, 2003

Related U.S. Application Data

(62) Division of application No. 09/770,896, filed on Jan. 26, 2001, now Pat. No. 6,555,577.
(60) Provisional application No. 60/245,392, filed on Nov. 2, 2000, provisional application No. 60/217,948, filed on Jul. 13, 2000, and provisional application No. 60/181,192, filed on Feb. 9, 2000.

(30) Foreign Application Priority Data

| | | | |
|---|---|---|---|
| Jan. 28, 2000 | (DK) | ......................... | 2000 00136 |
| Jul. 7, 2000 | (DK) | ......................... | 2000 01071 |
| Oct. 25, 2000 | (DK) | ......................... | 2000 01594 |

(51) Int. Cl.[7] ...................... A61K 31/47; C07D 215/02
(52) U.S. Cl. ...................... 514/311; 546/174; 546/342; 549/447; 549/462; 514/464; 514/469
(58) Field of Search .................. 514/311, 464, 514/469; 546/174, 342; 549/447, 462

(56) References Cited

U.S. PATENT DOCUMENTS 5,306,726 A  4/1994  Hulin ......................... 514/375

FOREIGN PATENT DOCUMENTS

| | | |
|---|---|---|
| EP | 0 903 343 A1 | 3/1999 |
| WO | WO 91/19702 | 12/1991 |
| WO | WO 94/01420 | 1/1994 |
| WO | WO 94/13650 | 6/1994 |
| WO | WO 95/03038 | 2/1995 |
| WO | WO 95/17394 | 6/1995 |
| WO | WO 96/04260 | 2/1996 |
| WO | WO 96/04261 | 2/1996 |
| WO | WO 97/25042 | 7/1997 |
| WO | WO 97/36579 | 10/1997 |
| WO | WO 99/08501 | 2/1999 |
| WO | WO 99/16758 | 4/1999 |
| WO | WO 99/19313 | 4/1999 |
| WO | WO 99/20614 | 4/1999 |
| WO | WO 99/38850 | 8/1999 |
| WO | WO 00/63153 | 10/2000 |

OTHER PUBLICATIONS

Abstract of Elzbieta Wyrzykiewicz et al., Zeszyty Nauk. Uniw. Poznaniu, Mat., Fiz., Chem., vol. 58, No. 9, pp. 29–45 (1965).

Primary Examiner—Charanjit S. Aulakh
(74) Attorney, Agent, or Firm—Rosemarie R. Wilk-Orescan; Reza Green; Richard W. Bork

(57) ABSTRACT

The present invention relates to compounds of the general formula (I)

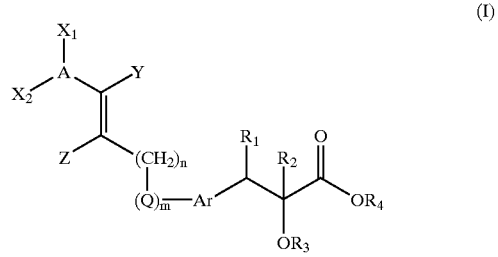

(I)

The compounds are useful in the treatment and/or prevention of conditions mediated by nuclear receptors, in particular the Peroxisome Proliferator-Activated Receptors (PPAR).

53 Claims, No Drawings

US 6,867,218 B2

COMPOUNDS, THEIR PREPARATION AND USE

CROSS-REFERENCE TO RELATED APPLICATIONS

This application is a divisional of application Ser. No. 09/770,896, filed on Jan. 26, 2000 now U.S. Pat. No. 6,555,577 and claims priority under 35 U.S.C. 119 of Danish application no. PA 2000 00136 filed on Jan. 28, 2000, Danish application no. PA 2000 01071 filed on Jul. 7, 2000, Danish application no. PA 2000 01594 filed on Oct. 25, 2000, U.S. provisional application No. 60/181,192 filed on Feb. 9, 2000, U.S. provisional application No. 60/217,948 filed on Jul. 13, 2000, and U.S. provisional application No. 60/245,392 filed on Nov. 2, 2000, the contents of which are fully incorporated herein by reference.

FIELD OF INVENTION

The present invention relates to novel compounds, pharmaceutical compositions containing them, methods for preparing the compounds and their use as medicaments. More specifically, compounds of the invention can be utilised in the treatment and/or prevention of conditions mediated by nuclear receptors, in particular the Peroxisome Proliferator-Activated Receptors (PPAR).

BACKGROUND OF THE INVENTION

Coronary artery disease (CAD) is the major cause of death in Type 2 diabetic and metabolic syndrome patients (i.e. patients that fall within the 'deadly quartet' category of impaired glucose tolerance, insulin resistance, hypertriglyceridaemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialised proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarised as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid β-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

A number of compounds have been reported to be useful in the treatment of hyperglycemia, hyperlipidemia and hypercholesterolemia (U.S. Pat. No. 5,306,726, PCT Publications nos. WO91/19702, WO 95/03038, WO 96/04260, WO 94/13650, WO 94/01420, WO 97/36579, WO 97/25042, WO 95/17394, WO 99/08501, WO 99/19313 and WO 99/16758).

SUMMARY OF THE INVENTION

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridaemia associated with these syndromes as well as alleviation of hyperglycaemia.

The clinical activity of fibrates and thiazolidinediones indicates that research for compounds displaying combined PPARα and PPARγ activation should lead to the discovery of efficacious glucose and triglyceride lowering drugs that have great potential in the treatment of Type 2 diabetes and the metabolic syndrome (i.e. impaired glucose tolerance, insulin resistance, hypertriglyceridaemia and/or obesity).

DETAILED DESCRIPTION OF THE INVENTION

Accordingly, the present invention relates to compounds of the general formula (I):

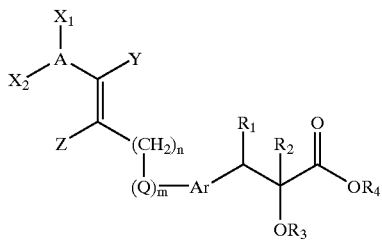

(I)

wherein A is aryl or heteroaryl and wherein A is optionally substituted with one or more substituents selected from hydroxy, halogen, perhalomethyl, perhalomethoxy, acyl, cyano, amino, $C_{1-6}$-alkylamino, $C_{1-6}$-dialkylamino, methylenedioxy, aralkenyl, aralkynyl, heteroaryloxy, heteroaralkoxy, aralkyl, heteroaralkyl, arylamino, or A is optionally substituted with $C_{1-6}$-alkyl, $C_{2-6}$-alkenyl or $C_{2-6}$-alkynyl each of which is optionally substituted with one or more substituents selected from $C_{1-6}$-alkoxycarbonyl or carboxy, or A is optionally substituted with $C_{1-6}$-alkoxy, $C_{1-6}$-alkylthio or $C_{2-6}$-alkenyloxy each of which is optionally substituted with one or more halogens, or A is optionally substituted with aryloxy, arylthio or aralkoxy each of which is optionally substituted with one or more substituents selected from $C_{1-6}$-alkoxy, nitro, carboxy or $C_{1-6}$-alkoxycarbonyl; and $X_1$ and $X_2$ independently are hydrogen, aryl or heteroaryl each of which is optionally substituted with one or more substituents selected from hydroxy, aryloxy, arylthio, aralkoxy, heteroaryloxy, aralkoxy, $C_{1-6}$-alkoxy, $C_{1-6}$-alkylthio, halogen, perhalomethyl, perhalomethoxy, acyl, aryl, heteroaryl, aralkyl, heteroaralkyl, cyano, amino, $C_{1-6}$-alkylamino, $C_{1-6}$-dialkylamino, arylamino or methylenedioxy, or aryl or heteroaryl each of which is optionally substituted with one or more substituents selected from $C_{1-6}$-alkyl, $C_{2-6}$-alkenyl or $C_{2-6}$-alkynyl each of which is optionally substituted with hydroxy; or A is selected from the ring systems consisting of

FIG. 1

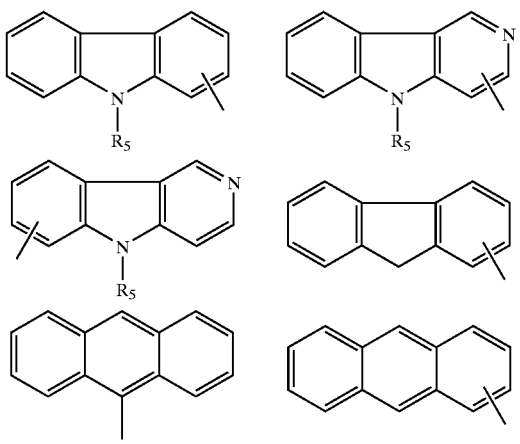

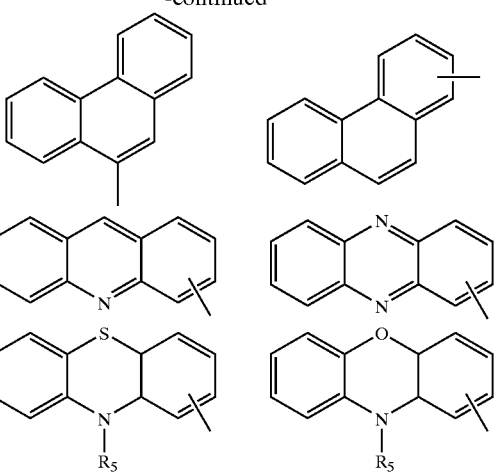

wherein the attachment point of A to the remaining part of the structure of formula (I) is as indicated on the chemical structures in Figure 1, and wherein A is optionally substituted with one or more substituents selected from $C_{1-6}$-alkyl, $C_{2-6}$-alkenyl, $C_{2-6}$-alkynyl, hydroxy, aryloxy, arylthio, aralkoxy, $C_{1-6}$-alkoxy, $C_{1-6}$-alkylthio, heteroaryloxy, heteroaralkoxy, halogen, perhalomethyl, perhalomethoxy, acyl, aralkyl, heteroaralkyl, cyano, amino, $C_{1-6}$-alkylamino, $C_{1-6}$-dialkylamino, arylamino or methylenedioxy; and wherein $X_1$ and $X_2$ are hydrogen; and $R_5$ is hydrogen or $C_{1-6}$-alkyl; and Y is hydrogen, or Y is $C_{1-12}$-alkyl, $C_{2-12}$-alkenyl, $C_{2-12}$-alkynyl, $C_{4-12}$-alkenynyl, aralkyl or heteroaralkyl each of which is optionally substituted with one or more substituents selected from halogen, $C_{1-6}$-alkyl, perhalomethyl, hydroxy, aryl, heteroaryl, carboxy or amino; and Z is hydrogen, halogen, hydroxy, or Z is $C_{1-6}$-alkyl or $C_{1-6}$-alkoxy each of which is optionally substituted with one or more substituents selected from halogen, hydroxy, carboxy, amino, cyano or $C_{1-6}$-alkoxy; and Q is O, S or $NR_6$, wherein $R_6$ is hydrogen, $C_{1-6}$-alkyl, $C_{2-6}$-alkenyl, $C_{2-6}$-alkynyl, $C_{4-6}$-alkenynyl, aralkyl, heteroaralkyl and wherein $R_6$ is optionally substituted with one or more substituents selected from halogen, hydroxy, $C_{1-6}$-alkoxy, amino or carboxy; and Ar is arylene, heteroarylene or a divalent heterocyclic group each of which can be optionally substituted with one or more substituents selected from $C_{1-6}$-alkyl, aryl or $C_{1-6}$-alkoxy each of which can be optionally substituted with halogen, hydroxy, carboxy, cyano or heterocyclyl; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, or $R_3$ is $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl each of which is optionally substituted with one or more substituents selected from halogen, perhalomethyl, hydroxy or cyano; and $R_4$ is hydrogen, $C_{1-6}$-alkyl, $C_{2-6}$-alkenyl, $C_{2-6}$-alkynyl, $C_{4-6}$-alkenynyl or aryl; and n is an integer ranging from 0 to 3; and m is an integer ranging from 0 to 1;

or a pharmaceutically acceptable salt thereof, or a pharmaceutically acceptable solvate thereof, or any tautomeric forms, stereoisomers, mixture of stereoisomers including a racemic mixture, or polymorphs.

In a preferred embodiment, the present invention is concerned with compounds of formula (I)

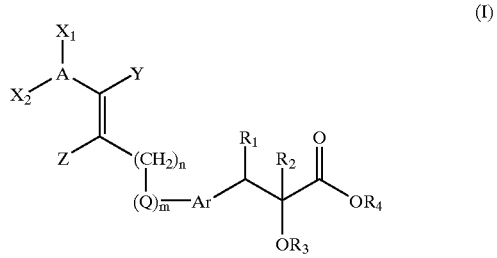

(I)

wherein A is aryl or heteroaryl and wherein A is optionally substituted with one or more substituents selected from hydroxy, halogen, perhalomethyl, perhalomethoxy, acyl, cyano, amino, $C_{1-6}$-alkylamino, $C_{1-6}$-dialkylamino, methylenedioxy, aralkenyl, aralkynyl, heteroaryloxy, heteroaralkoxy, aralkyl, heteroaralkyl, arylamino, or A is optionally substituted with $C_{1-6}$-alkyl, $C_{2-6}$-alkenyl or $C_{2-6}$-alkynyl each of which is optionally substituted with one or more substituents selected from $C_{1-6}$-alkoxycarbonyl or carboxy, or A is optionally substituted with $C_{1-6}$-alkoxy, $C_{1-6}$-alkylthio or $C_{2-6}$-alkenyloxy each of which is optionally substituted with one or more halogens, or A is optionally substituted with aryloxy, arylthio or aralkoxy each of which is optionally substituted with one or more substituents selected from $C_{1-6}$-alkoxy, nitro, carboxy or $C_{1-6}$-alkoxycarbonyl; and $X_1$ and $X_2$ independently are hydrogen, aryl or heteroaryl each of which is optionally substituted with one or more substituents selected from hydroxy, aryloxy, arylthio, aralkoxy, heteroaryloxy, aralkoxy, $C_{1-6}$-alkoxy, $C_{1-6}$-alkylthio, halogen, perhalomethyl, perhalomethoxy, acyl, aryl, heteroaryl, aralkyl, heteroaralkyl, cyano, amino, $C_{1-6}$-alkylamino, $C_{1-6}$-dialkylamino, arylamino or methylenedioxy, or aryl or heteroaryl each of which is optionally substituted with one or more substituents selected from $C_{1-6}$-alkyl, $C_{2-6}$-alkenyl or $C_{2-6}$-alkynyl each of which is optionally substituted with hydroxy; or A is selected from the ring systems consisting of

FIG. 1

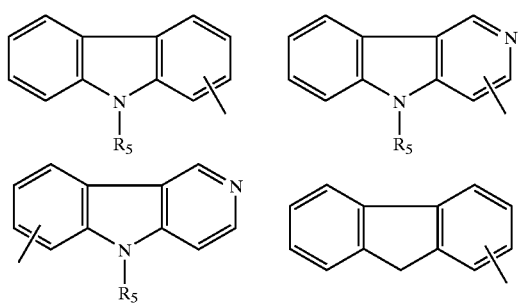

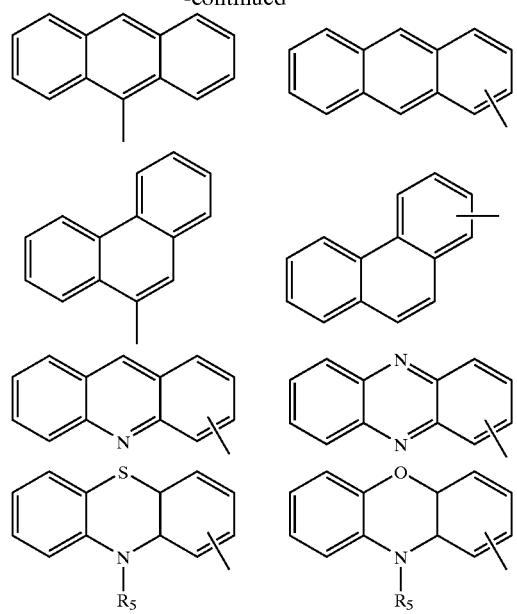

wherein the attachment point of A to the remaining part of the structure of formula (I) is as indicated on the chemical structures in Figure 1, and wherein A is optionally substituted with one or more substituents selected from $C_{1-6}$-alkyl, $C_{2-6}$-alkenyl, $C_{2-6}$-alkynyl, hydroxy, aryloxy, arylthio, aralkoxy, $C_{1-6}$-alkoxy, $C_{1-6}$-alkylthio, heteroaryloxy, heteroaralkoxy, halogen, perhalomethyl, perhalomethoxy, acyl, aralkyl, heteroaralkyl, cyano, amino, $C_{1-6}$-alkylamino, $C_{1-6}$-dialkylamino, arylamino or methylenedioxy; and wherein $X_1$ and $X_2$ are hydrogen; and $R_5$ is hydrogen or $C_{1-6}$-alkyl; and Y is hydrogen, or Y is $C_{1-12}$-alkyl, $C_{2-12}$-alkenyl, $C_{2-12}$-alkynyl, $C_{4-12}$-alkenynyl, aralkyl or heteroaralkyl each of which is optionally substituted with one or more substituents selected from halogen, $C_{1-6}$-alkyl, perhalomethyl, hydroxy, aryl, heteroaryl, carboxy or amino; and Z is hydrogen, halogen, hydroxy, or Z is $C_{1-6}$-alkyl or $C_{1-6}$-alkoxy each of which is optionally substituted with one or more substituents selected from halogen, hydroxy, carboxy, amino, cyano or $C_{1-6}$-alkoxy; and Q is O, S or $NR_6$, wherein $R_6$ is hydrogen, $C_{1-6}$-alkyl, $C_{2-6}$-alkenyl, $C_{2-6}$-alkynyl, $C_{4-6}$-alkenynyl, aralkyl, heteroaralkyl and wherein $R_6$ is optionally substituted with one or more substituents selected from halogen, hydroxy, $C_{1-6}$-alkoxy, amino or carboxy; and Ar is arylene, heteroarylene or a divalent heterocyclic group each of which can be optionally substituted with one or more substituents selected from $C_{1-6}$-alkyl, aryl or $C_{1-6}$-alkoxy each of which can be optionally substituted with halogen, hydroxy, carboxy, cyano or heterocyclyl; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, or $R_3$ is $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl each of which is optionally substituted with one or more substituents selected from halogen, perhalomethyl, hydroxy or cyano; and $R_4$ is hydrogen, $C_{1-6}$-alkyl, $C_{2-6}$-alkenyl, $C_{2-6}$-alkynyl, $C_{4-6}$-alkenynyl or aryl; and n is an integer ranging from 1 to 3; and m is 1;

or a pharmaceutically acceptable salt thereof, or a pharmaceutically acceptable solvate thereof, or any tautomeric forms, stereoisomers, mixture of stereoisomers including a racemic mixture, or polymorphs.

In another preferred embodiment, the present invention is concerned with compounds of formula (I)

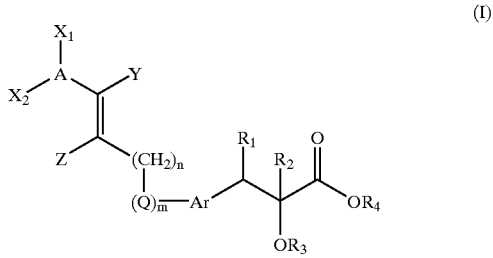

(I)

wherein A is aryl or heteroaryl and wherein A is optionally substituted with one or more substituents selected from $C_{1-6}$-alkyl, $C_{2-6}$-alkenyl, $C_{2-6}$-alkynyl, hydroxy, aryloxy, arylthio, aralkoxy, $C_{1-6}$-alkoxy, $C_{1-6}$-alkylthio, heteroaryloxy, heteroaralkoxy, halogen, perhalomethyl, perhalomethoxy, acyl, aralkyl, heteroaralkyl, cyano, amino, $C_{1-6}$-alkylamino, $C_{1-6}$-dialkylamino, arylamino or methylenedioxy, and $X_1$ and $X_2$ independently are hydrogen, aryl or heteroaryl optionally substituted with one or more substituents selected from $C_{1-6}$-alkyl, $C_{2-6}$-alkenyl, $C_{2-6}$-alkynyl, hydroxy, aryloxy, arylthio, aralkoxy, heteroaryloxy, aralkoxy, $C_{1-6}$-alkoxy, $C_{1-6}$-alkylthio, halogen, perhalomethyl, perhalomethoxy, acyl, aryl, heteroaryl, aralkyl, heteroaralkyl, cyano, amino, $C_{1-6}$-alkylamino, $C_{1-6}$-dialkylamino, arylamino or methylenedioxy;

or wherein A is selected from the ring systems consisting of

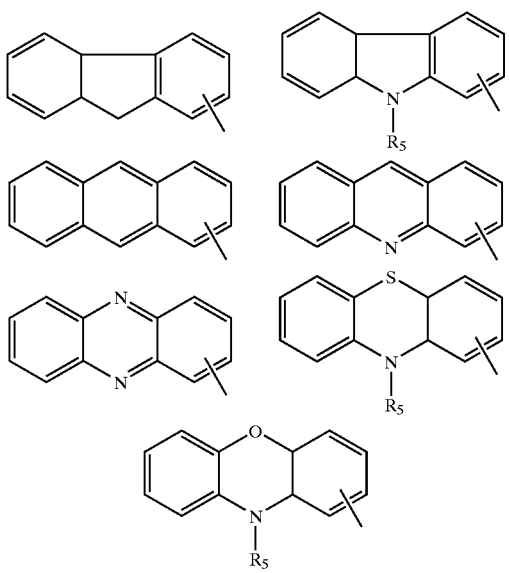

FIG. 1 wherein the attachment point of A to the remaining part of the structure of formula (I) is as indicated on the chemical structures in Figure 1, and wherein A is optionally substituted with one or more substituents selected from $C_{1-6}$-alkyl, $C_{2-6}$-alkenyl, $C_{2-6}$-alkynyl, hydroxy, aryloxy, arylthio, aralkoxy, $C_{1-6}$-alkoxy, $C_{1-6}$-alkylthio, heteroaryloxy, heteroaralkoxy, halogen, perhalomethyl, perhalomethoxy, acyl, aralkyl, heteroaralkyl, cyano, amino, $C_{1-6}$-alkylamino, $C_{1-6}$-dialkylamino, arylamino or methylenedioxy, and wherein $X_1$ and $X_2$ are hydrogen; and $R_5$ is hydrogen or $C_{1-6}$-alkyl; and Y is hydrogen, $C_{1-12}$-alkyl, $C_{2-12}$-alkenyl, $C_{2-12}$-alkynyl, $C_{4-12}$-alkenynyl, aralkyl or heteroaralkyl optionally substituted with one or more substituents selected from halogen, $C_{1-6}$-alkyl, perhalomethyl, hydroxy, aryl, heteroaryl, carboxy or amino; and Z is hydrogen, halogen, hydroxy, $C_{1-6}$-alkyl or $C_{1-6}$-alkoxy optionally substituted with one or more substituents selected from halogen, hydroxy, carboxy, amino, cyano or $C_{1-6}$-alkoxy; and Q is O, S or $NR_6$, wherein $R_6$ is hydrogen, $C_{1-6}$-alkyl, $C_{2-6}$-alkenyl, $C_{2-6}$-alkynyl, $C_{4-6}$-alkenynyl, aralkyl, heteroaralkyl and wherein $R_6$ is optionally substituted with one or more substituents selected from halogen, hydroxy, $C_{1-6}$-alkoxy, amino or carboxy; and Ar is arylene, heteroarylene or a divalent heterocyclic group each of which can be optionally substituted with one or more substituents selected from $C_{1-6}$-alkyl, aryl or $C_{1-6}$-alkoxy each of which can be optionally substituted with halogen, hydroxy, carboxy, cyano or heterocyclyl; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl groups optionally substituted with one or more substituents selected from halogen, perhalomethyl, hydroxy or cyano; and $R_4$ is hydrogen, $C_{1-6}$-alkyl, $C_{2-6}$-alkenyl, $C_{2-6}$-alkynyl, $C_{4-6}$-alkenynyl or aryl; and n is an integer ranging from 0 to 3; and m is an integer ranging from 0 to 1.

In another preferred embodiment, the present invention is concerned with compounds of formula (I)

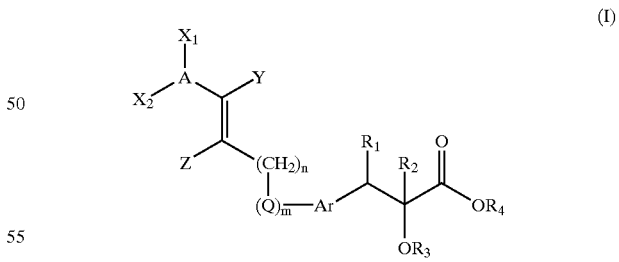

(I)

wherein A is aryl or heteroaryl and wherein A is optionally substituted with one or more substituents selected from $C_{1-6}$-alkyl, $C_{2-6}$-alkenyl, $C_{2-6}$-alkynyl, hydroxy, aryloxy, arylthio, aralkoxy, $C_{1-6}$-alkoxy, $C_{1-6}$-alkylthio, heteroaryloxy, heteroaralkoxy, halogen, perhalomethyl, perhalomethoxy, acyl, aralkyl, heteroaralkyl, cyano, amino, $C_{1-6}$-alkylamino, $C_{1-6}$-dialkylamino, arylamino or methylenedioxy; or provided $X_1$ and $X_2$ is hydrogen, A is selected from the ring systems consisting of

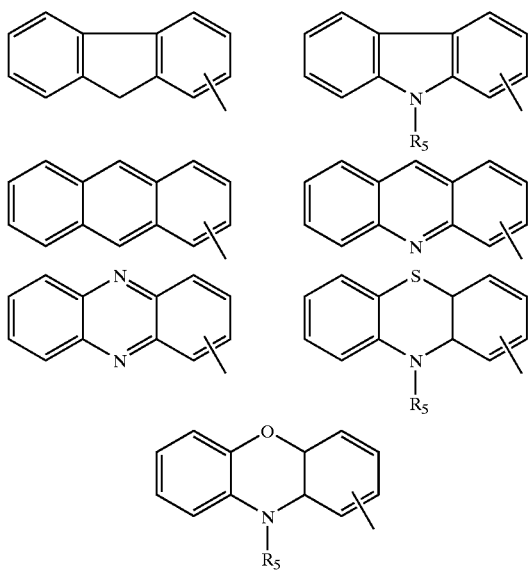

wherein A is optionally substituted with one or more substituents selected from $C_{1-6}$-alkyl, $C_{2-6}$-alkenyl, $C_{2-6}$-alkynyl, hydroxy, aryloxy, arylthio, aralkoxy, $C_{1-6}$-alkoxy, $C_{1-6}$-alkylthio, heteroaryloxy, heteroaralkoxy, halogen, perhalomethyl, perhalomethoxy, acyl, aralkyl, heteroaralkyl, cyano, amino, $C_{1-6}$-alkylamino, $C_{1-6}$-dialkylamino, arylamino or methylenedioxy; and $R_5$ is hydrogen or $C_{1-6}$-alkyl; and $X_1$ and $X_2$ independently are hydrogen, aryl or heteroaryl optionally substituted with one or more substituents selected from $C_{1-6}$-alkyl, $C_{2-6}$-alkenyl, $C_{2-6}$-alkynyl, hydroxy, aryloxy, arylthio, aralkoxy, heteroaryloxy, aralkoxy, $C_{1-6}$-alkoxy, $C_{1-6}$-alkylthio, halogen, perhalomethyl, perhalomethoxy, acyl, aryl, heteroaryl, aralkyl, heteroaralkyl, cyano, amino, $C_{1-6}$-alkylamino, $C_{1-6}$-dialkylamino, arylamino or methylenedioxy; and Y is hydrogen, $C_{1-12}$-alkyl, $C_{2-12}$-alkenyl, $C_{2-12}$-alkynyl, $C_{4-12}$-alkenynyl, aralkyl or heteroaralkyl optionally substituted with one or more substituents selected from halogen, $C_{1-6}$-alkyl, perhalomethyl, hydroxy, aryl, heteroaryl, carboxy or amino; and Z is hydrogen, halogen, hydroxy, $C_{1-6}$-alkyl or $C_{1-6}$-alkoxy optionally substituted with one or more substituents selected from halogen, hydroxy, carboxy, amino, cyano or $C_{1-6}$-alkoxy; and Q is O, S or $NR_6$, wherein $R_6$ is hydrogen, $C_{1-6}$-alkyl, $C_{2-6}$-alkenyl, $C_{2-6}$-alkynyl, $C_{4-6}$-alkenynyl, aralkyl, heteroaralkyl and wherein $R_6$ is optionally substituted with one or more substituents selected from halogen, hydroxy, $C_{1-6}$-alkoxy, amino or carboxy; and Ar is arylene, heteroarylene or a divalent heterocyclic group each of which can be optionally substituted with one or more substituents selected from $C_{1-6}$-alkyl, aryl or $C_{1-6}$-alkoxy each of which can be optionally substituted with halogen, hydroxy, carboxy, cyano or heterocyclyl; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl groups optionally substituted with one or more substituents selected from halogen, perhalomethyl, hydroxy or cyano; and $R_4$ is hydrogen, $C_{1-6}$-alkyl, $C_{2-6}$-alkenyl, $C_{2-6}$-alkynyl, $C_{4-6}$-alkenynyl or aryl; and n is an integer ranging from 0 to 3; and m is an integer ranging from 0 to 1.

In another preferred embodiment, the present invention is concerned with compounds of formula I wherein A is aryl or heteroaryl optionally substituted with one or more substituents selected from from $C_{1-6}$-alkyl, $C_{2-6}$-alkenyl each of which is optionally substituted with one or more substituents selected from $C_{1-6}$-alkoxycarbonyl or carboxy, or A is optionally substituted with aryloxy optionally substituted with one or more $C_{1-6}$-alkoxy, or A is optionally substituted with aralkoxy optionally substituted with one or more substituents selected from $C_{1-6}$-alkoxy, nitro, carboxy or $C_{1-6}$-alkoxycarbonyl, or A is optionally substituted with $C_{1-6}$-alkoxy optionally substituted with one or more halogens, or A is optionally substituted with aralkenyl, $C_{2-6}$-alkenyloxy, aralkynyl, halogen, perhalomethyl, perhalomethoxy, acyl, aralkyl or methylenedioxy.

In another preferred embodiment, the present invention is concerned with compounds of formula I wherein A is aryl, heteroaryl or

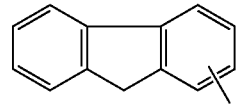

optionally substituted with one or more substituents selected from aryloxy, arylthio, aralkoxy, $C_{1-6}$-alkoxy, $C_{1-6}$-alkylthio, halogen, perhalomethyl, aralkyl, heteroaralkyl, heteroaryloxy or heteroaralkoxy.

In another preferred embodiment, the present invention is concerned with compounds of formula I wherein A is aryl optionally substituted with one or more substituents selected from aryloxy, arylthio, aralkoxy, $C_{1-6}$-alkoxy, $C_{1-6}$-alkylthio, halogen, perhalomethyl, aralkyl, heteroaralkyl, heteroaryloxy or heteroaralkoxy.

In another preferred embodiment, the present invention is concerned with compounds of formula I wherein A is aryl optionally substituted with one or more substituents selected from from $C_{1-6}$-alkyl, $C_{2-6}$-alkenyl each of which is optionally substituted with one or more substituents selected from $C_{1-6}$-alkoxycarbonyl or carboxy, or A is optionally substituted with aryloxy optionally substituted with one or more $C_{1-6}$-alkoxy, or A is optionally substituted with aralkoxy optionally substituted with one or more substituents selected from $C_{1-6}$-alkoxy, nitro, carboxy or $C_{1-6}$-alkoxycarbonyl, or A is optionally substituted with $C_{1-6}$-alkoxy optionally substituted with one or more halogens, or A is optionally substituted with aralkenyl, $C_{2-6}$-alkenyloxy, aralkynyl, halogen, perhalomethyl, perhalomethoxy, acyl, aralkyl or methylenedioxy.

In another preferred embodiment, the present invention is concerned with compounds of formula I wherein A is aryl optionally substituted with one or more substituents selected from from $C_{1-6}$-alkyl, or A is optionally substituted with aryloxy optionally substituted with one or more $C_{1-6}$-alkoxy, A is optionally substituted with aralkoxy optionally substituted with one or more substituents selected from $C_{1-6}$-alkoxy, or A is optionally substituted with $C_{1-6}$-alkoxy optionally substituted with one or more halogens, or A is optionally substituted with aralkenyl, aralkynyl, halogen, perhalomethyl, perhalomethoxy or aralkyl.

In another preferred embodiment, the present invention is concerned with compounds of formula I wherein A is heteroaryl optionally substituted With one or more substituents selected from aryloxy, arylthio, aralkoxy, $C_{1-6}$-alkoxy, $C_{1-6}$-alkylthio, halogen, perhalomethyl, aralkyl, heteroaralkyl, heteroaryloxy or heteroaralkoxy.

In another preferred embodiment, the present invention is concerned with compounds of formula I wherein A is heteroaryl.

In another preferred embodiment, the present invention is concerned with compounds of formula I wherein A is

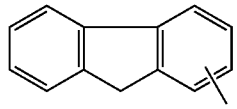

optionally substituted with one or more substituents selected from aryloxy, arylthio, aralkoxy, $C_{1-6}$-alkoxy, $C_{1-6}$-alkylthio, halogen, perhalomethyl, aralkyl, heteroaralkyl, heteroaryloxy or heteroaralkoxy.

In another preferred embodiment, the present invention is concerned with compounds of formula I wherein A is

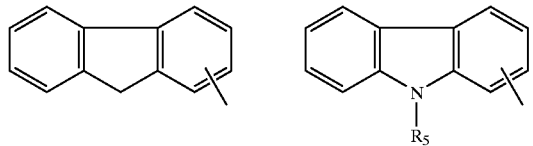

optionally substituted with one or more substituents selected from $C_{1-6}$-alkyl, and wherein $R_5$ is hydrogen or $C_{1-6}$-alkyl.

In another preferred embodiment, the present invention is concerned with compounds of formula I wherein $X_1$ and $X_2$ independently are hydrogen, aryl or heteroaryl optionally substituted with one or more substituents selected from aryloxy, arylthio, aralkoxy, halogen, perhalomethyl, aryl, heteroaryl, aralkyl, heteroaralkyl, heteroaryloxy or heteroaralkoxy.

In another preferred embodiment, the present invention is concerned with compounds of formula I wherein $X_1$ and $X_2$ independently are
hydrogen,
aryl or heteroaryl optionally substituted with one or more substituents selected from halogen, acyl, aryl, or
aryl or heteroaryl optionally substituted with one or more substituents selected from $C_{1-6}$-alkyl, $C_{2-6}$-alkynyl each of which is optionally substituted with hydroxy.

In another preferred embodiment, the present invention is concerned with compounds of formula I wherein $X_1$ and $X_2$ independently are
hydrogen, or
aryl or heteroaryl optionally substituted with one or more substituents selected from halogen.

In another preferred embodiment, the present invention is concerned with compounds of formula I wherein $X_1$ and $X_2$ independently are hydrogen or aryl optionally substituted with one or more substituents selected from aryloxy, arylthio, aralkoxy, halogen, perhalomethyl, aryl, heteroaryl, aralkyl, heteroaralkyl, heteroaryloxy or heteroaralkoxy.

In another preferred embodiment, the present invention is concerned with compounds of formula I wherein $X_1$ and $X_2$ independently are
hydrogen,
aryl optionally substituted with one or more substituents selected from halogen, acyl, aryl, or
aryl optionally substituted with one or more substituents selected from $C_{1-6}$-alkyl, $C_{2-6}$-alkynyl each of which is optionally substituted with hydroxy.

In another preferred embodiment, the present invention is concerned with compounds of formula I wherein $X_1$ and $X_2$ independently are
hydrogen, or
phenyl optionally substituted with one or more substituents selected from halogen.

In another preferred embodiment, the present invention is concerned with compounds of formula I wherein $X_1$ and $X_2$ independently are hydrogen or heteroaryl optionally substituted with one or more substituents selected from aryloxy, arylthio, aralkoxy, halogen, perhalomethyl, aryl, heteroaryl, aralkyl, heteroaralkyl, heteroaryloxy or heteroaralkoxy.

In another preferred embodiment, the present invention is concerned with compounds of formula I wherein $X_1$ and $X_2$ independently are hydrogen or heteroaryl.

In another preferred embodiment, the present invention is concerned with compounds of formula I wherein $X_1$ and $X_2$ is hydrogen.

In another preferred embodiment, the present invention is concerned with compounds of formula I wherein Y is hydrogen or $C_{1-12}$-alkyl.

In another preferred embodiment, the present invention is concerned with compounds of formula I wherein Y is hydrogen or methyl.

In another preferred embodiment, the present invention is concerned with compounds of formula I wherein Z is hydrogen or $C_{1-6}$-alkoxy.

In another preferred embodiment, the present invention is concerned with compounds of formula I wherein Z is hydrogen or $C_{1-6}$-alkyl.

In another preferred embodiment, the present invention is concerned with compounds of formula I wherein Z is hydrogen.

In another preferred embodiment, the present invention is concerned with compounds of formula I wherein Q is O.

In another preferred embodiment, the present invention is concerned with compounds of formula I wherein Ar is arylene optionally substituted with one or more substituents selected from $C_{1-6}$-alkyl or $C_{1-6}$-alkoxy each of which can be optionally substituted with carboxy.

In another preferred embodiment, the present invention is concerned with compounds of formula I wherein Ar is arylene.

In another preferred embodiment, the present invention is concerned with compounds of formula I wherein $R_1$ is hydrogen or $R_1$ forms a bond together with $R_2$.

In another preferred embodiment, the present invention is concerned with compounds of formula I wherein $R_1$ is hydrogen.

In another preferred embodiment, the present invention is concerned with compounds of formula I wherein $R_2$ is hydrogen or $R_2$ forms a bond together with $R_1$.

In another preferred embodiment, the present invention is concerned with compounds of formula I wherein $R_2$ is hydrogen.

In another preferred embodiment, the present invention is concerned with compounds of formula I wherein $R_3$ is $C_{1-6}$-alkyl or aralkyl.

In another preferred embodiment, the present invention is concerned with compounds of formula I wherein $R_3$ is $C_{1-6}$-alkyl.

In another preferred embodiment, the present invention is concerned with compounds of formula I wherein $R_4$ is hydrogen, $C_{1-3}$-alkyl.

In another preferred embodiment, the present invention is concerned with compounds of formula I wherein $R_4$ is hydrogen.

In another preferred embodiment, the present invention is concerned with compounds of formula I wherein n is 1.

In another preferred embodiment, the present invention is concerned with compounds of formula I wherein m is 1.

In another preferred embodiment, the present invention is concerned with compounds of formula I wherein alkyl is methyl, ethyl, n-propyl, iso-propyl, butyl, tert-butyl, pentyl, hexyl, cyclopropyl or cyclopentyl.

In another preferred embodiment, the present invention is concerned with compounds of formula I wherein alkenyl is vinyl or 1-propenyl.

In another preferred embodiment, the present invention is concerned with compounds of formula I wherein alkynyl is ethynyl, 1-propynyl and 2-propynyl.

In another preferred embodiment, the present invention is concerned with compounds of formula I wherein alkoxy is methoxy, ethoxy, propoxy, butoxy, pentoxy, hexoxy, isopropoxy or cyclopentyloxy.

In another preferred embodiment, the present invention is concerned with compounds of formula I wherein alkylthio is methylthio, ethylthio, propylthio or cyclopentylthio.

In another preferred embodiment, the present invention is concerned with compounds of formula I wherein aryl is phenyl optionally substituted with halogen.

In another preferred embodiment, the present invention is concerned with compounds of formula I wherein arylene is phenylene optionally substituted with halogen.

In another preferred embodiment, the present invention is concerned with compounds of formula I wherein halogen is fluorine or chlorine.

In another preferred embodiment, the present invention is concerned with compounds of formula I wherein perhalomethyl is trifluoromethyl.

In another preferred embodiment, the present invention is concerned with compounds of formula I wherein acyl is acetyl.

In another preferred embodiment, the present invention is concerned with compounds of formula I wherein heteroaryl is furan, thiophene, pyrrole, imidazole, pyrazole, pyridine, quinoline, isoquinoline, quinazoline, quinoxaline, indole, benzimidazole or benzofuran. In another preferred embodiment, the present invention is concerned with compounds of formula I wherein heteroaryl is furan, pyrrole, indole or benzofuran.

In another preferred embodiment, the present invention is concerned with compounds of formula I wherein heteroarylene is furan, thiophene, pyrrole, imidazole, pyrazole, triazole, pyridine, pyrazine, pyrimidine or pyridazine.

In another preferred embodiment, the present invention is concerned with compounds of formula I wherein aralkyl is benzyl or phenethyl.

In another preferred embodiment, the present invention is concerned with compounds of formula I wherein aryloxy is phenoxy.

In another preferred embodiment, the present invention is concerned with compounds of formula I wherein aralkoxy is benzyloxy.

In another preferred embodiment, the present invention is concerned with compounds of formula I wherein n is an integer ranging from 1 to 3 and m is 1.

In another preferred embodiment, the present invention is concerned with compounds of formula I wherein the substituents Z and Y are arranged in a trans-configuration.

In another preferred embodiment, the present invention is concerned with compounds of formula I wherein the substituents Z and Y are arranged in a cis-configuration.

Preferred compounds of the invention are:
(E)-(S)-Ethyl 3-[4-(3-biphenyl-4-yl-but-2-enyloxy)-phenyl]-2-ethoxy-propionate,
(E)-(S)-3-[4-(3-Biphenyl-4-yl-but-2-enyloxy)-phenyl]-2-ethoxy-propionic acid,
(E)-(S)-3-{4-[3-(4'-Bromo-biphenyl-4-yl)-but-2-enyloxy]-phenyl}-2-ethoxy-propionic acid ethyl ester,
(E)-(S)-3-{4-[3-(4'-Bromo-biphenyl-4-yl)-but-2-enyloxy]-phenyl}-2-ethoxy-propionic acid,
(E)-(S)-2-Ethoxy-3-{4-[3-(4-phenoxy-phenyl)-but-2-enyloxy]-phenyl}-propionic acid ethyl ester,
(E)-(S)-2-Ethoxy-3-{4-[3-(4-phenoxy-phenyl)-but-2-enyloxy]-phenyl}-propionic acid,
(E)-(S)-2-Ethoxy-3-(4-{3-[4-(4-methoxy-phenoxy)-phenyl]-but-2-enyloxy}-phenyl)-propionic acid ethyl ester,
(E)-(S)-2-Ethoxy-3-(4-{3-[4-(4-methoxy-phenoxy)-phenyl]-but-2-enyloxy}-phenyl)-propionic acid,
(E)-(S)-2-Ethoxy-3-{4-[3-(9H-fluoren-2-yl)-but-2-enyloxy]-phenyl}-propionic acid ethyl ester,
(E)-(S)-2-Ethoxy-3-{4-[3-(9H-fluoren-2-yl)-but-2-enyloxy]-phenyl}-propionic acid,
(E)-(S)-3-{4-[3-(3,4-Dimethoxy-phenyl)-but-2-enyloxy]-phenyl}-2-ethoxy-propionic acid ethyl ester,
(E)-(S)-3-{4-[3-(3,4-Dimethoxy-phenyl)-but-2-enyloxy]-phenyl}-2-ethoxy-propionic acid,
(E)-(S)-3-{4-[3-(3,5-Bis-trifluoromethyl-phenyl)-but-2-enyloxy]-phenyl}-2-ethoxy-propionic acid ethyl ester,
(E)-(S)-3-{4-[3-(3,5-Bis-trifluoromethyl-phenyl)-but-2-enyloxy]-phenyl}-2-ethoxy-propionic acid,
(E)-(S)-3-[4-(3-Biphenyl-4-yl-allyloxy)-phenyl]-2-ethoxy-propionic acid ethyl ester,
(E)-(S)-3-[4-(3-Biphenyl-4-yl-allyloxy)-phenyl]-2-ethoxy-propionic acid,
(E)-(S)-2-Ethoxy-3-[4-(3-naphthalen-2-yl-but-2-enyloxy)-phenyl]-propionic acid ethyl ester,
(E)-(S)-2-Ethoxy-3-[4-(3-naphthalen-2-yl-but-2-enyloxy)-phenyl]-propionic acid,
(E)-(S)-2-Ethoxy-3-[4-(3-pyridin-2-yl-but-2-enyloxy)-phenyl]-propionic acid ethyl ester,
(E)-(S)-2-Ethoxy-3-[4-(3-pyridin-2-yl-but-2-enyloxy)-phenyl]-propionic acid,
(E)-(S)-3-{4-[3-(3,5-Bis-benzyloxy-phenyl)-but-2-enyloxy]-phenyl}-2-ethoxy-propionic acid ethyl ester,
(E)-(S)-3-{4-[3-(3,5-Bis-benzyloxy-phenyl)-but-2-enyloxy]-phenyl}-2-ethoxy-propionic acid,
(E)-(S)-2-Ethoxy-3-[4-(3-naphthalen-2-yl-allyloxy)-phenyl]-propionic acid ethyl ester,
(E)-(S)-2-Ethoxy-3-[4-(3-naphthalen-2-yl-allyloxy)-phenyl]-propionic acid,
(E)-(S)-2-Ethoxy-3-{4-[3-(3-phenoxy-phenyl)-allyloxy]-phenyl}-propionic acid ethyl ester,
(E)-(S)-2-Ethoxy-3-{4-[3-(3-phenoxy-phenyl)-allyloxy]-phenyl}-propionic acid,
(S)-3-[4-(2-Benzofuran-3-yl-allyloxy)-phenyl]-2-ethoxy-propionic acid ethyl ester,
(S)-3-[4-(2-Benzofuran-3-yl-allyloxy)-phenyl]-2-ethoxy-propionic acid;
or a salt thereof with a pharmaceutically acceptable acid or base, or any optical isomer or mixture of optical isomers, including a racemic mixture, or any tautomeric forms.

Also preferred compounds of the invention are:
(E)-(S)-3-{4-[3-(4-Benzyloxy-phenyl)-allyloxy]-phenyl}-2-ethoxy-propionic acid ethyl ester,
(E)-(S)-3-{4-[3-(4-Benzyloxy-phenyl)-allyloxy]-phenyl}-2-ethoxy-propionic acid,
(E)-(S)-3-[4-(3-Benzo[1,3]dioxol-5-yl-allyloxy)-phenyl]-2-ethoxy-propionic acid ethyl ester, (E)-(S)-3-[4-(3-Benzo[1,3]dioxol-5-yl-allyloxy)-phenyl]-2-ethoxy-propionic acid,
(E)-(S)-3-{4-[3-(4-Allyloxy-phenyl)-allyloxy]-phenyl}-2-ethoxy-propionic acid ethyl ester,
(E)-(S)-3-{4-[3-(4-Allyloxy-phenyl)-allyloxy]-phenyl}-2-ethoxy-propionic acid,
(E)-(S)-3-[4-(3-Benzofuran-7-yl-allyloxy)-phenyl]-2-ethoxy-propionic acid ethyl ester,
(E)-(S)-3-[4-(3-Benzofuran-7-yl-allyloxy)-phenyl]-2-ethoxy-propionic acid,
(S)-3-[4-(3-Benzo[1,3]dioxol-4-yl-allyloxy)-phenyl]-2-ethoxy-propionic acid ethyl ester,
(S)-3-[4-(3-Benzo[1,3]dioxol-4-yl-allyloxy)-phenyl]-2-ethoxy-propionic acid,
(E)-(S)-2-Ethoxy-3-(4-[3-(9H-fluoren-2-yl)-allyloxy]-phenyl)-propionic acid ethyl ester,
(E)-(S)-2-Ethoxy-3-(4-[3-(9H-fluoren-2-yl)-allyloxy]-phenyl)-propionic acid,
(S)-2-Ethoxy-3-[4-(3-quinolin-2-yl-allyloxy)-phenyl]-propionic acid ethyl ester,
(S)-2-Ethoxy-3-[4-(3-quinolin-2-yl-allyloxy)-phenyl]-propionic acid,
(E)-(S)-3-{4-[3-(3,5-Bis-benzyloxy-phenyl)-allyloxy]-phenyl}-2-ethoxy-propionic acid ethyl ester,
(E)-(S)-3-{4-[3-(3,5-Bis-benzyloxy-phenyl)-allyloxy]-phenyl}-2-ethoxy-propionic acid,
(E)-(S)-3-{4-[3-(3,5-Dimethoxy-phenyl)-allyloxy]-phenyl}-2-ethoxy-propionic acid ethyl ester,
(E)-(S)-3-{4-[3-(3,5-Dimethoxy-phenyl)-allyloxy]-phenyl}-2-ethoxy-propionic acid,
(E)-(S)-2-Ethoxy-3-[4-(3-phenanthren-9-yl-allyloxy)-phenyl]-propionic acid ethyl ester,
(E)-(S)-2-Ethoxy-3-{4-[3-(2-methoxy-naphthalen-1-yl)-allyloxy]-phenyl}-propionic acid ethyl ester,
(E)-(S)-2-Ethoxy-3-{4-[3-(2-methoxy-naphthalen-1-yl)-allyloxy]-phenyl}-propionic acid,
(E)-(S)-Ethyl 3-{4-[3-(4-Bromophenyl)-but-2-enyloxy]-phenyl}-2-ethoxy-propionate,
(E)-(S)-3-{4-[3-(4-Bromophenyl)-but-2-enyloxy]-phenyl}-2-ethoxy-propionic acid,
(E)-(S)-Ethyl 3-{4-[3-(4'-Chloro-biphenyl-4-yl)-but-2-enyloxy]-phenyl}-2-ethoxy-propionate,
(E)-(S)-3-{4-[3-(4'-Chloro-biphenyl-4-yl)-but-2-enyloxy]-phenyl}-2-ethoxy-propionic acid,
(E)-(S)-Ethyl 2-Ethoxy-3-{4-[3-(5'-isopropyl-2'-methoxy-biphenyl-4-yl)-but-2-enyloxy]-phenyl}-propionate,
(E)-(S)-2-Ethoxy-3-{4-[3-(5'-isopropyl-2'-methoxy-biphenyl-4-yl)-but-2-enyloxy]-phenyl}-propionic acid,
(E)-(S)-Ethyl 2-Ethoxy-3-{4-[3-(5'-chloro-2'-methoxy-biphenyl-4-yl)-but-2-enyloxy]-phenyl}-propionate,
(E)-(S)-3-{4-[3-(5'-Chloro-2'-methoxy-biphenyl-4-yl)-but-2-enyloxy]-phenyl}-2-ethoxy-propionic acid,
(E)-(S)-Ethyl 3-{4-[3-(2',3'-Dichloro-biphenyl-4-yl)-but-2-enyloxy]-phenyl}-2-ethoxy-propionate,
(E)-(S)-3-{4-[3-(2',3'-Dichloro-biphenyl-4-yl)-but-2-enyloxy]-phenyl}-2-ethoxy-propionic acid,
(E)-(S)-Ethyl 3-{4-[3-(2',6'-Dimethoxy-biphenyl-4-yl)-but-2-enyloxy]-phenyl}-2-ethoxy-propionate,
(E)-(S)-3-{4-[3-(2',6'-Dimethoxy-biphenyl-4-yl)-but-2-enyloxy]-phenyl}-2-ethoxy-propionic acid,
(E)-(S)-Ethyl 3-{4-[3-(4-Bromophenyl)-2-methyl-but-2-enyloxy]-phenyl}-2-ethoxy-propionate,
(E)-(S)-3-{4-[3-(4-Bromophenyl)-2-methyl-but-2-enyloxy]-phenyl}-2-ethoxy-propionic acid,
(Z)-(S)-Ethyl 3-{4-[3-(4-Bromophenyl)-2-methyl-but-2-enyloxy]-phenyl}-2-ethoxy-propionate,
(Z)-(S)-3-{4-[3-(4-Bromophenyl)-2-methyl-but-2-enyloxy]-phenyl}-2-ethoxy-propionic acid,
(E)-(S)-Ethyl 2-Ethoxy-3-[4-(3-[1,1';3',1"]terphenyl-4"-yl-but-2-enyloxy)-phenyl]-propionate,
(E)-(S)-2-Ethoxy-3-[4-(3-[1,1';3',1"]terphenyl-4"-yl-but-2-enyloxy)-phenyl]-propionic acid,
(E)-(S)-Ethyl 2-Ethoxy-3-{4-[3-(3'-methyl-biphenyl-4-yl)-but-2-enyloxy]-phenyl}-propionate,
(E)-(S)-2-Ethoxy-3-{4-[3-(3'-methyl-biphenyl-4-yl)-but-2-enyloxy]-phenyl}-propionic acid,
(E)-(S)-3-{4-[3-(3'-Acetyl-biphenyl-4-yl)-but-2-enyloxy]-phenyl}-2-ethoxy-propionate,
(E)-(S)-2-Ethoxy-3-{4-[3-(5'-isopropyl-2'-methoxy-biphenyl-4-yl)-allyloxy]-phenyl}-propionic acid ethyl ester,
(E)-(S)-2- Ethoxy-3-{4-[3-(5'-isopropyl-2'-methoxy-biphenyl-4-yl)-allyloxy]-phenyl}-propionic acid,
(E)-(S)-3-{4-[3-(3,5-Distyryl-phenyl)-allyloxy]-phenyl}-2-ethoxy-propionic acid ethyl ester,
(E)-(S)-3-{4-[3-(3,5-Distyryl-phenyl)-allyloxy]-phenyl}-2-ethoxy-propionic acid;

or a salt thereof with a pharmaceutically acceptable acid or base, or any optical isomer or mixture of optical isomers, including a racemic mixture, or any tautomeric forms.

Also preferred compounds of the invention are:
(E)-(S)-3-{4-[3-(3,5-Diisopropoxy-phenyl)-allyloxy]-phenyl}-2-ethoxy-propionic acid ethyl ester,
(E)-(S)-3-{4-[3-(3,5-Diisopropoxy-phenyl)-allyloxy]-phenyl}-2-ethoxy-propionic acid,
(S)-3-{4-[3-(3-Bromo-5-styryl-phenyl)-allyloxy]-phenyl}-2-ethoxy-propionic acid ethyl ester,
(S)-3-{4-[3-(3-Bromo-5-styryl-phenyl)-allyloxy]-phenyl}-2-ethoxy-propionic acid,
(E)-(S)-2-Ethoxy-3-[4-(3-phenyl-allyloxy)-phenyl]-propionic acid ethyl ester,
(E)-(S)-2-Ethoxy-3-[4-(3-phenyl-allyloxy)-phenyl]-propionic acid,
(E)-(S)-3-{4-[3-(2',3'-Dichloro-biphenyl-4-yl)-allyloxy]-phenyl}-2-ethoxy-propionic acid ethyl ester,
(E)-(S)-3-{4-[3-(2',3'-Dichloro-biphenyl-4-yl)-allyloxy]-phenyl}-2-ethoxy-propionic acid,
(E)-(S)-3-{4-[3-(3,5-Bis-phenylethynyl-phenyl)-allyloxy]-phenyl}-2-ethoxy-propionic acid ethyl ester,
(E)-(S)-3-{4-[3-(3,5-Bis-phenylethynyl-phenyl)-allyloxy]-phenyl}-2-ethoxy-propionic acid,
(E)-(S)-3-{4-[3-(3,5-Diphenethyl-phenyl)-allyloxy]-phenyl}-2-ethoxy-propionic acid ethyl ester,
(E)-(S)-3-{4-[3-(3,5-Diphenethyl-phenyl)-allyloxy]-phenyl}-2-ethoxy-propionic acid,
3-{4-[3-(3,5-Bis-cyclopentyloxy-phenyl)-allyloxy]-phenyl}-2-ethoxy-propionic acid ethyl ester,
(E)-(S)-3-{4-[3-(3,5-Bis-cyclopentyloxy-phenyl)-allyloxy]-phenyl}-2-ethoxy-propionic acid,
(E)-(S)-3-(4-{3-[3,5-Bis-(2,2,2-trifluoro-ethoxy)-phenyl]-allyloxy}-phenyl)-2-ethoxy-propionic acid ethyl ester,
(E)-(S)-3-(4-{3-[3,5-Bis-(2,2,2-trifluoro-ethoxy)-phenyl]-allyloxy}-phenyl)-2-ethoxy-propionic acid,
(E)-(S)-Ethyl 2-Ethoxy-3-{4-[3-(4-furan-2-yl-phenyl)-but-2-enyloxy]-phenyl}-propionate,
(E)-(S)-Ethyl 2-Ethoxy-3-{4-[3-(2'-methyl-biphenyl-4-yl)-but-2-enyloxy]-phenyl}-propionate,
(E)-(S)-2-Ethoxy-3-{4-[3-(2'-methyl-biphenyl-4-yl)-but-2-enyloxy]-phenyl}-propionic acid,
(E)-(S)-Ethyl 3-{4-[3-(2',5'-Dimethoxy-biphenyl-4-yl)-but-2-enyloxy]-phenyl}-2-ethoxy-propionate,
(E)-(S)-3-{4-[3-(2',5'-Dimethoxy-biphenyl-4-yl)-but-2-enyloxy]-phenyl}-2-ethoxy-propionic acid,
(E)-(S)-Ethyl 3-{4-[3-(4-Bromophenyl)-2-ethyl-but-2-enyloxy]-phenyl}-2-ethoxy-propionate, (E)-(S)-3-{4-[3-(4-Bromophenyl)-2-ethyl-but-2-enyloxy]-phenyl}-2-ethoxy-propionic acid,
(Z)-(S)-Ethyl 3-{4-[3-(4-Bromophenyl)-2-ethyl-but-2-enyloxy]-phenyl}-2-ethoxy-propionate,
(Z)-(S)-3-{4-[3-(4-Bromophenyl)-2-ethyl-but-2-enyloxy]-phenyl}-2-ethoxy-propionic acid,
(E)-(S)-Ethyl 3-{4-[3-(4'-tert-Butyl-biphenyl-4-yl)-but-2-enyloxy]-phenyl}-2-ethoxy-propionate,
(E)-(S)-Ethyl 3-{4-[3-(3',5'-Bis-trifluoromethyl-biphenyl-4-yl)-but-2-enyloxy]-phenyl}-2-ethoxy-propionate,
(E)-(S)-3-{4-[3-(3',5'-Bis-trifluoromethyl-biphenyl-4-yl)-but-2-enyloxy]-phenyl}-2-ethoxy-propionic acid,
(E)-(S)-Ethyl 2-Ethoxy-3-{4-[3-(4'-isopropyl-biphenyl-4-yl)-but-2-enyloxy]-phenyl}-propionate,
(E)-(S)-2-Ethoxy-3-{4-[3-(4'-isopropyl-biphenyl-4-yl)-but-2-enyloxy]-phenyl}-propionic acid,
(E)-(S)-3-{4-[3-(3,5-Dimethoxy-phenyl)-but-2-enyloxy]-phenyl}-2-ethoxy-propionic acid ethyl ester,
(E)-(S)-3-{4-[3-(3'-Acetyl-biphenyl-4-yl)-but-2-enyloxy]-phenyl}-2-ethoxy-propionic acid,
(E)-(S)-Ethyl 3-{4-[3-(4'-Acetyl-biphenyl-4-yl)-but-2-enyloxy]-phenyl}-2-ethoxy-propionate,
(E)-(S)-3-{4-[3-(4'-Acetyl-biphenyl-4-yl)-but-2-enyloxy]-phenyl}-2-ethoxy-propionic acid,
(E)-(S)-Ethyl 2-Ethoxy-3-[4-(3-[1,1';3',1"]terphenyl-5'-yl-allyloxy)-phenyl]-propionate,
(E)-(S)-2-Ethoxy-3-[4-(3-[1,1';3',1"]terphenyl-5'-yl-allyloxy)-phenyl]-propionic acid,
(E,E)-(S)-Ethyl 3-(4'-{3-[4-(2-Ethoxy-2-ethoxycarbonyl-ethyl)-phenoxy]-1-methyl-propenyl}-biphenyl-3-yl)-but-2-enoate,
(E,E)-(S)-3-(4'-{3-[4-(2-Carboxy-2-ethoxy-ethyl)-phenoxy]-1-methyl-propenyl}-biphenyl-3-yl)-but-2-enoic acid,
(E)-(S)-Ethyl 2-Ethoxy-3-{4-[3-(3'-methoxy-biphenyl-4-yl)-but-2-enyloxy]-phenyl}-propionate,
(E)-(S)-2-Ethoxy-3-{4-[3-(3'-methoxy-biphenyl-4-yl)-but-2-enyloxy]-phenyl}-propionic acid,
(E)-(S,S/R)-Ethyl 2-Ethoxy-3-(4-{3-[3'-(1-hydroxy-ethyl)-biphenyl-4-yl]-but-2-enyloxy}-phenyl)-propionate,
(E)-(S,S/R)-2-Ethoxy-3-(4-{3-[3'-(1-hydroxy-ethyl)-biphenyl-4-yl]-but-2-enyloxy}-phenyl)-propionic acid,
(E)-(S)-Ethyl 3-{4-[3-(3,5-Dibromophenyl)-but-2-enyloxy]-phenyl}-2-ethoxy-propionate,
(E)-(S)-3-{4-[3-(3,5-Dibromophenyl)-but-2-enyloxy]-phenyl}-2-ethoxy-propionic acid,
(E)-(S)-Ethyl 3-{4-[3-(3,5-Dibromophenyl)-allyloxy]-phenyl}-2-ethoxy-propionate,
(E)-(S)-3-{4-[3-(3,5-Dibromophenyl)-allyloxy]-phenyl}-2-ethoxy-propionic acid,
(E)-(S)-Ethyl 3-{4-[3-(4,4"-Di-tert-butyl-[1,1';3',1"]terphenyl-5'-yl)-allyloxy]-phenyl}-2-ethoxy-propionate,
(E)-(S)-3-{4-[3-(4,4"-Di-tert-butyl-[1,1';3',1"]terphenyl-5'-yl)-allyloxy]-phenyl}-2-ethoxy-propionic acid,
(E)-(S)-Ethyl 3-{4-[3-(3',5'-Dibromo-biphenyl-4-yl)-but-2-enyloxy]-phenyl}-2-ethoxy-propionate,
(E)-(S)-3-{4-[3-(3',5'-Dibromo-biphenyl-4-yl)-but-2-enyloxy]-phenyl}-2-ethoxy-propionic acid,
(E)-(S)-Ethyl 3-{4-[3-(3',5'-Dichloro-biphenyl-4-yl)-but-2-enyloxy]-phenyl}-2-ethoxy-propionate,
(E)-(S)-3-{4-[3-(3',5'-Dichloro-biphenyl-4-yl)-but-2-enyloxy]-phenyl}-2-ethoxy-propionic acid,
(E)-(S)-Ethyl 3-{4-[3-(3',5'-Dichloro-biphenyl-4-yl)-allyloxy]-phenyl}-2-ethoxy-propionate,
(E)-(S)-3-{4-[3-(3',5'-Dichloro-biphenyl-4-yl)-allyloxy]-phenyl}-2-ethoxy-propionic acid,
(E)-(S)-Ethyl 3-{4-[3-(3',5'-di-tert-butyl-biphenyl-4-yl)-allyloxy]-phenyl}-2-ethoxy-propionate,
(E)-(S)-3-{4-[3-(3',5'-Di-tert-butyl-biphenyl-4-yl)-allyloxy]-phenyl}-2-ethoxy-propionic acid,
(E)-(S)-Ethyl 3-{4-[3-(3',5'-Di-tert-butyl-biphenyl-4-yl)-but-2-enyloxy]-phenyl}-2-ethoxy-propionate,
(E)-(S)-3-{4-[3-(3',5'-Di-tert-butyl-biphenyl-4-yl)-but-2-enyloxy]-phenyl}-2-ethoxy-propionic acid,
(E)-(S/R)-Ethyl 3-[4-(3-Biphenyl-4-yl-but-2-enyloxy)-phenyl]-2-isopropoxy-propionate,
(E)-(S/R)-3-[4-(3-Biphenyl-4-yl-but-2-enyloxy)-phenyl]-2-isopropoxy-propionic acid,
(E)-(S/R)-Ethyl 3-[4-(3-Biphenyl-4-yl-but-2-enyloxy)-phenyl]-2-butoxy-propionate,
(E)-(S/R)-3-[4-(3-Biphenyl-4-yl-but-2-enyloxy)-phenyl]-2-butoxy-propionic acid,
(E)-(S/R)-Ethyl 3-[4-(3-Biphenyl-4-yl-but-2-enyloxy)-phenyl]-2-hexyloxy-propionate,
(E)-(S/R)-3-[4-(3-Biphenyl-4-yl-but-2-enyloxy)-phenyl]-2-hexyloxy-propionic acid,
(E)-(S/R)-Ethyl 3-[4-(3-Biphenyl-4-yl-but-2-enyloxy)-phenyl]-2-(3-phenyl-propoxy)-propionate,
(E)-(S/R)-3-[4-(3-Biphenyl-4-yl-but-2-enyloxy)-phenyl]-2-(3-phenyl-propoxy)-propionic acid,
(E)-(S/R)-Ethyl 3-[4-(3-Biphenyl-4-yl-but-2-enyloxy)-phenyl]-2-(4-phenyl-butoxy)-propionate,
(E)-(S/R)-3-[4-(3-Biphenyl-4-yl-but-2-enyloxy)-phenyl]-2-(4-phenyl-butoxy)-propionic acid,
(E)-(S/R)-Propyl 3-[4-(3-Biphenyl-4-yl-but-2-enyloxy)-phenyl]-2-propoxy-propionate,
(E)-(S/R)-3-[4-(3-Biphenyl-4-yl-but-2-enyloxy)-phenyl]-2-propoxy-propionic acid,
(E)-(S)-3-{4-[3-(3,5-Diethoxyoxy-phenyl)-allyloxy]-phenyl}-2-ethoxy-propionic acid ethyl ester,
(E)-(S)-3-{4-[3-(3,5-Diethoxyoxy-phenyl)-allyloxy]-phenyl}-2-ethoxy-propionic acid,
(E)-(S)-3-{4-[3-(3,5-Bis-trifluoromethyl-phenyl)-allyloxy]-phenyl}-2-ethoxy-propionic acid ethyl ester,
(E)-(S)-3-{4-[3-(3,5-Bis-trifluoromethyl-phenyl)-allyloxy]-phenyl}-2-ethoxy-propionic acid,
(E)-(R,S)-3-[4-(3-Biphenyl-4-yl-allyloxy)-phenyl]-2-ethoxy-propionic acid ethyl ester,
(E)-(R,S)-3-[4-(3-Biphenyl-4-yl-allyloxy)-phenyl]-2-ethoxy-propionic acid,
(E)-(S)-4-(3-{3-[4-(2-Ethoxy-2-ethoxycarbonyl-ethyl)-phenoxy]-propenyl}-phenoxymethyl)-benzoic acid methyl ester,
(E)-(S)-4-(3-{3-[4-(2-Carboxy-2-ethoxy-ethyl)-phenoxy]-propenyl}-phenoxymethyl)-benzoic acid;
or a salt thereof with a pharmaceutically acceptable acid or base, or any optical isomer or mixture of optical isomers, including a racemic mixture, or any tautomeric forms.

Also preferred compounds of the invention are:
(E)-(S)-Ethyl 2-Ethoxy-3-{4-[3-(4'-fluoro-biphenyl-4-yl)-but-2-enyloxy]-phenyl}-propionate,
(E)-(S)-2-Ethoxy-3-{4-[3-(4'-fluoro-biphenyl-4-yl)-but-2-enyloxy]-phenyl}-propionic acid,
(E)-(S)-Ethyl 2-Ethoxy-3-{4-[3-(4-Iodophenyl)-but-2-enyloxy]-phenyl}-propionate;
or a salt thereof with a pharmaceutically acceptable acid or base, or any optical isomer or mixture of optical isomers, including a racemic mixture, or any tautomeric forms.

In the above structural formulas and throughout the present specification, the following terms have the indicated meaning:

The term "$C_{1-12}$-alkyl" as used herein, alone or in combination is intended to include those alkyl groups of the designated length in either a linear or branched or cyclic configuration represents e.g. cyclopropyl, cyclobutyl, cyclopentyl, cyclohexyl, cycloheptyl and cyclooctyl and the like. Typical $C_{1-12}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl, cyclopropyl, cyclobutyl, cyclopentyl, cyclohexyl, cycloheptyl and cyclooctyl and the like, especially preferred is methyl, ethyl, n-propyl, iso-propyl, butyl, tert-butyl, pentyl, hexyl, cyclopropyl and cyclopentyl.

The term "$C_{2-12}$-alkenyl" as used herein, represents an olefinically unsaturated branched or straight group having from 2 to the specified number of carbon atoms and at least one double bond. Examples of such groups include, but are not limited to, vinyl, 1-propenyl, 2-propenyl, allyl, isopropenyl, 1,3-butadienyl, 1-butenyl, hexenyl, pentenyl and the like, especially preferred is vinyl and 1-propenyl.

The term "$C_{2-12}$-alkynyl", as used herein, represent an unsaturated branched or straight group having from 2 to the specified number of carbon atoms and at least one triple bond. Examples of such groups include, but are not limited to ethynyl, 1-propynyl, 2-propynyl, 1-butynyl, 2-butynyl, 1-pentynyl, 2-pentynyl and the like, especially preferred is ethynyl, 1-propynyl and 2-propynyl.

The term "$C_{4-12}$-alkenynyl" as used herein, represent an unsaturated branched or straight hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like.

The term "$C_{1-6}$-alkoxy" as used herein, alone or in combination is intended to include those $C_{1-6}$-alkyl groups of the designated length in either a linear or branched or cyclic configuration linked thorugh an ether oxygen having its free valence bond from the ether oxygen. Examples of linear alkoxy groups are methoxy, ethoxy, propoxy, butoxy, pentoxy, hexoxy and the like, especially preferred is methoxy, ethoxy, propoxy, butoxy, pentoxy, hexoxy. Examples of branched alkoxy are isopropoxy, sec-butoxy, tert-butoxy, isopentoxy, isohexoxy and the like, especially preferred is isopropoxy. Examples of cyclic alkoxy are cyclopropyloxy, cyclobutyloxy, cyclopentyloxy, cyclohexyloxy and the like, especially preferred is cyclopentyloxy.

The term "$C_{1-6}$-alkylthio" as used herein, alone or in combination, refers to a straight or branched or cyclic monovalent substituent comprising a $C_{1-6}$-alkyl group linked through a divalent sulfur atom having its free valence bond from the sulfur atom and having 1 to 6 carbon atoms e.g. methylthio, ethylthio, propylthio, butylthio, pentylthio and the like, especially preferred is methylthio, ethylthio and propylthio. Examples of cyclic alkylthio are cyclopropylthio, cyclobutylthio, cyclopentylthio, cyclohexylthio and the like, especially preferred is cyclopentylthio.

The term "$C_{1-6}$-alkylamino" as used herein, alone or in combination, refers to a straight or branched or cyclic monovalent substituent comprising a $C_{1-6}$-alkyl group linked through amino having a free valence bond from the nitrogen atom e.g. methylamino, ethylamino, propylamino, butylamino, pentylamino and the like. Examples of cyclic alkylamino are cyclopropylamino, cyclobutylamino, cyclopentylamino, cyclohexylamino and the like.

The term "arylamino" as used herein, alone or in combination, refers to an aryl as defined herein linked through amino having a free valence bond from the nitrogen atom e.g. phenylamino, naphthylamino and the like.

The term "$C_{1-6}$-alkoxy$C_{1-6}$-alkyl" as used herein, alone or in combination, refers to a $C_{1-6}$-alkyl as defined herein whereto is attached a $C_{1-6}$-alkoxy as defined herein, e.g. methoxymethyl, ethoxymethyl, methoxyethyl, ethoxyethyl and the like.

The term "aryl" is intended to include a bicyclic aromatic ring, such as carbocyclic aromatic rings selected from the group consisting of phenyl and naphthyl, (1-naphthyl or 2-naphthyl), optionally substituted with halogen, amino, hydroxy, $C_{1-6}$-alkyl, $C_{1-6}$-alkoxy, carboxy or $C_{1-6}$-alkylester and the like, especially preferred is halogen.

The term "arylene" is intended to include divalent aromatic rings, such as carbocyclic aromatic rings selected from the group consisting of phenylene, naphthylene and the like optionally substituted with halogen, amino, hydroxy, $C_{1-6}$-alkyl, $C_{1-6}$-alkoxy, carboxy or $C_{1-6}$-alkylester and the like.

The term "halogen" means fluorine, chlorine, bromine or iodine, especially preferred is fluorine and chlorine.

The term "perhalomethyl" means trifluoromethyl, trichloromethyl, tribromomethyl or triiodomethyl, especially preferred is trifluoromethyl.

The term "$C_{1-6}$-dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl)amino and the like.

The term "acyl" as used herein refers to a monovalent substituent comprising a $C_{1-6}$-alkyl group linked through a carbonyl group; such as e.g. acetyl, propionyl, butyryl, isobutyryl, pivaloyl, valeryl and the like, especially preferred is acetyl.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine and the like, preferred is furan, thiophene, pyrrole, imidazole, pyrazole, pyridine, quinoline, isoquinoline, quinazoline, quinoxaline, indole, benzimidazole, benzofuran, especially preferred is furan, pyrrole, indole and benzofuran.

The term "heteroarylene" as used herein, alone or in combination, refers to a divalent group comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine and the like, especially preferred is furan, thiophene, pyrrole, imidazole, pyrazole, triazole, pyridine, pyrazine, pyrimidine, pyridazine.

The term "heteroaryloxy" as used herein, alone or in combination, refers to a heteroaryl as defined herein linked to an oxygen atom having its free valence bond from the oxygen atom e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine linked to oxygen, and the like.

The term "aralkyl" as used herein refers to a straight or branched saturated carbon chain containing from 1 to 6 carbons substituted with an aromatic carbohydride; such as benzyl, phenethyl, 3-phenylpropyl, 1-naphthylmethyl, 2-(1-naphthyl)ethyl and the like, especially preferred is benzyl and phenethyl.

The term "aryloxy" as used herein refers to phenoxy, 1-naphthyloxy, 2-naphthyloxy and the like, especially preferred is phenoxy.

The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphthyl)ethoxy and the like, especially preferred is benzyloxy.

The term "heteroaralkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "heteroaralkoxy" as used herein refers to a heteroaralkyl as defined herein linked to an oxygen atom having its free valence bond from the oxygen atom, e.g. (2-furyl)methyl, (3-furyl)methyl, (2-thienyl)methyl, (3-thienyl)methyl, (2-pyridyl)methyl, 1-methyl-1-(2-pyrimidyl)ethyl linked to oxygen, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)-thio, (2-chlorophenyl)thio and the like.

As used herein, the phrase "heterocyclyl" means a monovalent saturated or unsaturated non aromatic group being monocyclic and containing one or more, such as from one to four carbon atom(s), and from one to four N, O or S atom(s) or a combination thereof. The phrase "heterocyclyl" includes, but is not limited to, 5-membered heterocycles having one hetero atom (e.g. pyrrolidine, pyrroline and the like); 5-membered heterocycles having two heteroatoms in 1,2 or 1,3 positions (e.g. pyrazoline, pyrazolidine, 1,2-oxathiolane, imidazolidine, imidazoline, 4-oxazolone and the like); 5-membered heterocycles having three heteroatoms (e.g. tetrahydrofurazan and the like); 5-membered heterocycles having four heteroatoms; 6-membered heterocycles with one heteroatom (e.g. piperidine and the like); 6-membered heterocycles with two heteroatoms (e.g. piperazine, morpholine and the like); 6-membered heterocycles with three heteroatoms; and 6-membered heterocycles with four heteroatoms, and the like.

As used herein, the phrase "a divalent heterocyclic group" means a divalent saturated or unsaturated system being monocyclic and containing one or more, such as from one to four carbon atom(s), and one to four N, O or S atom(s) or a combination thereof. The phrase a divalent heterocyclic group includes, but is not limited to, 5-membered heterocycles having one hetero atom (e.g. pyrrolidine, pyrroline and the like); 5-membered heterocycles having two heteroatoms in 1,2 or 1,3 positions (e.g. pyrazoline, pyrazolidine, 1,2-oxathiolane, imidazolidine, imidazoline, 4-oxazolone and the like); 5-membered heterocycles having three heteroatoms (e.g. tetrahydrofurazan and the like); 5-membered heterocycles having four heteroatoms; 6-membered heterocycles with one heteroatom (e.g. piperidine and the like); 6-membered heterocycles with two heteroatoms (e.g. piperazine, morpholine and the like); 6-membered heterocycles with three heteroatoms; and 6-membered heterocycles with four heteroatoms, and the like.

As used herein the term "treatment" includes treatment, prevention and management of such condition.

Certain of the above defined terms may occur more than once in the above formula (I), and upon such occurrence each term shall be defined independently of the other.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, □immer□e□ acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, aminoacids, aminoalcohols derived from aminoacids; conventional reaction conditions may be employed to convert acid into an amide; the dia-stereomers may be separated either by fractional crystallization or chromatography and the stereoisomers of compound of formula I may be prepared by hydrolysing the pure diastereomeric amide.

Various polymorphs of compound of general formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Furthermore, the present compounds of formula I can be utilised in the treatment and/or prevention of conditions mediated by nuclear receptors, in particular the Peroxisome Proliferator-Activated Receptors (PPAR).

In a further aspect, the present invention relates to a method of treating and/or preventing Type I or Type II diabetes.

In a still further aspect, the present invention relates to the use of one or more compounds of the general formula I or pharmaceutically acceptable salts thereof for the preparation of a medicament for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, hyperlipidemia, coronary artery disease, myocardial ischemia and other cardiovascular disorders.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of the general formula I or their tautomeric forms, their stereoisomers, their polymorphs, their pharmaceutically acceptable salts or pharmaceutically acceptable solvates thereof for the preparation of a pharmaceutical composition for the treatment and/or prevention of conditions mediated by nuclear receptors, in particular the Peroxisome Proliferator-Activated Receptors (PPAR) such as the conditions mentioned above.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

The method comprises:

a) Reacting a compound of formula II

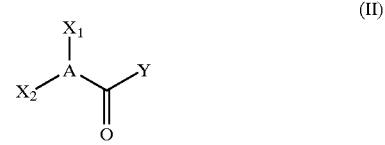

wherein A, $X_1$, $X_2$ and Y are defined as above, through a Wittig process with e.g. $(EtO)_2PO(CHZ)(CH_2)_tCOOR6$ (wherein $R_6$ is an alkyl group), in the presence of a base such as sodium hydride, EtONa and the like to give a compound of formula III.

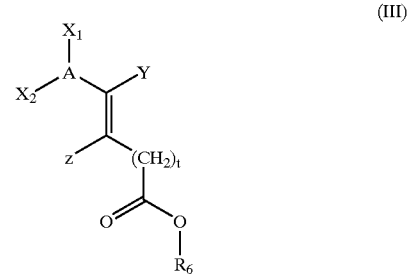

wherein A, $X_1$, $X_2$, Y, Z and $R_6$ are defined as above, and wherein t is 0–2, and b) reducing a compound of formula III, wherein A, $X_1$, $X_2$, Y, Z, $R_6$ and t are defined as above with a suitable reagent such a diisobutylaluminum hydride, to give a compound of formula IV.

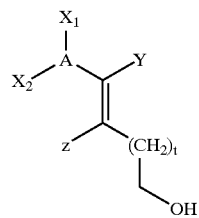
(IV)

wherein A, $X_1$, $X_2$, Y, Z and t are defined as above, and c)

reacting a compound of IV, wherein A, $X_1$, $X_2$, Y, Z and t are defined as above, with a compound of formula V

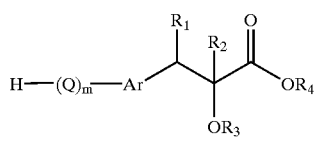
(V)

wherein Q, Ar, $R_1$, $R_2$, $R_3$, $R_4$ and m are defined as above, under Mitsunobu conditions, using a reagent such as triphenylphosphine/diethylazodicarboxylate and the like to obtain a compound of formula I, wherein A, $X_1$, $X_2$, Y, Z, Q, Ar, $R_1$, $R_2$, $R_3$, $R_4$, n and m are defined as above, except that $R_4$ is not H, n and m are not 0, and d)

converting the —OH functionality in a compound of formula IV wherein A, $X_1$, $X_2$, Y, Z and t are defined as above to an appropriate leaving group (L) such as p-toluenesulfonate, methanesulfonate, halogen (in examples by methods according to: Houben-Weyl, Methoden der organischen Chemie, Alkohole III, 6/1b, Thieme Verlag 1984, 4th Ed., pp. 927–939; Comprehensive Organic Transformations. A guide to functional group preparations, VCH Publishers 1989, 1$^{st}$ Ed., pp. 353–363), triflate and the like, to give a compound of formula VI

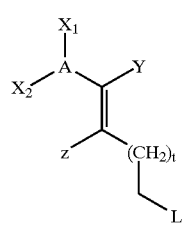
(IV)

e)

reacting a compound of formula VI

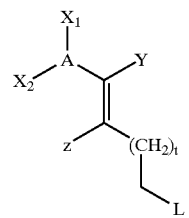
(IV)

wherein L is a leaving group such as p-toluenesulfonate, methanesulfonate, halogen, triflate and the like and wherein A, $X_1$, $X_2$, Y, Z and t are defined as above with a compound of formula V

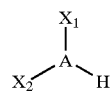
(V)

wherein Q, Ar, $R_1$, $R_2$, $R_3$, $R_4$ and m are defined as above, to give a compound of formula I wherein A, $X_1$, $X_2$, Y, Z, Q, Ar, $R_1$, $R_2$, $R_3$, $R_4$, n and m are defined as above except that $R_4$ is not H, n and m are not 0, or e)

reacting a compound of formula VII (VII)

wherein A, $X_1$ and $X_2$ are defined as above, through a Friedel-Crafts acylation with in example ClOCCHZ(CH$_2$)$_n$R$_7$ (wherein n and Z is defined as above and R$_7$ are halogen or OH), in the presence of a Friedel-Crafts catalysts such as aluminium trichloride and the like, to give a compound of formula VIII

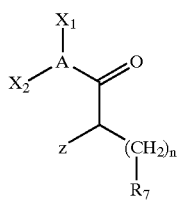
(VIII)

wherein A, $X_1$, $X_2$, Z, $R_7$ and n are defined as above, and f)

reacting a compound of formula VIII, wherein A, $X_1$, $X_2$, Z and $R_7$ are defined as above with a Grignard reagents such a MgBrY or a lithium reagent such as LiY or organozinc reagent such as ZnY, wherein Y is defined as above, followed by a acidic workup to give a compound of formula IX

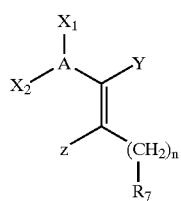

(IX)

wherein A, $X_1$, $X_2$, Z, Y, $R_7$ and n are defined as above, and g) reacting a compound of IX, wherein A, $X_1$, $X_2$, Z, Y, $R_7$ and n are defined as above, with a compound of formula V

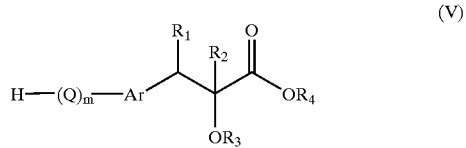

(V)

wherein Q, Ar, $R_1$, $R_2$, $R_3$, $R_4$ and m are defined as above except that m is not 0, under either basic condition e.g. potassium carbonate/acetone (if $R_7$ is halogen) or Mitsunobu conditions (if $R_7$ is OH) using a reagent such as triphenylphosphine/diethylazodicarboxylate and the like to obtain a compound of formula I, wherein A, $X_1$, $X_2$, Y, Z, Q, Ar, $R_1$, $R_2$, $R_3$, $R_4$, n and m are defined as above, except that $R_4$ is not H, n and m are not 0, or h) by chemical or enzymatic saponification of a compound of formula I

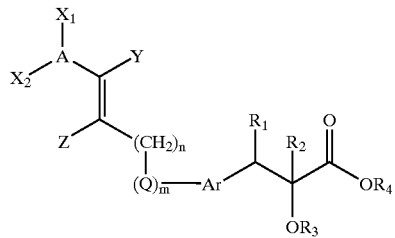

(I)

wherein A, $X_1$, $X_2$, Y, Z, Q, Ar, $R_1$, $R_2$, $R_3$, $R_4$, n and m are defined as above, except that $R_4$ is not H, to obtain a compound of formula I, wherein A, $X_1$, $X_2$, Y, Z, Q, Ar, $R_1$, $R_2$, $R_3$, $R_4$, n and m are defined as above, except that $R_4$ is H.

i) Trans-cis or cis-trans isomerization of compounds I, III, IV, VI, and IX (Arai et al., Chem. Rev., 93, pp 23–39, 1993; J. March, Advanced Organic Chemistry, $4^{th}$ Ed., J. Wiley & Sons, New York 1992, pp. 218, 245, 745).

Pharmacological Methods
In Vitro PPAR Alpha and PPAR Gamma Activation Activity.
Principle The PPAR gene transcription activation assays were based on transient transfection into human HEK293 cells of two plasmids encoding a chimeric test protein and a reporter protein respectively. The chimeric test protein was a fusion of the DNA binding domain (DBD) from the yeast GAL4 transcription factor to the ligand binding domain (LBD) of the human PPAR proteins. The PPAR LBD harbored in addition to the ligand binding pocket also the native activation domain (activating function 2=AF2) allowing the fusion protein to function as a PPAR ligand dependent transcription factor. The GAL4 DBD will force the fusion protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand, luciferase protein will be produced in amounts corresponding to the activation of the PPAR protein. The amount of luciferase protein is measured by light emission after addition of the appropriate substrate.

Methods

In Vitro Transactivation Assays

Cell culture and transfection: HEK293 cells were grown in DMEM+10% FCS. Cells were seeded in 96-well plates the day before transfection to give a confluency of 50–80% at transfection. A total of 0.8 µg DNA containing 0.64 µg pM1α/γLBD, 0.1 µg pCMVβGal, 0.08 µg pGL2Gal4DBD and 0.02 µg pADVANTAGE was transfected per well using FuGene transfection reagent according to the manufacturers instructions (Roche). Cells were allowed to express protein for 48 h followed by addition of compound.

Plasmids: Human PPAR α and γ was obtained by PCR amplification using cDNA synthesized by reverse transcription of mRNA from liver and adipose tissue respectively. Amplified cDNAs were cloned into pCR2.1 and sequenced. The ligand binding domain (LBD) of each PPAR isoform was generated by PCR (PPARα: aa 167—C-terminus; PPARγ: aa 165—C-terminus) and fused to the DNA binding domain (DBD) of the yeast transcription factor GAL4 by subcloning fragments in frame into the vector pM1 generating the plasmids pM1αLBD and pM1γLBD. Ensuing fusions were verified by sequencing. The reporter was constructed by inserting an oligonucleotide encoding five repeats of the GAL4 recognition sequence (5×CGGAGTACTGTCCTCCG(AG)) into the vector pGL2 promotor (Promega) generating the plasmid pGL2(GAL4)$_5$. pCMVβGal was purchased from Clontech and pADVANTAGE was purchased from Promega.

Luciferase assay: Medium including test compound was aspirated and 100 µl PBS incl. 1 mM Mg++ and Ca++ was added to each well. The luciferase assay was performed using the Lu-cLite kit according to the manufacturers instructions (Packard Instruments). Light emission was quantified by counting SPC mode on a Packard Instruments top-counter. To measure β-galactosidase activity 25 µl supernatant from each transfection lysate was transferred to a new microplate. β-galactosidase assays were performed in the microwell plates using a kit from Promega and read in a microplate reader. The β-galactosidase data were used to normalize (transfection efficiency, cell growth etc.) the luciferase data.

Compounds: All compounds were dissolved in DMSO and diluted 1:1000 upon addition to the cells. Compounds were tested in quadruple in five concentrations ranging form 0.01 to 30 µM. Cells were treated with compound for 24 h followed by luciferase assay. Each compound was tested in three separate experiments. EC$_{50}$ values were calculated via non-linear regression using GraphPad PRISM 3.02 (GraphPad Software, San Diego, Calif.). The results were expressed as means.

TABLE 1

In vitro PPAR alpha and PPAR gamma activation of examples according to the present invention.

|  | In vitro activation | | | |
|---|---|---|---|---|
|  | PPAR α | | PPAR γ | |
| Example no | $EC_{50}$, μM | % max[a] | $EC_{50}$, μM | % max[b] |
| 4 | 3.1 | 212 | 0.72 | 156 |
| 9 | 0.038 | 234 | 0.35 | 125 |
| 27 | 0.10 | 185 | 0.11 | 99 |
| 57 | 0.38 | 178 | 0.70 | 110 |
| 124 | 0.35 | 102 | 0.30 | 83 |
| 134 | 2.90 | 122 | 0.89 | 155 |

Compounds were tested in at least three separate experiments in five concentrations ranging from 0.01 to 30 μM. $EC_{50}$'s were not calculated for compounds producing transactivation lower than 25% at 30 μM. [a]Fold activation relative to maximum activation obtained with Wy14643 (approx. 20 fold corresponded to 100%) and with [b]rosiglitazone (approx. 120 fold corresponded to 100%).

Pharmaceutical Compositions

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

The present compounds may also be administered in combination with one or more further pharmacologically active substances eg., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagons like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguanide eg. metformin.

In yet another embodiment the present compounds are administered in combination with a meglitinide eg. repaglinide or senaglinide.

In a further embodiment the present compounds are administered in combination with an α-glucosidase inhibitor eg. miglitol or acarbose.

In another embodiment the present compounds are administered in combination with an agent acting on the ATP-dependent potassium channel of the β-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg. In combination with a sulphonylurea and metformin, a sulphonylurea and acarbose, repaglinide and mefformin, insulin and a sulphonylurea, insulin and mefformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

Pharmaceutical compositions containing a compound of the present invention may be prepared by conventional techniques, e.g. as described in Remington: The Science and Practise of Pharmacy, 19th Ed., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
| --- | --- |
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and non-domestic animals such as wildlife.

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients it may frequently be necessary to begin with a dosage of from about 2 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.1 to about 100 mg of active ingredient together with a pharmaceutically acceptable carrier per unit dosage.

Usually, dosage forms suitable for oral, nasal, pulmonary or transdermal administration comprise from about 0.001 mg to about 100 mg, preferably from about 0.01 mg to about 50 mg of the compounds of formula I admixed with a pharmaceutically acceptable carrier or diluent.

Any novel feature or combination of features described herein is considered essential to this invention.

EXAMPLES

The process for preparing compounds of formula I, and preparations containing them, is further illustrated in the following examples, which however, are not to be construed as limiting.

The structures of the compounds are confirmed by either elemental analysis (MA) nuclear magnetic resonance (NMR) or mass spectrometry (MS). NMR shifts (δ) are given in parts per million (ppm) and only selected peaks are given. Mp is melting point and is given in ° C. Column chromatography was carried out using the technique described by W. C. Still et al, J. Org. Chem. 1978, 43, 2923–2925 on Merck silica gel 60 (Art 9385). Compounds used as starting materials are either known compounds or compounds which can readily be prepared by methods known per se.

| Abbrevations: | |
| --- | --- |
| THF: | tetrahydrofuran |
| DIBAL-H: | diisobutylaluminum hydride |
| $Na_2SO_4$: | sodium sulfate |
| $MgSO_4$: | magnesium sulfate |
| DMSO: | dimethylsulfoxide |
| $CDCl_3$: | deuterated chloroform |
| DMF: | N,N-dimethylformamide |
| HCl: | hydrochloric acid |
| DME: | 1,2-dimethoxyethane |
| min: | minutes |
| h: | hours |

Example 1

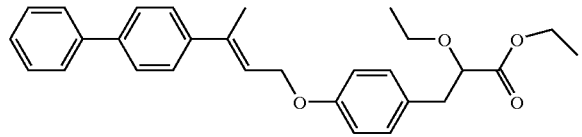

(E)-(S)-Ethyl 3-[4-(3-biphenyl-4-yl-but-2-enyloxy)-phenyl]-2-ethoxy-propionate a)

Sodium (1.75 g, 73.4 mmol) was added to ethanol (45 ml) at 20° C. and the mixture stirred until the metal had fully reacted. Triethyl phosphonoacetate (14.69 g, 73.4 mmol) was added, the mixture stirred for 5 min., then 4-acetylbiphenyl (12.00 g, 61.1 mmol) was added to the stirred solution. The mixture was stirred at room temperature for 24 h, the resulting suspension filtered, and the filter-cake collected and recrystallised from ethanol to give (E)-3-biphenyl-4-yl-but-2-enoic acid ethyl ester as white crystals; 5.73 g (36%)

$^1$H NMR (300 MHz, $CDCl_3$) δ: 1.32 (3H, t), 2.62 (3H, d), 4.21 (2H, q), 6.2 (1H, d), 7.31–7.65 (9H, m). MS: 267 ($M^+$), 266(100%), 221, 194, 178. Microanalysis Calculated % C, 81.00; H, 7.0. Found C, 80.86; H, 6.90.

b)

A 1M solution of DIBAL-H in toluene (40 ml, 40 mmol) was added dropwise at −70° C. over 20 min. to a stirred solution of 3-biphenyl-4-yl-but-2-enoic acid ethyl ester (2.66 g, 10.0 mmol) in dry THF (100 ml) and the mixture stirred for 30 min. Methanol (2 ml) was added, followed by saturated aqueous Rochelle's salt (100 ml), and the resulting mixture extracted with ethyl acetate (200 ml), separated and the organic phase washed with brine, dried ($Na_2SO_4$), evaporated and dried in vacuo yielding (E)-3-biphenyl-4-yl-but-2-en-1-ol as colorless crystals: 1.94 g (86%)

$^1$H NMR (300 MHz, $CDCl_3$) δ: 1.40 (1H, br s), 2.12 (3H, d), 4.45 (2H, dd), 6.05 (1H, dt), 7.35–7.7 (9H, m). MS: 225 ($M^+$), 224(100%), 209, 181,165. Microanalysis Calculated % C, 86.00; H, 7.00. Found C, 85.67; H, 7.29.

c)

Diethyl azodicarboxylate (0.346 ml, 2.2 mmol) was added at 0° C. to a stirred solution of triphenyl-phosphine (0.656 g, 2.2 mmol) and (E)-3-biphenyl-4-yl-but-2-en-1-ol (0.270 g, 1.2 mmol) in dry THF (20 ml) and the mixture stirred for 5 min. A solution of (S)-ethyl 2-ethoxy-3-(4-hydroxy-phenyl)-propionate (0.238 g, 1.0 mmol) in dry THF (10 ml) was added, the mixture allowed to warm to room temperature, and stirring continued for 48 h. The resulting mixture was evaporated in vacuo and the residue purified by column chromatography on silica gel (20% ethyl acetate in n-heptane) to give (E)-(S)-ethyl 3-[4-(3-biphenyl-4-yl-but-2-enyloxy)-phenyl]-2-ethoxy-propionate as an oil; 0.288 g (65%).

$^1$H NMR (300 MHz, $CDCl_3$) δ: 1.13–1.25 (6H, m), 2.13 (3H, d), 2.94 (2H, d), 3.29–3.37 (1H, m), 3.54–3.61 (1H, m), 3.97 (1H, t), 4.1 (2H, q), 4.70 (2H, d), 6.11 (1H, dt), 6.86 (2H, d), 7.16 (2H, d), 7.25–7.63 (9H, m).

Example 2

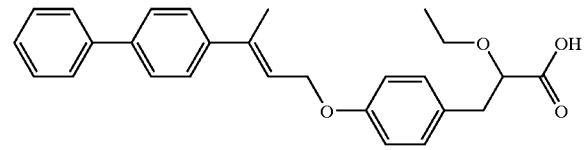

(E)-(S)-3-[4-(3-Biphenyl-4-yl-but-2-enyloxy)-phenyl]-2-ethoxy-propionic acid

Sodium hydroxide (1M, 0.45 ml, 0.45 mmol) was added to a solution of (E)-(S)-ethyl 3-[4-(3-biphenyl-4-yl-but-2-enyloxy)-phenyl]-2-ethoxy-propionate (example 1) (0.100 g, 0.225 mmol) in ethanol (20 ml) and the mixture stirred at 70° C. for 2.5 h. After cooling to room temperature the resulting mixture was partitioned between water (50 ml) and ethyl acetate and the aqueous phase collected. The aqueous phase was acidified with 1N hydrochloric acid (5 ml) and extracted with ethyl acetate (100 ml), and the organic phase collected, washed with brine, dried ($Na_2SO_4$) and evaporated to give (E)-(S)-3-[4-(3-biphenyl-4-yl-but-2-enyloxy)-phenyl]-2-ethoxy-propionic acid as a white solid; 0.014 g (15%).

$^1$H NMR (300 MHz, $CDCl_3$) δ: 1.19 (3H, t), 2.63 (3H, d), 2.93 (1H, dd), 3.1 (1H, dd), 3.4–3.65 (2H, m), 4.1 (2H, q), 4.72 (2H, d), 6.1 (1H, dt), 6.9 (2H, d), 7.2 (2H, d), 7.35–7.60 (9H, m).

Example 3

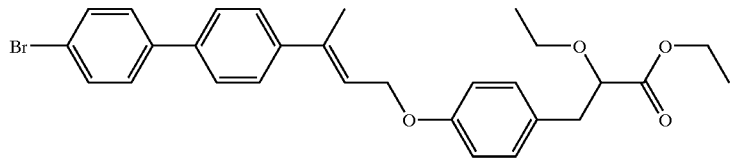

(E)-(S)-3-{4-[3-(4'-Bromo-biphenyl-4-yl)-but-2-enyloxy]-pheny}-2-ethoxy-propionic acid ethyl ester a)
(E)-3-(4'-Bromo-biphenyl-4-yl)-but-2-enoic acid ethyl ester was prepared from 4-(4-bromophenyl)acetophenone (12.0 g, 0.044 mol), sodium (1.25 g, 0.052 mol) and triethyl phosphonoacetate (11.73 g, 0.052 mol) by a procedure analogous to that described in example 1a yielding 11.97 g (80%).
¹H NMR (300 MHz, CDCl₃) δ: 1.32 (3H, t), 2.61 (3H, d), 4.23 (2H, q), 6.19 (1H, d), 7.40–7.58 (8H, m).

b)
(E)-3-(4'-bromo-biphenyl-4-yl)-but-2-en-1-ol was prepared from (E)-3-(4'-bromo-biphenyl-4-yl)-but-2-enoic acid ethyl ester (3.45 g, 10.0 mmol) and DIBAL-H (1M in toluene, 40 ml, 40 mmol) by a procedure analogous to that described in example 1b, yielding 1.68 g (55%).
¹H NMR (300 MHz, CDCl₃) δ: 2.14 (3H, d), 4.4 (2H, t), 6.05 (1H, dt), 7.45–7.55 (8H, m), c)
The title compound was prepared from (E)-3-(4'-bromo-biphenyl-4-yl)-but-2-en-1-ol (0.364 g, 1.2 mmol), triphenylphosphine (0.328 g, 1.3 mmol), diethyl azodicarboxylate (0.173 ml, 1.1 mmol) and (S)-ethyl 2-ethoxy-3-(4-hydroxy-phenyl)-propionate (0.238 g, 1.0 mmol) by a procedure analogous to that described in example 1c, yielding 0.180 g (34%) of (E)-(S)-3-{4-[3-(4'-bromo-biphenyl-4-yl)-but-2-enyloxy]-phenyl}-2-ethoxy-propionic acid ethyl ester.
¹H NMR (300 MHz, CDCl₃) δ: 1.15–1.25 (6H, m), 2.15 (3H, d), 2.95 (2H, d) 3.29–3.4 (1H, m), 3.5–3.65 (1H, m), 3.96 (1H, t), 4.15 (2H, q), 4.75 (2H, dd), 6.11 (1H, dt), 6.85 (2H, d), 7.14 (2H, d), 7.4–7.55 (8H, m).

Example 4

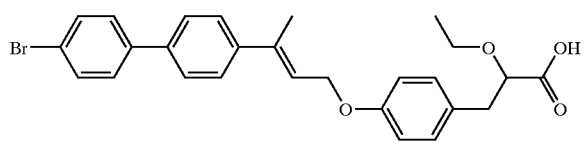

(E)-(S)-3-{4-[3-(4'-Bromo-biphenyl-4-yl)-but-2-enyloxy]-phenyl}-2-ethoxy-propionic acid The title compound was prepared from (E)-(S)-3-{4-[3-(4'-bromo-biphenyl-4-yl)-but-2-enyloxy]-phenyl}-2-ethoxy-propionic acid ethyl ester (example 3) (0.150 g, 0.29 mmol) and sodium hydroxide (1M, 0.45 ml, 0.45 mmol) by a procedure analogous to that described in example 2 yielding 0.180 g (34%) of (E)-(S)-3-{4-[3-(4'-bromo-biphenyl-4-yl)-but-2-enyloxy]-phenyl}-2-ethoxy-propionic acid ethyl ester.
¹H NMR (300 MHz, CDCl₃) δ: 1.14 (3H, t), 2.13 (3H, d), 2.86–3.10 (2H, m), 3.37–3.45 (1H, m), 3.55–3.65 (1H, m), 4.05 (2H, q), 4.70 (2H, dd), 6.12 (1H, dt), 6.9 (2H, d), 7.18 (2H, d), 7.4–7.60 (8H, m).

Example 5

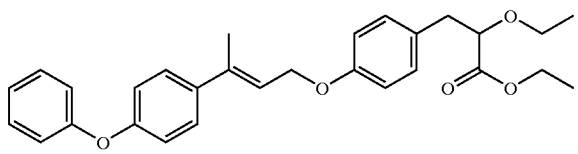

(E)-(S)-2-Ethoxy-3-{4-[3-(4-phenoxy-phenyl)-but-2-enyloxy]-phenyl}-propionic acid ethyl ester The title compound was prepared from 4-phenoxyacetophenone (12.0 g, 0.056 mol) by a sequence analogous to that described in example 3, yielding 0.190 g (41%) of (E)-(S)-2-ethoxy-3-{4-[3-(4-phenoxy-phenyl)-but-2-enyloxy]-phenyl}-propionic acid ethyl ester.

¹H NMR (300 MHz, CDCl₃) δ: 1.2 (6H, m), 2.12 (3H, s), 2.97 (2H, d), 3.30–3.42 (1H, m), 3.59–3.70 (1H, m), 3.98 (1H, t), 4.15 (2H, q), 4.73 (2H, dd), 6.05 (1H, dt), 6.85–7.45 (13H, m).

Example 6

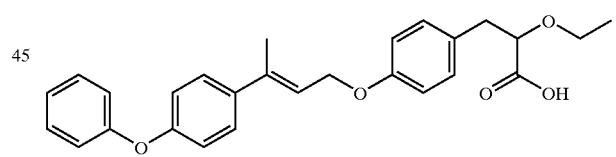

(E)-(S)-2-Ethoxy-3-{4-[3-(4-phenoxy-phenyl)-but-2-enyloxy]-phenyl}-propionic acid The title compound was prepared from (E)-(S)-2-ethoxy-3-{4-[3-(4-phenoxy-phenyl)-but-2-enyloxy]-phenyl}-propionic acid ethyl ester (example 5) (0.170 g, 0.37 mmol) and sodium hydroxide (1M, 0.74 ml, 0.74 mmol) by a procedure analogous to that described in example 2 yielding 0.136 g (85%) of (E)-(S)-2-ethoxy-3-{4-[3-(4-phenoxy-phenyl)-but-2-enyloxy]-phenyl}-propionic acid.

¹H NMR (300 MHz, CDCl₃) δ: 1.14 (3H, t), 2.13 (3H, d), 2.86–3.10 (2H, m), 3.38–3.45 (1H, m), 3.55–3.65(1H, m), 4.05 (2H, q), 4.70 (2H, dd), 6.12 (1H, dt), 6.9 (2H, d), 7.18 (2H, d), 7.4–7.60 (8H, m).

Example 7

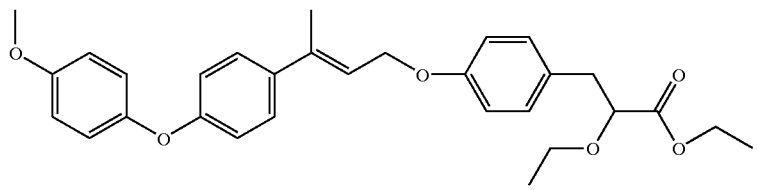

(E)-(S)-2-Ethoxy-3-(4-{3-[4-(4-methoxy-phenoxy)-phenyl]-but-2-enyloxy}-phenyl)-propionic acid ethyl ester The title compound was prepared from 4-(4-methoxyphenoxy)acetophenone (2.63 g, 0.011 mol) by a sequence analogous to that described in example 3 yielding 0.200 g (41%) of (E)-(S)-2-ethoxy-3-(4-{3-[4-(4-methoxy-phenoxy)-phenyl]-but-2-enyloxy}-phenyl)-propionic acid ethyl ester.

$^1$H NMR (300 MHz, CDCl$_3$) δ: 1.15–1.23 (6H, m), 2.12 (3H, s), 2.97 (2H, d), 3.30–3.40 (1H, m), 3.57–3.65 (1H, m), 3.80 (3H, s), 3.98 (1H, t), 4.18 (2H, q), 4.63 (2H, dd), 5.97–6.05 (1H, m), 6.85–6.96 (8H, m), 7.15 (2H, d), 7.35 (2H, d). MS 490 (M$^+$), 417, 359 (100%), 269.

Example 8

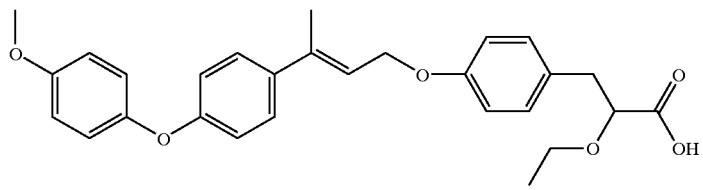

(E)-(S)-2-Ethoxy-3-(4-{3-[4-(4-methoxy-phenoxy)-phenyl]-but-2-enyloxy}-phenyl)-propionic acid The title compound was prepared from (E)-(S)-2-ethoxy-3-(4-{3-[4-(4-methoxy-phenoxy)-phenyl]-but-2-enyloxy}-phenyl)-propionic acid ethyl ester (example 7) (0.176 g, 0.36 mmol) and sodium hydroxide (1M, 0.74 ml, 0.74 mmol) by a procedure analogous to that described in example 2 yielding 0.140 g (84%) of (E)-(S)-2-ethoxy-3-(4-{3-[4-(4-methoxy-phenoxy)-phenyl]-but-2-enyloxy}-phenyl)-propionic acid.

$^1$H NMR (300 MHz, CDCl$_3$) δ: 1.15 (3H, t), 2.1 (3H, s), 2.9–3.1 (2H, m), 3.36–3.43 (1H, m), 3.55–3.64 (1H, m), 3.78 (3H, s), 4.00 (1H, dd), 4.70 (2H, dd), 6.0 (1H, dt), 6.8–6.9 (8H, m), 7.19 (2H, d), 7.35 (2H, d). MS 462 (M$^+$)(100%), 436, 359, 252.

Example 9

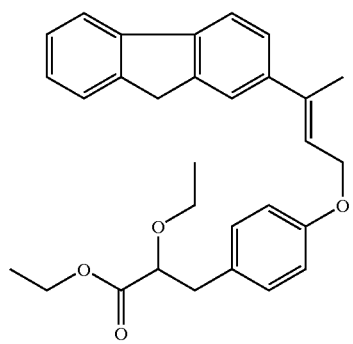

(E)-(S)-2-Ethoxy-3-{4-[3-(9H-fluoren-2-yl)-but-2-enyloxy]-phenyl}-propionic acid ethyl ester The title compound was prepared from 2-acetylfluorene (12.0 g, 0.058 mmol) by a sequence analogous to that described in example 3 yielding 0.200 g (41%) of (E)-(S)-2-ethoxy-3-{4-[3-(9H-fluoren-2-yl)-but-2-enyloxy]-phenyl}-propionic acid ethyl ester.

$^1$H NMR (300 MHz, CDCl$_3$) δ: 1.16–1.22 (6H, m), 2.2 (3H, s), 2.96 (2H, d), 3.30–3.40 (1H, m), 3.51–3.65 (1H, m), 3.9 (2H, s), 3.98 (1H, t), 4.15 (2H, q), 4.75 (2H, d), 6.04–6.13 (1H, m), 6.88 (2H, d), 7.17 (2H, d), 7.3–7.8 (7H, m). MS 456 (M$^+$), 410, 325 (100%), 238. Microanalysis Calculated % C, 78.92; H, 7.06. Found C, 78.72; H, 7.30.

Example 10

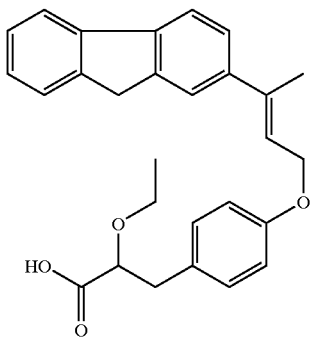

(E)-(S)-2-Ethoxy-3-{4-[3-(9H-fluoren-2-yl)-but-2-enyloxy]-phenyl}-propionic acid The title compound was prepared from (E)-(S)-2-ethoxy-3-{4-[3-(9H-fluoren-2-yl)-but-2-enyloxy]-phenyl}-propionic acid ethyl ester (example 9) (0.230 g, 0.504 mol) and sodium hydroxide (1M, 1.008 ml, 1.008 mmol) by a procedure analogous to that described in example 2 yielding 0.140 g (84%) of (E)-(S)-2-ethoxy-3-{4-[3-(9H-fluoren-2-yl)-but-2-enyloxy]-phenyl}-propionic acid.

$^1$H NMR (300 MHz, CDCl$_3$) δ: 1.20 (3H, t), 2.18 (3H, s), 2.9–3.15 (2H, m), 3.4–3.6 (2H, m), 3.87 (2H, s), 4.05 (1H, dd), 4.75 (2H, d), 6.11 (1H, dt), 6.88 (2H, d), 7.17 (2H, d), 7.3–7.8 (7H, m).

Example 11

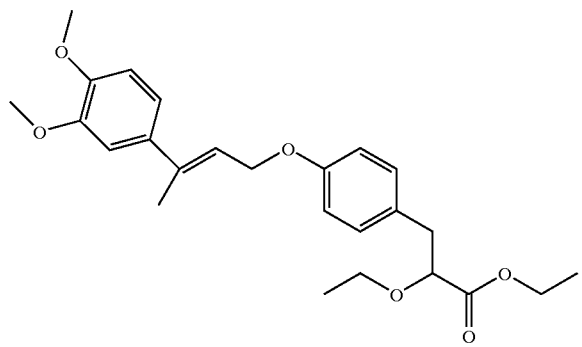

(E)-(S)-3-{4-[3-(3,4-Dimethoxy-phenyl)-but-2-enyloxy]-phenyl}-2-ethoxy-propionic acid ethyl ester The title compound was prepared from 3,4-dimethoxyacetophenone (10.00 g, 0.055 mol) by a sequence analogous to that described in example 3 yielding 0.160 g (31%) of (E)-(S)-3-{4-[3-(3,4-dimethoxy-phenyl)-but-2-enyloxy]-phenyl}-2-ethoxy-propionic acid ethyl ester.

$^1$H NMR (300 MHz, CDCl$_3$) δ: 1.1–1.19 (6H, m), 2.17 (3H, s), 2.98 (2H, d), 3.37–3.45 (1H, m), 3.58–3.65 (1H, m), 3.9 (6H, ds), 4.02 (1H, t), 4.15 (2H, q), 4.7 (2H, d), 6.0 (1H, dt), 6.81–6.86 (3H, m), 7.0 (2H, d), 7.15 (2H, d). MS 428 (M$^+$), 382, 355,297 (100%), 207.

Example 12

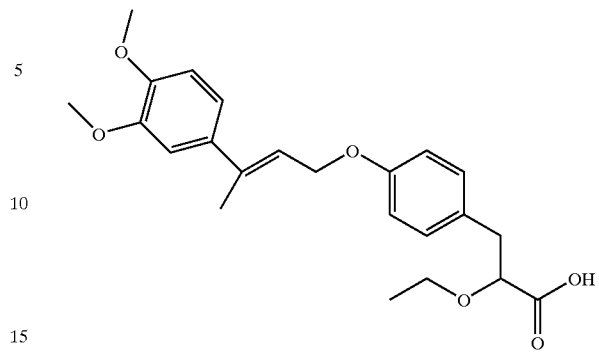

(E)-(S)-3-{4-[3-(3,4-Dimethoxy-phenyl)-but-2-enyloxy]-phenyl}-2-ethoxy-propionic acid The title compound was prepared from (E)-(S)-3-{4-[3-(3,4-dimethoxy-phenyl)-but-2-enyloxy]-phenyl}-2-ethoxy-propionic acid ethyl ester (example 11) (0.150 g, 0.350 mmol) and sodium hydroxide (1M, 1.05 ml, 1.05 mmol) by a procedure analogous to that described in example 2 yielding 0.120 g (86%) of (E)-(S)-3-{4-[3-(3,4-dimethoxy-phenyl)-but-2-enyloxy]-phenyl}-2-ethoxy-propionic acid.

$^1$H NMR (300 MHz, CDCl$_3$) δ: 1.15 (3H, t), 2.15 (3H, s), 2.9–3.15 (2H, m), 3.40–3.48 (1H, m), 3.56–3.63 (1H, m), 3.9 (6H, ds), 4.08 (1H, dd), 4.75 (2H, d), 6.01 (1H, dt), 6.80–6.91 (3H, m), 7.0 (2H, d), 7.15 (2H, d).

Example 13

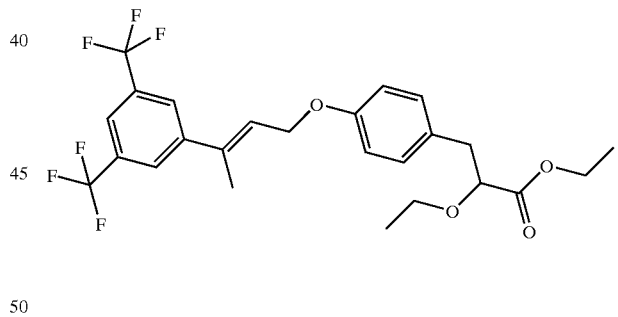

(E)-(S)-3-{4-[3-(3,5-Bis-trifluoromethyl-phenyl)-but-2-enyloxy]-phenyl}-2-ethoxy-propionic acid ethyl ester The title compound was prepared from 3,5-bis(trifluoromethyl)acetophenone (5.12 g, 0.02 mol) by a sequence analogous to that described in example 3 yielding 0.370 g (73%) of (E)-(S)-3-{4-[3-(3,5-bis-trifluoromethyl-phenyl)-but-2-enyloxy]-phenyl}-2-ethoxy-propionic acid ethyl ester.

$^1$H NMR (300 MHz, CDCl$_3$) δ: 1.1–1.25 (6H, m), 2.20 (3H, s), 2.97 (2H, d), 3.3–3.4 (1H, m), 3.62–3.7 (1H, m), 4.0 (1H, t), 4.15 (2H, q), 4.75 (2H, d), 6.2 (1H, dt), 6.85 (2H, d), 7.2 (2H, d), 7.78 (1H, br s), 7.87 (2H, br s). MS 504 (M$^+$), 458, 431(100%), 373, 267, 192

Example 14

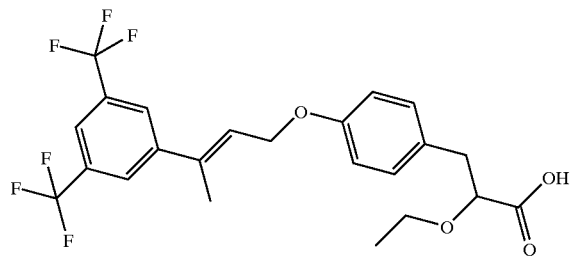

(E)-(S)-3-{4-[3-(3,5-Bis-trifluoromethyl-phenyl)-but-2-enyloxy]-phenyl}-2-ethoxy-propionic acid The title compound was prepared from (E)-(S)-3-{4-[3-(3,5-bis-trifluoromethyl-phenyl)-but-2-enyloxy]-phenyl}-2-ethoxy-propionic acid ethyl ester (example 13) (0.200 g, 0.396 mmol) and sodium hydroxide (1M, 0.792 ml, 0.792 mmol) by a procedure analogous to that described in example 2 yielding 0.150 g (79%) of (E)-(S)-3-{4-[3-(3,5-bis-trifluoromethyl-phenyl)-but-2-enyloxy]-phenyl}-2-ethoxy-propionic acid.

$^1$H NMR (300 MHz, CDCl$_3$) δ: 1.12 (3H, t), 2.18 (3H, s), 2.9 (1H, dd), 3.1 (1H, dd), 3.34–3.42 (1H, m), 3.5–3.65 (1H, m), 4.0 (1H, dd), 4.7 (2H, d), 6.11 (1H, dt), 6.83 (2H, d), 7.19 (2H, d) 7.72 (1H, br s), 7.83 (2H, br s).

Example 16

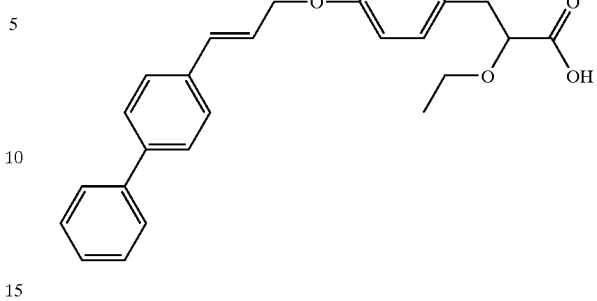

(E)-(S)-3-[4-(3-Biphenyl-4-yl-allyloxy)-phenyl]-2-ethoxy-propionic acid

The title compound was prepared from (E)-(S)-3-[4-(3-biphenyl-4-yl-allyloxy)-phenyl]-2-ethoxy-propionic acid ethyl ester (example 15) (0.200 g, 0.464 mmol) and sodium hydroxide (1M, 0.928 ml, 0.928 mmol) by a procedure analogous to that described in example 2 yielding 0.043 g (23%) of (E)-(S)-3-[4-(3-biphenyl-4-yl-allyloxy)-phenyl]-2-ethoxy-propionic acid.

$^1$H NMR (300 MHz, CDCl$_3$) δ: 1.15 (3H, t), 2.9 (1H, dd), 3.12 (1H, dd) 3.45–3.55 (2H, m), 3.84–3.96 (2H, m), 4.1 (1H, dd), 4.7 (2H, d), 6.35–6.5 (1H, dt), 6.78 (1H, d), 6.88 (2H, d), 7.15 (2H, d) 7.4–7.6 (9H, m).

Example 15

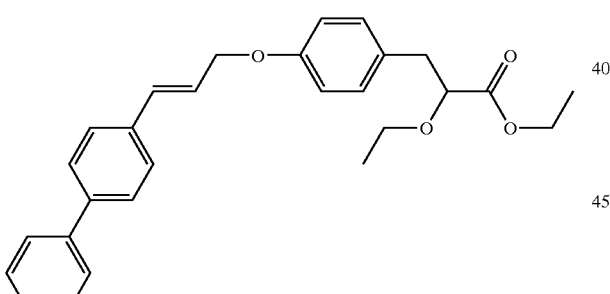

(E)-(S)-3-[4-(3-Biphenyl-4-yl-allyloxy)-phenyl]-2-ethoxy-propionic acid ethyl ester The title compound was prepared from 3-biphenyl-4-yl-acrylic acid ethyl ester (2.5 g, 0.01 mol) by a sequence analogous to that described in example 3b–c yielding 0.370 g (73%) of (E)-(S)-3-[4-(3-biphenyl-4-yl-allyloxy)-phenyl]-2-ethoxy-propionic acid ethyl ester.

$^1$H NMR (200 MHz, CDCl$_3$) δ: 1.1–1.25 (6H, m), 2.97 (2H, d), 3.3–3.4 (1H, m), 3.52–3.7 (1H, m), 4.0 (1H, t), 4.15 (2H, q), 4.75 (2H, dd), 6.35–6.5 (1H, dt), 6.75 (1H, d), 6.87 (2H, d), 7.15 (2H, d), 7.4–7.65 (9H, m).

Example 17

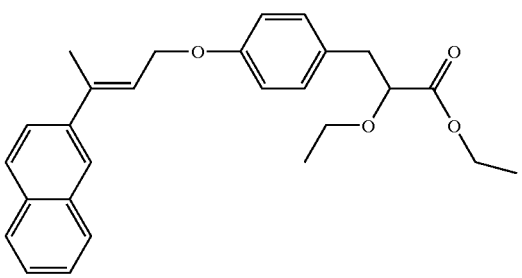

(E)-(S)-2-Ethoxy-3-[4-(3-naphthalen-2-yl-but-2-enyloxy)-phenyl]-propionic acid ethyl ester The title compound was prepared from 2-acetonaphthone (10.0 g, 0.06 mol) by a sequence analogous to that described in example 3 yielding 0.190 g (38%) of (E)-(S)-2-ethoxy-3-[4-(3-naphthalen-2-yl-but-2-enyloxy)-phenyl]-propionic acid ethyl ester.

$^1$H NMR (200 MHz, CDCl$_3$) δ: 1.1–1.2 (6H, m), 2.20 (3H, s), 2.95 (2H, d), 3.3–3.4 (1H, m), 3.52–3.65 (1H, m), 3.95 (1H, t), 4.15 (2H, q), 4.76 (2H, d), 6.2 (1H, t), 6.85 (2H, d), 7.15 (2H, d), 7.35–7.42 (2H, m), 7.6 (1H, dd), 7.75–7.85 (4H, m).

Example 18

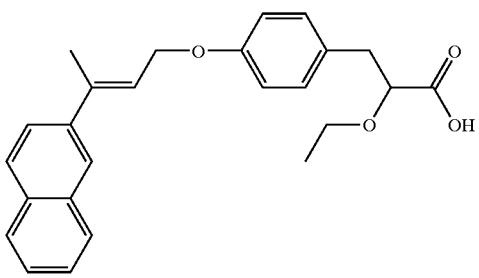

(E)-(S)-2-Ethoxy-3-[4-(3-naphthalen-2-yl-but-2-enyloxy)-phenyl]-propionic acid

The title compound was prepared from (E)-(S)-2-ethoxy-3-[4-(3-naphthalen-2-yl-but-2-enyloxy)-phenyl]-propionic acid ethyl ester (example 17) (0.165 g, 0.394 mmol) and sodium hydroxide (1M, 0.789 ml, 0.789 mmol) by a procedure analogous to that described in example 2 yielding 0.030 g (19%) of (E)-(S)-2-ethoxy-3-[4-(3-naphthalen-2-yl-but-2-enyloxy)-phenyl]-propionic acid.

$^1$H NMR (400 MHz, CDCl$_3$) δ: 1.13 (3H, t), 2.18 (3H, s), 2.95 (1H, dd), 3.05 (1H, dd), 3.3–3.45 (1H, m), 3.65–3.63 (1H, m), 3.95 (1H, dd), 4.72 (2H, d), 6.15 (1H, t), 6.84 (2H, d), 7.14 (2H, d), 7.35–7.45 (2H, m), 7.6 (1H, d), 7.7–7.8 (4H, m).

Example 19

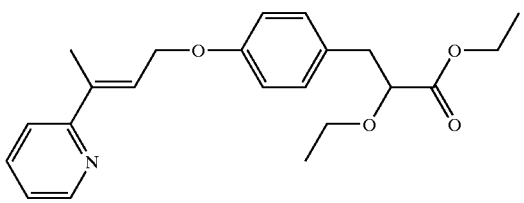

(E)-(S)-2-Ethoxy-3-[4-(3-pyridin-2-yl-but-2-enyloxy)-phenyl]-propionic acid ethyl ester The title compound was prepared from 2-acetylpyridine (9.6 g, 0.08 mol) by a sequence analogous to that described in example 3 yielding 0.230 g (23%) of (E)-(S)-2-ethoxy-3-[4-(3-pyridin-2-yl-but-2-enyloxy)-phenyl]-propionic acid ethyl ester.

$^1$H NMR (400 MHz, CDCl$_3$) δ: 1.1–2.5 (6H, m), 2.21 (3H, s), 2.97 (2H, d), 3.3–3.4 (1H, m), 3.58–3.64 (1H, m), 3.97 (1H, t), 4.15 (2H, q), 4.78 (2H, d), 6.65 (1H, t), 6.85 (2H, d), 7.05–7.15 (3H, m), 7.42 (2H, d), 7.6 (1 H, dd), 8,52 (1H, d).

Example 20

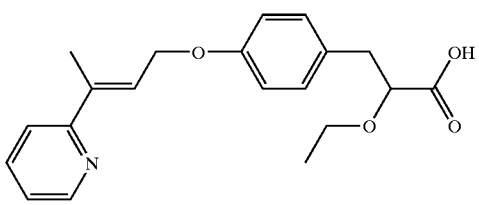

(E)-(S)-2-Ethoxy-3-[4-(3-pyridin-2-yl-but-2-enyloxy)-phenyl]-propionic acid

The title compound was prepared from (E)-(S)-2-ethoxy-3-[4-(3-pyridin-2-yl-but-2-enyloxy)-phenyl]-propionic acid ethyl ester (example 19) (0.220 g, 0.595 mmol) and sodium hydroxide (1M, 1.19 ml, 1.19 mmol) by a procedure analogous to that described in example 2 yielding 0.200 g (98%) of (E)-(S)-2-ethoxy-3-[4-(3-pyridin-2-yl-but-2-enyloxy)-phenyl]-propionic acid.

$^1$H NMR (300 MHz, CDCl$_3$) δ: 1.2 (3H, t), 2.1 (3H, s), 2.7–2.85 (1H, m), 3.0–3.25 (2H, m), 3.5–3.6 (1H, m), 3.8–3.92 (1H, m), 4.6 (2H, d), 6.5 (1H, t), 6.75 (2H, d), 7.1–7.2 (3H, m), 7.35 (1H, d), 7.6 (1H, t), 8,5 (1H, d).

Example 21

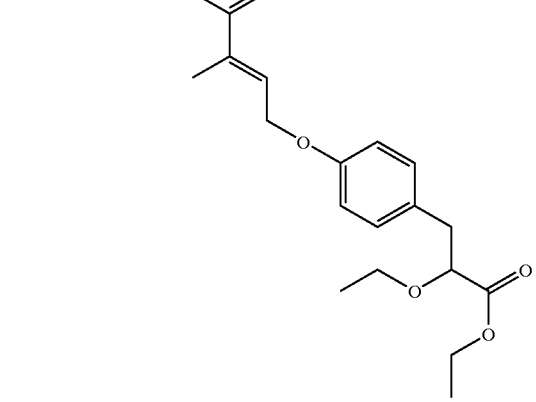

(E)-(S)-3-{4-[3-(3,5-Bis-benzyloxy-phenyl)-but-2-enyloxy]-phenyl}-2-ethoxy-propionic acid ethyl ester The title compound was prepared from 3,5-dibenzyloxyacetophenone (6.64 g, 0.02 mol) by a sequence analogous to that described in example 3 yielding 0.460 g (53%) of (E)-(S)-3-{4-[3-(3,5-bis-benzyloxy-phenyl)-but-2-enyloxy]-phenyl}-2-ethoxy-propionic acid ethyl ester.

$^1$H NMR (300 MHz, CDCl$_3$) δ: 1.1–1.21 (6H, m), 2.14 (3H, s), 2.95 (2H, d) 3.28–3.41 (1H, m), 3.51–3.65 (1H, m), 3.94 (1H, t), 4.12 (2H, q), 4.7 (2H, d), 5.05 (4H, s), 6.05 (1H, t), 6.53–6.57 (1H, m), 6.67 (2H, d), 6.85 (2H, d), 7.12 (2H, d), 7.3–7.45 (10H, m).

Example 22

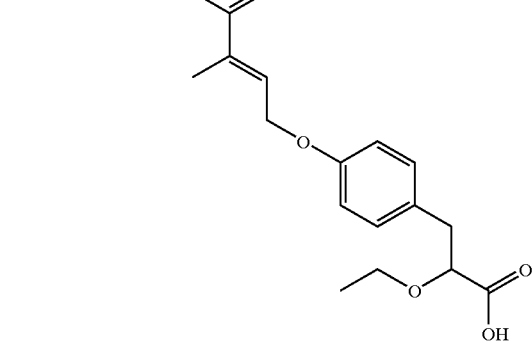

(E)-(S)-3-{4-[3-(3,5-Bis-benzyloxy-phenyl)-but-2-enyloxy]-phenyl}-2-ethoxy-propionic acid The title compound was prepared from (E)-(S)-3-{4-[3-(3,5-bis-benzyloxy-phenyl)-but-2-enyloxy]-phenyl}-2-ethoxy-propionic acid ethyl ester (example 21) (0.430 g, 0.741 mmol) and sodium hydroxide (1M, 1.5 ml, 1.5 mmol) by a procedure analogous to that described in example 2 yielding 0.300 g (73%) of (E)-(S)-3-{4-[3-(3,5-bis-benzyloxy-phenyl)-but-2-enyloxy]-phenyl}-2-ethoxy-propionic acid.

$^1$H NMR (300 MHz, CDCl$_3$) δ: 1.15 (3H, t), 2.1 (3H, s), 2.95 (1H, dd), 3.05 (1H, dd), 3.36–3.44 (1H, m), 3.57–3.65 (1H, m), 4.05 (1H, dd), 4.68 (2H, d), 5.05 (4H, s), 6.05 (1H, t), 6.52 (1H, m), 6.65 (2H, d), 6.85 (2H, d), 7.15 (2H, d), 7.3–7.45 (10H, m).

Example 23

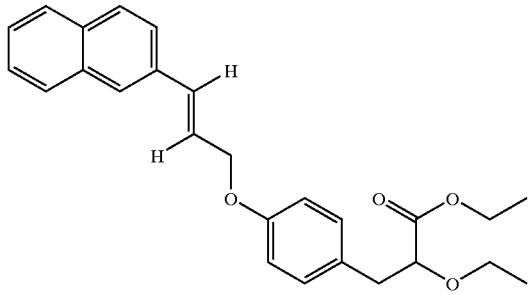

(E)-(S)-2-Ethoxy-3-[4-(3-naphthalen-2-yl-allyloxy)-phenyl]-propionic acid ethyl ester a)
Triethyl phosphonoacetate (8.9 g, 40.0 mmol) was added at 0° C. over a period of 10 min. to a stirred suspension of sodium hydride (60% in oil, 1.44 g, 36.0 mmol) in dry THF (145 mL). After stirring at 0° C. for 15 min. a solution of 2-naphthaldehyde (3.12 g, 20.0 mmol) in dry THF (15 mL) was added, the mixture slowly warmed to room temperature, and stirring continued for 16 h. The reaction mixture was quenched with water (100 mL) and acidified to pH 6 with 1N hydrochloric acid. Additional water (200 mL) was added, the organic phase separated, and the aqueous phase further extracted with ethyl acetate (300 mL). The combined organic phases were washed with water (200 mL×3), dried (MgSO$_4$), filtered and concentrated in vacuo to give 6.5 g of crude (E)-3-naphthalen-2-yl-acrylic acid ethyl ester.

b)
Crude (E)-3-naphthalen-2-yl-acrylic acid ethyl ester (4.5 g, 20.0 mmol) was reduced by a procedure analogous to that described in example 1b. The product was purified by flash column chromatography to give 3.1 g (86%) of (E)-3-naphthalen-2-yl-prop-2-en-1-ol.

c)
Under an atmosphere of nitrogen, (E)-3-naphthalen-2-yl-prop-2-en-1-ol (190 mg, 0.8 mmol), tributylphosphine (323 mg, 1.6 mmol) and (S)-2-ethoxy-3-(4-hydroxy-phenyl)-propionic acid ethyl ester (184 mg, 1.0 mmol) were successively dissolved in dry benzene (20 mL). Solid 1,1'-(azodicarbonyl) dipiperidine (403 mg, 1.6 mmol) was added at 0° C. with stirring. After 10 min. the reaction was warmed to room temperature and the stirring continued for 1 h. The reaction mixture was concentrated in vacuo and the product purified by flash column chromatography, eluting with heptane/ethyl acetate (3:2), to give 180 mg (55%) of the title compound.

$^1$H NMR (CDCl$_3$, 300 MHz) δ: 1.15 (t, 3H), 1,22 (t, 3H), 2.95 (d, 2H), 3.28–3.40 (m, 1H), 3.55–3.65 (m, 1H), 3.96 (t, 1H), 4.15 (q, 2H), 4.72 (dd, 2H), 6.53 (dt, 1H), 6.83–6.93 (m, 3H), 7.18 (d, 2H), 7.40–7.50 (m, 2H), 7.13 (dd, 1H), 7.72–7.85 (m, 4H).

Example 24

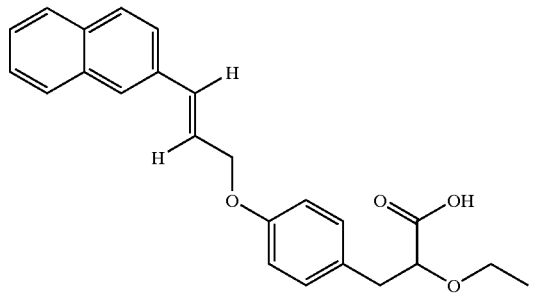

(E)-(S)-2-Ethoxy-3-[4-(3-naphthalen-2-yl-allyloxy)-phenyl]-propionic acid (E)-(S)-2-Ethoxy-3-[4-(3-naphthalen-2-yl-allyloxy)-phenyl]-propionic acid ethyl ester (example 23) (170 mg, 0.42 mmol) was dissolved in ethanol (20 mL) at 35° C. and sodium hydroxide (1N, 2.1 mL, 2.1 mmol) added. The mixture was stirred at 35° C. for 1 h, the ethanol evaporated in vacuo and the mixture acidified to pH 1 with 1N hydrochloric acid. The product was isolated by extraction with ethyl acetate (30 mL×2). The combined organic phases were dried (MgSO$_4$), filtered and evaporated to give 155 mg (98%) of the title compound as crystals.

$^1$H NMR (CDCl$_3$, 300 MHz) δ: 1.18 (t, 3H), 2.90–3.12 (m, 2H), 3.35–3.48 (m, 1H), 3.55–3.68 (m, 1H), 4.03 (q, 1H), 4.70 (dd, 2H), 6.52 (dt, 1H), 6.80–6.95 (m, 3H), 7.18 (d, 2H), 7.40–7.48 (m, 2H), 7.60 (dd, 1H), 7.70–7.80 (m, 4H).

Example 25

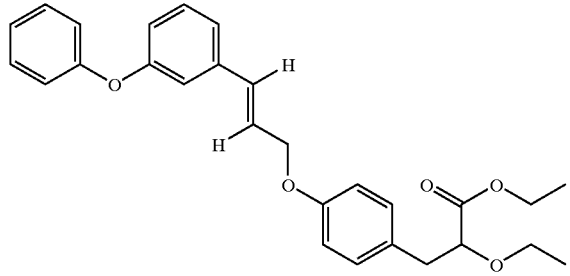

(E)-(S)-2-Ethoxy-3-{4-[3-(3-phenoxy-phenyl)-allyloxy]-phenyl}-propionic acid ethyl ester The title compound was prepared from 3-phenoxybenzaldehyde (4.0 g, 20.0 mmol) by a sequence analogous to that described in example 23.

$^1$H NMR (CDCl$_3$, 300 MHz) δ: 1.15 (t, 3H), 1,22 (t, 3H), 2.95 (d, 2H), 3.30–3.40 (m, 1H), 3.55–3.68 (m, 1H), 3.98 (t, 1H), 4.15 (q, 2H), 4.72 (dd, 2H), 6.38 (dt, 1H), 6.67 (d, 1H), 6.83–6.93 (m, 3H), 6.97–7.20 (m, 7H), 7.22–7.38 (m, 3H).

Example 26

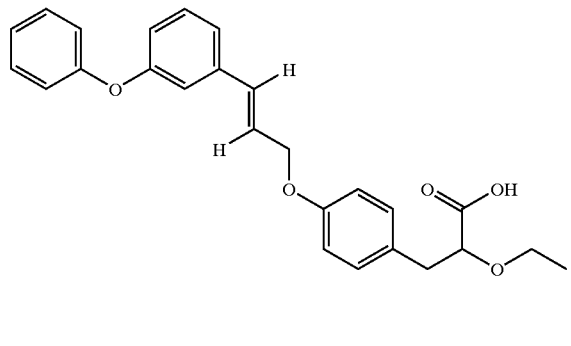

(E)-(S)-2-Ethoxy-3-{4-[3-(3-phenoxy-phenyl)-allyloxy]-phenyl}-propionic acid (E)-(S)-2-Ethoxy-3-{4-[3-(3-phenoxy-phenyl)-allyloxy]-phenyl}-propionic acid ethyl ester (example 25) (150 mg, 0.34 mmol) was dissolved in ethanol (7 mL) and sodium hydroxide (1N, 4.4 mL, 4.4 mmol) added. The mixture was heated slightly to obtain a clear solution and then stirred at room temperature for 1.5 h. The ethanol was evaporated in vacuo and the mixture acidified to pH 1 with 1N hydrochloric acid. The product was isolated by extraction with ethyl acetate (40 mL×2). The combined organic phases were dried (MgSO$_4$), filtered and evaporated to give 130 mg (91%) of the title compound as an oil.

$^1$H NMR (CDCl$_3$, 300 MHz) δ: 1.18 (t, 3H), 2.95 (dd, 1H), 3.08 (dd, 1H), 3.38–3.50 (m, 1H), 3.55–3-65 (m, 1H), 4.05 (q, 1H), 4.65 (dd, 1H), 6.35 (dt, 1H), 6.66 (d, 1H), 6.85–6.92 (m, 3H), 6.98–7.20 (m, 7H), 7.25–7.40 (m, 3H).

Example 27

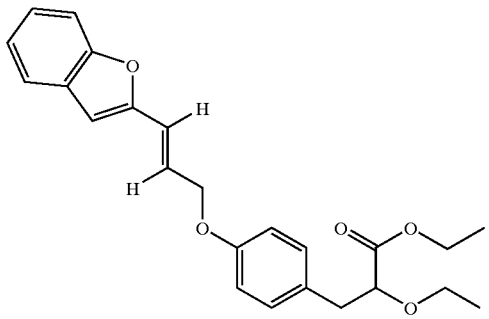

(S)-3-[4-(2-Benzofuran-3-yl-allyloxy)-phenyl]-2-ethoxy-propionic acid ethyl ester The title compound was prepared from benzo[b]furan-2-carboxaldehyde (9.8 g, 0.07 mol) by a sequence analogous to that described in example 23.

$^1$H NMR (CDCl$_3$, 300 MHz) δ: 1.15 (t, 3H), 1.22 (t, 3H), 2.95 (d, 2H), 3.30–3.42 (m, 1H), 3.55–3.65 (m, 1H), 3.98 (t, 1H), 4.15 (q, 2H), 4.73 (d, 2H), 6.65–6.70 (m, 3H), 6.88 (d, 2H), 7.15 (d, 2H), 7.20–7-30 (m, 2H), 7.45 (d, 1 H), 7.53 (d, 1 H).

Example 28

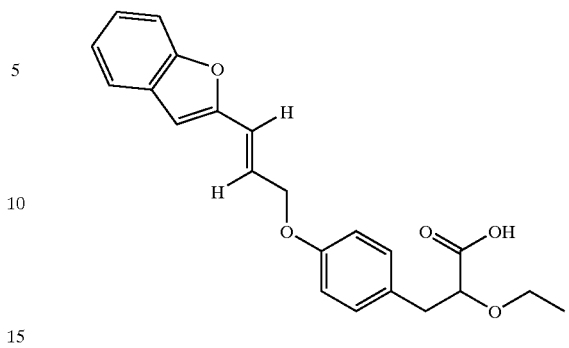

(S)-3-[4-(2-Benzofuran-3-yl-allyloxy)-phenyl]-2-ethoxy-propionic acid

The title compound was prepared from (S)-3-[4-(2-benzofuran-3-yl-allyloxy)-phenyl]-2-ethoxy-propionic acid ethyl ester (example 27) (127 mg, 0.3 mmol) by a procedure analogous to that described in example 26.

$^1$H NMR (CDCl$_3$, 300 MHz) δ: 1.15 (t, 3H), 3.30 (dd, 1H), 3.08 (dd, 1H), 2.38–3.50 (m, 1H), 3.55–3.65 (m, 1H), 4.05 (q, 1H), 4.72 (d, 2H), 6.55–6.68 (m, 3H), 6.90 (d, 1H), 7-13–7.30 (m, 5H), 7.42 (d, 1H), 7.50 (d, 1H).

Example 29

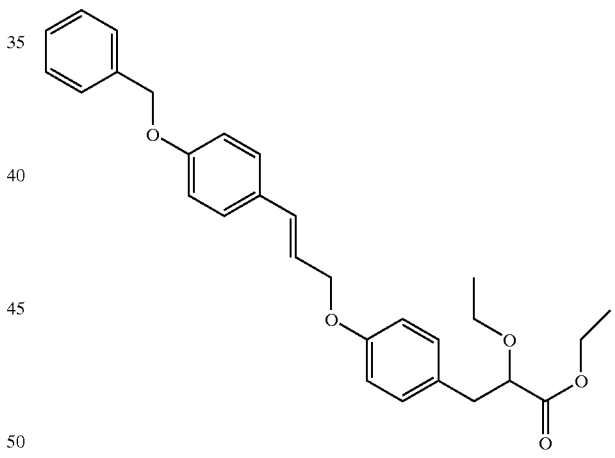

(E)-(S)-3-{4-[3-(4-Benzyloxy-phenyl)-allyloxy]-phenyl}-2-ethoxy-propionic acid ethyl ester The title compound was prepared from 4-benzyloxybenzaldehyde (21.2 g, 0.1 mol) by a sequence analogous to that described in example 23. The title compound was purified on HPLC, using ethyl acetate/heptane (20:80) as eluent.

$^1$H NMR (CDCl$_3$, 300 MHz) δ: 1.15 (t, 3H), 1.22 (t, 3H), 2.95 (d, 2H), 3.35 (m, 1H), 3.6 (m, 1H), 3.98 (t, 1H), 4.15 (q, 2H), 4.65 (dd, 2H), 5.05 (s, 2H), 2.28 (dt, 1H), 6.65 (d, 1H), 6.85 (d, 2H), 6.93 (d, 2H), 7.15 (d, 2H), 7.30–7.48 (m, 7H).

Example 30

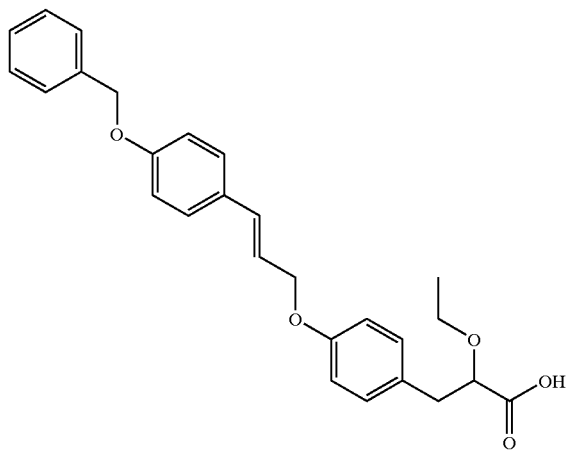

(E)-(S)-3-{4-[3-(4-Benzyloxy-phenyl)-allyloxy]-phenyl}-2-ethoxy-propionic acid

The title compound was prepared from (E)-(S)-3-{4-[3-(4-Benzyloxy-phenyl)-allyloxy]-phenyl}-2-ethoxy-propionic acid ethyl ester (example 29) (80 mg, 0.17 mmol) by a procedure analogous to that described in example 26.

$^1$H NMR (CDCl$_3$, 300 MHz): 1.18 (t, 3H), 2.95 (dd, 1H), 3.12 (dd, 1H), 3.45–3.60 (m, 2H), 4.15 (dd, 1H), 4.65 (dd, 2H), 5.06 (s, 2H), 6.25 (dt, 1 H), 6.65 (d, 1 H), 6.90 (d, 2H), 6.93 (d, 2H), 7.15 (d, 2H), 7.30–7.45 (m, 7H).

Example 31

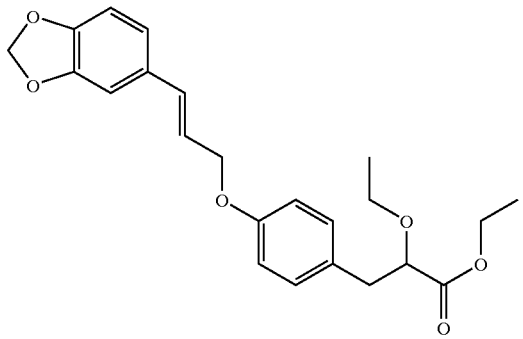

(E)-(S)-3-[4-(3-Benzo[1,3]dioxol-5-yl-allyloxy)-phenyl]-2-ethoxy-propionic acid ethyl ester The title compound was prepared from piperonal (3.0 g, 20 mmol) by a sequence analogous to that described in example 23. The title compound was purified on HPLC, using ethyl acetate/heptane (10:90) as eluent.

$^1$H NMR (CDCl$_3$, 300 MHz) δ: 1.15 (t, 3H), 1.22 (t, 3H), 2.96 (d, 2H), 3.30–3.42 (m, 1H), 3.55–3.65 (m, 1H), 3.97 (t, 1H), 4.15 (q, 2H), 4.63 (dd, 2H), 5.96 (s, 2H), 6.25 (dt, 1H), 6.63 (d, 1H), 6.75 (d, 1H), 6.80–6.90 (m, 3H), 6.95 (d, 1H), 7.15 (d, 2H).

Example 32

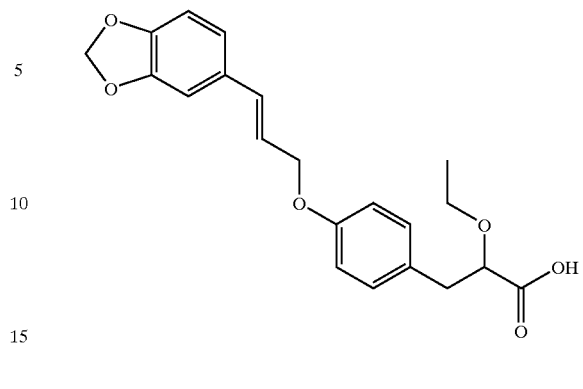

(E)-(S)-3-[4-(3-Benzo[1,3]dioxol-5-yl-allyloxy)-phenyl]-2-ethoxy-propionic acid

The title compound was prepared from (E)-(S)-3-[4-(3-benzo[1,3]dioxol-5-yl-allyloxy)-phenyl]-2-ethoxy-propionic acid ethyl ester (example 31) (100 mg, 0.25 mmol) by a procedure analogous to that described in example 26.

$^1$H NMR (CDCl$_3$, 300 MHz): 1.18 (t, 3H), 2.95 (dd, 1H), 3.08 (dd, 1H), 3.38–3.50 (m, 1H), 3.55–3.68 (m, 1H), 4.05 (dd, 1H), 4.65 (dd, 2H), 5.95 (s, 2H), 6.25 (dt, 1H), 6.63 (d, 1H), 6.75 (d, 1H), 6.83 (dd, 1H), 6.88 (d, 2H), 6.95 (d, 1 H), 7.17 (d, 2H).

Example 33

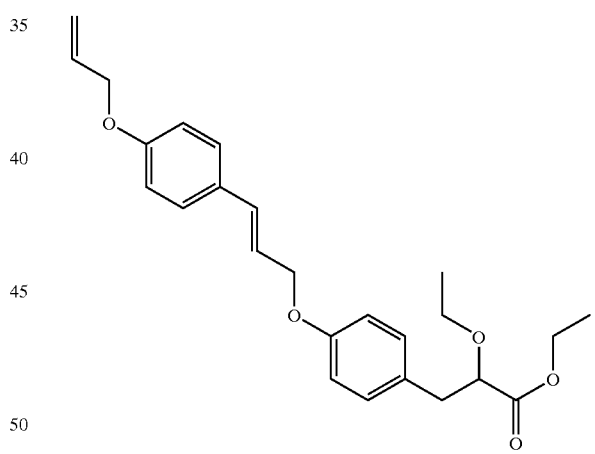

(E)-(S)-3-{4-[3-(4-Allyloxy-phenyl)-allyloxy]-phenyl)-2-ethoxy-propionic acid ethyl ester The title compound was prepared from 4-allyloxybenzaldehyde (3.24 g, 20 mmol) by a sequence analogous to that described in example 23. The title compound was purified on HPLC, using ethyl acetate/heptane (10:90) as eluent.

$^1$H NMR (CDCl$_3$, 300 MHz) δ: 1.18 (t, 3H), 1.22 (t, 3H), 2.95 (d, 2H), 3.30–3.42 (m, 1H), 3.55–3.68 (m, 1H), 3.98 (t, 1H), 4.17 (q, 2H), 4.53 (d, 2H), 4.65 (dd, 2H), 5.29 (dd, 1H), 5.40 (dd, 1H), 5.97–6.13 (m, 1H), 6.28 (dt, 1H), 6.65 (d, 1H), 6.88 (d, 4H), 7.15 (d, 2H), 7.35 (d, 2H).

Example 34

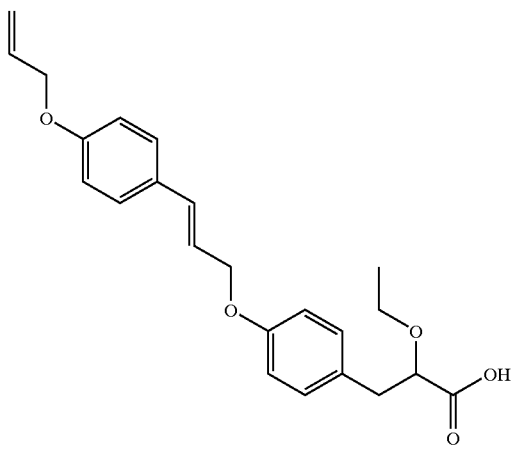

(E)-(S)-3-{4-[3-(4-Allyloxy-phenyl)-allyloxy]-phenyl}-2-ethoxy-propionic acid

The title compound was prepared from (E)-(S)-3-{4-[3-(4-allyloxy-phenyl)-allyloxy]-phenyl}-2-ethoxy-propionic acid ethyl ester (example 33) (40 mg, 0.1 mmol) by a procedure analogous to that described in example 26.

$^1$H NMR (CDCl$_3$, 300 MHz): 1.18 (t, 3H), 2.95 (dd, 1H), 3.10 (dd, 1H), 3.39–3.50 (m, 1H), 3.53–3.65 (m, 1H), 4.05 (dd, 1H), 4.53 (d, 2H), 4.65 (d, 2H), 5.29 (dd, 1H), 5.40 (dd, 1H), 5.98–6.14 (m, 1H), 6.28 (dt, 1H), 6.65 (d, 1H), 6.85–6.95 (m, 4H), 7.15 (d, 2H), 7.35 (d, 2H).

Example 35

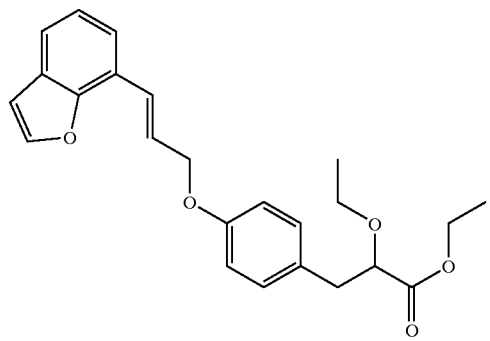

(E)-(S)-3-[4-(3-Benzofuran-7-yl-allyloxy)-phenyl]-2-ethoxy-propionic acid ethyl ester The title compound was prepared from benzofuran-7-carboxaldehyde (1.46 g, 10 mmol) by a sequence analogous to that described in example 23.

$^1$H NMR (CDCl$_3$, 300 MHz) δ: 1.15 (t, 3H), 1.22 (t, 3H), 2.95 (d, 2H), 3.30–3.42 (m, 1H), 3.55–3.65 (m, 1H), 3.98 (t, 1H), 4.15 (q, 2H), 4.75 (dd, 2H), 6,79 (d, 1H), 6.87–7.00 (m, 4H), 7.13–7.30 (m, 4H), 7.50 (dd, 1H), 7.65 (d, 1H).

Example 36

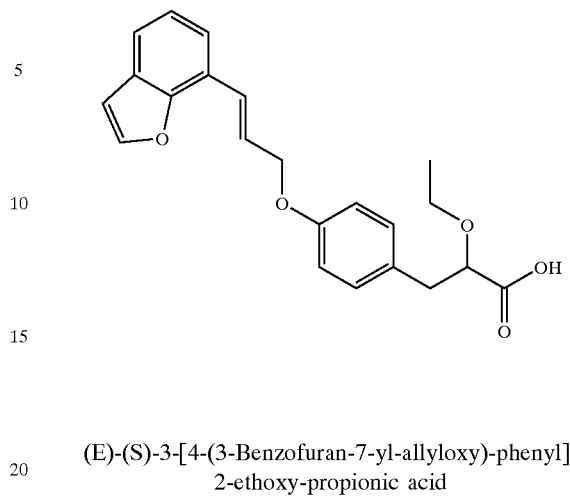

(E)-(S)-3-[4-(3-Benzofuran-7-yl-allyloxy)-phenyl]-2-ethoxy-propionic acid

The title compound was prepared from (E)-(S)-3-[4-(3-benzofuran-7-yl-allyloxy)-phenyl]-2-ethoxy-propionic acid ethyl ester (example 35) (100 mg, 0.25 mmol) by a procedure analogous to that described in example 26.

$^1$H NMR (CDCl$_3$, 300 MHz) δ: 1.15 (t, 3H), 2.95 (dd, 1H), 3.08 (dd, 1H), 3.35–3.48 (m, 1H) 3.55–3.68 (m, 1H), 4.03 (dd, 1H), 4.75 (dd, 2H), 6.78 (d, 1H), 6.90–7.00 (m, 4H), 7.13–7.32 (m, 4H), 7.50 (dd, 1H), 7.65 (d, 1H), 10.1 (bs, 1H).

Example 37

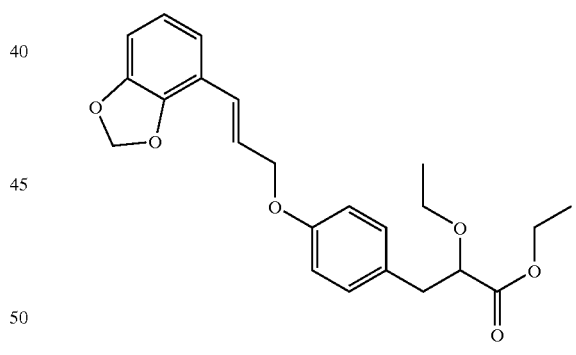

(S)-3-[4-(3-Benzo[1,3]dioxol-4-yl-allyloxy)-phenyl]-2-ethoxy-propionic acid ethyl ester The title compound was prepared from 2,3-methylenedioxybenzaldehyde (1.5 g, 10 mmol) by a sequence analogous to that described in example 23.

$^1$H NMR (CDCl$_3$, 300 MHz) δ: 1.18 (t, 3H), 1.22 (t, 3H), 2.95 (d, 2H), 3.30–3.42 (m, 1H), 3.55–3.65 (m, 1H), 3.97 (t, 1H), 4.15 (q, 2H), 4.65 (d, 2H), 6.00 (s, 2H), 6.55–6.92 (m, 7H), 7.15 (d, 2H).

Example 38

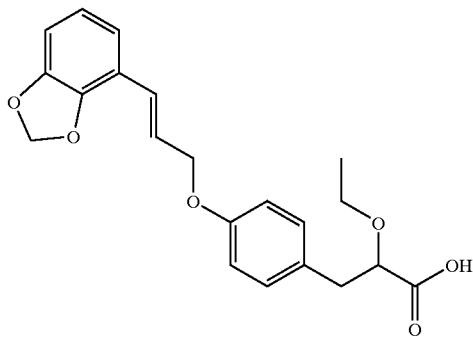

(S)-3-[4-(3-Benzo[1,3]dioxol-4-yl-allyloxy)-phenyl]-2-ethoxy-propionic acid

The title compound was prepared from (S)-3-[4-(3-benzo[1,3]dioxol-4-yl-allyloxy)-phenyl]-2-ethoxy-propionic acid ethyl ester (example 37) (100 mg, 0.24 mmol) by a procedure analogous to that described in example 26.

$^1$H NMR (CDCl$_3$, 300 MHz) δ: 1.17 (t, 3H), 2.95 (dd, 1H), 3.05 (dd, 1H), 3.35–3.48 (m, 1H), 3.55–3.68 (m, 1H), 4.03 (dd, 1H), 4.65 (d, 2H), 6.00 (s, 2H), 6.55–6.95 (m, 7H), 7.19 (d, 2H).

Example 39

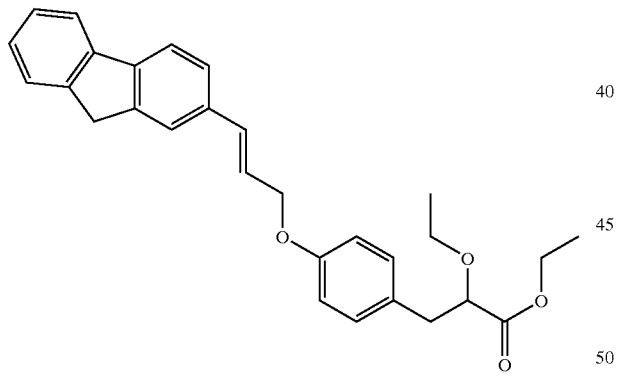

(E)-(S)-2-Ethoxy-3-(4-[3-(9H-fluoren-2-yl)-allyloxy]-phenyl)-propionic acid ethyl ester The title compound was prepared from fluorene-2-carboxaldehyde (9.7 g, 50 mmol) by a sequence analogous to that described in example 23.

$^1$H NMR (CDCl$_3$, 300 MHz) δ: 1.18 (t, 3H), 1.22 (t, 3H), 2.97 (d, 2H), 3.32–3.42 (m, 1H), 3.55–3.67 (m, 1H), 3.90 (s, 2H), 3.98 (t, 1H), 4.16 (q, 2H), 4.70 (dd, 2H), 6.45 (dt, 1H), 6.80 (d, 1H), 6.90 (d, 2H), 7.1 (d, 2H), 7.24–7.46 (m, 3H), 7.55 (d, 1H), 7.62 (s, 1H), 7.72–7.80 (m, 2H).

Example 40

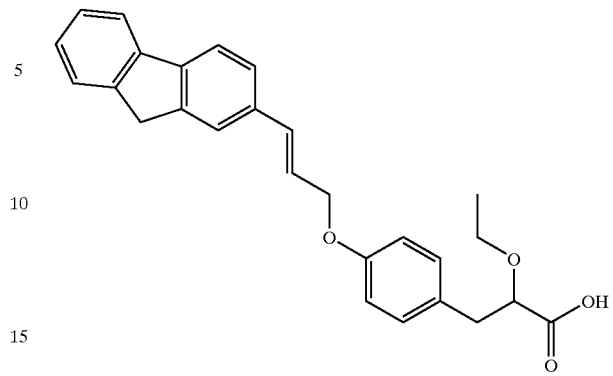

(E)-(S)-2-Ethoxy-3-(4-[3-(9H-fluoren-2-yl)-allyloxy]-phenyl)-propionic acid

The title compound was prepared from (E)-(S)-2-ethoxy-3-(4-[3-(9H-fluoren-2-yl)-allyloxy]-phenyl)-propionic acid ethyl ester (example 39) (275 mg, 0.6 mmol) by a procedure analogous to that described in example 26.

$^1$H NMR (CDCl$_3$, 300 MHz) δ: 1.20 (t, 3H), 3.46 (dd, 1H), 3.12 (dd, 1H), 3.43–3.65 (m, 2H), 3.90 (s, 2H), 4.05 (dd, 1H), 4.70 (dd, 2H), 6.46 (dt, 1H), 6.80 (d, 1H), 6.92 (d, 2H), 7.17 (d, 2H), 7.23–7.46 (m, 3H), 7.53 (d, 1H), 7.60 (s, 1H), 7.70–7.80 (m, 2H).

Example 41

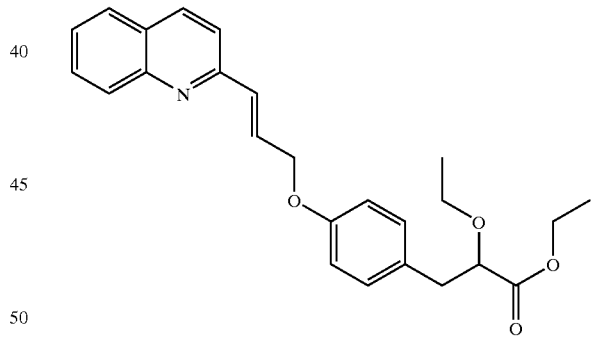

(S)-2-Ethoxy-3-[4-(3-quinolin-2-yl-allyloxy)-phenyl]-propionic acid ethyl ester

The title compound was prepared from 2-quinoline-carboxaldehyde (5.12 g, 32.5 mmol) by a sequence analogous to that described in example 23.

$^1$H NMR (CDCl$_3$, 300 MHz) δ: 1.18 (t, 3H), 1.22 (t, 3H), 2.98 (d, 2H), 3.32–3.42 (m, 1H), 3.55–3.66 (m, 1H), 3.98 (t, 1H), 4.17 (q, 2H), 4.80 (d, 2H), 6.92 (d, 2H), 7.02 (m, 2H), 7.18 (d, 2H), 7.47–7.60 (m, 2H), 7.70 (dt, 1H), 7.78 (d, 1H), 8.05 (d, 1H), 8.13 (d, 1H).

Example 42

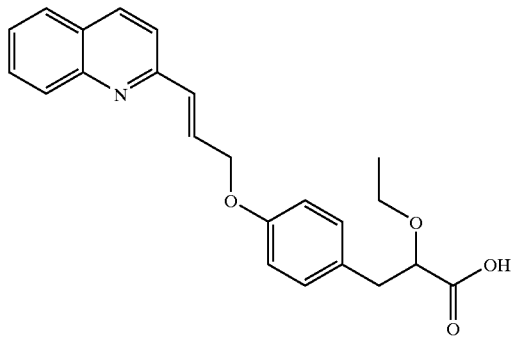

(S)-2-Ethoxy-3-[4-(3-quinolin-2-yl-allyloxy)-
phenyl]-propionic acid (S)-2-Ethoxy-3-[4-(3-quinolin-2-yl-allyloxy)-phenyl]-propionic acid ethyl ester (example 41) (150 mg, 0.37 mmol) was dissolved in ethanol (2 mL) and sodium hydroxide (1N, 2.0 mL, 2.0 mmol) added. The mixture was stirred at room temperature for 16 h. The reaction mixture was concentrated in vacuo, added 2-propanol (2 mL) and diethyl ether (2 mL). The title compound was isolated by filtration.

$^1$H NMR (CDCl$_3$/MeOD, 300 MHz) δ: 1.12 (t, 3H), 2.83 (dd, 1H), 3.02 (dd, 1H), 3.32 (m, 1H), 3.56 (dd, 1H), 3.84 (dd, 1H), 4.85 (d, 2H), 6.90–7.10 (m, 4H), 7.25 (m, 2H), 7.5–7.6 (m, 1H), 7.68–7.75 (m, 2H), 7.85 (d, 1H), 8.03 (d, 1H), 8.23 (d, 1H).

Example 43

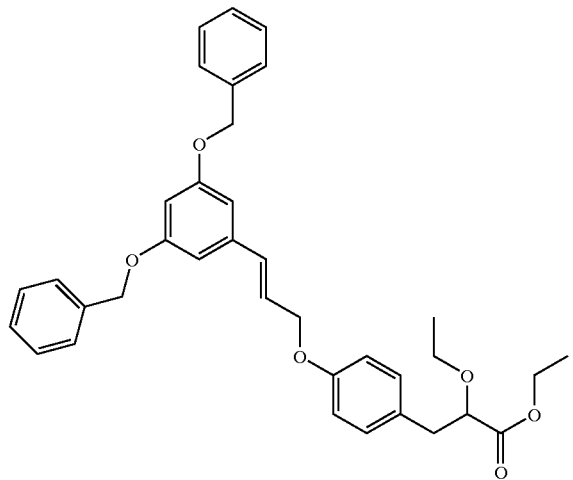

(E)-(S)-3-{4-[3-(3,5-Bis-benzyloxy-phenyl)-
allyloxy]-phenyl}-2-ethoxy-propionic acid ethyl
ester The title compound was prepared from 3,5-dibenzyloxybenzaldehyde (3.1 g, 9.7 mmol) by a sequence analogous to that described in example 23.

$^1$H NMR (CDCl$_3$, 300 MHz) δ: 1.16 (t, 3H), 1.22 (t, 3H), 2.96 (d, 2H), 3.30–3.42 (m, 1H), 3.54–3.65 (m, 1H), 3.98 (t, 1H), 4.17 (q, 2H), 4.65 (d, 2H), 5.02 (s, 4H), 6.38 (dt, 1H), 6.55 (s, 1H), 6.58–6.70 (m, 3H), 6.88 (d, 2H), 7.15 (d, 2H), 7.30–7.45 (m, 10H).

Example 44

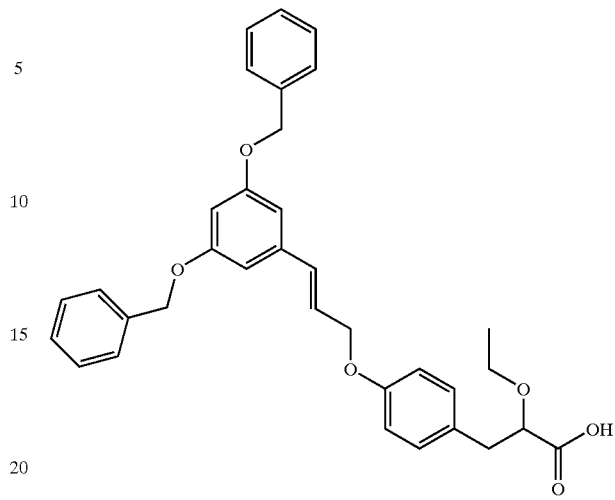

(E)-(S)-3-{4-[3-(3,5-Bis-benzyloxy-phenyl)-
allyloxy]-phenyl}-2-ethoxy-propionic acid The title compound was prepared from (E)-(S)-3-{4-[3-(3,5-bis-benzyloxy-phenyl)-allyloxy]-phenyl}-2-ethoxy-propionic acid ethyl ester (example 43) (587 mg, 1.1 mmol) by a procedure analogous to that described in example 26.

$^1$H NMR (CDCl$_3$, 300 MHz) δ: 1.15 (t, 3H), 2.95 (dd, 1H), 3.08 (dd, 1H), 3.38–3.48 (m, 1H), 3.54–3.65 (m 1H), 4.03 (dd, 1H), 4.65 (d, 2H), 5.03 (s, 4H), 6.35 (dt, 1H), 6.54 (t, 1H), 6.60–6.70 (m, 3H), 6.88 (d, 2H), 7.16 (d, 2H), 7.30–7.45 (m, 10H).

Example 45

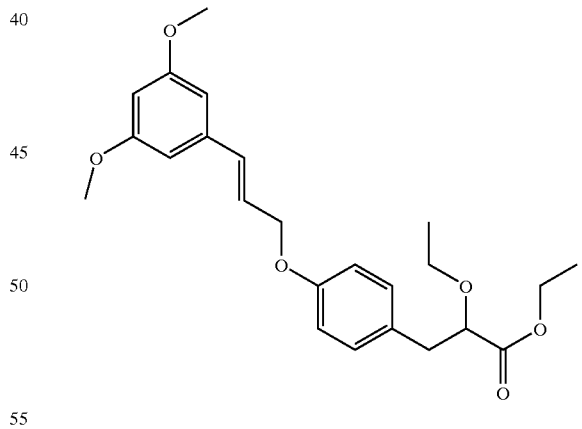

(E)-(S)-3-{4-[3-(3,5-Dimethoxy-phenyl)-allyloxy]-
phenyl}-2-ethoxy-propionic acid ethyl ester The title compound was prepared from 3,5-dimethoxybenzaldehyde (5.5 g, 33.1 mmol) by a sequence analogous to that described in example 23.

$^1$H NMR (CDCl$_3$, 300 MHz) δ: 1.18 (t, 3H), 1.22 (t, 3H), 2.95 (d, 2H), 3.30–3.40 (m, 1H), 3.53–3.65 (m, 1H), 3.78 (s, 6H), 3.97 (t, 1H), 4.15 (q, 2H), 4.65 (dd, 1H), 6.33–6.43 (m, 2H), 6.55 (d, 2H), 6.88 (d, 2H), 7.15 (d, 2H).

Example 46

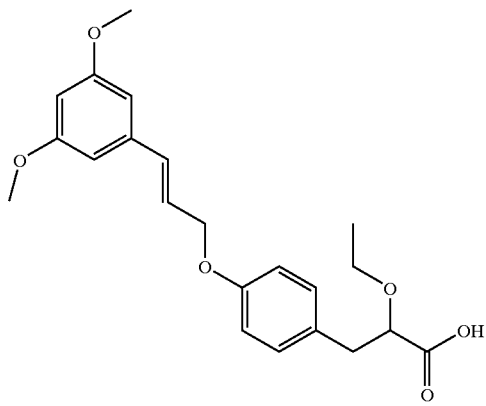

(E)-(S)-3-{4-[3-(3,5-Dimethoxy-phenyl)-allyloxy]-phenyl}-2-ethoxy-propionic acid The title compound was prepared from (E)-(S)-3-{4-[3-(3,5-dimethoxy-phenyl)-allyloxy]-phenyl}-2-ethoxy-propionic acid ethyl ester (example 45) (300 mg, 0.7 mmol) by a procedure analogous to that described in example 26.

$^1$H NMR (CDCl$_3$, 300 MHz) δ: 1.18 (t, 3H), 2.95 (dd, 1H), 3.07 (dd, 1H), 3.37–3.48 (m, 1H), 3.55–3.67 (m, 1H), 3.80 (s, 6H), 4.05 (dd, 1H), 4.67 (d, 2H), 6.33–6.45 (m, 1H), 6.55 (d, 2H), 6.65 (d, 1H), 6.88 (d, 2H), 7.18 (d, 2H).

Example 47

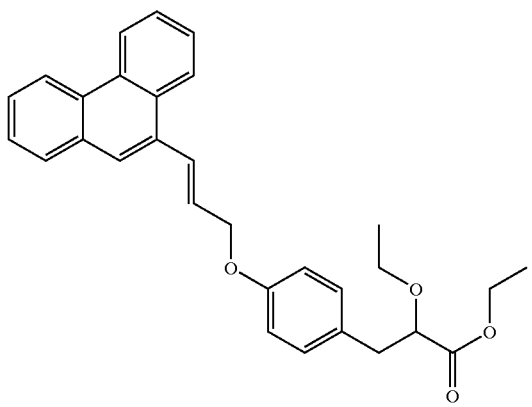

(E)-(S)-2-Ethoxy-3-[4-(3-phenanthren-9-yl-allyloxy)-phenyl]-propionic acid ethyl ester The title compound was prepared from phenanthrene-9-carboxaldehyde (4.1 g, 20.0 mmol) by a sequence analogous to that described in example 23.

$^1$H NMR (CDCl$_3$, 300 MHz) δ: 1.16 (t, 3H), 1.22 (t, 3H), 2.95 (d, 2H), 3.30–3.42 (m, 1H), 3.53–3.65 (m, 1H), 3.98 (t, 1H), 4.15 (q, 2H), 4.47 (d, 2H), 6.47 (dt, 1H), 6.74 (d, 2H), 7.08 (d, 2H), 7.38 (d, 1H), 7.53–7.70 (m, 4H), 7.82 (s, 1H), 7.85 (d, 1H), 8.15 (d, 1H), 8.65 (d, 1H), 8.72 (d, 1H).

Example 48

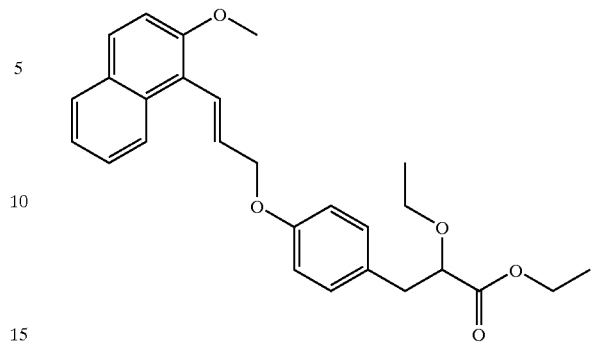

(E)-(S)-2-Ethoxy-3-{4-[3-(2-methoxy-naphthalen-1-yl)-allyloxy]-phenyl}-propionic acid ethyl ester The title compound was prepared from 2-methoxy-1-naphthaldehyde (4.1 g, 22.1 mmol) by a sequence analogous to that described in example 23.

$^1$H NMR (CDCl$_3$, 300 MHz) δ: 1.16 (t, 3H), 1.22 (t, 3H), 2.97 (d, 2H), 3.30–3.42 (m, 1H), 3.55–3.65 (m, 1H), 3.93 (s, 3H), 3.97 (t, 1H), 4.15 (q, 2H), 4.85 (d, 2H), 6.48 (dt, 1H), 6.95 (d, 2H), 7.10–7.35 (m, 5H), 7.45 (dt, 1H), 7.75–7.78 (m, 2H), 8.12 (d, 1H).

Example 49

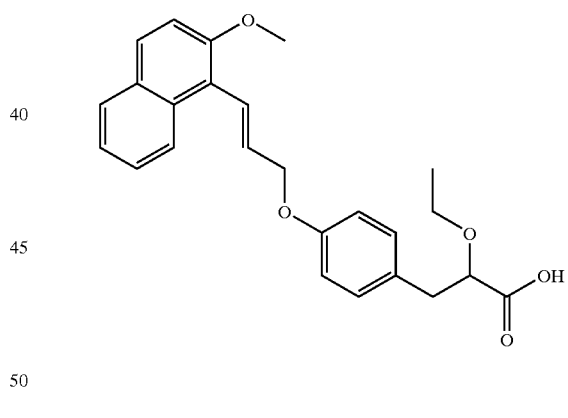

(E)-(S)-2-Ethoxy-3-{4-[3-(2-methoxy-naphthalen-1-yl)-allyloxy]-phenyl}-propionic acid The title compound was prepared from (E)-(S)-2-ethoxy-3-{4-[3-(2-methoxy-naphthalen-1-yl)-allyloxy]-phenyl}-propionic acid ethyl ester (example 48) (327 mg, 0.75 mmol) by a procedure analogous to that described in example 26.

$^1$H NMR (CDCl$_3$, 300 MHz) δ: 1.16 (t, 3H), 2.95 (dd, 1H), 3.08 (dd, 1H), 3.35–3.48 (m, 1H), 3.53–3.65 (m, 1H), 3.93 (s, 3H), 4.05 (dd, 1H), 4.82 (dd, 2H), 6.49 (dt, 1H), 6.95 (d, 2H), 7.13 (d, 1H), 7.20 (d, 2H), 7.23–7.35 (m, 2H), 7.44 (dt, 1H), 7.74 (d, 2H), 8.12 (d, 1H).

Example 50

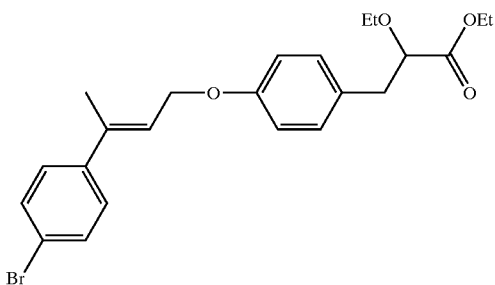

(E)-(S)-Ethyl 3-{4-[3-(4-Bromophenyl)-but-2-enyloxy]-phenyl}-2-ethoxy-propionate a)

Sodium (5.52 g, 0.24 mol) was added to ethanol (250 ml) at 20° C. and the mixture stirred until the metal had fully reacted. Triethyl phosphonoacetate (62.72 g, 0.28 mol) was added, the mixture stirred for 20 min, then a solution of 4-bromoacetophenone (39.81 g, 0.20 mol) in ethanol (250 ml) was added and the reaction mixture heated to 80° C. under reflux for 17 h. The solution was cooled, the ethanol evaporated and the resulting orange residue partitioned between 1N HCl (200 ml) and ethyl acetate (200 ml). The aqueous layer was collected and further extracted with ethyl acetate (2×200 ml). The organic layers were combined, washed with brine, dried (MgSO$_4$) and evaporated to an orange gum. This was purified by column chromatography on silica gel (3% diethyl ether in n-heptane eluent) to give the product, (E)-ethyl 3-(4-bromophenyl)-but-2-enoate, as a colourless oil; 44.08 g (82%)

$^1$H NMR (300 MHz, CDCl$_3$) δ: 1.31 (3H, t), 2.54 (3H, s), 4.21 (2H, q), 6.11 (1H, s), 7.34 (2H, dm), 7.48 (2H, dm). MS: 268/270 (M$^+$), 240/242, 239/241, 196/198, 116, 115 (100%). Microanalysis Calculated % C, 53.55; H, 4.87. Found % C, 53.86; H, 4.90.

b)

A 1M solution of DIBAL-H in toluene (42 ml, 42 mmol) was added dropwise, at −70° C. over 30 min, to a stirred solution of (E)-ethyl 3-(4-bromophenyl)-but-2-enoate (4.55 g, 16.92 mmol) in dry THF (100 ml), and the mixture stirred for 1 h. Methanol (5 ml) was carefully added, followed by 1N HCl (300 ml) and the resulting mixture extracted with ethyl acetate (3×200 ml). The combined organic extracts were washed with brine, dried (Na$_2$SO$_4$), and evaporated to give the crude product as an off-white solid, which was purified by recrystallisation from hot 1:4 ether/n-heptane (250 ml) to give the product (E)-3-(4-bromophenyl)-but-2-en-1-ol as colourless needles: 3.10 g (81%)

Mpt. 58–59.5° C. $^1$H NMR (300 MHz, CDCl$_3$) δ: 1.41 (1H, br s), 2.05 (3H, d), 4.36 (2H, d), 5.96 (1H, tq), 7.27 (2H, dm), 7.44 (2H, dm). MS: 226/228 (M$^+$), 211/213, 193/195, 183/185, 147 (100%), 132, 129, 115. Microanalysis Calculated % C, 52.89; H, 4.88; Br, 35.18. Found C, 53.24; H, 4.86; Br, 35.08.

c)

Azodicarboxylic dipiperidide (0.756 g, 3.0 mmol) was added at 0–5° C. to a stirred solution of tributylphosphine (0.74 ml, 0.61 g, 3.0 mmol), (S)-ethyl 2-ethoxy-3-(4-hydroxyphenyl)-propionate (0.500 g, 2.10 mmol) and (E)-3-(4-bromophenyl)-but-2-en-1-ol (0.454 g, 2.0 mmol) in dry benzene (20 ml), the mixture warmed to room temperature, and stirred for 2.5 days. The resulting mixture was diluted with water and ethyl acetate (50 ml each), the aqueous layer collected and further extracted with ethyl acetate (50 ml). The organic layers were combined, washed with brine, dried (MgSO$_4$) and evaporated. The crude product was then purified by column chromatography on silica gel (20% ethyl acetate in n-heptane eluent) to give (E)-(S)-ethyl 3-{4-[3-(4-bromophenyl)-but-2-enyloxy]-phenyl}-2-ethoxy-propionate as an oil; 0.780 g (87%).

$^1$H NMR (300 MHz, CDCl$_3$) δ: 1.17 (3H, t), 1.22 (3H, t), 2.10 (3H, s), 2.96 (2H, d), 3.30–3.45 (1H, m), 3.55–3.70 (1H, m), 3.98 (1H, t), 4.17 (2H, q), 4.70 (2H, d), 6.04 (1H, t), 6.86 (2H, m), 7.16 (2H, m), 7.29 (2H, m), 7.44 (2H, m).

Example 51

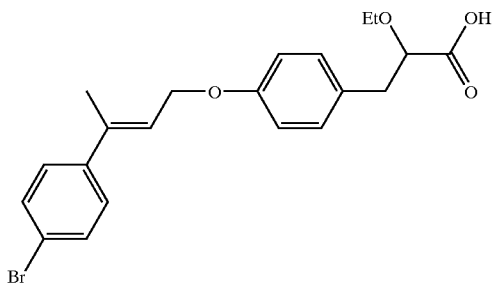

(E)-(S)-3-{4-[3-(4-Bromophenyl)-but-2-enyloxy]-phenyl}-2-ethoxy-propionic acid Sodium hydroxide (1M, 1.10 ml, 1.10 mmol) was added to a solution of (E)-(S)-ethyl 3-{4-[3-(4-bromophenyl)-but-2-enyloxy]-phenyl}-2-ethoxy-propionate (example 50) (0.245 g, 0.548 mmol) in ethanol (10 ml) and the mixture stirred at room temperature for 18 h. The resulting mixture was partitioned between water (50 ml) and ethyl acetate (50 ml) and the aqueous layer acidified to pH1 by addition of 1N HCl. The aqueous layer was separated and further extracted with ethyl acetate (2×50 ml). The combined organic layers were washed with brine, dried (MgSO$_4$), evaporated and vacuum dried at 40° C. for 18 h, to give (E)-(S)-3-{4-[3-(4-bromophenyl)-but-2-enyloxy]-phenyl}-2-ethoxy-propionic acid as a colourless gum which contained 0.1 molar equivalents of ethyl acetate; 0.22 g (96%).

$^1$H NMR (300 MHz, CDCl$_3$) δ: 1.18 (3H, t), 1.26 (ethyl acetate impurity, 0.3H, t), 2.04 (ethyl acetate impurity, 0.2H, s), 2.11 (3H, s), 2.96 (1H, dd), 3.08 (1H, dd), 3.40–3.55 (1H, m), 3.55–3–68 (1H, m), 4.06 (1H, dd), 4.15 (ethyl acetate impurity, 0.2H, q), 4.70 (2H, d), 6.04 (1H, t), 6.88 (2H, m), 7.17 (2H, m), 7.29 (2H, m), 7.44 (2H, m), carboxylic acid proton not observed. LCMS: 441/443 (M+Na), 209/211 (100%).

Example 52

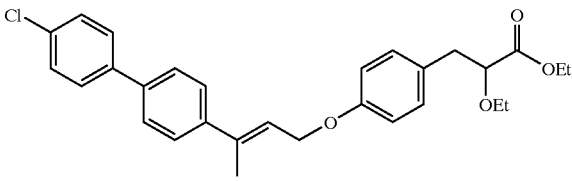

(E)-(S)-Ethyl 3-{4-[3-(4'-Chloro-biphenyl-4-yl)-but-2-enyloxy]-phenyl}-2-ethoxy-propionate a)

Tetrakis(triphenylphoshine)palladium(0) (0.26 g, 0.22 mmol, 4 mol %) was added, under nitrogen, to a stirred solution of (E)-ethyl 3-(4-bromophenyl)-but-2-enoate (1.5 g, 5.57 mmol) {prepared as detailed in example 50 a} in DME (70 ml), and the resulting orange coloured solution stirred at room temperature for 10 min. Aqueous 2M sodium carbonate (16.7 ml, 33.4 mmol) was then added, the mixture stirred for 10 min, then 4-chlorophenyl boronic acid (1.3 g, 8.36 mmol) was added, and the reaction mixture heated to 80° C. for 18 h, under reflux. The reaction mixture was diluted with 1N HCl (100 ml) and the products extracted into ethyl acetate (2×100 ml). The combined organic extracts were washed with brine, dried (MgSO$_4$), and evaporated to give the crude product, which was purified by column chromatography on silica gel (20% ethyl acetate in n-heptane eluent) to give the product, (E)-ethyl-3-(4'-chloro-biphenyl-4-yl)-but-2-enoate as a colourless solid; 1.17 g (70%).

$^1$H NMR (300 MHz, CDCl$_3$) δ: 1.33 (3H, t), 2.60 (3H, s), 4.23 (2H, q), 6.20 (1H, s), 7.41 (2H, m), 7.52 (2H, m). MS: 300/302 (100%, M$^+$), 271/273, 255/257, 228/230, 165.

b)

A 1M solution of DIBAL-H in toluene (10 ml, 10 mmol) was added dropwise, at −70° C. over 10 min, to a stirred solution of (E)-ethyl-3-(4'-chloro-biphenyl-4-yl)-but-2-enoate (1.0 g, 3.32 mmol) in dry THF (25 ml), and the mixture warmed to room temperature over 4 h. Methanol (1 ml) was carefully added, followed by 1N HCl (50 ml) and the resulting mixture extracted with ethyl acetate (2×50 ml). The combined organic extracts were washed with brine, dried (MgSO$_4$), and evaporated to give the product, (E)-3-(4'-chloro-biphenyl-4-yl)-but-2-en-1-ol as a colourless solid: 0.86 g (100%).

Mpt. 137–142° C. $^1$H NMR (300 MHz, CDCl$_3$) δ: 1.79 (1H, br s), 2.11 (3H, d), 4.40 (2H, d), 6.05 (1H, tq), 7.41 (2H, dm), 7.45–7.60 (6H, m).

c)

Azodicarboxylic dipiperidide (0.731 g, 2.9 mmol) was added at 0–5° C. to a stirred solution of tributylphosphine (0.71 ml, 0.58 g, 2.9 mmol), (S)-ethyl 2-ethoxy-3-(4-hydroxyphenyl)-propionate (0.483 g, 2.03 mmol) and (E)-3-(4'-chloro-biphenyl-4-yl)-but-2-en-1-ol (0.500 g, 1.93 mmol) in dry benzene (15 ml), the mixture warmed to room temperature, and stirred for 3 h. The resulting mixture was diluted with water and ethyl acetate (30 ml each), the aqueous layer collected and further extracted with ethyl acetate (30 ml). The organic layers were combined, washed with brine, dried (MgSO$_4$) and evaporated. The crude product was then purified by column chromatography on silica (20% ethyl acetate in n-heptane eluent) to give (E)-(S)-ethyl 3-{4-[3-(4'-chloro-biphenyl-4-yl)-but-2-enyloxy]-phenyl}-2-ethoxy-propionate as a gum; 0.69 g (75%).

$^1$H NMR (300 MHz, CDCl$_3$) δ: 1.17 (3H, t), 1.23 (3H, t), 2.16 (3H, s), 2.96 (2H, d), 3.30–3.45 (1H, m), 3.55–3.68 (1H, m), 3.98 (1H, t), 4.17 (2H, q), 4.74 (2H, d), 6.12 (1H, t), 6.88 (2H, m), 7.18 (2H, m), 7.40 (2H, m), 7.45–7.60 (6H, m).

Example 53

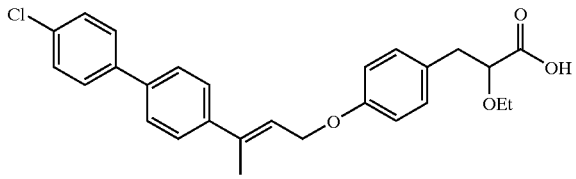

(E)-(S)-3-{4-[3-(4'-Chloro-biphenyl-4-yl)-but-2-enyloxy]-phenyl}-2-ethoxy-propionic acid Sodium hydroxide (1M, 2.3 ml, 2.3 mmol) was added to a solution of (E)-(S)-ethyl 3-{4-[3-(4'-chloro-biphenyl-4-yl)-but-2-enyloxy]-phenyl}-2-ethoxy-propionate (example 52) (0.600 g, 1.25 mmol) in ethanol (10 ml) and the mixture stirred at room temperature for 18 h, then heated to 80° C. for 2 h. The resulting mixture was partitioned between water (50 ml) and ethyl acetate (50 ml) and the aqueous layer acidified to pH1 by addition of 1N HCl. The aqueous layer was separated and further extracted with ethyl acetate (2×50 ml). The combined organic layers were washed with brine, dried (MgSO$_4$), evaporated, and the product and vacuum dried at 40° C. for 72 h, to give (E)-(S)-3-{4-[3-(4'-chloro-biphenyl-4-yl)-but-2-enyloxy]-phenyl}-2-ethoxy-propionic acid as a colourless solid; 0.53 g (94%).

$^1$H NMR (300 MHz, CDCl$_3$) δ: 1.18 (3H, t), 2.16 (3H, s), 2.97 (1H, dd), 3.08 (1H, dd), 3.40–3.53 (1H, m), 3.55–3–68 (1H, m), 4.07 (1H, dd), 4.74 (2H, d), 6.11 (1H, t), 6.90 (2H, m), 7.17 (2H, m), 7.39 (2H, m), 7.45–7.60 (6H, m), carboxylic acid proton not observed.

Example 54

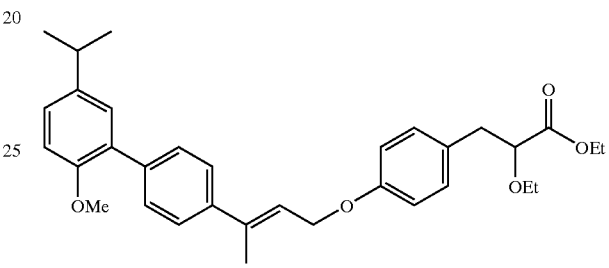

(E)-(S)-Ethyl 2-Ethoxy-3-{4-[3-(5'-isopropyl-2'-methoxy-biphenyl-4-yl)-but-2-enyloxy]-phenyl}-propionate a)

Tetrakis(triphenylphoshine)palladium(0) (0.20 g, 0.18 mmol, 4 mol %) was added, under nitrogen, to a stirred solution of (E)-3-(4-bromophenyl)-but-2-en-1-ol (1.0 g, 4.40 mmol) {prepared as detailed in example 50 b} in DME (55 ml), and the resulting orange coloured solution stirred at room temperature for 10 min. Aqueous 2M sodium carbonate (13.2 ml, 26.4 mmol) was then added, the mixture stirred for 10 min, then 5-isopropyl-2-methoxyphenylboronic acid (1.28 g, 6.60 mmol) was added, and the reaction mixture heated to 80° C. for 18 h, under reflux. The reaction mixture was diluted with 1N HCl (100 ml) and the products extracted into ethyl acetate (2×100 ml). The combined organic extracts were washed with brine, dried (MgSO$_4$), and evaporated to give the crude product, which was purified by column chromatography on silica gel (1% methanol in dichloromethane eluent) to give the product, 3-(5'-isopropyl-2'-methoxy-biphenyl-4-yl)-but-2-en-1-ol as a colourless oil; 1.15 g (88%).

$^1$H NMR (300 MHz, CDCl$_3$) δ: 1.26 (6H, d), 1.33 (1H, br t), 2.12 (3H, s), 2.91 (1H, septet), 3.80 (3H, s), 4.39 (2H, br t), 6.04 (1H, 7), 6.92 (1H, d), 7.15–7.20 (2H, m), 7.42–7.55 (4H, m). MS: 296 (100%, M$^+$), 281, 263, 253.

b)

Azodicarboxylic dipiperidide (0.756 g, 3.0 mmol) was added at 0–5° C. to a stirred solution of tributylphosphine (0.74 ml, 0.61 g, 3.0 mmol), (S)-ethyl 2-ethoxy-3-(4-hydroxyphenyl)-propionate (0.50 g, 2.10 mmol) and 3-(5'-isopropyl-2'-methoxy-biphenyl-4-yl)-but-2-en-1-ol (0.593 g, 2.0 mmol) in dry benzene (15 ml), the mixture warmed to room temperature, and stirred for 4 h. The resulting mixture was diluted with water (100 ml) and ethyl acetate (50 ml), the aqueous layer collected and further extracted with ethyl acetate (50 ml). The organic layers were combined, washed with brine, dried (MgSO₄) and evaporated. The crude product was then purified by column chromatography on silica (10% ethyl acetate in n-heptane eluent) to give (E)-(S)-ethyl 2-ethoxy-3-{4-[3-(5'-isopropyl-2'-methoxy-biphenyl-4-yl)-but-2-enyloxy]-phenyl}-propionate as a colourless oil; 0.67 g (65%).

¹H NMR (300 MHz, CDCl₃) δ: 1.17 (3H, t), 1.22 (3H, t), 1.26 (6H, d), 2.16 (3H, s), 2.91 (1H, septet), 2.96 (2H, d), 3.30–3.45 (1H, m), 3.54–3.66 (1H, m), 3.79 (3H, s), 3.98 (1H, t), 4.17 (2H, q), 4.74 (2H, d), 6.10 (1H, t), 6.84–6.95 (3H, m), 7.12–7.20 (4H, m), 7.42–7.57 (4H, m).

Example 55

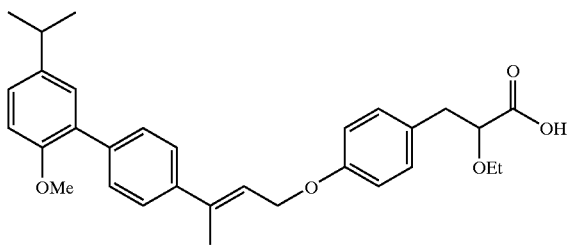

(E)-(S)-2-Ethoxy-3-{4-[3-(5'-isopropyl-2'-methoxy-biphenyl-4-yl)-but-2-enyloxy]-phenyl}-propionic acid The title compound was prepared from (E)-(S)-ethyl 2-ethoxy-3-{4-[3-(5'-isopropyl-2'-methoxy-biphenyl-4-yl)-but-2-enyloxy]-phenyl}-propionate (example 54) (0.50 g, 0.968 mmol) and sodium hydroxide (1M, 1.93 ml, 1.93 mmol) by a procedure analogous to that described in example 51, yielding (E)-(S)-2-ethoxy-3-{4-[3-(5'-isopropyl-2'-methoxy-biphenyl-4-yl)-but-2-enyloxy]-phenyl}-propionic acid as a colourless gum, which contained 0.44 mol equivalents of ethyl acetate; 0.48 g (94%).

¹H NMR (300 MHz, CDCl₃) δ: 1.18 (3H, t), 1.26 (6H, d), 1.26 (ethyl acetate impurity, 1.32H, t), 2.04 (ethyl acetate impurity, 0.88H, s), 2.16 (3H, s), 2.82–3.02 (2H, m), 3.08 (1H, dd), 3.40–3.52 (1H, m), 3.52–3.68 (1H, m), 3.79 (3H, s), 4.06 (1H, dd), 4.15 (ethyl acetate impurity, 0.88H, q), 4.75 (2H, d), 6.09 (1H, t), 6.88–6.95 (3H, m), 7.12–7.20 (4H, m), 7.42–7.57 (4H, m), carboxylic acid proton not observed.

Example 56

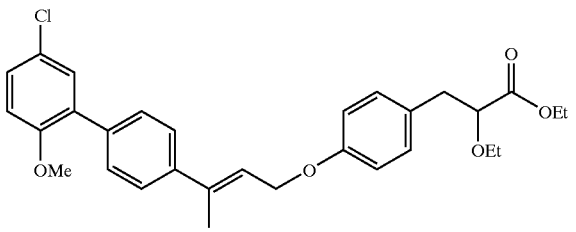

(E)-(S)-Ethyl 2-Ethoxy-3-{4-[3-(5'-chloro-2'-methoxy-biphenyl-4-yl)-but-2-enyloxy]-phenyl}-propionate a)

(E)-Ethyl 3-(5'-chloro-2'-methoxy-biphenyl-4-yl)-but-2-enoate (1.07 g, 91% yield) was prepared from 5-chloro-2-methoxyphenylboronic acid (1.0 g, 5.36 mmol) and (E)-ethyl 3-(4-bromophenyl)-but-2-enoate (0.96 g, 3.57 mmol) by a procedure analogous to that described in example 52 a.

¹H NMR (300 MHz, CDCl₃) δ: 1.33 (3H, t), 2.60 (3H, s), 3.81 (3H, s), 4.23 (2H, q), 6.20 (1H, s), 6.91 (1H, d), 7.25–7.33 (2H, m), 7.47–7.57 (4H, m). MS: 330/332 (100%, M⁺).

b)

(E)-Ethyl 3-(5'-chloro-2'-methoxy-biphenyl-4-yl)-but-2-enoate (0.90 g, 2.72 mmol) was reduced with DIBAL-H by a procedure analogous to that described in example 52 b to give (E)-3-(5'-chloro-2'-methoxy-biphenyl-4-yl)-but-2-en-1-ol as a colourless oil; 0.785 g (100%).

¹H NMR (300 MHz, CDCl₃) δ: 1.49 (1H, br s), 2.11 (3H, s), 3.80 (3H, s), 4.39 (2H, d), 6.04 (1H, t), 6.90 (1H, d), 7.22–7.32 (2H, m), 7.47–7.57 (4H, m). MS: 288/290 (100%, M⁺), 270/272, 2551257, 245/247.

c)

The title compound (0.54 g, 61% yield) was prepared from (E)-3-(5'-chloro-2'-methoxy-biphenyl-4-yl)-but-2-en-1-ol (0.50 g, 1.73 mmol) and (S)-ethyl 2-ethoxy-3-(4-hydroxyphenyl)-propionate (0.433 g, 1.82 mmol) by a procedure analogous to that described in example 52 c.

¹H NMR (300 MHz, CDCl₃) δ: 1.17 (3H, t), 1.23 (3H, t), 2.16 (3H, s), 2.96 (2H, d), 3.30–3.43 (1H, m), 3.55–3.65 (1H, m), 3.79 (3H, s), 3.98 (1H, t), 4.17 (2H, q), 4.74 (2H, d), 6.10 (1H, t), 6.84–6.92 (3H, m), 7.12–7.20 (2H, m), 7.22–7.32 (2H, m), 7.45–7.50 (4H, m). LCMS: 331/333 (M+Na).

Example 57

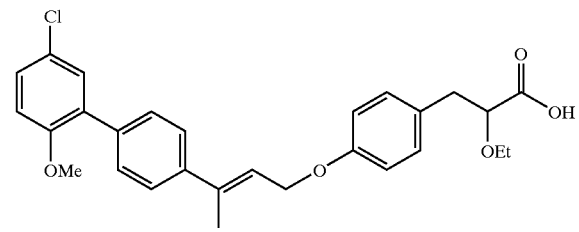

(E)-(S)-3-{4-[3-(5'-Chloro-2'-methoxy-biphenyl-4-yl)-but-2-enyloxy]-phenyl}-2-ethoxy-propionic acid The title compound was prepared from (E)-(S)-ethyl 2-ethoxy-3-{4-[3-(5'-chloro-2'-methoxy-biphenyl-4-yl)-but-2-enyloxy]-phenyl}-propionate (example 56) (0.47 g, 0.92 mmol) and sodium hydroxide (1M, 1.8 ml, 1.8 mmol) by a procedure analogous to that described in example 51, yielding (E)-(S)-3-{4-[3-(5'-chloro-2'-methoxy-biphenyl-4-yl)-but-2-enyloxy]-phenyl}-2-ethoxy-propionic acid as a colourless gum, which contained 0.2 mol equivalents of ethyl acetate; 0.43 g (98%).

¹H NMR (300 MHz, CDCl₃) δ: 1.19 (3H, t), 1.26 (ethyl acetate impurity, 0.6H, t), 2.04 (ethyl acetate impurity, 0.4H, s), 2.16 (3H, s), 2.96 (1H, dd), 3.10 (1H, dd), 3.42–3.52 (1H, m), 3.53–3.68 (1H, m), 3.80 (3H, s), 4.07 (1H, dd), 4.12 (ethyl acetate impurity, 0.4H), 4.74 (2H, d), 6.10 (1H, t), 6.85–6.95 (3H, m), 7.12–7.20 (2H, m), 7.21–7.32 (2H, m), 7.45–7.50 (4H, m), carboxylic acid proton not observed. LCMS: 503/505 (M+Na).

Example 58

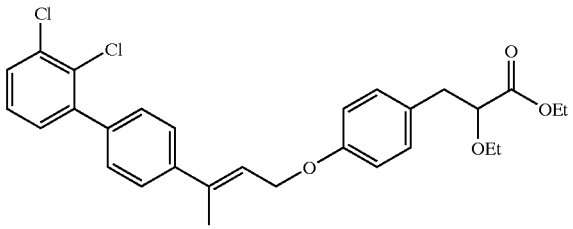

(E)-(S)-Ethyl 3-{4-[3-(2',3'-Dichloro-biphenyl-4-yl)-but-2-enyloxy]-phenyl}-2-ethoxy-propionate a)

(E)-Ethyl 3-(2',3'-Dichloro-biphenyl-4-yl)-but-2-enoate (1.07 g, 73% yield) was prepared from 2,3-dichlorophenylboronic acid (1.26 g, 6.60 mmol) and (E)-ethyl 3-(4-bromophenyl)-but-2-enoate (1.0 g, 4.40 mmol) by a procedure analogous to that described in example 52 a.

Mpt. 64–66° C. ¹H NMR (300 MHz, CDCl₃) δ: 1.33 (3H, t), 2.62 (3H, d), 4.23 (2H, q), 6.21 (1H, m), 7.20–7.30 (2H, m), 7.40–7.50 (3H, m), 7.50–7.60 (2H, m). MS: 334/336/338 (100%, M⁺), 305/307/309, 289/291/293, 262/264/266, 189/191.

b)

(E)-Ethyl 3-(2',3'-dichloro-biphenyl-4-yl)-but-2-enoate (1.07 g, 3.19 mmol) was reduced with DIBAL-H by a procedure analogous to that described in example 52 b to give (E)-3-(2',3'-dichloro-biphenyl-4-yl)-but-2-en-1-ol as a colourless solid; 0.74 g (79%).

Mpt. 95–100° C. ¹H NMR (300 MHz, CDCl₃) δ: 1.45 (1H, br s), 2.13 (3H, s), 4.40 (2H, d), 6.07 (1H, t), 7.20–7.28 (2H, m), 7.35–7.42 (2H, m), 7.42–7.53 (3H, m).

c)

The title compound (0.41 g, 80% yield) was prepared from (E)-3-(2',3'-dichloro-biphenyl-4-yl)-but-2-en-1-ol (0.293 g, 1.0 mmol) and (S)-ethyl 2-ethoxy-3-(4-hydroxyphenyl)-propionate (0.25 g, 1.05 mmol) by a procedure analogous to that described in example 52 c.

¹H NMR (300 MHz, CDCl₃) δ: 1.17 (3H, t), 1.23 (3H, t), 2.18 (3H, s), 2.96 (2H, d), 3.30–3.43 (1H, m), 3.55–3.65 (1H, m), 3.98 (1H, t), 4.17 (2H, q), 4.75 (2H, d), 6.13 (1H, t), 6.84–6.92 (2H, m), 7.12–7.20 (2H, m), 7.21–7.32 (2H, m), 7.35–7.42 (2H, m), 7.43–7.53 (3H, m).

Example 59

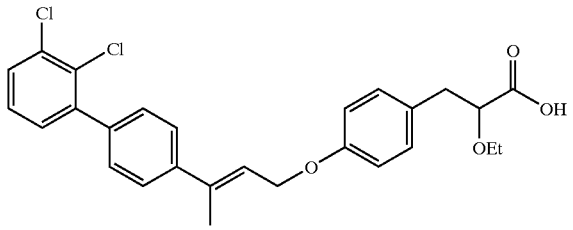

(E)-(S)-3-{4-[3-(2',3'-Dichloro-biphenyl-4-yl)-but-2-enyloxy]-phenyl}-2-ethoxy-propionic acid The title compound was prepared from (E)-(S)-ethyl 3-{4-[3-(2',3'-dichloro-biphenyl-4-yl)-but-2-enyloxy]-phenyl}-2-ethoxy-propionate (example 58) (0.325 g, 0.63 mmol) and sodium hydroxide (1M, 1.27 ml, 1.27 mmol) by a procedure analogous to that described in example 51, giving (E)-(S)-3-{4-[3-(2',3'-dichloro-biphenyl-4-yl)-but-2-enyloxy]-phenyl}-2-ethoxy-propionic acid as a gum, which contained 0.28 mol equivalents of ethyl acetate; 0.24 g (80%).

¹H NMR (300 MHz, CDCl₃) δ: 1.19 (3H, t), 1.26 (ethyl acetate impurity, 0.84H, t), 2.05 (ethyl acetate impurity, 0.56H, s), 2.18 (3H, m), 2.98 (1H, dd), 3.08 (1H, dd), 3.42–3.52 (1H, m), 3.53–3.68 (1H, m), 3.80 (3H, s), 4.07 (1H, dd), 4.12 (ethyl acetate impurity, 0.56H), 4.75 (2H, d), 6.13 (1H, tm), 6.85–6.95 (2H, m), 7.14–7.20 (2H, m), 7.21–7.30 (2H, m), 7.35–7.42 (2H, m), 7.42–7.53 (3H, m), carboxylic acid proton not observed.

Example 60

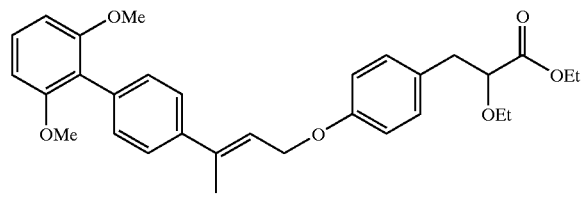

(E)-(S)-Ethyl 3-{4-[3-(2',6'-Dimethoxy-biphenyl-4-yl)-but-2-enyloxy]-phenyl}-2-ethoxy-propionate a)

(E)-Ethyl 3-(2',6'-dimethoxy-biphenyl-4-yl)-but-2-enoate (1.02 g, 73% yield) was prepared from 2,6-dimethoxyphenylboronic acid (1.20 g, 6.60 mmol) and (E)-ethyl 3-(4-bromophenyl)-but-2-enoate (1.0 g, 4.40 mmol) by a procedure analogous to that described in example 52 a.

Mpt. 120–123.5° C. ¹H NMR (300 MHz, CDCl₃) δ: 1.32 (3H, t), 2.62 (3H, d), 3.75 (6H, s), 4.23 (2H, q), 6.22 (1H, m), 6.67 (2H, d), 7.29 (1H, t), 7.38 (2H, dm), 7.53 (2H, dm). MS: 326 (100%, M⁺), 297, 281.

b)

(E)-Ethyl 3-(2',6'-dimethoxy-biphenyl-4-yl)-but-2-enoate (0.90 g, 2.76 mmol) was reduced with DIBAL-H by a procedure analogous to that described in example 52 b to give (E)-3-(2',6'-dimethoxy-biphenyl-4-yl)-but-2-en-1-ol as a colourless solid; 0.82 g (100%).

Mpt. 70–75° C. ¹H NMR (300 MHz, CDCl₃) δ: 1.44 (1H, br s), 2.12 (3H, d), 3.74 (6H, s), 4.38 (2H, d), 6.06 (1H, tm), 6.66 (2H, d), 7.13–7.37 (3H, m), 7.42–7.50 (2H, m). MS: 284 (100%, M⁺), 266, 251, 241.

c)

The title compound (0.41 g, 80% yield) was prepared from (E)-3-(2',6'-dimethoxy-biphenyl-4-yl)-but-2-en-1-ol (0.50 g, 1.76 mmol) and (S)-ethyl 2-ethoxy-3-(4-hydroxyphenyl)-propionate (0.44 g, 1.85 mmol) by a procedure analogous to that described in example 52 c.

¹H NMR (300 MHz, CDCl₃) δ: 1.17 (3H, t), 1.22 (3H, t), 2.16 (3H, m), 2.96 (2H, d), 3.30–3.43 (1H, m), 3.53–3.65 (1H, m), 3.73 (6H, s), 3.97 (1H, t), 4.17 (2H, q), 4.75 (2H, d), 6.10 (1H, tm), 6.66 (2H, d), 6.84–6.90 (2H, m), 7.13–7.20 (2H, m), 7.27 (1H, t), 7.30–7.38 (2H, m), 7.45–7.52 (2H, m). LCMS: 527 (M+Na), 267 (100%).

Example 61

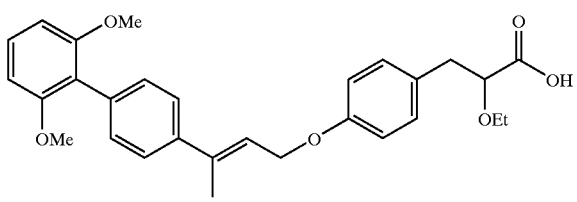

(E)-(S)-3-{4-[3-(2',6'-Dimethoxy-biphenyl-4-yl)-but-2-enyloxy]-phenyl}-2-ethoxy-propionic acid The title compound was prepared from (E)-(S)-ethyl 3-{4-[3-(2',6'-dimethoxy-biphenyl-4-yl)-but-2-enyloxy]-phenyl}-2-ethoxy-propionate (example 60) (0.565 g, 1.12 mmol) and sodium hydroxide (1M, 2.20 ml, 2.20 mmol) by a procedure analogous to that described in example 51; giving (E)-(S)-3-{4-[3-(2',6'-dimethoxy-biphenyl-4-yl)-but-2-enyloxy]-phenyl}-2-ethoxy-propionic acid as a gum; 0.49 g (92%).

$^1$H NMR (300 MHz, CDCl$_3$) δ: 1.18 (3H, t), 2.16 (3H, m), 2.98 (1H, dd), 3.08 (1H, dd), 3.42–3.52 (1H, m), 3.53–3.68 (1H, m), 3.73 (6H, s), 4.07 (1H, dd), 4.75 (2H, d), 6.10 (1H, tm), 6.66 (2H, d), 6.86–6.92 (2H, m), 7.13–7.20 (2H, m), 7.27 (1H, t), 7.28–7.35 (2H, m), 7.45–7.50 (2H, m), carboxylic acid proton not observed. LCMS: 499 (M$^+$), 267 (100%).

Example 62

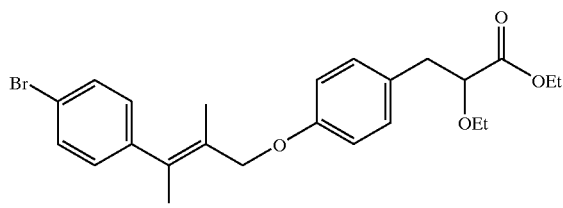

(E)-(S)-Ethyl 3-{4-[3-(4-Bromophenyl)-2-methyl-but-2-enyloxy]-phenyl}-2-ethoxy-propionate a)

Sodium (1.37 g, 59.6 mmol) was added to ethanol (50 ml) at 20° C. and the mixture stirred until the metal had fully reacted. Triethyl phosphonoacetate (17.78 g, 74.62 mmol) was added, the mixture stirred for 20 min, then a solution of 4-bromoacetophenone (9.90 g, 49.74 mmol) in ethanol (50 ml) was added and the reaction mixture heated to 80° C. under reflux for 17 h. The solution was cooled, the ethanol evaporated and the residue partitioned between 1N HCl (100 ml) and ethyl acetate (100 ml). The aqueous layer was collected and further extracted with ethyl acetate (2×200 ml). The organic layers were combined, washed with brine, dried (MgSO$_4$) and evaporated to an orange gum. This was purified by column chromatography on silica gel (2% diethyl ether in n-heptane eluent) to give the two double-bond isomer products as colourless oils.

(E)-Ethyl 3-(4-bromophenyl)-2-methyl-but-2-enoate; 5.38 g (38%).

$^1$H NMR (300 MHz, CDCl$_3$) δ: 1.34 (3H, t), 1.75 (3H, m), 2.22 (3H, m), 4.26 (2H, q), 7.04 (2H, dm), 7.49 (2H, dm). MS: 282/284 (M$^+$), 253/255, 237/239, 208/210, 175, 157, 130, 129 (100%), 115.

And (Z)-Ethyl 3-(4-bromophenyl)-2-methyl-but-2-enoate; 3.15 g (22%).

$^1$H NMR (300 MHz, CDCl$_3$) δ: 0.90 (3H, t), 2.01 (3H, s), 2.06 (3H, s), 3.88 (2H, q), 7.00 (2H, dm), 7.41 (2H, dm). MS: 282/284 (M$^+$), 253/255, 237/239, 208/210, 157, 130, 129 (100%), 115.

b)

(E)-Ethyl 3-(4-bromophenyl)-2-methyl-but-2-enoate (2.83 g, 9.99 mmol) was reduced with DIBAL-H by a procedure analogous to that described in example 52b to give (E)-3-(4-bromophenyl)-2-methyl-but-2-en-1-ol as a colourless oil; 1.82 g (75%).

$^1$H NMR (300 MHz, CDCl$_3$) δ: 1.60 (1H, br s), 1.66 (3H, m), 2.00 (3H, m), 4.29 (2H, s), 7.01 (2H, dm), 7.44 (2H, dm). MS: 240/242 (M$^+$), 225/227,183/185 (100%), 161,146, 143,128, 115.

c)

The title compound (0.83 g, 87% yield) was prepared from (E)-3-(4-bromophenyl)-2-methyl-but-2-en-1-ol (0.50 g, 2.07 mmol) and (S)-ethyl 2-ethoxy-3-(4-hydroxyphenyl)-propionate (0.519 g, 2.18 mmol) by a procedure analogous to that described in example 52c.

$^1$H NMR (300 MHz, CDCl$_3$) δ: 1.18 (3H, t), 1.23 (3H, t), 1.68 (3H, m), 2.04 (3H, m), 2.97 (2H, d), 3.30–3.43 (1H, m), 3.53–3.68 (1H, m), 3.98 (1H, t), 4.18 (2H, q), 4.61 (2H, s), 6.88 (2H, dm), 7.04 (2H, dm), 7.17 (2H, dm), 7.45 (2H, dm).

Example 63

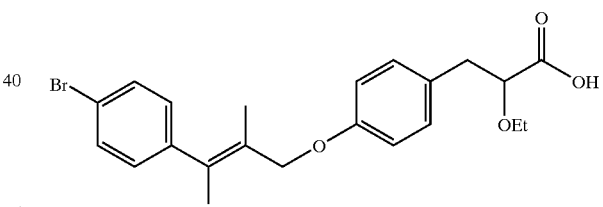

(E)-(S)-3-{4-[3-(4-Bromophenyl)-2-methyl-but-2-enyloxy]-phenyl}-2-ethoxy-propionic acid The title compound was prepared from (E)-(S)-ethyl 3-{4-[3-(4-bromophenyl)-2-methyl-but-2-enyloxy]-phenyl}-2-ethoxy-propionate (example 62) (0.710 g, 1.54 mmol) and sodium hydroxide (1M, 3.10 ml, 3.10 mmol) by a procedure analogous to that described in example 51; giving (E)-(S)-3-{4-[3-(4-bromophenyl)-2-methyl-but-2-enyloxy]-phenyl}-2-ethoxy-propionic acid as a colourless solid, which contained approximately 13 mol % of ethyl acetate impurity; 0.67 g (98%).

$^1$H NMR (300 MHz, CDCl$_3$) δ: 1.19 (3H, t), 1.68 (3H, m), 2.04 (3H, m), 2.98 (1 H, dd), 3.08 (1H, dd), 3.42–3.54 (1H, m), 3.54–3.68 (1H, m), 4.07 (1H, dd), 4.61 (2H, s), 6.90 (2H, dm), 7.04 (2H, dm), 7.17 (2H, dm), 7.45 (2H, dm), carboxylic acid proton not observed.

Example 64

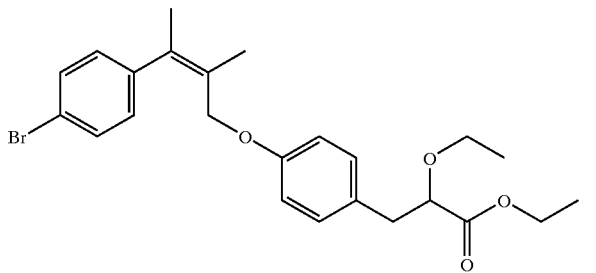

(Z)-(S)-Ethyl 3-{4-[3-(4-Bromophenyl)-2-methyl-but-2-enyloxy]-phenyl}-2-ethoxy-propionate a)
(Z)-Ethyl 3-(4-bromophenyl)-2-methyl-but-2-enoate (1.42 g, 5.01 mmol), which was prepared as described in example 62 a, was reduced with DIBAL-H by a procedure analogous to that described in example 52 b to give (Z)-3-(4-bromophenyl)-2-methyl-but-2-en-1-ol as a colourless oil; 1.19 g (98%).

$^1$H NMR (300 MHz, CDCl$_3$) δ: 1.38 (1H, br s), 1.89 (3H, s), 1.97 (3H, s), 3.92 (2H, s), 7.01 (2H, dm), 7.42 (2H, dm). MS: 240/242 (M$^+$), 225/227, 183/185 (100%), 161, 146, 143, 128, 115.

c)
The title compound (0.91 g, 95% yield) was prepared from (Z)-3-(4-bromophenyl)-2-methyl-but-2-en-1-ol (0.50 g, 2.07 mmol) and (S)-ethyl 2-ethoxy-3-(4-hydroxyphenyl)-propionate (0.519 g, 2.18 mmol) by a procedure analogous to that described in example 52 c.

$^1$H NMR (300 MHz, CDCl$_3$) δ: 1.16 (3H, t), 1.21 (3H, t), 1.93 (3H, s), 2.02 (3H, s), 2.93 (2H, d), 3.28–3.42 (1H, m), 3.53–3.68 (1H, m), 3.95 (1H, t), 4.16 (2H, q), 4.25 (2H, s), 6.69 (2H, dm), 7.04 (2H, dm), 7.09 (2H, dm), 7.41 (2H, dm).

Example 65

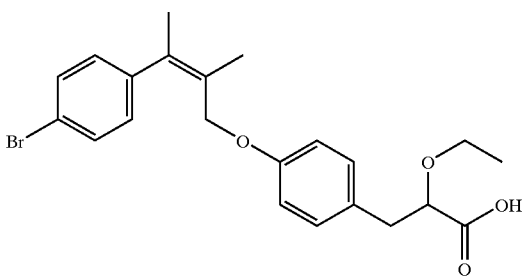

(Z)-(S)-3-{4-[3-(4-Bromophenyl)-2-methyl-but-2-enyloxy]-phenyl}-2-ethoxy-propionic acid The title compound was prepared from (Z)-(S)-ethyl 3-{4-[3-(4-bromophenyl)-2-methyl-but-2-enyloxy]-phenyl}-2-ethoxy-propionate (example 64) (0.82 g, 1.78 mmol) and sodium hydroxide (1M, 3.60 ml, 3.60 mmol) by a procedure analogous to that described in example 51; giving (Z)-(S)-3-{4-[3-(4-bromophenyl)-2-methyl-but-2-enyloxy]-phenyl}-2-ethoxy-propionic acid as a colourless solid, which contained approximately 15 mol % of ethyl acetate impurity; 0.766 g (100%).

$^1$H NMR (300 MHz, CDCl$_3$) δ: 1.17 (3H, t), 1.93 (3H, s), 2.02 (3H, s), 2.93 (1H, dd), 3.04 (1H, dd), 3.40–3.52 (1H, m), 3.52–3.65 (1H, m), 4.03 (1H, dd), 4.26 (2H, s), 6.71 (2H, dm), 7.04 (2H, dm), 7.09 (2H, dm), 7.41 (2H, dm), carboxylic acid proton not observed.

Example 66

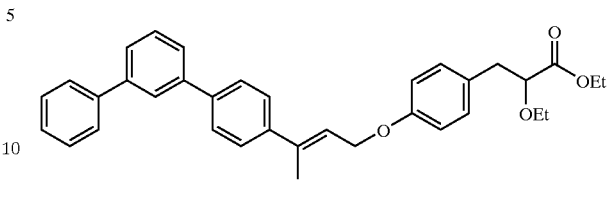

(E)-(S)-Ethyl 2-Ethoxy-3-[4-(3-[1,1';3',1"]terphenyl-4"-yl-but-2-enyloxy)-phenyl]-propionate a)
(E)-Ethyl 3-[1,1';3',1"]terphenyl-4"-yl-but-2-enoate (1.02 g, 68% yield) was prepared from 3-biphenylboronic acid (1.31 g, 6.60 mmol) and (E)-ethyl 3-(4-bromophenyl)-but-2-enoate (1.0 g, 4.40 mmol) by a procedure analogous to that described in example 52 a.

$^1$H NMR (300 MHz, CDCl$_3$) δ: 1.33 (3H, t), 2.62 (3H, d), 4.23 (2H, q), 6.21 (1H, s), 7.30–7.70 (12H, m), 7.82 (1H, m). LCMS: 343 (100%, M$^+$), 297.

b)
(E)-Ethyl 3-[1,1';3',1"]terphenyl-4"-yl-but-2-enoate (0.95 g, 2.77 mmol) was reduced with DIBAL-H by a procedure analogous to that described in example 52 b to give (E)-3-[1,1';3',1"]terphenyl-4"-yl-but-2-en-1-ol as a colourless solid; 0.81 g (97%).

$^1$H NMR (300 MHz, CDCl$_3$) δ: 1.37 (1H, br s), 2.13 (3H, s), 4.40 (2H, d), 6.06 (1H, tm), 7.30–7.70 (12H, m), 7.81 (1H, m). LCMS: 283 (100%, M+H-H$_2$O). Microanalysis Calculated % C, 87.96; H, 6.71. Found % C, 87.85; H, 6.74.

c)
The title compound (0.41 g, 80% yield) was prepared from (E)-3-[1,1';3',1"]terphenyl-4"-yl-but-2-en-1-ol (0.30 g, 1.0 mmol) and (S)-ethyl 2-ethoxy-3-(4-hydroxyphenyl)-propionate (0.25 g, 1.05 mmol) by a procedure analogous to that described in example 52 c.

$^1$H NMR (300 MHz, CDCl$_3$) δ: 1.17 (3H, t), 1.22 (3H, t), 2.18 (3H, s), 2.96 (2H, d), 3.30–3.43 (1H, m), 3.55–3.68 (1H, m), 3.98 (1H, t), 4.17 (2H, q), 4.75 (2H, d), 6.13 (1H, t), 6.89 (2H, dm), 7.17 (2H, dm), 7.30–7.70 (12H, m), 7.81 (1H, m). Microanalysis Calculated % C, 80.74; H, 6.97. Found % C, 80.84; H, 7.28.

Example 67

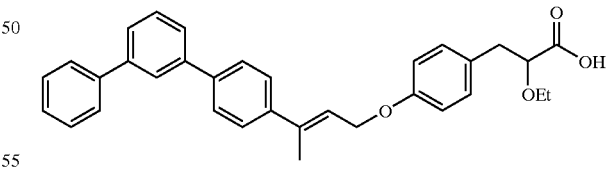

(E)-(S)-2-Ethoxy-3-[4-(3-[1,1';3',1"]terphenyl-4"-yl-but-2-enyloxy)-phenyl]-propionic acid The title compound was prepared from (E)-(S)-ethyl 2-ethoxy-3-[4-(3-[1,1';3',1"]terphenyl-4"-yl-but-2-enyloxy)-phenyl]-propionate (example 66) (0.185 g, 0.36 mmol) and sodium hydroxide (1M, 0.71 ml, 0.71 mmol) by a procedure analogous to that described in example 51; giving (E)-(S)-2-ethoxy-3-[4-(3-[1,1';3',1"]terphenyl-4"-yl-but-2-enyloxy)-phenyl]-propionic acid as a gum; 0.145 g (83%).

¹H NMR (300 MHz, CDCl₃) δ: 1.19 (3H, t), 2.18 (3H, m), 2.99 (1H, dd), 3.09 (1H, dd), 3.40–3.53 (1H, m), 3.53–3.68 (1H, m), 4.07 (1H, dd), 4.75 (2H, d), 6.13 (1H, tm), 6.90 (2H, dm), 7.17 (2H, dm), 7.30–7.70 (12H, m), 7.81 (1H, m), carboxylic acid proton not observed.

Example 68

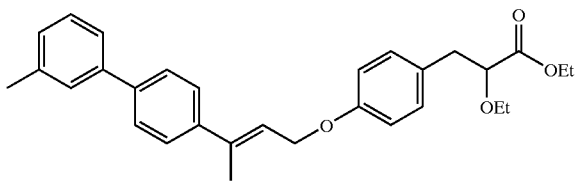

(E)-(S)-Ethyl 2-Ethoxy-3-{4-[3-(3'-methyl-biphenyl-4-yl)-but-2-enyloxy]-phenyl}-propionate a)
(E)-3-(3'-Methyl-biphenyl-4-yl)-but-2-enoate (0.795 g, 65% yield) was prepared from 3-tolylboronic acid (0.90 g, 6.60 mmol) and (E)-ethyl 3-(4-bromophenyl)-but-2-enoate (1.0 g, 4.40 mmol) by a procedure analogous to that described in example 52 a.

¹H NMR (300 MHz, CDCl₃) δ: 1.33 (3H, t), 2.43 (3H, s), 2.61 (3H, s), 4.23 (2H, q), 6.20 (1H, s), 7.18 (1H, dm), 7.34 (1H, tm), 7.41 (2H, dm), 7.52–7.63 (4H, m). LCMS: 281 (M+H), 235 (100%).

b)
(E)-3-(3'-Methyl-biphenyl-4-yl)-but-2-enoate (0.74 g, 2.64 mmol) was reduced with DIBAL-H by a procedure analogous to that described in example 52 b to give (E)-3-(3'-methyl-biphenyl-4-yl)-but-2-en-1-ol as a colourless solid; 0.63 g (85%).

¹H NMR (300 MHz, CDCl₃) δ: 1.36 (1 H, br s), 2.12 (3H, s), 2.42 (3H, s), 4.39 (2H, d), 6.05 (1H, tm), 7.16 (1H, dm), 7.33 (1H, tm), 7.40 (2H, dm), 7.48 (2H, dm), 7.56 (2H, dm). LCMS: 221 (100%, M+H-H₂O).

c)
The title compound (0.365 g, 78% yield) was prepared from (E)-3-(3'-methyl-biphenyl-4-yl)-but-2-en-1-ol (0.238 g, 1.0 mmol) and (S)-ethyl 2-ethoxy-3-(4-hydroxyphenyl)-propionate (0.25 g, 1.05 mmol) by a procedure analogous to that described in example 52 c.

¹H NMR (300 MHz, CDCl₃) δ: 1.17 (3H, t), 1.22 (3H, t), 2.17 (3H, s), 2.42 (3H, s), 2.96 (2H, d), 3.30–3.43 (1H, m), 3.55–3.68 (1H, m), 3.98 (1H, t), 4.17 (2H, q), 4.74 (2H, d), 6.11 (1H, t), 6.90 (2H, dm), 7.13–7.23 (3H, m), 7.33 (1H, t), 7.36–7.44 (2H, m), 7.45–7.60 (4H, m). Microanalysis Calculated % C, 78.57; H, 7.47. Found % C, 78.90; H, 7.70.

Example 69

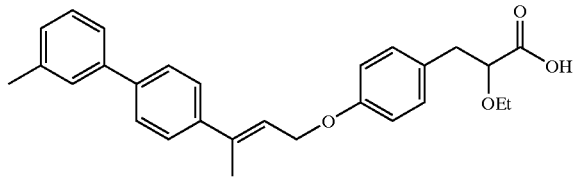

(E)-(S)-2-Ethoxy-3-{4-[3-(3'-methyl-biphenyl-4-yl)-but-2-enyloxy]-phenyl}-propionic acid The title compound was prepared from (E)-(S)-2-ethoxy-3-{4-[3-(3'-methyl-biphenyl-4-yl)-but-2-enyloxy]-phenyl}-propionate (example 68) (0.225 g, 0.49 mmol) and sodium hydroxide (1M, 0.98 ml, 0.98 mmol) by a procedure analogous to that described in example 51; giving (E)-(S)-ethoxy-3-{4-[3-(3'-methyl-biphenyl-4-yl)-but-2-enyloxy]-phenyl}-propionic acid as a gum; 0.20 g (95%).

¹H NMR (300 MHz, CDCl₃) δ: 1.18 (3H, t), 2.17 (3H, m), 2.42 (3H, s), 2.97 (1H, dd), 3.09 (1H, dd), 3.42–3.54 (1H, m), 3.55–3.68 (1H, m), 4.07 (1H, dd), 4.75 (2H, d), 6.11 (1H, tm), 6.90 (2H, dm), 7.10–7.23 (3H, m), 7.35 (1H, t), 7.37–7.44 (2H, m), 7.45–7.60 (4H, m), carboxylic acid proton not observed.

Example 70

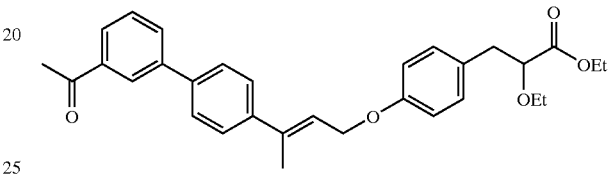

(E)-(S)-Ethyl 3-{4-[3-(3'-Acetyl-biphenyl-4-yl)-but-2-enyloxy]-phenyl}-2-ethoxy-propionate a)

3-Acetylphenylboronic acid (7.10 g, 43.3 mmol) was coupled with (E)-3-(4-bromophenyl)-but-2-en-1-ol (5.76 g, 25.0 mmol) by a procedure analogous to that described in example 54 a to give (E)-3-(3'-acetyl-biphenyl-4-yl)-but-2-en-1-ol as an off-white solid; 5.33 g (79%). This solid was recrystallised from aqueous ethanol to give a first crop of very pure (E)-3-(3'-acetyl-biphenyl-4-yl)-but-2-en-1-ol as colourless platelets; 2.78 g (41%) and a second crop of (E)-3-(3'-acetyl-biphenyl-4-yl)-but-2-en-1-ol as an amorphous off-white solid; 2.53 g (37%).

Mpt. 85–86° C. ¹H NMR (300 MHz, CDCl₃) δ: 1.46 (1H, br t), 2.13 (3H, d), 2.66 (3H, s), 4.41 (2H, br t), 6.07 (1H, tm), 7.50–7.62 (5H, m), 7.80 (1H, dm), 7.92 (1H, dm), 8.19 (1H, m). MS: 266 (M⁺), 251, (M-Me), 248 (M-H₂O), 223 (100%). Microanalysis Calculated % C, 81.17; H, 6.81. Found % C, 81.22; H, 6.83.

b)

The title compound (0.16 g, 65% yield) was prepared from (E)-3-(3'-acetyl-biphenyl-4-yl)-but-2-en-1-ol (0.133 g, 0.50 mmol) and (S)-ethyl 2-ethoxy-3-(4-hydroxyphenyl)-propionate (0.125 g, 0.525 mmol) by a procedure analogous to that described in example 52 c.

¹H NMR (300 MHz, CDCl₃) δ: 1.17 (3H, t), 1.23 (3H, t), 2.18 (3H, s), 2.66 (3H, s), 2.92 (2H, d), 3.30–3.43 (1H, m), 3.55–3.68 (1H, m), 3.98 (1H, t), 4.17 (2H, q), 4.75 (2H, d), 6.13 (1H, t), 6.89 (2H, dm), 7.17 (2H, dm), 7.50–7.64 (5H, m), 7.80 (1H, dm), 7.92 (1H, dm), 8.19 (1H, m).

Example 71

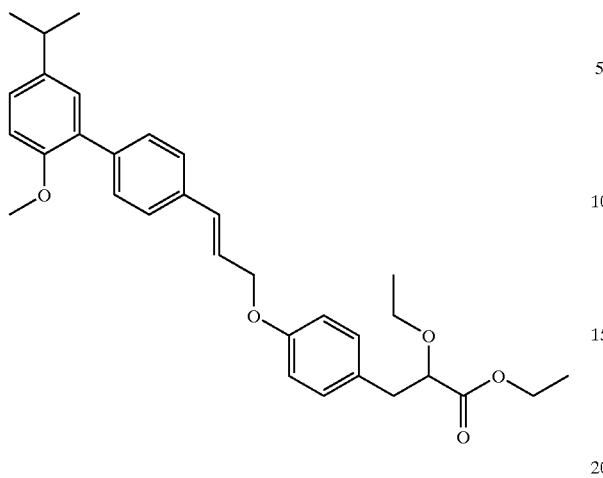

(E)-(S)-2-Ethoxy-3-{4-[3-(5'-isopropyl-2'-methoxy-biphenyl-4-yl)-allyloxy]-phenyl}-propionic acid ethyl ester a)

(E)-3-(4-Bromo-phenyl)-acrylic acid ethyl ester was prepared from 4-bromobenzaldehyde (20.0 g, 0.11 mol) by a procedure analogous to that described in example 23 a.

b)

(E)-3-(4-Bromo-phenyl)-acrylic acid ethyl ester (450 mg, 2.0 mmol) was reacted with 5-isopropyl-2-methoxy-benzene boronic acid (776 mg, 4.0 mmol) by a procedure described in example 52 a, to give (E)-3-(5'-Isopropyl-2'-methoxy-biphenyl-4-yl)-acrylic acid ethyl ester.

c)

(E)-3-(5'-Isopropyl-2'-methoxy-biphenyl-4-yl)-acrylic acid ethyl ester was reduced by DIBAL-H by a procedure analogous to that described in example 52 b to give (E)-3-(5'-isopropyl-2'-methoxy-biphenyl-4-yl)-prop-2-en-1-ol.

d)

The title compound was prepared from (E)-3-(5'-isopropyl-2'-methoxy-biphenyl-4-yl)-prop-2-en-1-ol by a procedure analogous to that described in 52 c.

$^1$H NMR (300 MHz, CDCl$_3$) δ: 1.13–1.30 (m, 12H), 2.85–3.0 (m, 3H), 3.30–3.42 (m, 1H), 3.53–3.67 (m, 1H), 2.78 (s, 3H), 3.98 (t, 1H), 4.15 (q, 2H), 4.70 (dd, 2H), 6.43 (dt, 1H), 6.75 (d, 1H), 6.85–6.95 (m, 3H), 7.15 (d, 4H), 7.44 (d, 2H), 7.52 (d, 2H).

Example 72

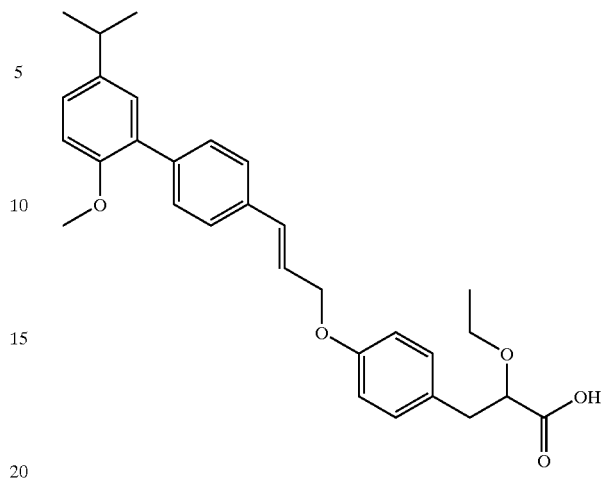

(E)-(S)-2-Ethoxy-3-{4-[3-(5'-isopropyl-2'-methoxy-biphenyl-4-yl)-allyloxy]-phenyl}-propionic acid The title compound was prepared from (E)-(S)-2-ethoxy-3-{4-[3-(5'-isopropyl-2'-methoxy-biphenyl-4-yl)-allyloxy]-phenyl}-propionic acid ethyl ester (example 71) (370 mg, 0.78 mmol) by a procedure analogous to that described in example 26.

$^1$H NMR (CDCl$_3$, 300 MHz) δ: 1.18 (t, 3H), 1.26 (d, 6H), 2.85–3.03 (m, 2H), 3.08 (dd, 1H), 3.35–3.48 (m, 1H), 3.55–3.68 (m, 1H), 3.75 (s, 3H), 4.03 (dd, 1H), 4.67 (d, 2H), 6.43 (dt, 1H), 6.75 (d, 1H), 6.87–6.95 (m, 3H), 7.13–7.23 (m, 4H), 7.43 (d, 2H), 7.53 (d, 2H).

Example 73

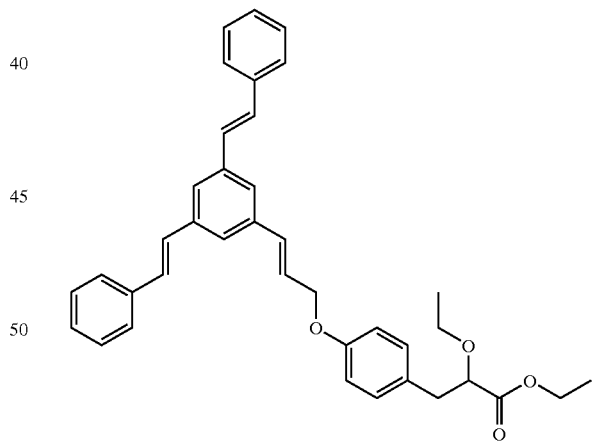

(E)-(S)-3-{4-[3-(3,5-Distyryl-phenyl)-allyloxy]-phenyl}-2-ethoxy-propionic acid ethyl ester a)

Bu$_4$NBr (2.0 g, 6.3 mmol), K$_2$CO$_3$ (7.8 g, 56.7 mmol), Pd(Oac)$_2$ (250 mg, 1.1 mmol) and styrene (20 mL, 175 mmol) were stirred for 5 min under nitrogen. To the mixture was added 3,5-dibromobenzaldehyde (5.0 g, 18.9 mmol) in dry DMF (5.0 mL), and the mixture was stirred at 65° C. for 16 h. The reaction mixture was diluted with ethyl acetate (20 mL) and the solution filtered. The filtrate was diluted with water and extracted with ethyl acetate (3×50 mL). The organic layers were combined, dried over MgSO$_4$, and concentrated under vacuum. To the residue was added a mixture of toluene/petroleum ether (1:1) (50 mL) and 3,5-distyryl-benzaldehyde (4.95 g, 85%) was isolated by filtration.

b)

The title compound was prepared from 3,5-distyryl-benzaldehyde (3.8 g, 10.0 mmol) by a sequence analogous to that described in example 23b–c.

$^1$H NMR (CDCl$_3$, 300 MHz) δ: 1.15 (t, 3H), 1.22 (t, 3H), 2.98 (d, 2H), 3.32–3.42 (m, 1H), 3.55–3.68 (m, 1H), 3.98 (t, 1H), 4.12 (t, 1H), 4.18 (q, 2H), 4.72 (dd, 2H), 6.50 (dt, 1H), 6.78 (d, 1H), 6.90 (d, 1H), 7.08–7.32 (m, 8H), 7.39 (t, 4H), 7.45 (s, 2H), 7.53 (d, 5H).

Example 74

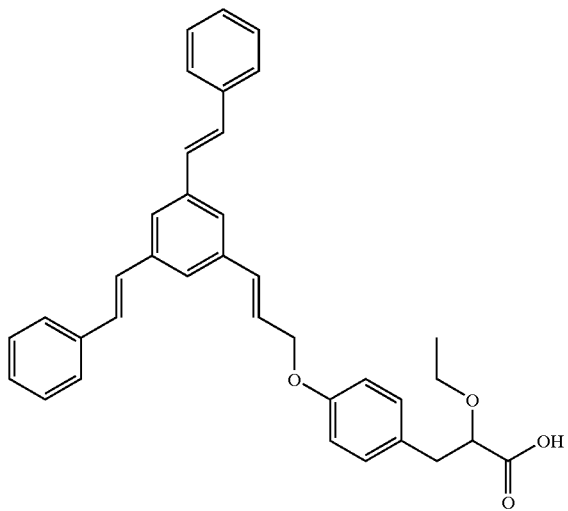

(E)-(S)-3-{4-[3-(3,5-Distyryl-phenyl)-allyloxy]-phenyl}-2-ethoxy-propionic acid (E)-(S)-3-{4-[3-(3,5-Distyryl-phenyl)-allyloxy]-phenyl}-2-ethoxy-propionic acid ethyl ester (example 73) (335 mg, 0.6 mmol) was dissolved in warm ethanol (20 mL) and sodium hydroxide (1N, 0.9 mL, 0.9 mmol) added. The mixture was stirred at room temperature for 16 h. The title compound as a sodium salt was isolated by filtration and washed with ethanol/water (10:1), yielding 190 mg (57%).

$^1$H NMR (CDCl$_3$, 300 MHz) δ: 0.98 (t, 3H), 2.63 (dd, 1H), 2.85 (dd, 1H), 3.05–3.15 (m, 1H), 3.50–3.64 (m, 2H), 4.75 (d, 2H), 6.68 (dt, 1H), 6.80 (d, 1H), 6.90 (d, 2H), 7.15 (d, 2H), 7.25–7.48 (m, 10H), 7.60–7.70 (m, 6H), 7.75 (s, 1H).

Example 75

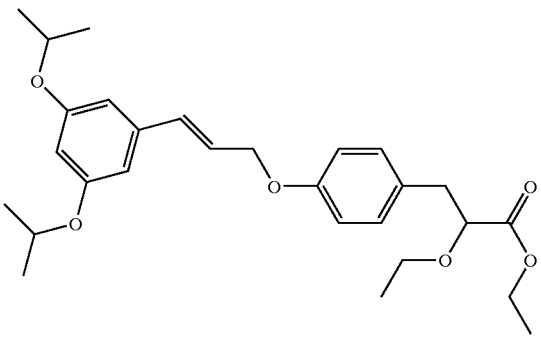

(E)-(S)-3-{4-[3-(3,5-Diisopropoxy-phenyl)-allyloxy]-phenyl}-2-ethoxy-propionic acid ethyl ester a)
To a solution of 3,5-dihydroxybenzaldehyde (3.0 g, 22.0 mmol) in DMF (17 mL) was added potassium carbonate (12.1 g, 87.0 mmol) and 2-bromopropane (28.5 g, 232 mmol). The reaction mixture was heated at 100° C. for 3 h. The mixture was filtered and washed with ethyl acetate. The filtrate was added water and the organic phase isolated. The aqueous phase was extracted once more with ethyl acetated. The combined organic phases were dried (MgSO$_4$), filtered and concentrated in vacuo. The residue was purified by flash chromatography eluting with toluene to give 3.8 g (79%) of 3,5-diisopropoxy-benzaldehyde as a yellow oil.

$^1$H NMR (CDCl$_3$, 300 MHz) δ: 1.35 (d, 12H), 4.60 (heptet, 2H), 6.68 (t, 1H), 6.97 (d, 2H).

b)
The title compound was prepared from 3,5-diisopropoxy-benzaldehyde by a sequence analogous to that described in example 23.

$^1$H NMR (CDCl$_3$, 300 MHz) δ: 1.15 (t, 3H), 1.22 (t, 3H), 1.32 (d, 12H), 2.96 (d, 2H), 3.32–3.42 (m, 1H), 3.55–3.65 (m, 1H), 3.98 (t, 1H), 4.16 (q, 2H), 4.53 (heptet, 2H), 4.65 (dd, 2H), 6.30–6.40 (m, 2H), 6.52 (d, 2H), 6.62 (d, 1H), 6.88 (d, 2H), 7.15 (d, 2H).

Example 76

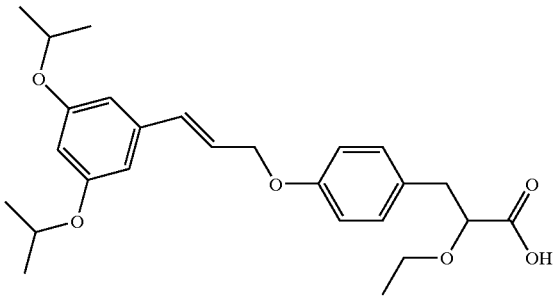

(E)-(S)-3-{4-[3-(3,5-Diisopropoxy-phenyl)-allyloxy]-phenyl}-2-ethoxy-propionic acid The title compound was prepared from (E)-(S)-3-{4-[3-(3,5-diisopropoxy-phenyl)-allyloxy]-phenyl}-2-ethoxy-propionic acid ethyl ester (example 75) (800 mg, 1.7 mmol) by a procedure analogous to that described in example 26.

$^1$H NMR (CDCl$_3$, 300 MHz) δ: 1.18 (t, 3H), 1.32 (d, 12H), 2.95 (dd, 1H), 3.10 (dd, 1H), 3.40–3.52 (m, 1H), 3.55–3.65 (m, 1H), 4.05 (dd, 1H), 4.53 (heptet, 2H), 6.30–6.40 (m, 2H), 6.52 (d, 2H), 6.62 (d, 1H), 6.88 (d, 2H), 7.15 (d, 2H).

Example 77

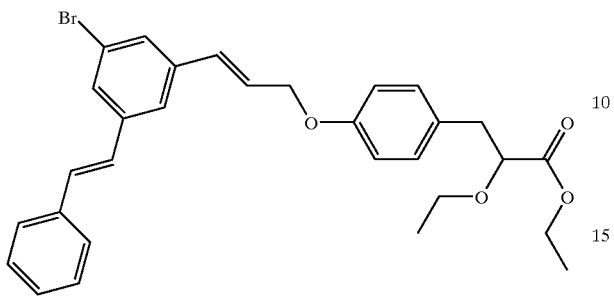

(S)-3-{4-[3-(3-Bromo-5-styryl-phenyl)-allyloxy]-phenyl}-2-ethoxy-propionic acid ethyl ester a)
A mixture of styrene (2.0 g, 18.9 mmol), potassium carbonate (7.8 g, 56.7 mmol), tetra-N-butylammonium bromide (2.0 g, 6.3 mmol) and palladium(II) acetate (250 mg, 1.11 mmol), under nitrogen, was stirred for 10 min. A solution of 3,5-dibromobenzaldehyde (5.0 g, 18.9 mmol) in dry DMF (10 mL) was added and the mixture heated at 65° C. for 16 h. The reaction mixture was concentrated in vacuo, and the product purified by flash chromatography (heptane/ethyl acetate 1:4) to give 1.7 g of 3-bromo-5-styryl-benzaldehyde.

b)
The title compound was prepared from 3-bromo-5-styryl-benzaldehyde by a sequence analogous to that described in example 23.

$^1$H NMR (CDCl$_3$, 300 MHz) δ: 1.18 (t, 3H), 1.23 (t, 3H), 2.96 (d, 2H), 3.30–3.42 (m, 1H), 3.55–3.65 (m, 1H), 3.98 (t, 1H), 4.15 (q, 2H), 4.68 (d, 2H), 6.43 (dt, 1H), 6.66 (d, 1H), 6.88 (d, 2H), 6.93–7.56 (m, 12H).

Example 78

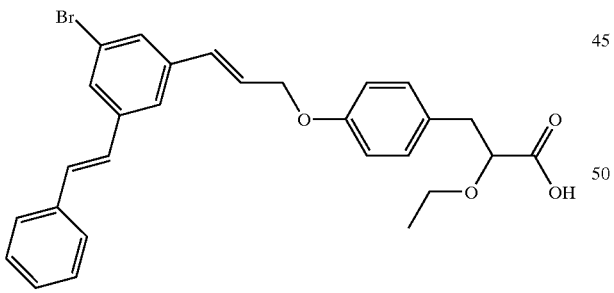

(S)-3-{4-[3-(3-Bromo-5-styryl-phenyl)-allyloxy]-phenyl}-2-ethoxy-propionic acid

The title compound was prepared from (S)-3-{4-[3-(3-bromo-5-styryl-phenyl)-allyloxy]-phenyl}-2-ethoxy-propionic acid ethyl ester (example 77) (800 mg, 1.7 mmol) by a procedure analogous to that described in example 26.

$^1$H NMR (CDCl$_3$, 300 MHz) δ: 1.18 (t, 3H), 2.98 (dd, 1H), 3.10 (dd, 1H), 3.40–3.53 (m, 1H), 3.54–3.68 (m, 1H), 4.05 (dd, 1H), 4.68 (dd, 2H), 6.43 (dt, 1H), 6.68 (s, 1H), 6.88 (d, 2H), 6.94–7.56 (m, 12H).

Example 79

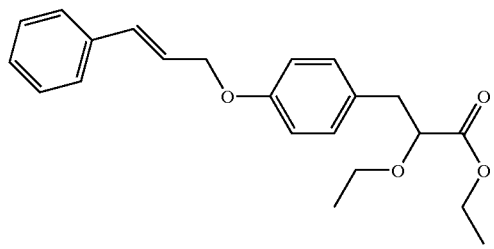

(E)-(S)-2-Ethoxy-3-[4-(3-phenyl-allyloxy)-phenyl]-propionic acid ethyl ester

The title compound was prepared from 3-phenyl-prop-2-en-1-ol (270 mg, 2.0 mmol) by a sequence analogous to that described in example 23c.

$^1$H NMR (CDCl$_3$, 300 MHz) δ: 1.18 (t, 3H), 1.22 (t, 3H), 2.95 (d, 2H), 3.30–3.42 (m, 1H), 3.53–3.65 (m, 1H), 3.98 (t, 1H), 4.15 (q, 2H), 4.68 (dd, 2H), 6.41 (dt, 1H), 6.73 (dt, 1H), 6.88 (d, 2H), 7.15 (d, 2H), 7.21–7.38 (m, 3H), 7.38–7.43 (m, 2H).

Example 80

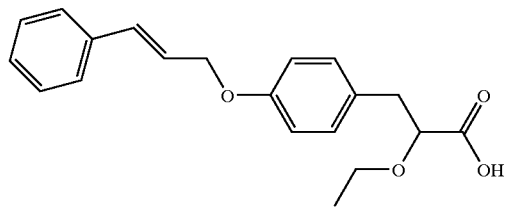

(E)-(S)-2-Ethoxy-3-[4-(3-phenyl-allyloxy)-phenyl]-propionic acid

The title compound was prepared from (E)-(S)-2-ethoxy-3-[4-(3-phenyl-allyloxy)-phenyl]-propionic acid ethyl ester (example 79) (700 mg, 2.0 mmol) by a procedure analogous to that described in example 26.

$^1$H NMR (CDCl$_3$, 300 MHz) δ: 1.18 (t, 3H), 2.95 (dd, 1H), 3.10 (dd, 1H), 4.42–3.53 (m, 1H), 3.53–3.64 (m, 1H), 4.05 (dd, 1H), 4.68 (dd, 2H), 6.42 (dt, 1H), 6.72 (d, 1H), 6.89 (d, 2H), 7.15 (d, 1H), 7.22–7.37 (m, 3H), 7.40 (d, 2H).

Example 81

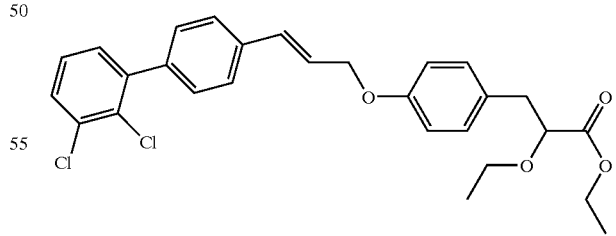

(E)-(S)-3-{4-[3-(2',3'-Dichloro-biphenyl-4-yl)-allyloxy]-phenyl}-2-ethoxy-propionic acid ethyl ester a)
(E)-3-(4-Bromo-phenyl)-acrylic acid ethyl ester was prepared from 3-bromobenzaldehyde (20.0 g, 0.11 mol) by a sequence analogous to that described in example 23a.

b)
The title compound was prepared from (E)-3-(4-bromophenyl)-acrylic acid ethyl ester and 2,3-dichlorobenzene boronic acid by a sequence analogous to that described in example 52a–c.

$^1$H NMR (CDCl$_3$, 300 MHz) δ: 1.18 (t, 3H), 1.23 (t, 3H), 2.95 (d, 2H), 3.30–3.42 (m, 1H), 3.53–3.65 (m, 1H), 3.98 (t, 1H), 4.15 (q, 2H), 4.70 (dd, 2H), 6.47 (dt, 1H), 6.7 (d, 1H), 6.88 (d, 2H), 7.15 (d, 2H), 7.20–7.28 (m, 2H), 7.35 (d, 2H), 7.43–7.52 (m, 3H).

Example 82

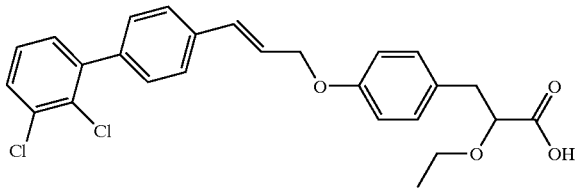

(E)-(S)-3-{4-[3-(2',3'-Dichloro-biphenyl-4-yl)-allyloxy]-phenyl}-2-ethoxy-propionic acid The title compound was prepared from (E)-(S)-3-{4-[3-(2',3'-dichloro-biphenyl-4-yl)-allyloxy]-phenyl}-2-ethoxy-propionic acid ethyl ester (example 81) by a procedure analogous to that described in example 26.

$^1$H NMR (MeOD, 300 MHz) δ: 1.12 (t, 3H), 2.88 (dd, 1H), 3.0 (dd, 1H), 3.30–3.42 (m, $_1$H), 3.3–3.65 (m, 1H), 4.0 (dd, 1H), 4.70 (dd, 2H), 6.52 (dt, 1H), 6.80 (d, 1H), 6.90 (d, 2H), 7.18 (d, 2H), 7.25–7.40 (m, 4H), 7.48–7.55 (m, 3H).

Example 83

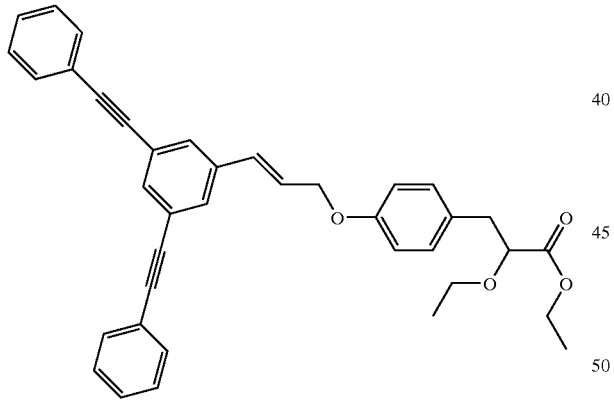

(E)-(S)-3-{4-[3-(3,5-Bis-phenylethynyl-phenyl)-allyloxy]-phenyl}-2-ethoxy-propionic acid ethyl ester a)
A mixture of potassium carbonate (2.1 g, 15.2 mmol), tetra-N-butylammonium bromide (0.75 g, 2.4 mmol) and palladium(II) acetate (75 mg, 0.33 mmol) in dry DMF (8 ML), under nitrogen, was stirred for 10 min. 3-(3,5-Dibromophenyl)-acrylic acid ethyl ester (1.2 g, 3.6 mmol) was added and the mixture cooled on ice. Phenylacetylene (4.0 mL, 36.0 mmol) was added and the mixture stirred at room temperature for 7 days. The reaction mixture was added water and the product extracted with ethyl acetate (×3). The combined organic phases were dried and concentrated in vacuo to give crude 3-(3,5-bis-phenylethynyl-phenyl)-acrylic acid ethyl ester.

b)
The title compound was prepared from 3-(3,5-bis-phenylethynyl-phenyl)-acrylic acid ethyl ester by a sequence analogous to that described in example 23b–c.

$^1$H NMR (CDCl$_3$, 300 MHz) δ: 1.18 (t, 3H), 1.23 (t, 3H), 2.96 (d, 2H), 3.30–3.42 (m, 1H), 3.55–3.67 (m, 1H), 3.98 (t, 1H), 4.15 (q, 2H), 4.70 (d, 2H), 6.46 (dt, 1H), 6.68 (d, 1H), 6.88 (d, 2H), 7.15 (d, 2H), 7.30–7.38 (m, 6H), 7.48–7.58 (m, 6H), 7.60 (s, 1H).

Example 84

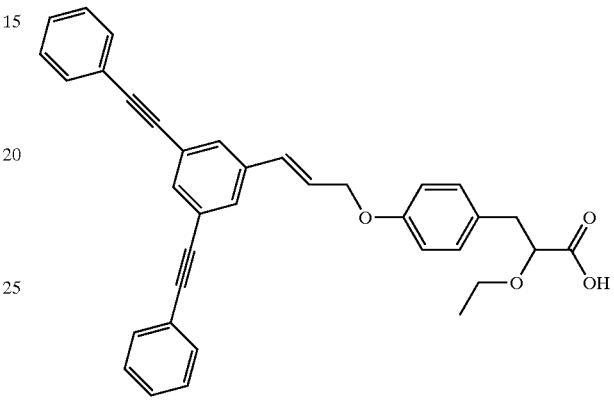

(E)-(S)-3-{4-[3-(3,5-Bis-phenylethynyl-phenyl)-allyloxy]-phenyl}-2-ethoxy-propionic acid The title compound was prepared from (E)-(S)-3-{4-[3-(3,5-bis-phenylethynyl-phenyl)-allyloxy]-phenyl}-2-ethoxy-propionic acid ethyl ester (example 83) (130 mg, 0.24 mmol) by a procedure analogous to that described in example 26.

$^1$H NMR (CDCl$_3$, 300 MHz) δ: 1.18 (t, 3H), 2.96 (dd, 1H), 3.98 (dd, 1H), 3.37–3.48 (m, 1H), 3.53–3.67 (m, 1H), 4.03 (dd, 1H), 4.68 (d, 2H), 6.47 (dt, 1H), 6.68 (d, 1H), 6.88 (d, 2H), 7.18 (d, 2H), 7.30–7.42 (m, 6H), 7.48–7.58 (m, 6H), 7.60 (s, 1H).

Example 85

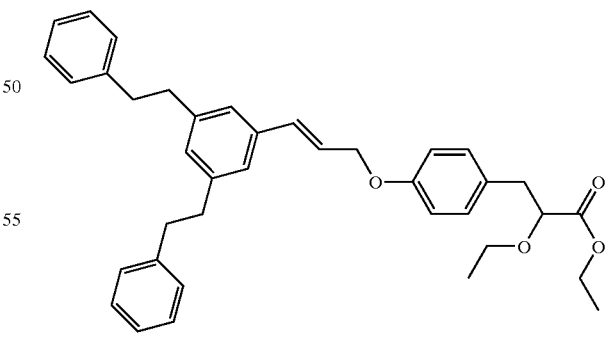

(E)-(S)-3-{4-[3-(3,5-Diphenethyl-phenyl)-allyloxy]-phenyl}-2-ethoxy-propionic acid ethyl ester a)
A solution of 3,5-distyryl-benzaldehyde (2.0 g, 6.44 mmol) (prepared as described in example 79) in ethyl acetate (150 mL) was hydrogenated at 3 atm for 16 h using 5% Pd-C (2 g) as catalyst. The catalyst was removed by filtration and the solvent evaporated to give (3,5-diphenethyl-phenyl)-methanol (2.0 g) as an oil.

b)

To a solution of (3,5-diphenethyl-phenyl)-methanol (2.0 g, 6.4 mmol) in dry dichloromethane (30 mL) was added pyridinium chlorochromate (1.4 g, 6.4 mmol) and the mixture was stirred at room temperature for 16 h. The product was purified by flash chromatography using dichloromethane as solvent to give 1.3 g 3,5-diphenethyl-benzaldehyde.

c)

The title compound was prepared from 3,5-diphenethyl-benzaldehyde by a sequence analogous to that described in example 23.

Example 86

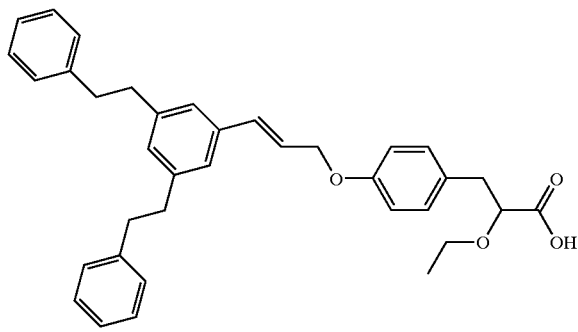

(E)-(S)-3-{4-[3-(3,5-Diphenethyl-phenyl)-allyloxy]-phenyl}-2-ethoxy-propionic acid The title compound was prepared from (E)-(S)-3-{4-[3-(3,5-Diphenethyl-phenyl)-allyloxy]-phenyl}-2-ethoxy-propionic acid ethyl ester (example 85) (449 mg, 0.80 mmol) by a procedure analogous to that described in example 26.

$^1$H NMR (CDCl$_3$, 300 MHz) δ: 1.18 (t, 3H), 2.96 (dd, 1H), 3.08 (dd, 1H), 3.35–3.48 (m, 1H), 3.55–3.67 (m, 1H), 4.03 (dd, 1H), 4.65 (dd, 1H), 6.35 (dt, 1H), 6.68 (d, 1H), 6.82–6.92 (m, 3H), 7.04 (d, 2H), 7.12–7.32 (m, 12H).

Example 87

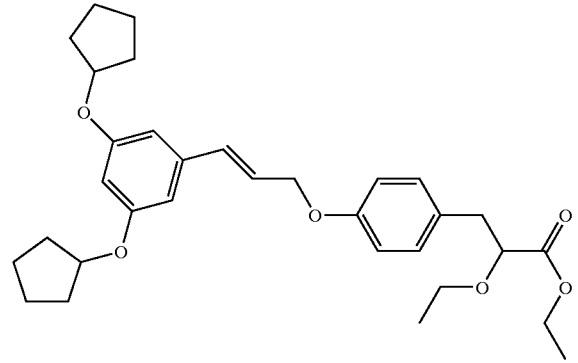

3-{4-[3-(3,5-Bis-cyclopentyloxy-phenyl)-allyloxy]-phenyl}-2-ethoxy-propionic acid ethyl ester The title compound was prepared from dihydroxybenzaldehyde (1.0 g, 7.2 mmol) and cyclopentylbromide (4.0 g, 29.0 mmol) by a sequence analogous to that described in example 75.

$^1$H NMR (CDCl$_3$, 300 MHz) δ: 1.18 (t, 3H), 1.21 (t, 3H), 1.50–1.68 (m, 4H), 1.68–1.97 (m, 12H), 2.95 (d, 2H), 3.28–3.42 (m, 1H), 3.54–3.65 (m, 1H), 3.97 (t, 1H), 4.15 (q, 2H), 4.67 (dd, 2H), 4.67–4.77 (m, 2H), 6.28–6.40 (m, 2H), 6.50 (d, 2H), 6.60 (d, 1H), 6.87 (d, 2H), 7.15 (d, 2H).

Example 88

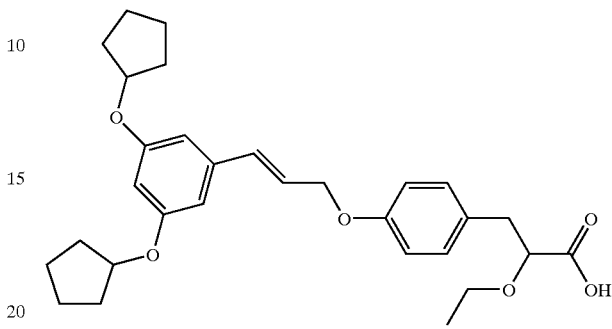

(E)-(S)-3-{4-[3-(3,5-Bis-cyclopentyloxy-phenyl)-allyloxy]-phenyl}-2-ethoxy-propionic acid The title compound was prepared from (E)-(S)-3-{4-[3-(3,5-bis-cyclopentyloxy-phenyl)-allyloxy]-phenyl}-2-ethoxy-propionic acid ethyl ester (example 87) (220 mg, 0.42 mmol) by a procedure analogous to that described in example 26.

$^1$H NMR (CDCl$_3$, 300 MHz) δ: 1.18 (t, 3H), 1.52–1.70 (m, 4H), 1.70–1.98 (m, 12H), 2.95 (dd, 1H), 3.07 (dd, 1H), 3.37–3.48 (m, 1H), 3.55–3.65 (m, 1H), 4.03 (dd, 1H), 4.65 (dd, 2H), 4.70–4.78 (m, 2H), 6.29–6.40 (m, 2H), 6.50 (d, 2H), 6.60 (d, 1H), 6.88 (d, 2H), 7.15 (d, 2H).

Example 89

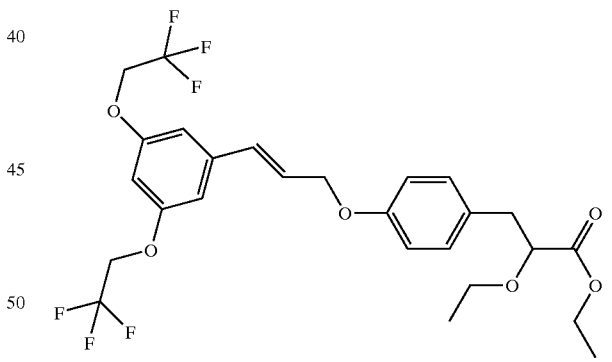

(E)-(S)-3-(4-{3-[3,5-Bis-(2,2,2-trifluoro-ethoxy)-phenyl]-allyloxy}-phenyl)-2-ethoxy-propionic acid ethyl ester a)

To a solution of 3,5-dihydroxybenzaldehyde (2.0 g, 14.5 mmol) in DMF (35 mL) was added potassium carbonate (11.0 g, 80.0 mmol) and 1,1,1-trifluoro-2-iodoethane (33.3 g, 160 mmol). The reaction mixture was heated I a sealed reactor at 50° C. for 7 days. The mixture was filtered and washed with ethyl acetate. The filtrate was added water and the organic phase isolated. The aqueous phase was extracted once more with ethyl acetated. The combined organic phases were dried (MgSO$_4$), filtered and concentrated in vacuo. The residue was purified by flash chromatography eluting with toluene to give 906 mg (18%) of 3,5-bis-(2,2,2-trifluoro-ethoxy)-benzaldehyde. $^1$H NMR (CDCl$_3$, 300 MHz) δ: 4.43 (q, 4H), 6.85 (t, 1H), 7.15 (d, 2H), 9.95 (s, 1H).

b)

The title compound was prepared from 3,5-bis-(2,2,2-trifluoro-ethoxy)-benzaldehyde by a sequence analogous to that described in example 23.

$^1$H NMR (CDCl$_3$, 300 MHz) δ: 1.15 (t, 3H), 1.22 (t, 3H), 2.95 (d, 2H), 3.30–3.40 (m, 1H), 3.55–3.67 (m, 1H), 3.97 (t, 1H), 4.15 (q, 2H), 4.33 (q, 4H), 4.65 (d, 2H), 6.32–6.48 (m, 2H), 6.55–6.70 (m, 3H), 6.85 (d, 2H), 7.15 (d, 2H).

Example 90

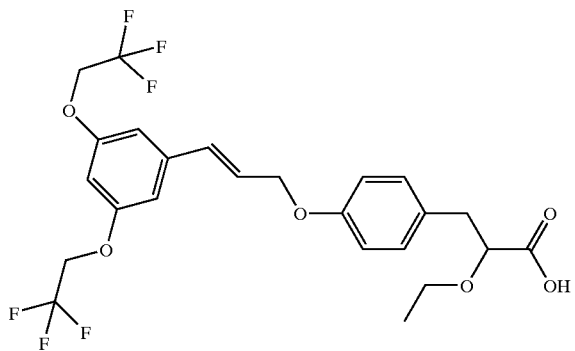

(E)-(S)-3-(4-{3-[3,5-Bis-(2,2,2-trifluoro-ethoxy)-phenyl]-allyloxy}-phenyl)-2-ethoxy-propionic acid The title compound was prepared from (E)-(S)-3-(4-{3-[3,5-bis-(2,2,2-trifluoro-ethoxy)-phenyl]-allyloxy}-phenyl)-2-ethoxy-propionic acid ethyl ester (example 89) (200 mg, 0.36 mmol) by a procedure analogous to that described in example 26.

$^1$H NMR (CDCl$_3$, 300 MHz) δ: 1.20 (t, 3H), 2.97 (dd, 1H), 3.10 (dd, 1H), 3.41–3.53 (m, 1H), 3.55–3.68 (m, 1H), 4.05 (dd, 1H), 4.35 (q, 4H), 4.67 (d, 2H), 6.35–6.48 (m, 2H), 6.60–6.70 (m, 3H), 6.87 (d, 2H), 7.15 (d, 2H).

Example 91

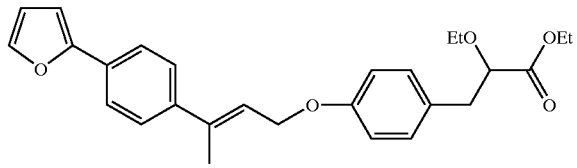

(E)-(S)-Ethyl 2-Ethoxy-3-{4-[3-(4-furan-2-yl-phenyl)-but-2-enyloxy]-phenyl}-propionate a)

Sodium (5.52 g, 0.24 mol) was added to ethanol (250 ml) at 20° C. and the mixture stirred until the metal had fully reacted. Triethyl phosphonoacetate (62.72 g, 0.28 mol) was added as an ethanol (50 ml) solution, the mixture stirred for 20 min, then a solution of 4-iodoacetophenone (49.21 g, 0.20 mol) in ethanol (300 ml) was added and the reaction mixture heated to 80° C. under reflux for 17 h. The solution was cooled, the ethanol evaporated and the resulting orange residue partitioned between 1N HCl (200 ml) and ethyl acetate (200 ml). The aqueous layer was collected and further extracted with ethyl acetate (3×200 ml). The organic layers were combined, washed with brine, dried (MgSO$_4$) and evaporated to an orange/yellow oil, which was purified by column chromatography on silica gel (2% diethyl ether in n-heptane eluent) to give the product, (E)-ethyl 3-(4-iodophenyl)-but-2-enoate, as a pale yellow oil; 54.83 g (87%)

$^1$H NMR (300 MHz, CDCl$_3$) δ: 1.31 (3H, t), 2.53 (3H, s), 4.21 (2H, q), 6.11 (1H, s), 7.20 (2H, dm), 7.69 (2H, dm). $^{13}$CNMR (75 MHz, CDCl$_3$) δ: 13.0 (q), 16.4 (q), 58.6 (t), 93.7 (s), 116.2 (d), 126.7 (d), 136.3 (d), 140.3 (s), 152.8 (s), 165.2 (s). MS: 316 (M$^+$), 287, 271, 244, 144, 115 (100%). Microanalysis Calculated % C, 45.59; H, 4.14. Found % C, 45.72; H, 4.20.

b)

Tetrakis(triphenylphoshine)palladium(0) (0.69 g, 0.60 mmol, 6 mol %) was added, under nitrogen, to a stirred solution of (E)-ethyl 3-(4-iodophenyl)-but-2-enoate (3.16 g, 10.0 mmol) in DME (100 ml), and the resulting orange coloured solution stirred at room temperature for 10 min. Aqueous 2M sodium carbonate (30.0 ml, 60.0 mmol) was then added, the mixture stirred for 10 min, then furan-2-boronic acid (2.25 g, 20.11 mmol) was added, and the reaction mixture heated to 80° C. for 20 h, under reflux. The reaction mixture was cooled, diluted with water (100 ml) and the products extracted into ethyl acetate (3×100 ml). The combined organic extracts were washed with brine, dried (MgSO$_4$), and evaporated to give the crude product, which was purified by column chromatography on silica gel (3% diethyl ether in n-heptane eluent) to give the product, (E)-ethyl 3-(4-furan-2-yl-phenyl)-but-2-enoate as an off-white solid; 2.46 g (96%).

Mpt. 85.5–56.5° C. $^1$H NMR (300 MHz, CDCl$_3$) δ: 1.32 (3H, t), 2.59 (3H, d), 4.22 (2H, q), 6.18 (1H, m), 6.49 (1H, dd), 6.70 (1H, d), 7.46–7.56 (3H, m), 7.66 (2H, dm). MS: 256 (100%, M$^+$), 227, 211, 184, 153, 115. Microanalysis Calculated % C, 74.98; H, 6.29. Found % C, 74.99; H, 6.39.

c)

(E)-Ethyl 3-(4-furan-2-yl-phenyl)-but-2-enoate was reduced with DIBAL-H by a procedure analogous to that described in example 50b, to give the colourless solid (E)-3-(4-furan-2-yl-phenyl)-but-2-en-1-ol.

d)

The title compound (678 mg, 77%) was prepared from (E)-3-(4-furan-2-yl-phenyl)-but-2-en-1-ol (430 mg, 2.0 mmol) and (S)-ethyl 2-ethoxy-3-(4-hydroxyphenyl)-propionate (526 mg, 2.21 mmol) by a procedure analogous to that described in example 52c.

$^1$H NMR (300 MHz, CDCl$_3$) δ: 1.17 (3H, t), 1.22 (3H, t), 2.14 (3H, d), 2.96 (2H, d), 3.31–3.41 (1H, m), 3.55–3.66 (1H, m), 3.98 (1H, t), 4.16 (2H, q), 4.73 (2H, d), 6.10 (1H, tm), 6.47 (1H, dd), 6.64 (1H, d), 6.88 (2H, dm), 7.17 (2H, dm), 7.43–7.48 (3H, m), 7.62 (2H, dm). LCMS: 457 (M+Na), 452 (M+NH$_4$), 197 (100%).

Example 92

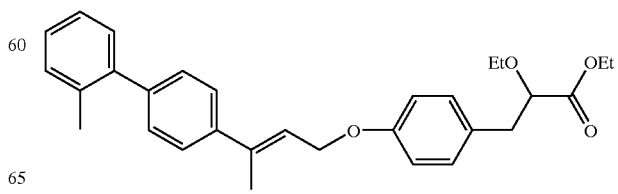

(E)-(S)-Ethyl 2-Ethoxy-3-{4-[3-(2'-methyl-biphenyl-4-yl)-but-2-enyloxy]-phenyl}-propionate a)

The colourless solid, (E)-ethyl 3-(2'-methyl-biphenyl-4-yl)-but-2-enoate was prepared from (E)-ethyl 3-(4-iodophenyl)-but-2-enoate (example 91a) and ortho-tolyl boronic acid by a procedure analogous to that described in example 91b.

b)

The colourless oil (E)-3-(2'-methyl-biphenyl-4-yl)-but-2-en-1-ol was prepared by DIBAL-H reduction of (E)-ethyl 3-(2'-methyl-biphenyl-4-yl)-but-2-enoate by a procedure analogous to that described in example 50b.

c)

The title compound (1.80 g, 78%) was prepared as a colourless oil from (E)-3-(2'-methyl-biphenyl-4-yl)-but-2-en-1-ol (1.19 g, 4.99 mmol) and (S)-ethyl 2-ethoxy-3-(4-hydroxyphenyl)-propionate (1.31 g, 6.48 mmol) by a procedure analogous to that described in example 52c.

$^1$H NMR (300 MHz, CDCl$_3$) δ: 1.17 (3H, t), 1.22 (3H, t), 2.17 (3H, d), 2.28 (3H, s), 2.96 (2H, d), 3.30–3.41 (1H, m), 3.54–3.66 (1H, m), 3.98 (1H, t), 4.16 (2H, q), 4.74 (2H, d), 6.11 (1H, tm), 6.88 (2H, dm), 7.16 (2H, dm), 7.20–7.32 (6H, m), 7.47 (2H, dm). LCMS: 679 (M+221), 633 (679-EtOH), 481 (M+Na), 476 (M+NH$_4$), 221 (100%).

Example 93

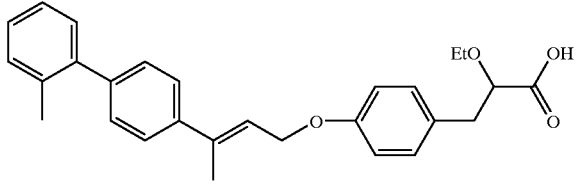

(E)-(S)-2-Ethoxy-3-{4-[3-(2'-methyl-biphenyl-4-yl)-but-2-enyloxy]-phenyl}-propionic acid The title compound was prepared by hydrolysis of (E)-(S)-ethyl 2-ethoxy-3-{4-[3-(2'-methyl-biphenyl-4-yl)-but-2-enyloxy]-phenyl}-propionate (example 92) (918 mg, 2.0 mmol) with sodium hydroxide by a procedure analogous to that described in example 51, yielding (E)-(S)-2-ethoxy-3-{4-[3-(2'-methyl-biphenyl-4-yl)-but-2-enyloxy]-phenyl}-propionic acid as a colourless gum, which contained 0.25 mol equivalents of ethyl acetate; 586 mg (64%).

$^1$H NMR (300 MHz, CDCl$_3$) δ: 1.17 (3H, t), 1.27 (0.75H, t, AcOEt), 2.04 (0.75H, s, AcOEt), 2.19 (3H, d), 2.29 (3H, s), 2.96 (1H, dd), 3.09 (1H, dd), 3.41–3.53 (1H, m), 3.53–3.65 (1H, m), 4.06 (1H, dd), 4.12 (0.5H, q, AcOEt), 4.75 (2H, d), 6.12 (1H, tm), 6.89 (2H, dm), 7.16 (2H, dm), 7.20–7.34 (6H, m), 7.48 (2H, dm), carboxylic acid proton not observed. LCMS: 651 (M+221), 453 (M+Na), 221 (100%).

Example 94

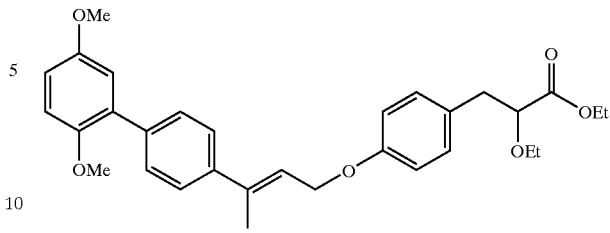

(E)-(S)-Ethyl 3-{4-[3-(2',5'-Dimethoxy-biphenyl-4-yl)-but-2-enyloxy]-phenyl}-2-ethoxy-propionate a)

The colourless oil, (E)-ethyl 3-(2',5'-dimethoxy-biphenyl-4-yl)-but-2-enoate was prepared from (E)-ethyl 3-(4-bromophenyl)-but-2-enoate (example 50a) and 2,5-dimethoxyphenyl boronic acid by a procedure analogous to that described in example 52a.

b)

The colourless gum (E)-3-(2',5'-dimethoxy-biphenyl-4-yl)-but-2-en-1-ol was prepared by DIBAL-H reduction of (E)-ethyl 3-(2',5'-dimethoxy-biphenyl-4-yl)-but-2-enoate by a procedure analogous to that described in example 52b.

c)

The title compound (0.765 g, 61%) was prepared as a colourless gum from (E)-3-(2',5'-dimethoxy-biphenyl-4-yl)-but-2-en-1-ol (0.711 g, 2.50 mmol) and (S)-ethyl 2-ethoxy-3-(4-hydroxyphenyl)-propionate (0.655 g, 2.75 mmol) by a procedure analogous to that described in example 52c.

$^1$H NMR (300 MHz, CDCl$_3$) δ: 1.17 (3H, t), 1.22 (3H, t), 2.16 (3H, d), 2.96 (2H, d), 3.31–3.41 (1H, m), 3.55–3.65 (1H, m), 3.76 (3H, s), 3.81 (3H, s), 3.98 (1H, t), 4.17 (2H, q), 4.74 (2H, d), 6.10 (1H, tm), 6.81–6.95 (5H, m), 7.16 (2H, dm), 7.45–7.53 (4H, m). LCMS: 771 (M+267), 527 (M+Na), 422 (M+NH$_4$), 267 (100%).

Example 95

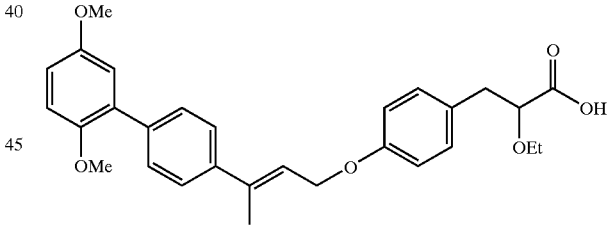

(E)-(S)-3-{4-[3-(2',5'-Dimethoxy-biphenyl-4-yl)-but-2-enyloxy]-phenyl}-2-ethoxy-propionic acid The title compound was prepared from (E)-(S)-ethyl 3-{4-[3-(2',5'-dimethoxy-biphenyl-4-yl)-but-2-enyloxy]-phenyl}-2-ethoxy-propionate (Example 94) (0.62 g, 1.23 mmol) and sodium hydroxide (1M, 2.0 ml, 2.0 mmol) by a procedure analogous to that described in example 51, yielding (E)-(S)-ethyl 3-{4-[3-(2',5'-dimethoxy-biphenyl-4-yl)-but-2-enyloxy]-phenyl}-2-ethoxy-propionic acid as a colourless glass; 0.485 g (83%).

$^1$H NMR (300 MHz, CDCl$_3$) δ: 1.18 (3H, t), 2.16 (3H, d), 2.96 (1H, dd), 3.10 (1H, dd), 3.42–3.51 (1H, m), 3.51–3.65 (1H, m), 3.75 (3H, s), 3.80 (3H, s), 4.05 (1H, dd), 4.74 (2H, d), 6.10 (1H, tm), 6.81–6.94 (5H, m), 7.17 (2H, dm), 7.43–7.53 (4H, m), carboxylic acid proton not observed. LCMS: 743 (M+267), 499 (M+Na), 494 (M+NH$_4$), 267 (100%).

Example 96

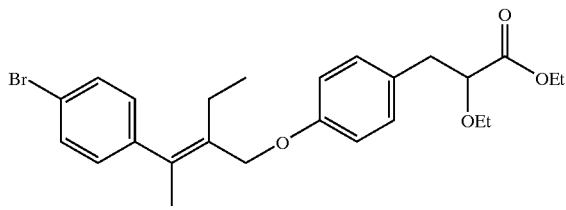

(E)-(S)-Ethyl 3-{4-[3-(4-Bromophenyl)-2-ethyl-but-2-enyloxy]-phenyl}-2-ethoxy-propionate a)

A solution of triethyl 2-phosphonobutyrate (17.7 g, 70.0 mmol) in dry THF (30 ml) was added dropwise, at 0° C., to a stirred suspension of sodium hydride (50% dispersion in mineral oil, 2.90 g, 60.4 mmol) in dry THF (30 ml) and the mixture stirred for 30 min. A solution of 4-bromoacetophenone (7.96 g, 39.99 mmol) in THF (80 ml) was added over 20 min., the resulting mixture warmed to room temperature and stirring continued overnight. Second portions of triethyl 2-phosphonobutyrate (10.11 g, 40.1 mmol) and sodium hydride (2.90 g, 60.4 mmol) were then added at room temperature, and stirring continued for a further 24 h; TLC at this stage showed that a substantial amount of unreacted 4-bromo acetophenone starting material was still present. The reaction was worked up by adding 1N HCl (200 ml) and ethyl acetate (100 ml), the organic layer collected and the aqueous layer extracted with ethyl acetate (3×100 ml). The combined organic layers were washed with brine, dried (MgSO$_4$) and concentrated to give an orange gum, which was purified by column chromatography on silica gel (2% diethyl ether in n-heptane eluent) to give the orange oil, (E/Z)-ethyl 3-(4-bromophenyl)-2-ethyl-but-2-enoate (3.47 g, 29%) as a mixture of double-bond isomers.

b)

A toluene solution of DIBAL-H (1M, 29.0 ml, 29.0 mmol) was added dropwise at −70° C. to a stirred THF (100 ml) solution of (E/Z)-ethyl 3-(4-bromophenyl)-2-ethyl-but-2-enoate (3.45 g, 11.6 mmol), and the solution stirred for 40 min. Methanol (1 ml) was carefully added, followed by 1N HCl (300 ml) and ethyl acetate (200 ml). The aqueous layer was separated and further extracted with ethyl acetate (2×150 ml). The combined organic layers were washed with brine, dried (MgSO$_4$), and concentrated to give an orange gum, which was separated into its two major constituents by column chromatography on silica gel (15% ethyl acetate in n-heptane eluent). The two products, in order of elution, were (Z)-3-(4-bromo-phenyl)-2-ethyl-but-2-en-1-ol (0.365 g, 12%) and (E)-3-(4-bromophenyl)-2-ethyl-but-2-en-1-ol (0.89 g, 30%).

c)

The title compound (843 mg, 89%) was prepared from (E)-3-(4-bromophenyl)-2-ethyl-but-2-en-1-ol (510 mg, 2.0 mmol) and (S)-ethyl 2-ethoxy-3-(4-hydroxyphenyl)-propionate (500 mg, 2.10 mmol) by a procedure analogous to that described in example 52c.

$^1$H NMR (300 MHz, CDCl$_3$) δ: 0.94 (3H, t), 1.20 (3H, t), 1.23 (3H, t), 2.01 (3H, s), 2.05 (2H, q), 2.97 (2H, d), 3.31–3.43 (1H, m), 3.54–3.68 (1H, m), 3.99 (1H, t), 4.17 (2H, q), 4.61 (2H, s), 6.89 (2H, dm), 7.04 (2H, dm), 7.18 (2H, dm), 7.45 (2H, dm).

Example 97

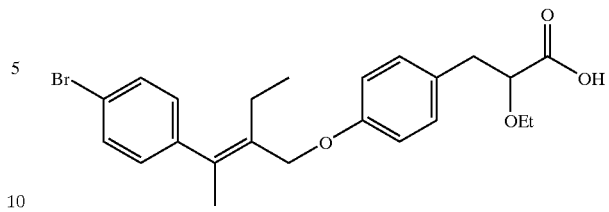

(E)-(S)-3-{4-[3-(4-Bromophenyl)-2-ethyl-but-2-enyloxy]-phenyl}-2-ethoxy-propionic acid The title compound was prepared from (E)-(S)-ethyl 3-{4-[3-(4-bromophenyl)-2-ethyl-but-2-enyloxy]-phenyl}-2-ethoxy-propionate (Example 96) (0.78 g, 1.64 mmol) and sodium hydroxide (1M, 3.3 ml, 3.3 mmol) by a procedure analogous to that described in example 51, yielding (E)-(S)-3-{4-[3-(4-bromophenyl)-2-ethyl-but-2-enyloxy]-phenyl}-2-ethoxy-propionic acid (0.703 g, 96%) as a pale yellow oil, which contained a small amount of dichloromethane; 0.703 g (96%).

$^1$H NMR (300 MHz, CDCl$_3$) δ: 1.19 (3H, t), 1.26 (ethyl acetate impurity, 0.6H, t), 2.04 (ethyl acetate impurity, 0.4H, s), 2.16 (3H, s), 2.96 (1H, dd), 3.10 (1H, dd), 3.42–3.52 (1H, m), 3.53–3.68 (1H, m), 3.80 (3H, s), 4.07 (1H, dd), 4.12 (ethyl acetate impurity, 0.4H), 4.74 (2H, d), 5.30 (CH$_2$Cl$_2$, trace), 6.10 (1H, t), 6.85–6.95 (3H, m), 7.12–7.20 (2H, m), 7.21–7.32 (2H, m), 7.45–7.50 (4H, m), carboxylic acid proton not observed.

Example 98

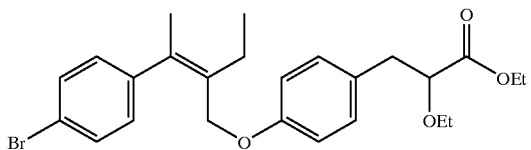

(Z)-(S)-Ethyl 3-{4-[3-(4-Bromophenyl)-2-ethyl-but-2-enyloxy]-phenyl}-2-ethoxy-propionate The title compound (535 mg, 81%) was prepared from (Z)-3-(4-bromophenyl)-2-ethyl-but-2-en-1-ol (prepared as described in example 96b) (355 mg, 1.39 mmol) and (S)-ethyl 2-ethoxy-3-(4-hydroxyphenyl)-propionate (348 mg, 1.46 mmol) by a procedure analogous to that described in example 52c.

$^1$H NMR (300 MHz, CDCl$_3$) δ: 1.11 (3H, t), 1.16 (3H, t), 1.21 (3H, t), 2.04 (3H, s), 2.37 (2H, q), 2.93 (2H, d), 3.29–3.40 (1H, m), 3.53–3.65 (1H, m), 3.95 (1H, t), 4.16 (2H, q), 4.25 (2H, s), 6.70 (2H, dm), 7.03–7.12 (4H, m), 7.40 (2H, dm). Microanalysis Calculated % C, 63.16; H, 6.57. Found % C, 63.34; H, 6.66.

Example 99

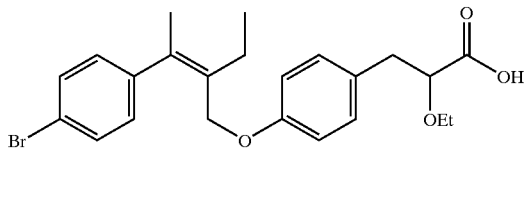

(Z)-(S)-3-{4-[3-(4-Bromophenyl)-2-ethyl-but-2-enyloxy]-phenyl}-2-ethoxy-propionic acid The title compound was prepared from (Z)-(S)-ethyl 3-{4-[3-(4-bromophenyl)-2-ethyl-but-2-enyloxy]-phenyl}-2-ethoxy-propionate (Example 98) (475 mg, 1.0 mmol) and sodium hydroxide (1M, 2.0 ml, 2.0 mmol) by a procedure analogous to that described in example 51, yielding (Z)-(S)-3-{4-[3-(4-bromophenyl)-2-ethyl-but-2-enyloxy]-phenyl}-2-ethoxy-propionic acid (0.424 g, 95%) as a pale yellow oil.

$^1$H NMR (300 MHz, CDCl$_3$) δ: 1.11 (3H, t), 1.18 (3H, t), 2.04 (3H, s), 2.37 (2H, q), 2.94 (1H, dd), 3.04 (1H, dd), 3.40–3.53 (1H, m), 3.53–3.64 (1H, m), 4.03 (1H, dd), 4.25 (2H, s), 6.71 (2H, dm), 7.02–7.14 (4H, m), 7.40 (2H, dm), carboxylic acid proton not observed.

Example 100

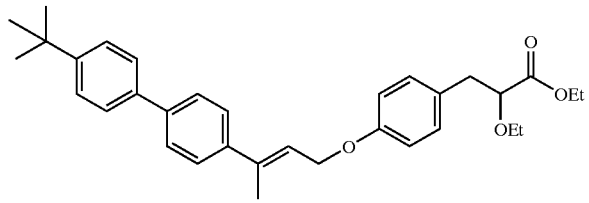

(E)-(S)-Ethyl 3-{4-[3-(4'-tert-Butyl-biphenyl-4-yl)-but-2-enyloxy]-phenyl}-2-ethoxy-propionate a)

The colourless oil, (E)-ethyl 3-(4'-tert-butyl-biphenyl-4-yl)-but-2-enoate was prepared from (E)-ethyl 3-(4-bromophenyl)-but-2-enoate (example 50a) and 4-tert-butylphenylboronic acid by a procedure analogous to that described in example 52a b)

The colourless gum (E)-3-(4'-tert-butyl-biphenyl-4-yl)-but-2-en-1-ol was prepared by DIBAL-H reduction of (E)-ethyl 3-(4'-tert-butyl-biphenyl-4-yl)-but-2-enoate by a procedure analogous to that described in example 52b.

c)

The title compound (0.375 g, 75%) was prepared as a colourless gum from (E)-3-(4'-tert-butyl-biphenyl-4-yl)-but-2-en-1-ol (0.280 g, 1.00 mmol) and (S)-ethyl 2-ethoxy-3-(4-hydroxyphenyl)-propionate (0.250 g, 1.05 mmol) by a procedure analogous to that described in example 52c.

$^1$H NMR (300 MHz, CDCl$_3$) δ: 1.17 (3H, t), 1.22 (3H, t), 1.37 (9H, s), 2.17 (3H, d), 2.97 (2H, d), 3.30–3.43 (1H, m), 3.53–3.67 (1H, m), 3.98 (1H, t), 4.17 (2H, q), 4.73 (2H, d), 6.11 (1H, tm), 6.88 (2H, dm), 7.17 (2H, dm), 7.43–7.60 (8H, m). LCMS: 763 (M+263), 523 (M+Na), 263 (100%).

Example 101

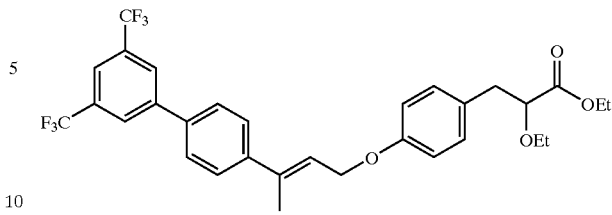

(E)-(S)-Ethyl 3-{4-[3-(3',5'-Bis-trifluoromethyl-biphenyl-4-yl)-but-2-enyloxy]-phenyl}-2-ethoxy-propionate a)

The colourless solid, (E)-ethyl 3-(3',5'-bis-trifluoromethyl-biphenyl-4-yl)-but-2-enoate was prepared from (E)-ethyl 3-(4-iodophenyl)-but-2-enoate (example 91a) and 3,5-bis-(trifluoromethyl)phenyl boronic acid by a procedure analogous to that described in example 91b.

b)

The colourless solid (E)-3-(3',5'-bis-trifluoromethyl-biphenyl-4-yl)-but-2-en-1-ol was prepared by DIBAL-H reduction of (E)-ethyl 3-(3',5'-bis-trifluoromethyl-biphenyl-4-yl)-but-2-enoate by a procedure analogous to that described in example 50b.

c)

The title compound (656 mg, 81%) was prepared as a colourless oil from (E)-3-(3',5'-bis-trifluoromethyl-biphenyl-4-yl)-but-2-en-1-ol (500 mg, 1.39 mmol) and (S)-ethyl 2-ethoxy-3-(4-hydroxyphenyl)-propionate (348 mg, 1.46 mmol) by a procedure analogous to that described in example 52c.

$^1$H NMR (300 MHz, CDCl$_3$) δ: 1.17 (3H, t), 1.23 (3H, t), 2.18 (3H, d), 2.97 (2H, d), 3.30–3.43 (1H, m), 3.56–3.69 (1H, m), 3.98 (1H, t), 4.17 (2H, q), 4.75 (2H, d), 6.15 (1H, tm), 6.89 (2H, dm), 7.18 (2H, dm), 7.52–7.62 (4H, m), 7.85 (1H, s), 8.01 (2H, s). LCMS: 603 (100%, M+Na), 598 (M+NH$_4$), 343.

Example 102

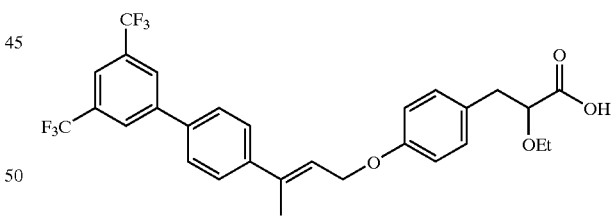

(E)-(S)-3-{4-[3-(3',5'-Bis-trifluoromethyl-biphenyl-4-yl)-but-2-enyloxy]-phenyl}-2-ethoxy-propionic acid The title compound was prepared from (E)-(S)-ethyl 3-{4-[3-(3',5'-bis-trifluoromethyl-biphenyl-4-yl)-but-2-enyloxy]-phenyl}-2-ethoxy-propionate (Example 101) (625 mg, 1.08 mmol) and sodium hydroxide (1M, 4.3 ml, 4.3 mmol) by a procedure analogous to that described in example 51, yielding (E)-(S)-3-{4-[3-(3',5'-bis-trifluoromethyl-biphenyl-4-yl)-but-2-enyloxy]-phenyl}-2-ethoxy-propionic acid (535 mg, 90%) as a colourless gum.

$^1$H NMR (300 MHz, CDCl$_3$) δ: 1.20 (3H, t), 2.18 (3H, d), 2.98 (1H, dd), 3.10 (1H, dd), 3.43–3.53 (1H, m), 3.53–3.66

(1H, m), 4.07 (1H, dd), 4.76 (2H, d), 6.15 (1H, tm), 6.90 (2H, dm), 7.19 (2H, dm), 7.50–7.62 (4H, m), 7.85 (1H, s), 8.01 (2H, s), carboxylic acid proton not observed.

Example 103

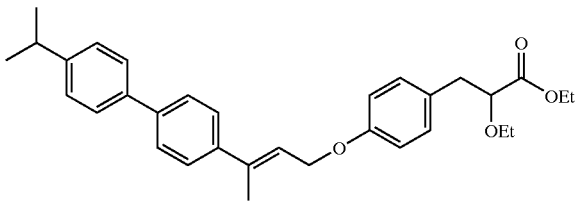

(E)-(S)-Ethyl 2-Ethoxy-3-{4-[3-(4'-isopropyl-biphenyl-4-yl)-but-2-enyloxy]-phenyl}-propionate a)
The colourless solid, (E)-ethyl 3-(4'-isopropyl-biphenyl-4-yl)-but-2-enoate was prepared from (E)-ethyl 3-(4-bromophenyl)-but-2-enoate (example 50a) and 4-isopropylphenyl boronic acid by a procedure analogous to that described in example 52a.

Mpt. 96.5–97.5° C. $^1$H NMR (300 MHz, CDCl$_3$) δ: 1.29 (6H, d), 1.32 (3H, t), 2.61 (3H, d), 2.97 (1H, septet), 4.22 (2H, q), 6.20 (1H, m), 7.32 (2H, dm), 7.50–7.65 (6H, m). MS: 308 (100%, M$^+$), 293, 178. Microanalysis Calculated % C, 81.78; H, 7.84. Found % C, 81.96; H, 8.22.

b)
The colourless solid (E)-3-(4'-isopropyl-biphenyl-4-yl)-but-2-en-1-ol was prepared by DIBAL-H reduction of (E)-ethyl 3-(4'-isopropyl-biphenyl-4-yl)-but-2-enoate by a procedure analogous to that described in example 50b.

Mpt. 110.5–112.5° C. $^1$H NMR (300 MHz, CDCl$_3$) δ: 1.29 (6H, d), 2.10 (3H, s), 2.94 (1H, septet), 4.37 (2H, d), 6.03 (1H, t), 7.29 (2H, dm), 7.40–7.60 (6H, m). MS: 266 (M$^+$), 251 (M-Me), 223 (100%, M-i-Pr). Microanalysis Calculated % C, 85.67; H, 8.32. Found % C, 85.55; H, 8.55.

c)
The title compound (410 mg, 84%) was prepared as a colourless solid from (E)-3-(4'-isopropyl-biphenyl-4-yl)-but-2-en-1-ol (266 mg, 1.00 mmol) and (S)-ethyl 2-ethoxy-3-(4-hydroxyphenyl)-propionate (250 mg, 1.05 mmol) by a procedure analogous to that described in example 52c.

Mpt. 70–73° C. $^1$H NMR (300 MHz, CDCl$_3$) δ: 1.17 (3H, t), 1.22 (3H, t), 1.29 (6H, d), 2.17 (3H, d), 2.89–3.01 (3H, m), 3.30–3.41 (1H, m), 3.55–3.66 (1H, m), 3.98 (1H, t), 4.17 (2H, q), 4.74 (2H, d), 6.11 (1H, tm), 6.88 (2H, dm), 7.17 (2H, dm), 7.30 (2H, dm), 7.46–7.57 (6H, m). LCMS: 735 (M+249), 509 (M+Na), 249 (100%).

Example 104

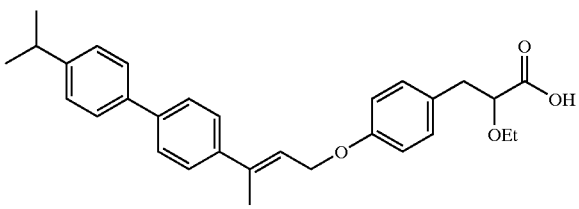

(E)-(S)-2-Ethoxy-3-{4-[3-(4'-isopropyl-biphenyl-4-yl)-but-2-enyloxy]-phenyl}-propionic acid The title compound was prepared from (E)-(S)-ethyl 2-ethoxy-3-{4-[3-(4'-isopropyl-biphenyl-4-yl)-but-2-enyloxy]-phenyl}-propionate (Example 103) (400 mg, 0.822 mmol) and sodium hydroxide (1M, 3.29 ml, 3.29 mmol) by a procedure analogous to that described in example 51, yielding (E)-(S)-2-ethoxy-3-{4-[3-(4'-isopropyl-biphenyl-4-yl)-but-2-enyloxy]-phenyl}-propionic acid (380 mg, 100%) as a beige coloured solid.

$^1$H NMR (300 MHz, CDCl$_3$) δ: 1.19 (3H, t), 1.29 (6H, d), 2.17 (3H, d), 2.89–3.01 (2H, m), 3.10 (1H, dd), 3.42–3.64 (2H, m), 4.06 (1H, dd), 4.74 (2H, d), 6.11 (1H, tm), 6.90 (2H, dm), 7.16 (2H, dm), 7.30 (2H, dm), 7.46–7.57 (6H, m), carboxylic acid proton not observed. LCMS: 707 (M+249), 481 (M+Na), 249 (100%).

Example 105

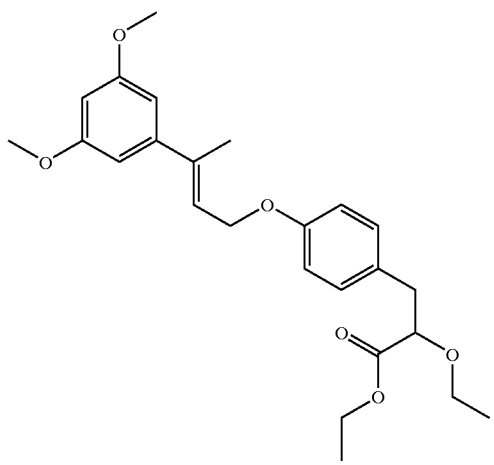

(E)-(S)-3-{4-[3-(3,5-Dimethoxy-phenyl)-but-2-enyloxy]-phenyl}-2-ethoxy-propionic acid ethyl ester The title compound was prepared from 3',5'-dimethoxyacetophenone (7.0 g, 0.0388 mol) by a sequence analogous to that described in example 3, yielding 0.165 g (35%) of (E)-(S)-3-{4-[3-(3,5-Dimethoxy-phenyl)-but-2-enyloxy]-phenyl}-2-ethoxy-propionic acid ethyl ester.

$^1$H NMR (200 MHz, CDCl$_3$) δ: 1.1–1.27 (6H, m), 2.97 (2H, d), 3.3–3.4 (1H, m), 3.52–3.7 (1H, m), 4.0 (1H, t), 4.15 (2H, q), 4.7 (2H, d),), 6.39 (1H, dd), 6.57 (2H, dd), 6.88 (2H, d), 7.17 (2H, d).

Example 106

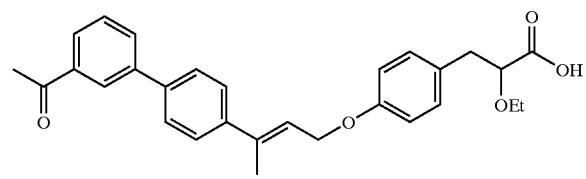

(E)-(S)-3-{4-[3-(3'-Acetyl-biphenyl-4-yl)-but-2-enyloxy]-phenyl}-2-ethoxy-propionic acid The title compound was prepared from (E)-(S)-ethyl 3-{4-[3-(3'-acetyl-biphenyl-4-yl)-but-2-enyloxy]-phenyl}-2-ethoxy-propionate (Example 105) (140 mg, 0.288 mmol) and sodium hydroxide (1M, 0.58 ml, 0.58 mmol) by a procedure analogous to that described in example 51, yielding (E)-(S)-3-{4-[3-(3'-acetyl-biphenyl-4-yl)-but-2-enyloxy]-phenyl}-2-ethoxy-propionic acid (33 mg, 25%) as a yellow coloured solid.

$^1$H NMR (300 MHz, CDCl$_3$) δ: 1.19 (3H, t), 2.18 (3H, d), 2.66 (3H, s), 2.97 (1H, dd), 3.10 (1H, dd), 3.41–3.65 (2H, m), 4.07 (1H, dd), 4.75 (2H, d), 6.13 (1H, tm), 6.90 (2H, dm), 7.17 (2H, dm), 7.49–7.63 (5H, m), 7.80 (1H, dm), 7.93 (1H, dm), 8.19 (1H, m), carboxylic acid proton not observed. LCMS: 707 (M+249), 481 (M+Na), 249 (100%).

Example 107

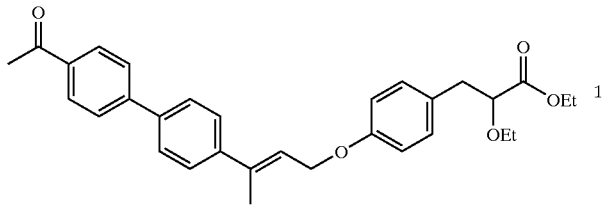

(E)-(S)-Ethyl 3-{4-[3-(4'-Acetyl-biphenyl-4-yl)-but-2-enyloxy]-phenyl}-2-ethoxy-propionate a)
(E)-3-(4-Iodophenyl)-but-2-en-1-ol was prepared by DIBAL-H reduction of (E)-ethyl 3-(4-iodophenyl)-but-2-enoate (example 91a) by a procedure analogous to that described in example 50b.

$^1$H NMR (300 MHz, CDCl$_3$) δ: 1.36 (1H, br s), 2.04 (3H, d), 2.66 (3H, s), 4.36 (2H, br d), 5.96 (1H, tm), 7.15 (2H, dm), 7.65 (2H, dm).

b)
The pale yellow solid, (E)-1-[4'-(3-hydroxy-1-methyl-propenyl)-biphenyl-4-yl]-ethanone was prepared from 4-acetylphenyl boronic acid and (E)-3-(4-iodophenyl)-but-2-en-1-ol by a procedure analogous to that described in example 54a.

$^1$H NMR (300 MHz, CDCl$_3$) δ: 1.55 (1H, br s), 2.12 (3H, d), 2.64 (3H, s), 4.41 (2H, d), 6.07 (1H, tm), 7.52 (2H, dm), 7.61 (2H, dm), 7.70 (2H, dm), 8.03 (2H, dm).

c)
The title compound (275 mg, 75%) was prepared from (E)-1-[4'-(3-hydroxy-1-methyl-propenyl)-biphenyl-4-yl]-ethanone (200 mg, 0.75 mmol) and (S)-ethyl 2-ethoxy-3-(4-hydroxyphenyl)-propionate (188 mg, 0.79 mmol) by a procedure analogous to that described in example 52c.

$^1$H NMR (300 MHz, CDCl$_3$) δ: 1.17 (3H, t), 1.23 (3H, t), 2.18 (3H, d), 2.64 (3H, s), 2.97 (2H, d), 3.30–3.42 (1H, m), 3.55–3.67 (1H, m), 3.98 (1H, t), 4.17 (2H, q), 4.75 (2H, d), 6.14 (1H, tm), 6.89 (2H, dm), 7.17 (2H, dm), 7.54 (2H, dm), 7.61 (2H, dm), 7.70 (2H, dm), 8.03 (2H, dm).

Example 108

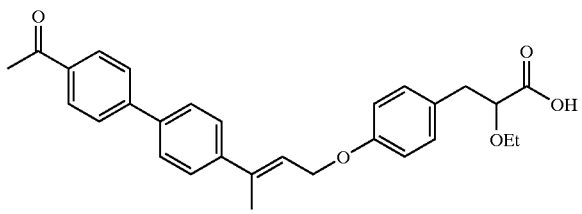

(E)-(S)-3-{4-[3-(4'-Acetyl-biphenyl-4-yl)-but-2-enyloxy]-phenyl}-2-ethoxy-propionic acid The title compound was prepared from (E)-(S)-ethyl 3-{4-[3-(4'-acetyl-biphenyl-4-yl)-but-2-enyloxy]-phenyl}-2-ethoxy-propionate (Example 107) (200 mg, 0.411 mmol) and sodium hydroxide (1M, 1.64 ml, 1.64 mmol) by a procedure analogous to that described in example 51, yielding (E)-(S)-3-{4-[3-(4'-acetyl-biphenyl-4-yl)-but-2-enyloxy]-phenyl}-2-ethoxy-propionic acid (70 mg, 37%) as a yellow coloured solid.

$^1$H NMR (300 MHz, CDCl$_3$) δ: 1.19 (3H, t), 2.18 (3H, d), 2.64 (3H, s), 2.97 (1H, dd), 3.11 (1H, dd), 3.45–3.65 (2H, m), 4.08 (1H, dd), 4.75 (2H, d), 6.14 (1H, tm), 6.90 (2H, dm), 7.17 (2H, dm), 7.54 (2H, dm), 7.61 (2H, dm), 7.70 (2H, dm), 8.03 (2H, dm), carboxylic acid proton not observed. LCMS: 707 (M+249), 459 (M+H), 249 (100%).

Example 109

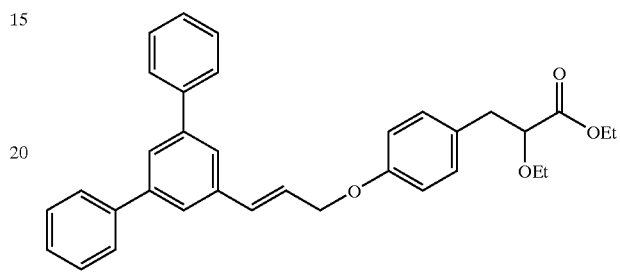

(E)-(S)-Ethyl 2-Ethoxy-3-[4-(3-[1,1';3',1"]terphenyl-5'-yl-allyloxy)-phenyl]-propionate a)
Sodium (0.90 g, 39.1 mmol) was added to ethanol (50 ml) at 20° C. and the mixture stirred until the metal had fully reacted. Triethyl phosphonoacetate (10.1 g, 45 mmol) was added, the mixture stirred. for 10 min, then a solution of 3,5-dibromobenzaldehyde (7.92 g, 30 mmol) in ethanol (50 ml) was added and the reaction mixture heated to 80° C. under reflux for 72 h. The solution was cooled, the ethanol evaporated and the resulting yellow residue partitioned between 1N HCl (100 ml) and ethyl acetate (100 ml). The aqueous layer was collected and further extracted with ethyl acetate (3×100 ml). The organic layers were combined, washed with brine, dried (MgSO$_4$) and evaporated to a yellow solid, which was purified by column chromatography on silica gel (2% diethyl ether in n-heptane eluent) to give the product, (E)-ethyl 3-(3,5-dibromophenyl)-acrylate, as a colourless solid; 4.54 g (45%).

Mpt. 80–82° C. $^1$H NMR (300 MHz, CDCl$_3$) δ: 1.33 (3H, t), 4.27 (2H, q), 6.42 (1H, d), 7.51 (1H, d), 7.58 (2H, d), 7.66 (1H, t). MS: 336/334/332 (M$^+$), 308/306/304, 291/289/287 (100%, M-Oet), 180/182.

b)
The colourless solid, (E)-ethyl 3-[1,1';3',1"]terphenyl-5'-yl-acrylate was prepared from (E)-ethyl 3-(3,5-dibromophenyl)-acrylate and phenylboronic acid by a procedure analogous to that described in example 52a.

Mpt. 78.5–81.5° C. $^1$H NMR (300 MHz, CDCl$_3$) δ: 1.36 (3H, t), 4.29 (2H, q), 6.58 (1H, d), 7.33–7.54 (6H, m), 7.60–7.68 (4H, m), 7.72 (2H, d), 7.81 (1H, t), 7.82 (1 H, d). MS: 328 (100%, M$^+$), 283, 256, 252, 241, 239.

c)
The colourless solid (E)-3-[1,1';3',1"]terphenyl-5'-yl-prop-2-en-1-ol was prepared by DIBAL-H reduction of (E)-ethyl 3-[1,1';3',1"]terphenyl-5'-yl-acrylate by a procedure analogous to that described for example 52b.

Mpt. 140–141.5° C. $^1$H NMR (300 MHz, CDCl$_3$) δ: 1.54 (1H, br s), 4.38 (2H, d), 6.50 (1H, dt), 6.75 (1H, d), 7.30–7.52 (6H, m), 7.53–7.73 (7H, m). MS: 286 (M$^+$), 258 (100%), 243, 230, 165, 91, 77.

d)

The title compound (426 mg, 80%) was prepared from (E)-3-[1,1';3',1"]terphenyl-5'-yl-prop-2-en-1-ol (300 mg, 1.05 mmol) and (S)-ethyl 2-ethoxy-3-(4-hydroxyphenyl)-propionate (262 mg, 1.10 mmol) by a procedure analogous to that described in example 52c.

¹H NMR (300 MHz, CDCl₃) δ: 1.16 (3H, t), 1.22 (3H, t), 2.96 (2H, d), 3.29–3.41 (1H, m), 3.54–3.66 (1H, m), 3.98 (1H, t), 4.16 (2H, q), 4.73 (2H, d), 6.54 (1H, dt), 6.85 (1H, d), 6.90 (2H, dm), 7.17 (2H, dm), 7.30–7.50 (6H, m), 7.55–7.71 (7H, m). LCMS: 775 (M+269), 729 (100%, M+269-EtOH), 461 (M+H-EtOH), 269.

Example 110

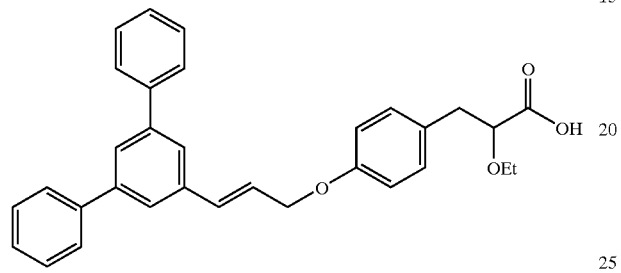

(E)-(S)-2-Ethoxy-3-[4-(3-[1,1';3',1"]terphenyl-5'-yl-allyloxy)-phenyl]-propionic acid The title compound was prepared from (E)-(S)-ethyl 2-ethoxy-3-[4-(3-[1,1';3',1"]terphenyl-5'-yl-allyloxy)-phenyl]-propionate (Example 109) (405 mg, 0.8 mmol) and sodium hydroxide (1M, 1.6 ml, 1.6 mmol) by a procedure analogous to that described in example 51, yielding (E)-(S)-2-ethoxy-3-[4-(3-[1,1';3',1"]terphenyl-5'-yl-allyloxy)-phenyl]-propionic acid (352 mg, 92%) as a colourless glass.

¹H NMR (300 MHz, CDCl₃) δ: 1.18 (3H, t), 2.97 (1H, dd), 3.09 (1H, dd), 3.41–3.53 (1H, m), 3.53–3.65 (1H, m), 4.07 (1H, dd), 4.73 (2H, dd), 6.54 (1H, dt), 6.85 (1H, dm), 6.92 (2H, dm), 7.17 (2H, dm), 7.32–7.50 (6H, m), 7.55–7.71 (7H, m), carboxylic acid proton not observed. LCMS: 747 (M+269), 501 (M+Na), 496 (M+NH₄), 269 (100%).

Example 111

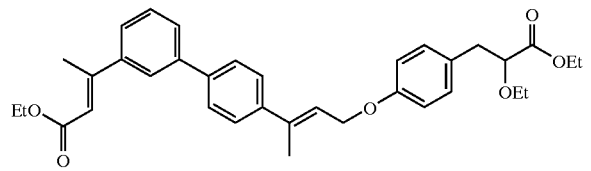

(E,E)-(S)-Ethyl 3-(4'-{3-[4-(2-Ethoxy-2-ethoxycarbonyl-ethyl)-phenoxy]-1-methyl-propenyl}-biphenyl-3-yl)-but-2-enoate a)

The yellow oil (E,E)-ethyl 3-[4'-(3-hydroxy-1-methyl-propenyl)-biphenyl-3-yl]-but-2-enoate was prepared from (E)-1-[4'-(3-hydroxy-1-methyl-propenyl)-biphenyl-3-yl]-ethanone (example 105a) and triethyl phosphonoacetate by a reaction analogous to that described for example 50a.

¹H NMR (300 MHz, CDCl₃) δ: 1.33 (3H, t), 1.37 (1H, br t), 2.13 (3H, d), 2.62 (3H, d), 4.23 (2H, q), 4.41 (2H, br t), 6.06 (1H, tm), 6.19 (1H, m), 7.40–7.62 (7H, m), 7.68 (1H, m). MS: 336 (M⁺), 334, 308, 293, 43 (100%).

b)

The title compound (230 mg, 58%) was prepared from (E,E)-ethyl 3-[4'-(3-hydroxy-1-methyl-propenyl)-biphenyl-3-yl]-but-2-enoate (235 mg, 0.70 mmol) and (S)-ethyl 2-ethoxy-3-(4-hydroxyphenyl)-propionate (175 mg, 0.73 mmol) by a procedure analogous to that described in example 52c.

¹H NMR (300 MHz, CDCl₃) δ: 1.17 (3H, t), 1.23 (3H, t), 1.33 (3H, t), 2.17 (3H, d), 2.62 (3H, d), 2.96 (2H, d), 3.30–3.42 (1H, m), 3.55–3.67 (1H, m), 3.98 (1H, t), 4.17 (2H, q), 4.23 (2H, q), 4.75 (2H, d), 6.13 (1H, tm), 6.20 (1H, m), 6.89 (2H, dm), 7.17 (2H, dm), 7.42–7.62 (7H, m), 7.67 (1H, m). MS: 556 (M⁺), 319 (100%).

Example 112

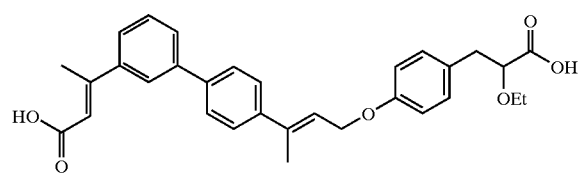

(E,E)-(S)-3-(4'-{3-[4-(2-Carboxy-2-ethoxy-ethyl)-phenoxy]-1-methyl-propenyl}-biphenyl-3-yl)-but-2-enoic acid The title compound was prepared from (E,E)-(S)-ethyl 3-(4'-{3-[4-(2-ethoxy-2-ethoxycarbonyl-ethyl)-phenoxy]-1-methyl-propenyl}-biphenyl-3-yl)-but-2-enoate (example 111) (190 mg, 0.34 mmol) and sodium hydroxide (1M, 1.4 ml, 1.4 mmol) by a procedure analogous to that described in example 51, yielding (E,E)-(S)-3-(4'-{3-[4-(2-carboxy-2-ethoxy-ethyl)-phenoxy]-1-methyl-propenyl}-biphenyl-3-yl)-but-2-enoic acid (135 mg, 79%) as a colourless solid.

¹H NMR (300 MHz, CDCl₃) δ: 1.19 (3H, t), 2.18 (3H, m), 2.64 (3H, s), 3.01 (1H, dd), 3.08 (1H, dd), 3.40–3.70 (2H, m), 4.07 (1H, dd), 4.75 (2H, dd), 6.12 (1H, br m), 6.23 (1H, s), 6.89 (2H, dm), 7.18 (2H, dm), 7.40–7.70 (8H, m), carboxylic acid protons not observed.

Example 113

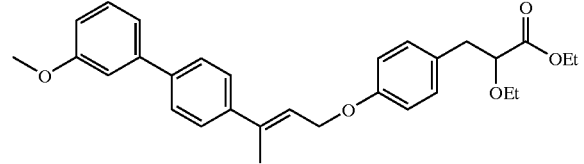

(E)-(S)-Ethyl 2-Ethoxy-3-{4-[3-(3'-methoxy-biphenyl-4-yl)-but-2-enyloxy]-phenyl}-propionate a)

The colourless oil (E)-ethyl 3-(3'-methoxy-biphenyl-4-yl)-but-2-enoate was prepared from (E)-ethyl 3-(4-bromophenyl)-but-2-enoate (example 50a) and 3-methoxyphenyl boronic acid by a procedure analogous to that described in example 52a.

¹H NMR (300 MHz, CDCl₃) δ: 1.33 (3H, t), 2.61 (3H, d), 3.87 (3H, s), 4.23 (2H, q), 6.20 (1H, m), 6.91 (1H, ddd), 7.13 (1H, dd), 7.19 (1H, ddd), 7.37 (1H, dd), 7.51–7.62 (4H, m). MS: 296 (100%, M⁺), 281, 267, 251, 224. Microanalysis Calculated % C, 77.00; H, 6.80. Found % C, 77.02; H, 6.93.

b)

The colourless solid (E)-3-(3'-methoxy-biphenyl-4-yl)-but-2-en-1-ol was prepared by DIBAL-H reduction of (E)-ethyl 3-(3'-methoxy-biphenyl-4-yl)-but-2-enoate as described for example 52b.

Mpt. 62–68° C. $^1$H NMR (300 MHz, CDCl$_3$) δ: 1.40 (1H, br s), 2.12 (3H, d), 3.87 (3H, s), 4.39 (2H, d), 6.05 (1H, tm), 6.89 (1H, ddd), 7.13 (1H, dd), 7.19 (1H, ddd), 7.35 (1H, dd), 7.49 (2H, dm), 7.56 (2H, dm). MS: 254 (M$^+$), 239, 211 (100%).

c)

The title compound (280 mg, 59%) was prepared as a colourless solid from (E)-3-(3'-methoxy-biphenyl-4-yl)-but-2-en-1-ol (254 mg, 1.00 mmol) and (S)-ethyl 2-ethoxy-3-(4-hydroxyphenyl)-propionate (250 mg, 1.05 mmol) by a procedure analogous to that described in example 52c.

$^1$H NMR (300 MHz, CDCl$_3$) δ: 1.17 (3H, t), 1.22 (3H, t), 2.17 (3H, d), 2.96 (2H, d), 3.30–3.42 (1H, m), 3.55–3.67 (1H, m), 3.87 (3H, s), 3.98 (1H, t), 4.17 (2H, q), 4.74 (2H, d), 6.12 (1H, tm), 6.85–6.92 (3H, m), 7.11–7.22 (4H, m), 7.35 (1H, dd), 7.47–7.59 (4H, m). MS: 474 (M$^+$), 237 (100%). Microanalysis Calculated % C, 75.92; H, 7.22. Found % C, 76.04; H, 7.39.

Example 114

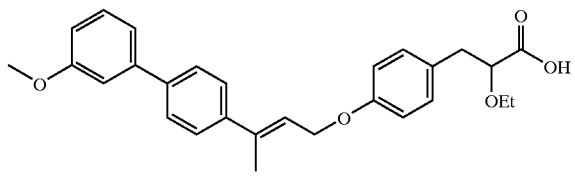

(E)-(S)-2-Ethoxy-3-{4-[3-(3'-methoxy-biphenyl-4-yl)-but-2-enyloxy]-phenyl}-propionic acid The title compound was prepared from (E)-(S)-ethyl 2-ethoxy-3-{4-[3-(3'-methoxy-biphenyl-4yl)-but-2-enyloxy]-phenyl}-propionate (example 113) (230 mg, 0.49 mmol) and sodium hydroxide (1M, 0.97 ml, 0.97 mmol) by a procedure analogous to that described in example 51, yielding (E)-(S)-2-ethoxy-3-{4-[3-(3'-methoxy-biphenyl-4-yl)-but-2-enyloxy]-phenyl}-propionic acid (183 mg, 85%) as a colourless solid.

$^1$H NMR (300 MHz, CDCl$_3$) δ: 1.18 (3H, t), 2.17 (3H, d), 2.97 (1H, dd), 3.10 (1H, dd), 3.41–3.53 (1H, m), 3.53–3.65 (1H, m), 3.87 (3H, s), 4.07 (1H, dd), 4.74 (2H, dd), 6.11 (1H, tm), 6.86–6.93 (3H, m), 7.11–7.22 (4H, m), 7.35 (1H, dd), 7.47–7.59 (4H, m), carboxylic acid proton not observed. LCMS: 683 (M+237), 469 (M+Na), 237 (100%).

Example 115

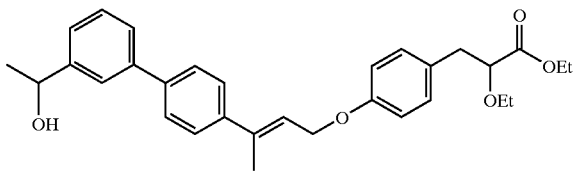

(E)-(S,S/R)-Ethyl 2-Ethoxy-3-(4-{3-[3'-(1-hydroxy-ethyl)-biphenyl-4-yl]-but-2-enyloxy}-phenyl)-propionate a)

The colourless solid (E)-(S/R)-3-[3'-(1-hydroxy-ethyl)-biphenyl-4-yl]-but-2-en-1-ol was prepared by DIBAL-H reduction of (E)-1-[4'-(3-hydroxy-1-methyl-propenyl)-biphenyl-3-yl]-ethanone (example 105a) by a procedure analogous to that described in example 52b.

Mpt. 94–100° C. $^1$H NMR (300 MHz, DMSO-d$_6$) δ: 1.37 (3H, d), 2.02 (3H, d), 4.18 (2H, br dd), 4.75 (1H, br t, OH), 4.78 (1H, dq), 5.21 (1H, d, OH), 5.98 (1H, tm), 7.33 (1H, dm), 7.40 (1H, dd), 7.48–7.54 (3H, m), 7.60–7.66 (3H, m). MS: 268 (100%, M$^+$), 253, 235, 225. Microanalysis Calculated % C, 80.56; H, 7.51. Found % C, 80.21; H, 7.78.

b)

The title compound (490 mg, 57%) was prepared as a colourless oil from (E)-(S/R)-3-[3'-(1-hydroxy-ethyl)-biphenyl-4-yl]-but-2-en-1-ol (500 mg, 1.86 mmol) and (S)-ethyl 2-ethoxy-3-(4-hydroxyphenyl)-propionate (422 mg, 1.77 mmol) by a procedure analogous to that described in example 52c.

$^1$H NMR (300 MHz, CDCl$_3$) δ: 1.17 (3H, t), 1.22 (3H, t), 1.56 (3H, d), 1.89 (1H, d, OH), 2.18 (3H, d), 2.97 (2H, d), 3.30–3.42 (1H, m), 3.54–3.66 (1H, m), 3.98 (1H, t), 4.17 (2H, q), 4.75 (2H, d), 4.99 (1H, dq), 6.12 (1H, tm), 6.85 (2H, dm), 7.18 (2H, dm), 7.32–7.48 (2H, m), 7.48–7.67 (6H, m).

Example 116

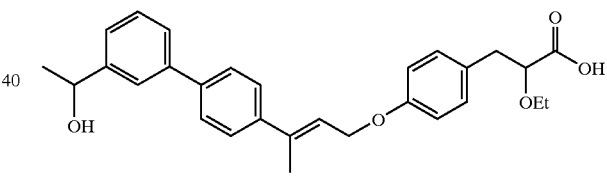

(E)-(S,S/R)-2-Ethoxy-3-(4-{3-[3'-(1-hydroxy-ethyl)-biphenyl-4-yl]-but-2-enyloxy}-phenyl)-propionic acid The title compound was prepared from (E)-(S,S/R)-ethyl 2-ethoxy-3-(4-{3-[3'-(1-hydroxy-ethyl)-biphenyl-4-yl]-but-2-enyloxy}-phenyl)-propionate (example 115) (460 mg, 0.94 mmol) and sodium hydroxide (1M, 1.9 ml, 1.9 mmol) by a procedure analogous to that described in example 51, yielding (E)-(S,S/R)-ethyl 2-ethoxy-3-(4-{3-[3'-(1-hydroxy-ethyl)-biphenyl-4-yl]-but-2-enyloxy}-phenyl)-propionic acid (434 mg, 100%) as a colourless gum.

$^1$H NMR (300 MHz, CDCl$_3$) δ: 1.18 (3H, t), 1.55 (3H, d), 2.17 (3H, d), 2.96 (1H, dd), 3.09 (1H, dd), 3.41–3.53 (1H, m), 3.54–3.66 (1H, m), 4.06 (1H, dd), 4.75 (2H, d), 4.98 (1H, q), 6.12 (1H, tm), 6.90 (2H, dm), 7.17 (2H, dm), 7.32–7.46 (2H, m), 7.47–7.63 (6H, m), carboxylic acid proton not observed.

Example 117

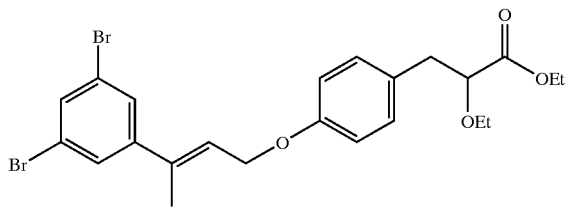

(E)-(S)-Ethyl 3-{4-[3-(3,5-Dibromophenyl)-but-2-enyloxy]-phenyl}-2-ethoxy-propionate a)

Sodium (0.49 g, 21.3 mmol) was added to ethanol (50 ml) at room temperature and the mixture stirred until the metal had fully reacted. Triethyl phosphonoacetate (5.49 g, 24.5 mmol) was added, the solution stirred for 15 min, then an ethanol (100 ml) solution of 3,5-dibromoacetophenone (4.60 g, 16.6 mol) was added and the reaction mixture heated to 80° C. under reflux for 72 h. The solution was cooled, the ethanol evaporated and the resulting orange residue partitioned between 1N HCl (150 ml) and ethyl acetate (150 ml). The aqueous layer was collected and further extracted with ethyl acetate (2×100 ml). The organic layers were combined, washed with brine, dried (MgSO$_4$) and evaporated to an orange/yellow gum, which was purified by column chromatography on silica gel (3% diethyl ether in n-heptane eluent) to give the product, (E)-ethyl 3-(3,5-dibromophenyl)-but-2-enoate, as a colourless wax; 4.06 g (70%).

$^1$H NMR (300 MHz, CDCl$_3$) δ: 1.32 (3H, t), 2.51 (3H, d), 4.22 (2H, q), 6.09 (1H, m), 7.52 (2H, d), 7.64 (1H, t). MS: 350/348/346 (M$^+$), 304/302/300 (M-EtOH), 115 (100%). Microanalysis Calculated % C, 41.41; H, 3.48; Br, 45.92. Found % C, 41.75; H, 3.52; Br, 45.62.

b)

(E)-Ethyl 3-(3,5-dibromophenyl)-but-2-enoate was reduced with DIBAL-H by a procedure analogous to that described in example 50b, to give the colourless oil (E)-3-(3,5-dibromophenyl)-but-2-en-1-ol.

$^1$H NMR (300 MHz, CDCl$_3$) δ: 1.64 (1H, br s), 2.01 (3H, d), 4.36 (2H, d), 5.96 (1H, tm), 7.46 (2H, d), 7.54 (1H, t). MS: 308/306/304 (M$^+$), 293/291/289 (M-Me), 266/264/262, 227/225/223, 131, 128, 115 (100%), 102.

c)

The title compound (851 mg, 81%) was prepared from (E)-3-(3,5-dibromo-phenyl)-but-2-en-1-ol (612 mg, 2.0 mmol) and (S)-ethyl 2-ethoxy-3-(4-hydroxyphenyl)-propionate (500 mg, 2.10 mmol) by a procedure analogous to that described in example 52c.

$^1$H NMR (300 MHz, CDCl$_3$) δ: 1.17 (3H, t), 1.23 (3H, t), 2.09 (3H, d), 2.96 (2H, d), 3.30–3.42 (1H, m), 3.54–3.66 (1H, m), 3.98 (1H, t), 4.17 (2H, q), 4.69 (2H, d), 6.04 (1H, tm), 6.85 (2H, dm), 7.16 (2H, dm), 7.48 (2H, d), 7.57 (1H, t). LCMS: 551/549/547 (100%, M+Na), 546/544/542 (M+NH$_4$), 483/481/479 (M+H-EtOH).

Example 118

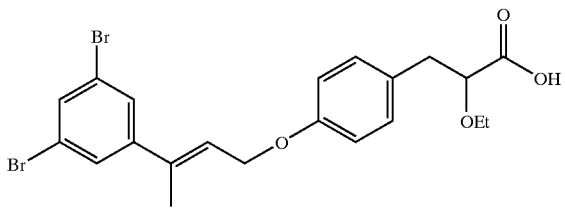

(E)-(S)-3-{4-[3-(3,5-Dibromophenyl)-but-2-enyloxy]-phenyl}-2-ethoxy-propionic acid The title compound was prepared from (E)-(S)-ethyl 3-{4-[3-(3,5-dibromophenyl)-but-2-enyloxy]-phenyl}-2-ethoxy-propionate (example 117) (840 mg, 1.60 mmol) and sodium hydroxide (1M, 16 ml, 16 mmol) by a procedure analogous to that described in example 51, yielding (E)-(S)-3-{4-[3-(3,5-dibromophenyl)-but-2-enyloxy]-phenyl}-2-ethoxy-propionic acid (781 mg, 98%) as a colourless gum.

$^1$H NMR (300 MHz, CDCl$_3$) δ: 1.19 (3H, t), 2.08 (3H, d), 2.96 (1H, dd), 3.09 (1H, dd), 3.41–3.53 (1H, m), 3.55–3.67 (1H, m), 4.07 (1H, dd), 4.70 (2H, d), 6.04 (1H, tm), 6.87 (2H, dm), 7.17 (2H, dm), 7.48 (2H, d), 7.58 (1H, t), carboxylic acid proton not observed. LCMS: 523/521/519 (100%, M+Na), 518/516/514 (M+NH$_4$), 455/453/451 (M+H-EtOH), 291/289/287.

Example 119

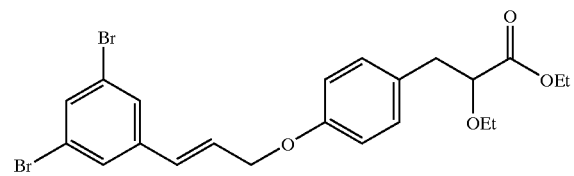

(E)-(S)-Ethyl 3-{4-[3-(3,5-Dibromophenyl)-allyloxy]-phenyl}-2-ethoxy-propionate a)

(E)-Ethyl 3-(3,5-dibromophenyl)-acrylate (example109a) was reduced with DIBAL-H by a procedure analogous to that described in example 50b, to give the colourless solid (E)-3-(3,5-dibromophenyl)-prop-2-en-1-ol.

$^1$H NMR (300 MHz, CDCl$_3$) δ: 1.52 (1H, t, OH), 4.35 (2H, ddd), 6.36 (1H, dt), 6.50 (1H, dm), 7.44 (2H, d), 7.53 (1H, t). LCMS: 277/275/273 (100%, M+H-H$_2$O), 196/194 (M+H-H$_2$O—Br), 100.

b)

The title compound (780 mg, 78%) was prepared from (E)-3-(3,5-dibromophenyl)-prop-2-en-1-ol (584 mg, 2.0 mmol) and (S)-ethyl 2-ethoxy-3-(4-hydroxyphenyl)-propionate (500 mg, 2.10 mmol) by a procedure analogous to that described in example 52c.

$^1$H NMR (300 MHz, CDCl$_3$) δ: 1.17 (3H, t), 1.22 (3H, t), 2.96 (2H, d), 3.30–3.42 (1H, m), 3.55–3.67 (1H, m), 3.97 (1H, t), 4.17 (2H, q), 4.68 (2H, dd), 6.41 (1H, dt), 6.59 (1H, dm), 6.86 (2H, dm), 7.17 (2H, dm), 7.46 (2H, d), 7,53 (1H, t).

Example 120

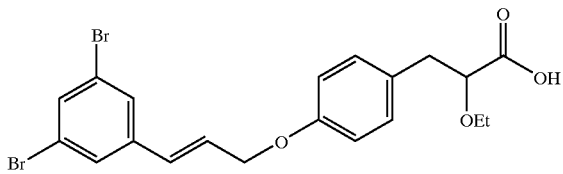

(E)-(S)-3-{4-[3-(3,5-Dibromophenyl)-allyloxy]-phenyl}-2-ethoxy-propionic acid

The title compound was prepared from (E)-(S)-ethyl 3-(4-[3-(3, 5-dibromophenyl)-allyloxy]-phenyl}-2-ethoxy-propionate (example 119) (512 mg, 1.0 mmol) and sodium hydroxide (1M, 10 ml, 10 mmol) by a procedure analogous to that described in example 51, yielding (E)-(S)-3-{4-[3-(3,5-dibromophenyl)-allyloxy]-phenyl}-2-ethoxy-propionic acid (96 mg, 20%) as a colourless gum.

$^1$H NMR (300 MHz, CDCl$_3$) δ: 1.19 (3H, t), 2.97 (1H, dd), 3.09 (1H, dd), 3.40–3.66 (2H, m), 4.06 (1H, dd), 4.68 (2H, dd), 6.42 (1H, dt), 6.59 (1H, dm), 6.88 (2H, dm), 7.18 (2H, dm), 7.46 (2H, d), 7.58 (1H, t), carboxylic acid proton not observed. LCMS: 509/507/505 (M+Na), 504/502/500 (100%, M+NH$_4$), 441/439/437 (M+H-EtOH), 277/275/273.

Example 121

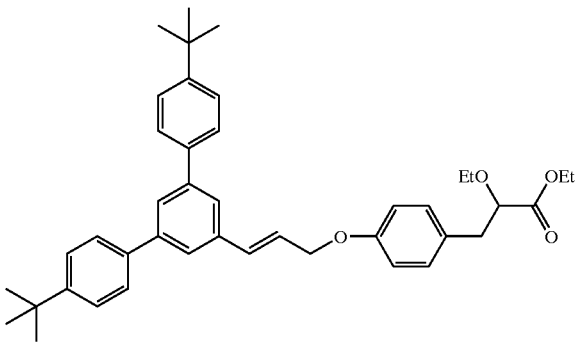

(E)-(S)-Ethyl 3-{4-[3-(4,4"-Di-tert-butyl-[1,1';3',1"]terphenyl-5'-yl)-allyloxy]-phenyl}-2-ethoxy-propionate a)
The colourless glass, (E)-ethyl 3-(4,4"-di-tert-butyl-[1,1';3',1"]terphenyl-5'-yl)-acrylate was prepared from (E)-ethyl 3-(3,5-dibromophenyl)-acrylate (example 109a) and 4-tert-butylphenylboronic acid by a procedure analogous to that described in example 52a.

$^1$H NMR (300 MHz, CDCl$_3$) δ: 1.36 (3H, t), 1.38 (18H, s), 4.29 (2H, q), 6.55 (1H, d), 7.43–7.52 (4H, m), 7.52–7.61 (4H, m), 7.70 (2H, d), 7.81 (1H, t), 7.82 (1H, d). MS: 440 (M$^+$), 425 (100%, M-Me), 205.

b)
The colourless gum (E)-3-(4,4"-di-tert-butyl-[1,1';3',1"]terphenyl-5'-yl)-prop-2-en-1-ol was prepared by DIBAL-H reduction of (E)-ethyl 3-(4,4"-di-tert-butyl-[1,1';3',1"]terphenyl-5'-yl)-acrylate by a procedure analogous to that described for example 52b.

$^1$H NMR (300 MHz, CDCl$_3$) δ: 1.37 (18H, s), 1.48 (1H, br t), 4.37 (2H, m), 6.49 (1H, dt), 6.75 (1H, dm), 7.45–7.52 (4H, m), 7.54–7.61 (6H, m), 7.68 (1H, t). LCMS: 779 (M+381), 761 (779-H$_2$O), 437, 421 (M+Na), 399 (M+H, 381 (100%, M+H-H$_2$O).

c)
The title compound (368 mg, 79%) was prepared from (E)-3-(4,4"-di-tert-butyl-[1,1';3',1"]terphenyl-5'-yl)-prop-2-en-1-ol (300 mg, 0.75 mmol) and (S)-ethyl 2-ethoxy-3-(4-hydroxyphenyl)-propionate (188 mg, 0.79 mmol) by a procedure analogous to that described in example 52c.

$^1$H NMR (300 MHz, CDCl$_3$) δ: 1.17 (3H, t), 1.22 (3H, t), 1.37 (18H, s), 2.96 (2H, d), 3.30–3.43 (1H, m), 3.54–3.67 (1H, m), 3.98 (1H, t), 4.16 (2H, q), 4.72 (2H, d), 6.52 (1H, dt), 6.85 (1H, d), 6.90 (2H, dm), 7.18 (2H, dm), 7.44–7.52 (4H, m), 7.54–7.63 (6H, m), 7.69 (1H, m). LCMS: 641 (100%, M+Na), 636 (M+NH$_4$), 381.

Example 122

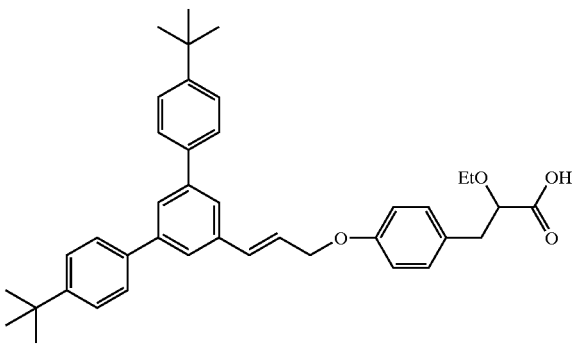

(E)-(S)-3-{4-[3-(4,4"-Di-tert-butyl-[1,1';3',1"]terphenyl-5'-yl)-allyloxy]-phenyl}-2-ethoxy-propionic acid The title compound was prepared from (E)-(S)-ethyl 3-{4-[3-(4,4"-di-tert-butyl-[1,1';3',1"]terphenyl-5'-yl)-allyloxy]-phenyl}-2-ethoxy-propionate (example 121) (345 mg, 0.56 mmol) and sodium hydroxide (1M, 1.1 ml, 1.1 mmol) by a procedure analogous to that described in example 51, yielding (E)-(S)-3-{4-[3-(4,4"-di-tert-butyl-[1,1';3',1"]terphenyl-5'-yl)-allyloxy]-phenyl}-2-ethoxy-propionic acid (284 mg, 86%) as a colourless foam.

$^1$H NMR (300 MHz, CDCl$_3$) δ: 1.18 (3H, t), 1.38 (18H, s), 2.97 (1H, dd), 3.10 (1H, dd), 3.41–3.65 (2H, m), 4.07 (1H, dd), 4.72 (2H, dm), 6.52 (1H, dt), 6.85 (1H, d), 6.92 (2H, dm), 7.17 (2H, dm), 7.44–7.52 (4H, m), 7.55–7.62 (6H, m), 7.69 (1H, m), carboxylic acid proton not observed.

Example 123

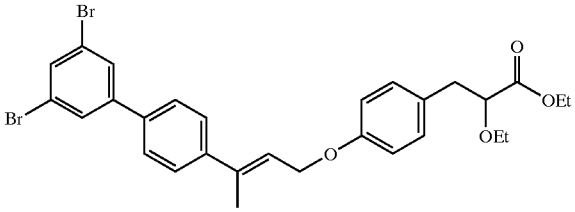

(E)-(S)-Ethyl 3-{4-[3-(3',5'-Dibromo-biphenyl-4-yl)-but-2-enyloxy]-phenyl}-2-ethoxy-propionate a)
The colourless gum (E)-ethyl 3-(3',5'-dibromo-biphenyl-4-yl)-but-2-enoate was prepared from (E)-ethyl 3-(4-iodophenyl)-but-2-enoate (example 91a) and 3,5-dibromobenzene boronic acid by a procedure analogous to that described in example 52a.

¹H NMR (300 MHz, CDCl₃) δ: 1.33 (3H, t), 2.61 (3H, d), 4.22 (2H, q), 6.20 (1H, m), 7.44–7.80 (7H, m). LCMS: 427/425/423 (100%, M+H), 381/379/377 (M+H-EtOH).

b)

The colourless gum (E)-3-(3',5'-dibromo-biphenyl-4-yl)-but-2-en-1-ol was prepared by DIBAL-H reduction of (E)-ethyl 3-(3',5'-dibromo-biphenyl-4-yl)-but-2-enoate as described for example 52b, with the purification of the product being carried out by preparative HPLC.

¹H NMR (300 MHz, CDCl₃) δ: 1.45 (1H, br s), 2.12 (3H, d), 4.41 (2H, d), 6.05 (1H, tm), 7.45–7.54 (4H, m), 7.62 (1H, t), 7.66 (2H, d). LCMS: 367/365/363 (100%, M+H-H₂O), 286/284.

c)

The title compound (177 mg, 83%) was prepared as a colourless gum from (E)-3-(3',5'-dibromo-biphenyl-4-yl)-but-2-en-1-ol (135 mg, 0.35 mmol) and (S)-ethyl 2-ethoxy-3-(4-hydroxyphenyl)-propionate (90 mg, 0.38 mmol) by a procedure analogous to that described in example 52c.

¹H NMR (300 MHz, CDCl₃) δ: 1.17 (3H, t), 1.23 (3H, t), 2.16 (3H, d), 2.96 (2H, d), 3.31–3.43 (1H, m), 3.55–3.67 (1H, m), 3.98 (1H, t), 4.17 (2H, q), 4.74 (2H, d), 6.13 (1H, tm), 6.88 (2H, dm), 7.17 (2H, dm), 7.45–7.56 (4H, m), 7.63 (1H, t), 7.66 (2H, d). LCMS: 627/625/623 (100%, M+Na), 365.

Example 124

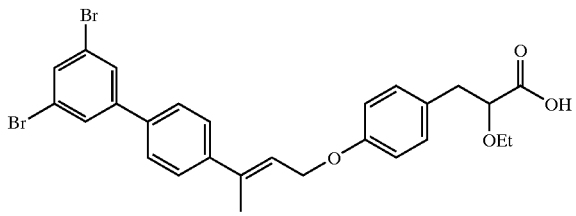

(E)-(S)-3-{4-[3-(3',5'-Dibromo-biphenyl-4-yl)-but-2-enyloxy]-phenyl}-2-ethoxy-propionic acid The title compound was prepared from (E)-(S)-ethyl 3-{4-[3-(3',5'-dibromo-biphenyl-4-yl)-but-2-enyloxy]-phenyl}-2-ethoxy-propionate (example 123) (110 mg, 0.18 mmol) and sodium hydroxide (1M, 1.0 ml, 1.0 mmol) by a procedure analogous to that described in example 51, yielding (E)-(S)-3-{4-[3-(3',5'-dibromo-biphenyl-4-yl)-but-2-enyloxy]-phenyl}-2-ethoxy-propionic acid (90 mg, 86%) as a colourless gum.

¹H NMR (300 MHz, CDCl₃) δ: 1.20 (3H, t), 2.18 (3H, d), 2.99 (1H, dd), 3.12 (1H, dd), 3.43–3.68 (2H, m), 4.08 (1H, dd), 4.75 (2H, d), 6.13 (1H, tm), 6.91 (2H, dm), 7.19 (2H, dm), 7.45–7.60 (4H, m), 7.60–7.74 (3H, m), carboxylic acid proton not observed. LCMS: 599/597/595 (100%, M+Na), 365.

Example 125

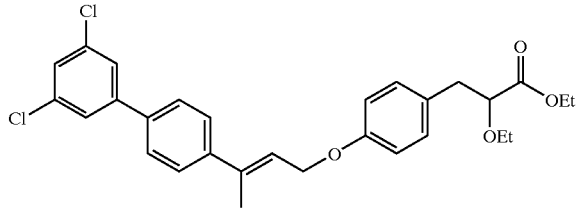

(E)-(S)-Ethyl 3-{4-[3-(3',5'-Dichloro-biphenyl-4-yl)-but-2-enyloxy]-phenyl}-2-ethoxy-propionate a)

The colourless solid (E)-ethyl 3-(3',5'-dichloro-biphenyl-4-yl)-but-2-enoate was prepared from (E)-ethyl 3-(4-iodophenyl)-but-2-enoate (example 91 a) and 3,5-dichlorobenzene boronic acid by a procedure analogous to that described in example 52a.

Mpt. 96.3–97.3° C. ¹H NMR (300 MHz, CDCl₃) δ: 1.33 (3H, t), 2.61 (3H, d), 4.23 (2H, q), 6.19 (1H, m), 7.35 (1H, t), 7.47 (2H, d), 7.51–7.61 (4H, m). LCMS: 335/337/339 (100%, M+H), 289/291/293 (M+H-EtOH). Microanalysis Calculated % C, 64.49; H, 4.81; Cl, 21.15. found C, 64.41; H, 4.80; Cl, 20.80.

b)

The colourless oil (E)-3-(3',5'-dichloro-biphenyl-4-yl)-but-2-en-1-ol was prepared by DIBAL-H reduction of (E)-ethyl 3-(3',5'-dichloro-biphenyl-4-yl)-but-2-enoate as described for example 52b.

¹H NMR (300 MHz, CDCl₃) δ: 1.39 (1H, br s), 2.12 (3H, d), 4.40 (2H, d), 6.05 (1H, tm), 7.33 (1H, t), 7.46 (2H, d), 7.45–7.65 (4H, m). MS: 296/294/292 (100%, M⁺), 281/279/277 (M-Me), 278/276/274 (M-H₂O), 253/251/249.

c)

The title compound (794 mg, 77%) was prepared as a colourless gum from (E)-3-(3',5'-dichloro-biphenyl-4-yl)-but-2-en-1-ol (586 mg, 2.0 mmol) and (S)-ethyl 2-ethoxy-3-(4-hydroxyphenyl)-propionate (500 mg, 2.10 mmol) by a procedure analogous to that described in example 52c.

¹H NMR (300 MHz, CDCl₃) δ: 1.17 (3H, t), 1.23 (3H, t), 2.17 (3H, d), 2.96 (2H, d), 3.30–3.42 (1H, m), 3.55–3.67 (1H, m), 3.98 (1H, t), 4.17 (2H, q), 4.74 (2H, d), 6.13 (1H, tm), 6.88 (2H, dm), 7.18 (2H, dm), 7.33 (1H, t), 7.46 (2H, d), 7.48–7.54 (4H, m). LCMS: 539/537/535 (100%, M+Na), 534/532/530 (M+NH₄), 279/277/275.

Example 126

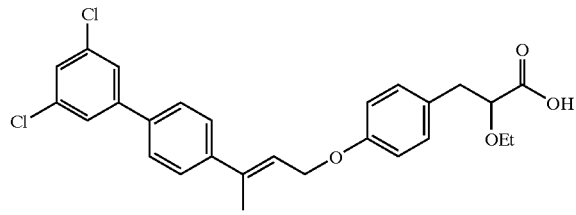

(E)-(S)-3-{4-[3-(3',5'-Dichloro-biphenyl-4-yl)-but-2-enyloxy]-phenyl}-2-ethoxy-propionic acid The title compound was prepared from (E)-(S)-ethyl 3-{4-[3-(3',5'-dichloro-biphenyl-4-yl)-but-2-enyloxy]-phenyl}-2-ethoxy-propionate (example 125) (513 mg, 1.0 mmol) and sodium hydroxide (1M, 5.0 ml, 5.0 mmol) by a procedure analogous to that described in example 51, yielding (E)-(S)-3-{4-[3-(3',5'-dichloro-biphenyl-4-yl)-but-2-enyloxy]-phenyl}-2-ethoxy-propionic acid (422 mg, 87%) as a colourless glass.

$^1$H NMR (300 MHz, CDCl$_3$) δ: 1.19 (3H, t), 2.16 (3H, d), 2.97 (1H, dd), 3.09 (1H, dd), 3.40–3.54 (H, m), 3.54–3.67 (1H, m), 4.07 (1H, dd), 4.74 (2H, d), 6.12 (1H, tm), 6.90 (2H, dm), 7.18 (2H, dm), 7.32 (1H, t), 7.46 (2H, d), 7.48–7.55 (4H, m), carboxylic acid proton not observed. LCMS: 511/509/507 (100%, M+Na), 279/277/275.

Example 127

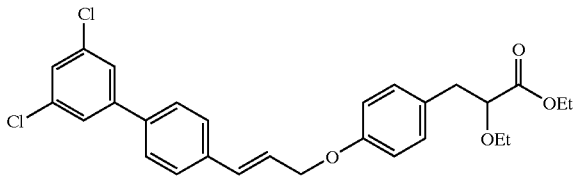

(E)-(S)-Ethyl 3-{4-[3-(3',5'-Dichloro-biphenyl-4-yl)-allyloxy]-phenyl}-2-ethoxy-propionate a)

The colourless solid (E)-ethyl 3-(3',5'-dichloro-biphenyl-4-yl)-acrylate was prepared from (E)-ethyl 3-(4-bromo-phenyl)-acrylate (example 71a) and 3,5-dichlorobenzene boronic acid by a procedure analogous to that described in example 52a.

Mpt. 70–78° C. $^1$H NMR (300 MHz, CDCl$_3$) δ: 1.35 (3H, t), 4.29 (2H, q), 6.49 (1H, d), 7.36 (1H, t), 7.47 (2H, d), 7.53–7.64 (4H, m), 7.71 (1H, d). LCMS: 325/323/321 (100%, M+H). Microanalysis Calculated % C, 63.57; H, 4.39. found C, 63.37; H, 4.43.

b)

The colourless gum (E)-3-(3',5'-dichloro-biphenyl-4-yl)-prop-2-en-1-ol was prepared by DIBAL-H reduction of (E)-ethyl 3-(3',5'-dichloro-biphenyl-4-yl)-acrylate as described for example 52b.

$^1$H NMR (300 MHz, CDCl$_3$) δ: 1.47 (1H, br t), 4.36 (2H, ddd), 6.43 (1H, dt), 6.65 (1H, dm), 7.33 (1H, t), 7.37–7.55 (6H, m). MS: 282/280/278 (100%, M$^+$), 239/237/235, 226/224/222.

c)

The title compound (732 mg, 70%) was prepared as a yellow gum, (containing 0.25 molar equivalents of ethyl acetate) from (E)-3-(3',5'-dichloro-biphenyl-4-yl)-prop-2-en-1-ol (559 mg, 2.0 mmol) and (S)-ethyl 2-ethoxy-3-(4-hydroxyphenyl)-propionate (500 mg, 2.10 mmol) by a procedure analogous to that described in example 52c.

$^1$H NMR (300 MHz, CDCl$_3$) δ: 1.17 (3H, t), 1.22 (3H, t), 1.25 (0.75H, t, AcOEt), 2.04 (0.75H, s, AcOEt), 2.97 (2H, d), 3.30–3.41 (1H, m), 3.53–3.67 (1H, m), 3.98 (1H, t), 4.12 (0.5H, q, AcOEt), 4.17 (2H, q), 4.71 (2H, dd), 6.47 (1H, dt), 6.76 (1H, dm), 6.89 (2H, dm), 7.17 (2H, dm), 7.33 (1H, t), 7.43–7.55 (6H, m). LCMS: 525/523/521 (100%, M+Na), 265/263/261.

Example 128

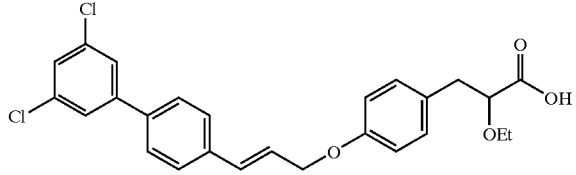

(E)-(S)-3-{4-[3-(3',5'-Dichloro-biphenyl-4-yl)-allyloxy]-phenyl}-2-ethoxy-propionic acid The title compound was prepared from (E)-(S)-ethyl 3-{4-[3-(3',5'-dichloro-biphenyl-4-yl)-allyloxy]-phenyl}-2-ethoxy-propionate (example 127) (522 mg, 1.0 mmol) and sodium hydroxide (1M, 10.0 ml, 10.0 mmol) by a procedure analogous to that described in example 51, yielding (E)-(S)-3-{4-[3-(3',5'-dichloro-biphenyl-4-yl)-allyloxy]-phenyl}-2-ethoxy-propionic acid (325 mg, 67%) as a colourless wax, which contained 0.167 molar equivalents of AcOEt.

$^1$H NMR (300 MHz, CDCl$_3$) δ: 1.19 (3H, t), 1.26 (0.5H, t, AcOEt), 2.04 (0.5H, s, AcOEt), 2.97 (1H, dd), 3.09 (1H, dd), 3.41–3.53 (1H, m), 3.53–3.68 (1H, m), 4.07 (1H, dd), 4.12 (0.33H, q, AcOEt), 4.71 (2H, dd), 6.48 (1H, dt), 6.76 (1H, dm), 6.91 (2H, dm), 7.18 (2H, dm), 7.33 (1H, t), 7.40–7.60 (6H, m), carboxylic acid proton not observed. LCMS: 497/495/493 (100%, M+Na), 492/490/488 (M+NH$_4$), 265/263/261.

Example 129

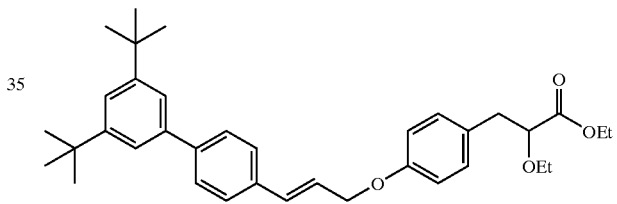

(E)-(S)-Ethyl 3-{4-[3-(3',5'-di-tert-butyl-biphenyl-4-yl)-allyloxy]-phenyl}-2-ethoxy-propionate a)

The colourless solid (E)-3-(4-bromo-phenyl)-prop-2-en-1-ol was prepared by DIBAL-H reduction of (E)-ethyl 3-(4-bromo-phenyl)-acrylate (example 71a) as described for example 52b.

Mpt. 65.5–67.5° C. $^1$H NMR (300 MHz, CDCl$_3$) δ: 1.50 (1H, br s), 4.33 (2H, d), 6.35 (1H, dt), 6.55 (1H, d), 7.23 (2H, dm), 7.43 (2H, dm). MS: 214/212 (M$^+$), 171/169, 158/156, 133 (M−Br, 100%), 115, 91, 77.

b)

tert-Butyl chlorodimethylsilane (1.33 g, 19.5 mmol) was added to a stirred solution of (E)-3-(4-bromo-phenyl)-prop-2-en-1-ol (3.20 g, 15.0 mmol), and imidazole (2.72 g, 18.0 mmol) in dry dichloromethane (75 ml) and the resulting mixture stirred at room temperature for 18 h, a colourless precipitate being formed. The mixture was diluted with dichloromethane (100 ml) and 1N hydrochloric acid (100 ml). The aqueous layer was separated, further extracted with dichloromethane (2×100ml) and the combined organic layers washed with brine, dried (MgSO$_4$) and evaporated. The product was purified by column chromatography on silica gel (1% diethyl ether in n-heptane eluent) to give the colourless solid, (E)-[3-(4-bromo-phenyl)-allyloxy]-tert-butyldimethylsilane (4.39 g, 89%).

Mpt. 46.5–48° C. ¹H NMR (300 MHz, CDCl₃) δ: 0.11 (6H, s), 0.94 (9H, s), 4.34 (2H, dd), 6.27 (1H, dt), 6.54 (1H, dt), 7.24 (2H, dm), 7.42 (2H, dm), 7.71 (1H, d). Microanalysis Calculated % C, 55.04; H, 7.08, Br, 24.41. found C, 54.81; H, 7.22, Br, 24.51.

c)

tert-Butyllithium (1.7M in pentane, 3.5 ml, 6.0 mmol) was added dropwise, at −78° C. to a stirred THF (10 ml) solution of (E)-[3-(4-bromo-phenyl)-allyloxy]-tert-butyldimethylsilane (982 mg, 3.0 mmol) and the resulting solution stirred for 45 min. Trimethylborate (0.51 ml, 4.50 mmol) was added, the solution allowed to warm to room temperature over 2h, and the solvents evaporated to give the crude boronate ester as a yellow gum, which was dissolved in DME (10 ml). Tetrakis(triphenylphosphine)palladium(0) (69 mg, 0.06 mmol), was added to a stirred DME (20 ml) solution of 1-bromo-3,5-di-tert-butylbenzene (538 mg, 2.0 mmol), the solution stirred for 10 min, aqueous sodium carbonate (2M, 9 ml, 18.0 mmol) added, and stirring continued for a further 10 min. The boronate ester solution was added and the mixture heated to 80° C., under reflux, for 24 h. The resulting mixture was diluted with 1N HCl (50 ml), the products extracted into ethyl acetate (3×50 ml), and the combined extracts washed with brine, dried (MgSO₄), and evaporated. The resulting yellow gum was dissolved in dry THF (20 ml), tetra-n-butyl ammonium fluoride (1.26 g, 4.0 mmol) added and the solution stirred at room temperature for 18h. The resulting mixture was diluted with 1N HCl (50 ml), and the products extracted into ethyl acetate (2×50 ml). The combined organic phases were washed with brine, dried (MgSO₄), and evaporated to give the colourless glass, (E)-3-(3',5'-di-tert-butyl-biphenyl-4-yl)-prop-2-en-1-ol (127 mg, 20%).

¹H NMR (300 MHz, CDCl₃) δ: 1.38 (18H, s), 1.45 (1H, br t), 4.35 (2H, br t), 6.41 (1H, dt), 6.66 (1H, br dm), 7.40–7.49 (5H, m), 7.53–7.58 (2H, m). MS: 322 (M⁺), 307 (100%, M-Me), 57.

d)

The title compound (110 mg, 51%) was prepared as a colourless gum from (E)-3-(3',5'-di-tert-butyl-biphenyl-4-yl)-prop-2-en-1-ol (127 mg, 0.39 mmol) and (S)-ethyl 2-ethoxy-3-(4-hydroxyphenyl)-propionate (99 mg, 0.41 mmol) by a procedure analogous to that described in example 52c.

¹H NMR (300 MHz, CDCl₃) δ: 1.17 (3H, t), 1.23 (3H, t), 1.38 (18H, s), 2.97 (2H, d), 3.29–3.42 (1H, m), 3.53–3.67 (1H, m), 3.98 (1H, t), 4.17 (2H, q), 4.70 (2H, dd), 6.45 (1H, dt), 6.77 (1H, dm), 6.90 (2H, dm), 7.18 (2H, dm), 7.40–7.60 (7H, m).

Example 130

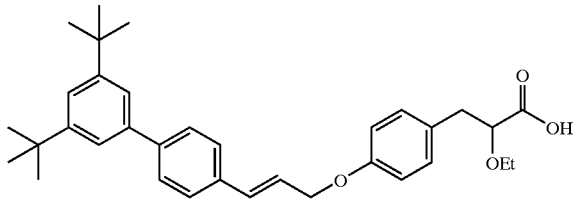

(E)-(S)-3-{4-[3-(3',5'-Di-tert-butyl-biphenyl-4-yl)-allyloxy]-phenyl}-2-ethoxy-propionic acid The title compound was prepared from (E)-(S)-ethyl 3-{4-[3-(3',5'-di-tert-butyl-biphenyl-4-yl)-allyloxy]-phenyl}-2-ethoxy-propionate (example 129) (110 mg, 0.20 mmol) and sodium hydroxide (1M, 0.8 ml, 0.8 mmol) by a procedure analogous to that described in example 51, yielding ((E)-(S)-3-{4-[3-(3',5'-di-tert-butyl-biphenyl-4-yl)-allyloxy]-phenyl}-2-ethoxy-propionic acid (92 mg, 88%) as a colourless solid.

¹H NMR (300 MHz, CDCl₃) δ: 1.20 (3H, t), 1.38 (18H, s), 2.97 (1H, dd), 3.10 (1H, dd), 3.40–3.65 (2H, m), 4.07 (1H, dd), 4.70 (2H, dd), 6.45 (1H, dt), 6.77 (1H, dm), 6.90 (2H, dm), 7.18 (2H, dm), 7.38–7.60 (7H, m), carboxylic acid proton not observed.

Example 131

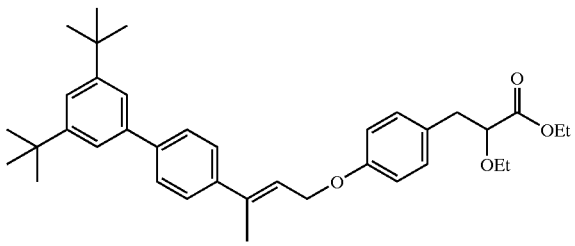

(E)-(S)-Ethyl 3-{4-[3-(3',5'-Di-tert-butyl-biphenyl-4-yl)-but-2-enyloxy]-phenyl}-2-ethoxy-propionate a)

The colourless oil, (E)-[3-(4-bromophenyl)-but-2-enyloxy]-tert-butyl-dimethylsilane was prepared from (E)-3-(4-bromophenyl)-but-2-en-1-ol (example 50b), imidazole and tert-butyl chlorodimethylsilane by a procedure analogous to that described in example 129b.

¹H NMR (300 MHz, CDCl₃) δ: 0.10 (6H, s), 0.92 (9H, s), 4.37 (2H, d), 5.88 (1H, tm), 7.25 (2H, dm), 7.42 (2H, dm). MS: 342/340 (M⁺), 327/325 (M-Me), 285/283 (M-Bu), 130, 75 (100%).

b)

The colourless wax, (E)-3-(3',5'-di-tert-butyl-biphenyl-4-yl)-but-2-en-1-ol was prepared via a metallation, boronation, cross coupling and deprotection sequence analogous to that described for example 129c.

¹H NMR (300 MHz, CDCl₃) δ: 1.26 (1H, br m), 1.38 (18H, s), 2.12 (3H, d), 4.40 (2H, br t), 6.05 (1H, dt), 7.40–7.42 (3H, m), 7.43–7.59 (4H, m). LCMS: 331 (M+H), 319 (100%, M+H-H₂O).

c)

The title compound (429 mg, 74%) was prepared as a colourless gum from (E)-3-(3',5'-di-tert-butyl-biphenyl-4-yl)-but-2-en-1-ol (350 mg, 1.04 mmol) and (S)-ethyl 2-ethoxy-3-(4-hydroxyphenyl)-propionate (260 mg, 1.09 mmol) by a procedure analogous to that described in example 52c.

¹H NMR (300 MHz, CDCl₃) δ: 1.17 (3H, t), 1.22 (3H, t), 1.38 (18H, s), 2.17 (3H, d), 2.96 (2H, d), 3.30–3.43 (1H, m), 3.55–3.68 (1H, m), 3.98 (1H, t), 4.17 (2H, q), 4.75 (2H, d), 6.11 (1H, tm), 6.89 (2H, dm), 7.17 (2H, dm), 7.40–7.45 (3H, m), 7.46–7.60 (4H, m). LCMS: 579 (100%, M+Na), 574 (M+NH₄), 511 (M+H-EtOH).

Example 132

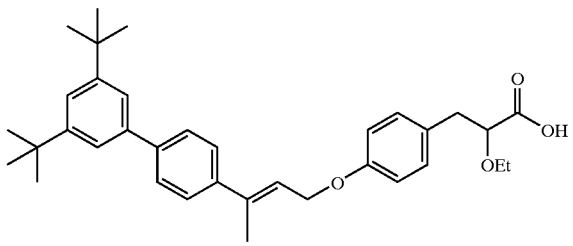

(E)-(S)-3-{4-[3-(3',5'-Di-tert-butyl-biphenyl-4-yl)-but-2-enyloxy]-phenyl}-2-ethoxy-propionic acid The title compound was prepared from (E)-(S)-ethyl 3-{4-[3-(3',5'-di-tert-butyl-biphenyl-4-yl)-but-2-enyloxy]-phenyl}-2-ethoxy-propionate (example 131) (400 mg, 0.72 mmol) and sodium hydroxide (1M, 2.9 ml, 2.9 mmol) by a procedure analogous to that described in example 51, yielding (E)-(S)-3-{4-[3-(3',5'-di-tert-butyl-biphenyl-4-yl)-but-2-enyloxy]-phenyl}-2-ethoxy-propionic acid (315 mg, 83%) as a colourless gum.

$^1$H NMR (300 MHz, CDCl$_3$) δ: 1.19 (3H, t), 1.39 (18H, s), 2.18 (3H, d), 2.97 (1H, dd), 3.10 (1H, dd), 3.40–3.67 (2H, m), 4.07 (1H, dd), 4.70 (2H, d), 6.11 (1H, tm), 6.90 (2H, dm), 7.18 (2H, dm), 7.40–7.45 (3H, m), 7.46–7.60 (4H, m), carboxylic acid proton not observed. LCMS: 847 (M+319), 551 (M+Na), 319 (100%).

Example 133

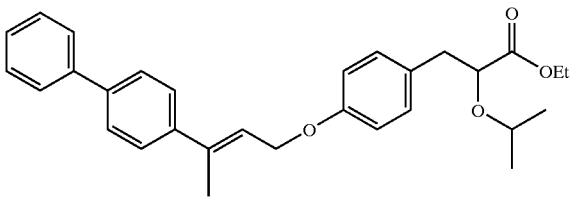

(E)-(S/R)-Ethyl 3-[4-(3-Biphenyl-4-yl-but-2-enyloxy)-phenyl]-2-isopropoxy-propionate a) (S/R)-Ethyl 2-(diethoxyphosphoryl)-2-isopropoxy-acetate was prepared as a pale green oil by the rhodium(II) acetate dimer catalysed reaction of ethyl diazo-(diethoxyphosphoryl)-acetate with isopropyl alcohol, according to the method described by C. J. Moody et al (*Tetrahedron*, 1992, 48, 3991–4004).

$^1$H NMR (300 MHz, CDCl$_3$) δ: 1.21 (3H, d), 1.23 (3H, d), 1.28–1.39 (9H, m), 3.74 (1H, septet), 4.15–4.35 (6H, m), 4.39 (1H, d, J$_{HP}$=19.9 Hz). LCMS: 283 (M+H), 241 (100%), 213.

b) A THF (20 ml) solution of (S/R)-ethyl 2-(diethoxyphosphoryl)-2-isopropoxy-acetate (6.40 g, 22.7 mmol) was added dropwise, at 0° C., to a stirred suspension of sodium hydride (60% dispersion in mineral oil, 0.92 g, 23.0 mmol) in THF (20 ml), and the resulting mixture stirred for 30 min. A THF (20 ml) solution of 4-benzyloxybenzaldehyde (3.21 g, 15.1 mmol) was added, the resulting solution allowed to warm to room temperature, and stirring continued for 72 h. The mixture was carefully diluted with 1N HCl (150 ml), the products extracted into ethyl acetate (3×100 ml), and the combined organic phases washed with brine, dried (MgSO$_4$) and (MgSO$_4$) and evaporated to give a yellow gum, which was purified by column chromatography on silica gel (10% ethyl acetate in n-heptane eluent) to give the intermediate, (E/Z)-ethyl 3-(4-benzyloxyphenyl)-2-isopropoxy-acrylate as a colourless gum. The (E/Z)-ethyl 3-(4-benzyloxyphenyl)-2-isopropoxy-acrylate was dissolved in ethanol (100 ml), palladium on activated charcoal (10 wt. %, 0.80 g, 0.75 mmol) added and the mixture hydrogenated at 30 lb/in$^2$ H$_2$ pressure for 18 h. The catalyst was removed by filtration through celite and the solvent evaporated to give (S/R)-ethyl 3-(4-hydroxyphenyl)-2-isopropoxy-propionate (3.44 g, 90%) as a pale orange gum.

$^1$H NMR (300 MHz, CDCl$_3$) δ: 0.98 (3H, d), 1.15 (3H, d), 1.24 (3H, t), 2.82–2.98 (2H, m), 3.51 (1H, septet), 4.02 (1H, dd), 4.17 (2H, q), 5.49 (1H, br s), 6.75 (2H, dm), 7.09 (2H, dm). LCMS: 275 (M+Na), 253 (M+H), 235, 211, 193, 151, 137 (100%).

c) The title compound (324 mg, 70%) was prepared as a colourless solid from (S/R)-ethyl 3-(4-hydroxyphenyl)-2-isopropoxy-propionate (280 mg, 1.11 mmol) and (E)-3-biphenyl-4-yl-but-2-en-1-ol (225 mg, 1.0 mmol) by a procedure analogous to that described in example 52c.

Mpt. 79–81° C. $^1$H NMR (300 MHz, CDCl$_3$) δ: 0.97 (3H, d), 1.16 (3H, d), 1.24 (3H, t), 2.17 (3H, d), 2.85–3.02 (2H, m), 3.51 (1H, septet), 4.01 (1H, dd), 4.08–4.25 (2H, m), 4.75 (2H, d), 6.11 (1H, tm), 6.88 (2H, dm), 7.17 (2H, dm), 7.30–7.38 (1H, m), 7.40–7.65 (8H, m). LCMS: 665 (M+207), 481 (M+Na), 476 (M+NH$_4$), 207 (100%).

Example 134

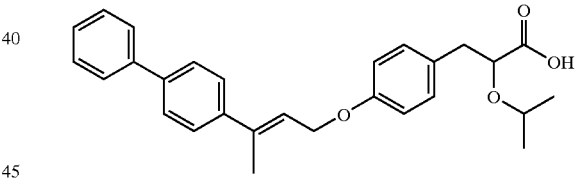

(E)-(S/R)-3-[4-(3-Biphenyl-4-yl-but-2-enyloxy)-phenyl]-2-isopropoxy-propionic acid The title compound was prepared from (E)-(S/R)-ethyl 3-[4-(3-biphenyl-4-yl-but-2-enyloxy)-phenyl]-2-isopropoxy-propionate (example 133) (230 mg, 0.50 mmol) and sodium hydroxide (1M, 1.5 ml, 1.5 mmol) by a procedure analogous to that described in example 51, yielding (E)-(S/R)-3-[4-(3-biphenyl-4-yl-but-2-enyloxy)-phenyl]-2-isopropoxy-propionic acid (190 mg, 88%) as a colourless solid.

Mpt. 125–127.5° C. $^1$H NMR (300 MHz, CDCl$_3$) δ: 1.03 (3H, d), 1.16 (3H, d), 2.17 (3H, d), 2.90 (1H, dd), 3.08 (1H, dd), 3.55 (1H, septet), 4.10 (1H, dd), 4.75 (2H, d), 6.12 (1H, tm), 6.90 (2H, dm), 7.17 (2H, dm), 7.30–7.38 (1H, m), 7.40–7.65 (8H, m), carboxylic acid proton not observed. LCMS: 637 (M+207), 453 (M+Na), 448 (M+NH$_4$), 207 (100%).

Example 135

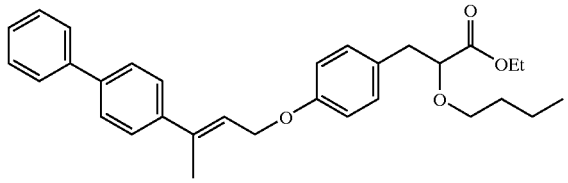

(E)-(S/R)-Ethyl 3-[4-(3-Biphenyl-4-yl-but-2-enyloxy)-phenyl]-2-butoxy-propionate a)
Butyl di-butoxy acetate (23.75 g, 91.2 mmol) was mixed with acetyl chloride (15.5 ml, 218 mmol) and iodine (0.2 g, 0.79 mmol) and the resulting brown solution heated to 60° C., under reflux, for 6 h. The product was then fractionally distilled, under reduced pressure, yielding (S/R)-butyl 2-butoxy-2-chloro-acetate (17.58 g, 79%) as an orange coloured oil. Bpt. 130–135° C./approx. 15 mmHg. $^1$H NMR (300 MHz, CDCl$_3$) δ: 0.89–0.99 (6H, m), 1.41 (4H, sextet), 1.60–1.75 (4H, m), 3.60 (1H, dt), 3.98 (1H, dt), 4.25 (2H, t), 5.81 (1H, s).

b)
A mixture of triethylphosphite (13.05 ml, 75.0 mmol) and (S/R)-butyl 2-butoxy-2-chloro-acetate (16.70 g, 75.0 mmol) was heated to 140° C., under reflux, for 6 h. The resulting oil was fractionally distilled under reduced pressure to give the product, (S/R)-butyl 2-butoxy-2-(diethoxyphosphoryl)-acetate (20.42 g, 84%) as a colourless oil.

Bpt. 170–175° C./1–5 mmHg. $^1$H NMR (300 MHz, CDCl$_3$) δ: 0.87–0.99 (6H, m), 1.30–1.49 (10H, m), 1.57–1.73 (4H, m), 3.52 (1H, dt), 3.66 (1H, dt), 4.15–4.30 (6H, m), 4.30 (1H, d, J$_{HP}$=19 Hz). LCMS: 325 (100%, M+H), 269, 167.

c)
A THF (40 ml) solution of (S/R)-butyl 2-butoxy-2-(diethoxyphosphoryl)-acetate (14.60 g, 45.0 mmol) was added dropwise, at 0° C., to a stirred suspension of sodium hydride (55% dispersion in mineral oil, 2.61 g, 59.8 mmol) in THF (50 ml), and the resulting mixture stirred for 30 min. A THF (50 ml) solution of 4-benzyloxybenzaldehyde (6.37 g, 30.0 mmol) was added, the resulting solution allowed to warm to room temperature, and stirring continued for 48 h. The mixture was carefully diluted with 1N HCl (200 ml), the products extracted into ethyl acetate (4×100 ml), and the combined organic phases washed with brine, dried (MgSO$_4$) and evaporated to give a yellow gum, which was purified by column chromatography on silica gel (10% ethyl acetate in n-heptane eluent) to give the intermediate, (E/Z)-butyl 3-(4-benzyloxyphenyl)-2-butoxy-acrylate as a colourless gum.

The (E/Z)-butyl 3-(4-benzyloxyphenyl)-2-butoxy-acrylate was dissolved in ethanol (200 ml), palladium on activated charcoal (10 wt. %, 1.60 g, 1.5 mmol) added and the mixture hydrogenated at 30 lb/in$^2$ H$_2$ pressure for 18 h. The catalyst was removed by filtration through celite and the solvent evaporated to give an orange gum, which contained both (S/R)-butyl 3-(4-hydroxyphenyl)-2-butoxy-propionate and the trans-esterification product, (S/R)-ethyl 3-(4-hydroxyphenyl)-2-butoxy-propionate. These were separated by column chromatography on silica gel (15% ethyl acetate in n-heptane eluent) to give, in respective order of elution, (S/R)-butyl 3-(4-hydroxyphenyl)-2-butoxy-propionate (6.74 g, 76%) and (S/R)-ethyl 3-(4-hydroxyphenyl)-2-butoxy-propionate (0.40 g, 5%) as colourless oils.

(S/R)-butyl 3-(4-hydroxyphenyl)-2-butoxy-propionate: $^1$H NMR (300 MHz, CDCl$_3$) δ: 0.85 (3H, t), 0.91 (3H, t), 1.22–1.43 (4H, m), 1.43–1.65 (4H, m), 2.89–2.98 (2H, m), 3.28 (1H, dt), 3.54 (1H, dt), 3.97 (1H, dd), 4.11 (2H, t), 5.56 (1H, br s), 6.74 (2H, dm), 7.08 (2H, dm). LCMS: 317 (M+Na), 295 (M+H), 221 (100%, M+H-BuOH), 193, 179, 165, 137.

(S/R)-ethyl 3-(4-hydroxyphenyl)-2-butoxy-propionate: $^1$H NMR (300 MHz, CDCl$_3$) δ: 0.85 (3H, t), 1.23 (3H, t), 1.21–1.39 (2H, m), 1.43–1.60 (2H, m), 2.89–2.99 (2H, m), 3.28 (1H, dt), 3.55 (1H, dt), 3.97 (1H, dd), 4.17 (2H, q), 5.63 (1H, br s), 6.74 (2H, dm), 7.08 (2H, dm). LCMS: 289 (M+Na), 267 (M+H), 193 (100%, M+H-BuOH), 151, 137.

d)
The title compound (420 mg, 71%) was prepared as a colourless solid from (S/R)-ethyl 3-(4-hydroxyphenyl)-2-butoxy-propionate (385 mg, 1.45 mmol) and (E)-3-biphenyl-4-yl-but-2-en-1-ol (280 mg, 1.25 mmol) by a procedure analogous to that described in example 52c.

Mpt. 62–63.5° C. $^1$H NMR (300 MHz, CDCl$_3$) δ: 0.85 (3H, t), 1.23 (3H, t), 1.20–1.40 (2H, m), 2.17 (3H, d), 2.90–3.00 (2H, m), 3.27 (1H, dt), 3.55 (1H, dt), 3.95 (1H, dd), 4.10–4.23 (2H, m), 4.74 (2H, d), 6.11 (1H, tm), 6.88 (2H, dm), 7.17 (2H, dm), 7.30–7.38 (1H, m), 7.40–7.63 (8H, m). LCMS: 679 (M+207), 495 (M+Na), 490 (M+NH$_4$), 207 (100%).

Example 136

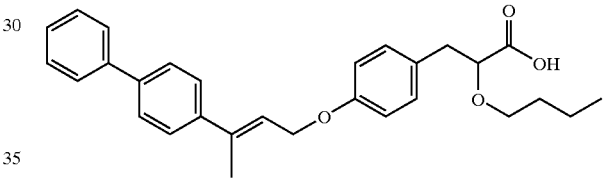

(E)-(S/R)-3-[4-(3-Biphenyl-4-yl-but-2-enyloxy)-phenyl]-2-butoxy-propionic acid

The title compound was prepared from (E)-(S/R)-ethyl 3-[4-(3-biphenyl-4-yl-but-2-enyloxy)-phenyl]-2-butoxy-propionate (example 135) (331 mg, 0.70 mmol) and sodium hydroxide (1M, 2.1 ml, 2.1 mmol) by a procedure analogous to that described in example 51, yielding (E)-(S/R)-3-[4-(3-biphenyl-4-yl-but-2-enyloxy)-phenyl]-2-butoxy-propionic acid (42 mg, 13%) as a colourless solid.

$^1$H NMR (300 MHz, CDCl$_3$) δ: 0.87 (3H, t), 1.21–1.38 (2H, m), 1.47–1.60 (2H, m), 2.17 (3H, br s), 2.96 (1H, dd), 3.09 (1H, dd), 3.33–3.44 (1H, m), 3.47–3.60 (1H, m), 4.04 (1H, dd), 4.75 (2H, d), 6.12 (1H, br t), 6.90 (2H, dm), 7.17 (2H, dm), 7.30–7.38 (1H, m), 7.38–7.65 (8H, m), carboxylic acid proton not observed. LCMS: 651 (M+207), 467 (100%, M+Na), 207.

Example 137

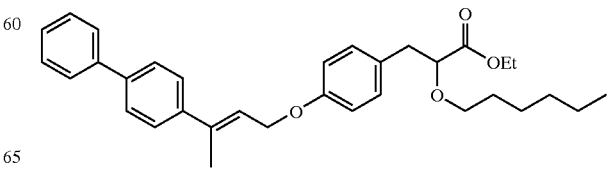

(E)-(S/R)-Ethyl 3-[4-(3-Biphenyl-4-yl-but-2-enyloxy)-phenyl]-2-hexyloxy-propionate a)

(S/R)-Ethyl 2-(diethoxyphosphoryl)-2-hexyloxy-acetate was prepared as a pale green oil by the rhodium(II) acetate dimer catalysed reaction of ethyl diazo-(diethoxyphosphoryl)-acetate with 1-hexanol, by a method analogous to that described for example 133a.

$^1$H NMR (300 MHz, CDCl$_3$) δ: 0.88 (3H, t), 1.23–1.44 (15H, m), 1.57–1.69 (2H, m), 3.51 (1H, dt), 3.65 (1H, dt), 4.15–4.38 (7H, m). LCMS: 671 (2M+Na), 649 (2M+H), 325 (100%, M+H), 297, 241.

b)

Sodium hydride (60% dispersion in mineral oil, 1.0 g, 25.0 mmol) was added at 0° C., in small portions, to a stirred THF (50 ml) solution of (S/R)-ethyl 2-(diethoxyphosphoryl)-2-hexyloxy-acetate (8.12 g, 25.0 mmol), and the resulting suspension stirred for 30 min. A THF (50 ml) solution of 4-benzyloxybenzaldehyde (4.25 g, 20.0 mmol) was added, the resulting solution allowed to warm to room temperature, and stirring continued for 4 h. The mixture was carefully diluted with 0.5N HCl (150 ml), the products extracted into ethyl acetate (4×75 ml), and the combined organic phases washed with brine, dried (MgSO$_4$) and evaporated to give an orange coloured gum, which was purified by column chromatography on silica gel (15% ethyl acetate in n-heptane eluent) to give the intermediate, (E/Z)-ethyl 3-(4-benzyloxyphenyl)-2-hexyloxy-acrylate as a pale yellow oil.

The (E/Z)-ethyl 3-(4-benzyloxyphenyl)-2-hexyloxy-acrylate was dissolved in ethanol (150 ml), palladium on activated charcoal (10 wt. %, 1.40 g, 1.32 mmol) added and the mixture hydrogenated at 30 lb/in$^2$ H$_2$ pressure for 18 h. The catalyst was removed by filtration through celite and the solvent evaporated to give a colourless gum, which was purified by column chromatography on silica gel (10% ethyl acetate in n-heptane eluent) to give (S/R)-ethyl 3-(4-hydroxyphenyl)-2-hexyloxy-propionate (1.83 g, 30%) as a colourless gum.

$^1$H NMR (300 MHz, CDCl$_3$) δ: 0.85 (3H, t), 1.14–1.32 (9H, m), 1.45–1.60 (2H, m), 2.94 (2H, d), 3.28 (1H, dt), 3.54 (1H, dt), 3.97 (1H, dd), 4.17 (2H, q), 5.95 (1H, br s), 6.74 (2H, dm), 7.07 (2H, dm). MS: 294 (M$^+$), 221 (M–COOEt), 192 (M–hexanol), 137, 107 (100%).

c)

The title compound (248 mg, 81%) was prepared as a waxy solid from (S/R)-ethyl 3-(4-hydroxyphenyl)-2-hexyloxy-propionate (215 mg, 0.72 mmol) and (E)-3-biphenyl-4-yl-but-2-en-1-ol (137 mg, 0.61 mmol) by a procedure analogous to that described in example 52c.

$^1$H NMR (300 MHz, CDCl$_3$) δ: 0.86 (3H, t), 1.13–1.35 (9H, m), 1.46–1.60 (2H, m), 2.17 (3H, br s), 2.88–3.00 (2H, m), 3.26 (1H, dt), 3.55 (1H, dt), 3.95 (1H, dd), 4.10–4.23 (2H, m), 4.74 (2H, d), 6.12 (1H, tm), 6.88 (2H, dm), 7.17 (2H, dm), 7.30–7.37 (1H, m), 7.40–7.63 (8H, m).

Example 138

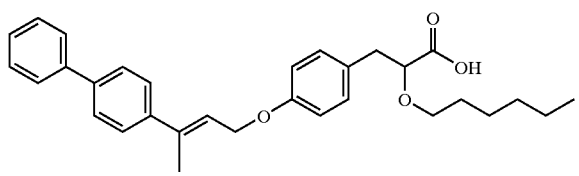

(E)-(S/R)-3-[4-(3-Biphenyl-4-yl-but-2-enyloxy)-phenyl]-2-hexyloxy-propionic acid The title compound was prepared from (E)-(S/R)-ethyl 3-[4-(3-biphenyl-4-yl-but-2-enyloxy)-phenyl]-2-hexyloxy-propionate (example 137) (172 mg, 0.34 mmol) and sodium hydroxide (1M, 1.0 ml, 1.0 mmol) by a procedure analogous to that described in example 51, yielding (E)-(S/R)-3-[4-(3-biphenyl-4-yl-but-2-enyloxy)-phenyl]-2-hexyloxy-propionic acid (160 mg, 99%) as a colourless solid.

Mpt. 117–119° C. $^1$H NMR (300 MHz, CDCl$_3$) δ: 0.87 (3H, t), 1.13–1.38 (6H, m), 1.45–1.60 (2H, m), 2.17 (3H, d), 2.96 (1H, dd), 3.10 (1H, dd), 3.40 (1H, dt), 3.53 (1H, dt), 4.05 (1H, dd), 4.75 (2H, d), 6.12 (1H, tm), 6.90 (2H, dm), 7.16 (2H, dm), 7.30–7.38 (1H, m), 7.40–7.63 (8H, m), carboxylic acid proton not observed.

Example 139

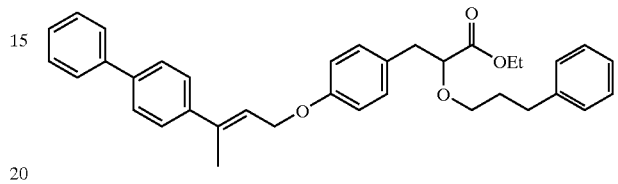

(E)-(S/R)-Ethyl 3-[4-(3-Biphenyl-4-yl-but-2-enyloxy)-phenyl]-2-(3-phenyl-propoxy)-propionate a)

(S/R)-Ethyl 2-(diethoxyphosphoryl)-2-(3-phenyl-propoxy)-acetate was prepared as a pale green oil by the rhodium(II) acetate □immer catalysed reaction of 3-phenyl-1-propanol with ethyl diazo-(diethoxyphosphoryl)-acetate, by a method analogous to that described for example 133a.

$^1$H NMR (300 MHz, CDCl$_3$) δ: 1.23–1.40 (9H, m), 1.98 (2H, quintet), 2.72 (2H, t), 3.52 (1H, dt), 3.67 (1H, dt), 4.15–4.35 (7H, m), 7.12–7.22 (3H, m), 7.22–7.32 (2H, m).

b)

A THF (50 ml) solution of (S/R)-ethyl 2-(diethoxyphosphoryl)-2-(3-phenyl-propoxy)-acetate (14.2 g, 39.6 mmol) was added dropwise, at 0° C., to a stirred mixture of sodium hydride (60% dispersion in mineral oil, 2.35 g, 58.8 mmol) and 4-benzyloxybenzaldehyde (4.20 g, 19.8 mmol) in THF (50 ml), and the resulting mixture allowed to warm slowly to room temperature over 18 h. The mixture was carefully diluted with water (150 ml), the products extracted into ethyl acetate (2×150 ml), and the combined organic phases washed with brine, dried (MgSO$_4$) and evaporated to give (E/Z)-ethyl 3-(4-benzyloxyphenyl)-2-(3-phenyl-propoxy)-acrylate as a yellow oil.

The (E/Z)-ethyl 3-(4-benzyloxyphenyl)-2-(3-phenyl-propoxy)-acrylate was dissolved in ethanol (50 ml), palladium on activated charcoal (10 wt. %, 1.0 g, 0.94 mmol) added and the mixture hydrogenated at 30 lb/in$^2$ H$_2$ pressure for 18 h. The catalyst was removed by filtration through celite and the solvent evaporated to give a colourless oil.

$^1$H NMR (300 MHz, CDCl$_3$) δ: 1.23 (3H, t), 1.72–1.97 (2H, m), 2.52–2.64 (2H, m), 2.87–3.02 (2H, m), 3.17–3.27 (1H, m), 3.53–3.63 (1H, m), 3.94 (1H, dd), 4.17 (2H, q), 4.93 (1H, s), 6.76 (2H, dm), 7.02–7.29 (7H, m).

c)

The title compound (150 mg, 56%) was prepared as a waxy solid from (S/R)-ethyl 3-(4-hydroxyphenyl)-2-(3-phenyl-propoxy)-propionate (172 mg, 0.53 mmol) and (E)-3-biphenyl-4-yl-but-2-en-1-ol (112 mg, 0.50 mmol) by a procedure analogous to that described in example 52c.

$^1$H NMR (300 MHz, CDCl$_3$) δ: 1.23 (3H, t), 1.72–1.97 (2H, m), 2.16 (3H, br s), 2.51–2.65 (2H, m), 2.89–3.05 (2H, m), 3.17–3.27 (1H, m), 3.59 (1H, dt), 3.95 (1H, dd), 4.18 (2H, q), 4.74 (2H, d), 6.11 (1H, tm), 6.90 (2H, dm), 7.01–7.63 (16H, m). LCMS: 741 (M+207), 557 (100%, M+Na), 552 (M+NH$_4$), 207.

Example 140

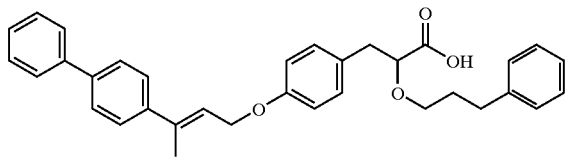

(E)-(S/R)-3-[4-(3-Biphenyl-4-yl-but-2-enyloxy)-phenyl]-2-(3-phenyl-propoxy)-propionic acid The title compound was prepared from (E)-(S/R)-ethyl 3-[4-(3-biphenyl-4-yl-but-2-enyloxy)-phenyl]-2-(3-phenyl-propoxy)-propionate (example 139) (130 mg, 0.24 mmol) and sodium hydroxide (1M, 0.73 ml, 0.73 mmol) by a procedure analogous to that described in example 51, yielding (E)-(S/R)-3-[4-(3-biphenyl-4-yl-but-2-enyloxy)-phenyl]-2-(3-phenyl-propoxy)-propionic acid (90 mg, 73%) as a colourless solid.

Mpt. 115–117° C. $^1$H NMR (300 MHz, CDCl$_3$) δ: 1.75–1.98 (2H, m), 2.16 (3H, d), 2.52–2.68 (2H, m), 2.96 (1H, dd), 3.10 (1H, dd), 3.36 (1H, dt), 3.57 (1H, dt), 4.03 (1H, dd), 4.74 (2H, d), 6.11 (1H, tm), 6.91 (2H, dm), 7.06 (2H, dm), 7.12–7.63 (14H, m), carboxylic acid proton not observed. LCMS: 529 (M+Na), 525 (M+NH$_4$), 207 (100%).

Example 141

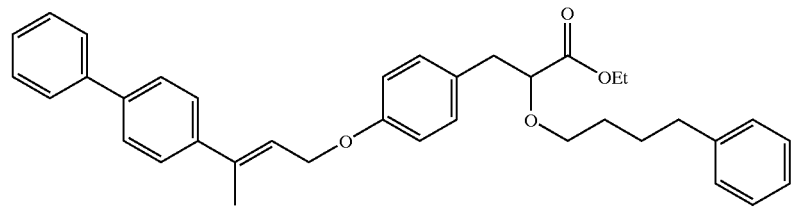

(E)-(S/R)-Ethyl 3-[4-(3-Biphenyl-4-yl-but-2-enyloxy)-phenyl]-2-(4-phenyl-butoxy)-propionate a)

(S/R)-Ethyl 2-(diethoxyphosphoryl)-2-(4-phenyl-butoxy)-acetate was prepared as a pale green oil by the rhodium(II) acetate dimmer catalysed reaction of 4-phenyl-1-butanol with ethyl diazo-(diethoxyphosphoryl)-acetate, by a method analogous to that described for example 133a.

$^1$H NMR (300 MHz, CDCl$_3$) δ: 1.25–1.40 (9H, m), 1.60–1.78 (4H, m), 2.63 (2H, t), 3.47–3.56 (1H, m), 3.61–3.70 (1H, m), 4.12–4.35 (7H, m), 7.12–7.21 (3H, m), 7.21–7.31 (2H, m). LCMS: 745 (2M+H), 373 (100%, M+H), 241.

b)

A THF (30 ml) solution of (S/R)-ethyl 2-(diethoxyphosphoryl)-2-(4-phenyl-butoxy)-acetate (15.64 g, 42.0 mmol) was added dropwise, at 0° C., to a stirred suspension of sodium hydride (60% dispersion in mineral oil, 2.52 g, 63.0 mmol) in THF (30 ml), and the resulting mixture stirred for 20 min. A THF (50 ml) solution of 4-benzyloxybenzaldehyde (4.46 g, 21.0 mmol) was added, and the mixture warmed, resulting in a vigorous reaction. The mixture was cooled, carefully diluted with 0.5N HCl (150 ml), the products extracted into ethyl acetate (2×150 ml), and the combined organic phases washed with brine, dried (MgSO$_4$) and evaporated to give (E/Z)-ethyl 3-(4-benzyloxyphenyl)-2-(4-phenyl-butoxy)-acrylate as a yellow oil. The (E/Z)-ethyl 3-(4-benzyloxyphenyl)-2-(4-phenyl-butoxy)-acrylate was dissolved in ethanol (175 ml), palladium on activated charcoal (10 wt. %, 0.50 g, 0.47 mmol) added and the mixture hydrogenated at 30 lb/in$^2$ H$_2$ pressure for 18 h. The catalyst was removed by filtration through celite and the solvent evaporated to give a colourless gum, which was purified by column chromatography on silica gel to give (S/R)-ethyl 3-(4-hydroxyphenyl)-2-(4-phenyl-butoxy)-propionate (1.73 g, 24%) as a colourless oil.

$^1$H NMR (300 MHz, CDCl$_3$) δ: 1.22 (3H, t), 1.50–1.67 (4H, m), 2.50–2.60 (2H, m), 2.85–3.0 (2H, m), 3.21–3.31 (1H, m), 3.53–3.63 (1H, m), 3.94 (1H, dd), 4.16 (2H, q), 6.72 (2H, dm), 7.06–7.31 (7H, m), phenol proton not observed.

c)

The title compound (245 mg, 80%) was prepared as a yellow, waxy solid from (S/R)-ethyl 3-(4-hydroxyphenyl)-2-(4-phenyl-butoxy)-propionate (200 mg, 0.58 mmol) and (E)-3-biphenyl-4-yl-but-2-en-1-ol (125 mg, 0.56 mmol) by a procedure analogous to that described in example 52c.

$^1$H NMR (300 MHz, CDCl$_3$) δ: 1.22 (3H, t), 1.50–1.68 (4H, m), 2.16 (3H, d), 2.50–2.60 (2H, m), 2.88–3.02 (2H, m), 3.21–3.33 (1H, m), 3.52–3.64 (1H, m), 3.95 (1H, dd), 4.17 (2H, q), 4.72 (2H, d), 6.11 (1H, tm), 6.87 (2H, dm), 7.06–7.63 (16H, m).

Example 142

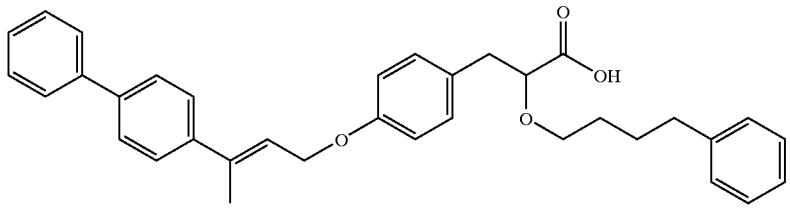

(E)-(S/R)-3-[4-(3-Biphenyl-4-yl-but-2-enyloxy)-phenyl]-2-(4-phenyl-butoxy)-propionic acid The title compound was prepared from (E)-(S/R)-ethyl 3-[4-(3-biphenyl-4-yl-but-2-enyloxy)-phenyl]-2-(4-phenylbutoxy)-propionate (example 141) (225 mg, 0.41 mmol) and sodium hydroxide (1M, 1.64 ml, 1.64 mmol) by a procedure analogous to that described in example 51, yielding (E)-(S/R)-3-[4-(3-biphenyl-4-yl-but-2-enyloxy)-phenyl]-2-(4-phenyl-butoxy)-propionic acid (210 mg, 99%) as a pale yellow solid.

$^1$H NMR (300 MHz, CDCl$_3$) δ: 1.50–1.70 (4H, m), 2.17 (3H, d), 2.53–2.61 (2H, m), 2.95 (1H, dd), 3.09 (1H, dd), 3.34–3.44 (1H, m), 3.50–3.60 (1H, m), 4.04 (1H, dd), 4.72 (2H, d), 6.11 (1H, tm), 6.88 (2H, dm), 7.06–7.63 (16H, m), carboxylic acid proton not observed.

Example 143

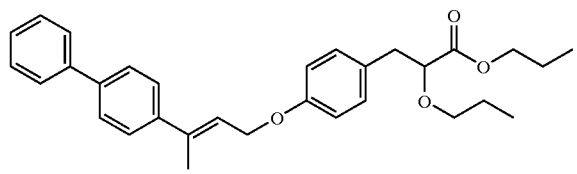

(E)-(S/R)-Propyl 3-[4-(3-Biphenyl-4-yl-but-2-enyloxy)-phenyl]-2-propoxy-propionate a)
Morpholinium dimorpholinoacetate was prepared according to the method described by Bourguignon and Wermuth (Bourguignon, J. J.; Wermuth, C. G. *J. Org. Chem.* 1981, 46, 4889–4894): an ethanol (100 ml) solution of morpholine (310 ml, 3.55 mol) was added, at 0° C., to a stirred ethanol (500 ml) solution of glyoxylic acid monohydrate (92.06 g, 1.0 mol) and the resulting mixture refrigerated for 60 h, a colourless precipitate being formed. The solid was collected by filtration, washed with diethyl ether (2×300 ml) and vacuum dried at 30° C. to give morphilinium dimorhpholinoacetate (298 g, 94%) as a colourless solid, which contained a small amount of water.

Mpt. 139–139.5° C. $^1$H NMR (300 MHz, CDCl$_3$) δ: 2.83 (12H, br m), 3.26 (1H, s), 3.78 (12H, br m), 7.78 (2H, br s). Microanalysis Calculated % C, 52.93; H, 8.58; N, 13.24; water: 0.1%. found C, 52.84; H, 8.84; N, 13.15, water: 0.1%.

b)
Using a method based on that described by Kerfanto and Jegou, (Kerfanto, M.; Jegou, D. Compt. Rendus. 1965, 261(11), 2232–2233) morphilinium dimorpholinoacetate (127 g, 0.40 mol) was added to a stirred solution of hydrochloric acid (94.3 g, 6.5 mol) in 1-propanol (600 ml) and the resulting mixture heated to 80° C., under reflux, for 2 h. The resulting colourless suspension was filtered to remove morphiline hydrochloride, and the filtrate fractionally distilled, under reduced pressure, to give excess 1-propanol and the colourless oil, propyl 2,2-dipropoxyacetate (57.14 g, 65%).

$^1$H NMR (300 MHz, CDCl$_3$) δ: 0.86–1.05 (9H, m), 1.55–1.78 (6H, m), 3.47–3.65 (4H, m), 4.15 (2H, t), 4.89 (1H, s).

c)
A mixture of propyl 2,2-dipropoxyacetate (43.66 g, 0.20 mol), acetyl chloride (28 ml, 0.394 mol) and iodine (0.25 g, 1.0 mmol) was heated to 55° C., under reflux, for 16 h. Since GC analysis showed that some propyl 2,2-dipropoxyacetate starting material was still present, second portions of acetyl chloride (14 ml, 0.197 mol) and iodine (0.25 g, 1.0 mmol) were added, and heating continued for a further 6 h. The product was then purified by fractional distillation under reduced pressure to give (S/R)-propyl 2-chloro-2-propoxyacetate (32.67 g, 84%) as a pale orange oil (trace of iodine present).

Bpt. 116–119.5° C./approx. 10 mmHg. $^1$H NMR (300 MHz, CDCl$_3$) δ: 0.97 (3H, t), 0.98 (3H, t), 1.63–1.82 (4H, m), 3.58 (1H, dt), 3.93 (1H, dt), 4.13–4.26 (2H, m), 5.83 (1H, s).

d)
Triethylphosphite (27 ml, 0.155 mol) was added to (S/R)-propyl 2-chloro-2-propoxyacetate (29.21 g, 0.15 mol), resulting in an immediate decolourisation of the pale orange acetate, and the resulting mixture heated to 140° C., under reflux, for 6 h, a colourless gas being evolved. The mixture was then fractionally distilled under reduced pressure to give the product, (S/R)-propyl 2-(diethoxyphosphoryl)-2-propoxyacetate (35.78 g, 80%) as a colourless oil.

Bpt. 155–160° C./approx. 3 mmHg. $^1$H NMR (300 MHz, CDCl$_3$) δ: 0.95 (3H, t), 0.98 (3H, t), 1.31–1.39 (6H, m), 1.60–1.76 (4H, m), 3.49 (1H, dt), 3.62 (1H, dt), 4.12–4.30 (6H, m), 4.31 (1H, d, $J_{HP}$=19 Hz).

e)
A THF (50 ml) solution of (S/R)-propyl 2-(diethoxyphosphoryl)-2-propoxyacetate (18.52 g, 62.5 mmol) was added dropwise, at 0° C., to a stirred suspension of sodium hydride (60% dispersion in mineral oil, 2.50 g, 62.5 mmol) in THF (50 ml), and the resulting mixture stirred for 30 min. A THF (100 ml) solution of 4-benzyloxybenzaldehyde (10.62 g, 50.0 mmol) was added, the resulting solution allowed to warm to room temperature, and stirring continued for 24 h. TLC showed a considerable amount of unreacted 4-benzyloxybenzaldehyde was still present so a further portion of sodium hydride (60% dispersion in mineral oil, 1.0 g, 25.0 mmol) was added and stirring continued for a further 18 h. The mixture was carefully diluted with 0.5N HCl (400 ml), the products extracted into ethyl acetate (3×200 ml), and the combined organic phases washed with brine, dried (MgSO$_4$) and evaporated to give a yellow gum, which was purified by column chromatography on silica gel (10% ethyl acetate in n-heptane eluent) to give the intermediate, (E/Z)-propyl 3-(4-benzyloxyphenyl)-2-propoxy-acrylate as a colourless gum.

The (E/Z)-propyl 3-(4-benzyloxyphenyl)-2-propoxy-acrylate was dissolved in ethanol (200 ml), palladium on activated charcoal (10 wt. %, 2.18 g, 2.05 mmol) added and the mixture hydrogenated at 30 lb/in$^2$ H$_2$ pressure for 20 h. The catalyst was removed by filtration through celite and the solvent evaporated to give an orange gum, which contained both the propyl and the ethyl (formed by trans-esterification) esters of (S/R)-3-(4-hydroxyphenyl)-2-propoxy-propionic acid. These were separated by column chromatography on silica gel (15% ethyl acetate in n-heptane eluent) to give, in respective order of elution, (S/R)-propyl 3-(4-hydroxyphenyl)-2-propoxy-propionate (4.52 g, 41%) and a mixture of both (S/R)-propyl and (S/R)-ethyl 3-(4-hydroxyphenyl)-2-propoxy-propionates (4.98 g, approx. 45%) as colourless oils.

(S/R)-propyl 3-(4-hydroxyphenyl)-2-propoxy-propionate: $^1$H NMR (300 MHz, CDCl$_3$) δ: 0.84 (3H, t), 0.90 (3H, t), 1.48–1.69 (4H, m), 2.95 (2H, d), 3.25 (1H, dt), 3.52 (1H, dt), 4.00 (1H, t), 4.07 (2H, t), 6.43 (1H, br s), 6.74 (2H, dm), 7.07 (2H, dm). $^{13}$C NMR (75 MHz, CDCl$_3$) δ: 10.2 (q), 10.3 (q), 21.8 (t), 22.7 (t), 38.4 (t), 66.6 (t), 72.5 (t), 80.6 (d), 115.2 (d), 128.5 (s), 130.4 (d), 154.7 (s), 173.2 (s). MS: 266 (M$^+$), 206 (M−PrOH), 179, 164, 137, 107 (100%).

f)
The title compound (350 mg, 74%) was prepared as a colourless gum from (S/R)-propyl 3-(4-hydroxyphenyl)-2-propoxy-propionate (280 mg, 1.05 mmol) and (E)-3-biphenyl-4-yl-but-2-en-1-ol (224 mg, 1.0 mmol) by a procedure analogous to that described in example 52c.

¹H NMR (300 MHz, CDCl₃) δ: 0.85 (3H, t), 0.90 (3H, t), 1.49–1.69 (4H, m), 2.17 (3H, d), 3.91–3.02 (2H, m), 3.23 (1H, dt), 3.52 (1H, dt), 3.97 (1H, dd), 4.07 (2H, t), 4.74 (2H, d), 6.11 (1H, tm), 6.88 (2H, dm), 7.17 (2H, dm), 7.30–7.38 (1H, m), 7.40–7.63 (8H, m). LCMS: 679 (M+207), 495 (100%, M+Na), 490 (M+NH₄), 207.

Example 144

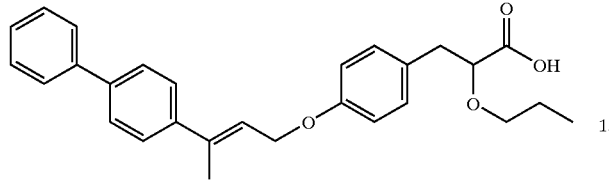

(E)-(S/R)-3-[4-(3-Biphenyl-4-yl-but-2-enyloxy)-phenyl]-2-propoxy-propionic acid

The title compound was prepared from (E)-(S/R)-propyl 3-[4-(3-biphenyl-4-yl-but-2-enyloxy)-phenyl]-2-propoxy-propionate (example 143) (330 mg, 0.70 mmol) and sodium hydroxide (1M, 1.4 ml, 1.4 mmol) by a procedure analogous to that described in example 51, yielding (E)-(S/R)-3-[4-(3-biphenyl-4-yl-but-2-enyloxy)-phenyl]-2-propoxy-propionic acid (300 mg, 100%) as a colourless gum.

¹H NMR (300 MHz, CDCl₃) δ: 0.88 (3H, t), 1.58 (2H, sextet), 2.17 (3H, s), 2.96 (1H, dd), 3.10 (1H, dd), 3.37 (1H, dt), 3.50 (1H, dt), 4.06 (1H, dd), 4.75 (2H, d), 6.11 (1H, t), 6.90 (2H, dm), 7.17 (2H, dm), 7.30–7.38 (1H, m), 7.40–7.63 (8H, m), carboxylic acid proton not observed. LCMS: 637 (M+207), 453 (100%, M+Na), 207.

Example 145

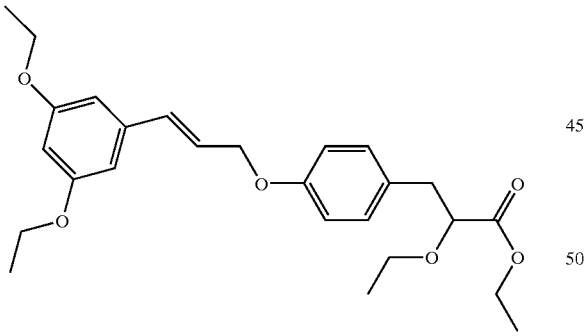

(E)-(S)-3-{4-[3-(3,5-Diethoxyoxy-phenyl)-allyloxy]-phenyl}-2-ethoxy-propionic acid ethyl ester The title compound was prepared from 3,5-dihydroxybenzaldehyde (3.0 g, 22.0 mmol) and ethyl iodide (17.2 g, 110 mmol) by a sequence analogous to that described in example 75.

¹H NMR (300 MHz, CDCl₃) δ: 1.15 (t, 3H), 1.20 (t, 3H), 1.38 (t, 6H), 2.95 (d, 2H), 3.30–3.40 (m, 1H), 3.53–3.65 (m, 1H), 3.98 (q, 4H), 4.15 (q, 2H), 4.63 (d, 2H), 6.28–6.40 (m, 2H), 6.53 (d, 2H), 6.60 (d, 1H), 6.87 (d, 2H), 7.15 (d, 2H).

Example 146

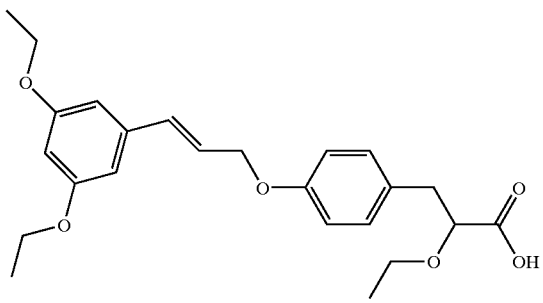

(E)-(S)-3-{4-[3-(3,5-Diethoxyoxy-phenyl)-allyloxy]-phenyl}-2-ethoxy-propionic acid The title compound was prepared from (E)-(S)-3-{4-[3-(3,5-diethoxyoxy-phenyl)-allyloxy]-phenyl}-2-ethoxy-propionic acid ethyl ester (730 mg, 1.6 mmol) by a procedure analogous to that described in example 26.

¹H NMR (300 MHz, CDCl₃) δ: 1.15 (t, 3H), 1.22 (t, 3H), 1.38 (t, 6H), 2.95 (d, 2H), 3.28–3.38 (m, 1H), 3.53–3.65 (m, 1H), 3.98 (q, 4H), 4.15 (q, 2H), 4.63 (d, 2H), 6.28–6.40 (m, 2H), 6.53 (d, 2H), 6.60 (d, 1H), 6.85 (d, 2H), 7.15 (d, 2H).

Example 147

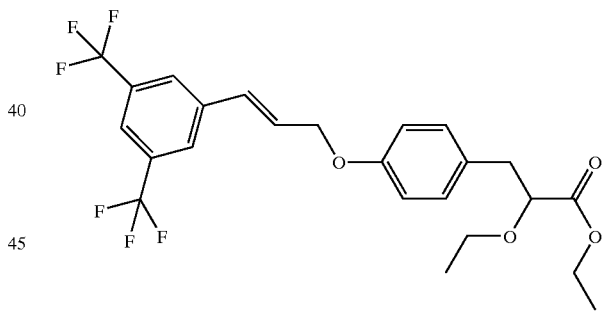

(E)-(S)-3-{4-[3-(3,5-Bis-trifluoromethyl-phenyl)-allyloxy]-phenyl}-2-ethoxy-propionic acid ethyl ester The title compound was prepared from 3,5-bis(trifluoromethyl)benzaldehyde (5.0 g, 20.7 mmol) by a sequence analogous to that described in example 23. The title compound was purified on HPLC, using ethyl acetate/heptane (20:80) as eluent.

¹H NMR (300 MHz, CDCl₃) δ: 1.15 (t, 3H), 1.22 (t, 3H), 2.97 (d, 2H), 3.30–3.42 (m, 1H), 3.55–3.67 (m, 1H), 3.98 (t, 1H), 4.18 (q, 2H), 4.72 (d, 2H), 6.55 (dt, 1H), 6.80 (d, 1H), 6.89 (d, 2H), 7.18 (d, 2H), 7.75 (bs, 1H), 7.82 (bs, 2H).

Example 148

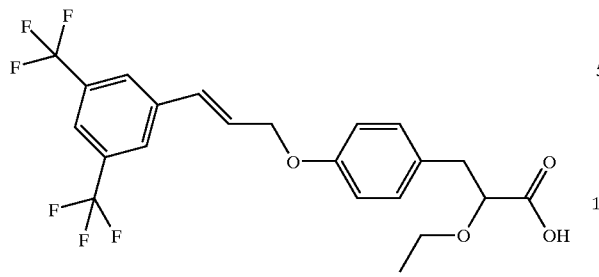

(E)-(S)-3-{4-[3-(3,5-Bis-trifluoromethyl-phenyl)-allyloxy]-phenyl}-2-ethoxy-propionic acid The title compound was prepared from (E)-(S)-3-{4-[3-(3,5-bis-trifluoromethyl-phenyl)-allyloxy]-phenyl}-2-ethoxy-propionic acid ethyl ester (0.58 g, 1.2 mmol) by a procedure analogous to that described in example 26.

$^1$H NMR (300 MHz, CDCl$_3$) δ: 1.18 (t, 3H), 2.98 (dd, 1H), 3.08 (dd, 1H), 3.36–3.48 (m, 1H), 3.58–3.71 (m, 1H), 4.05 (dd, 1H), 4.72 (d, 2H), 6.55 (dt, 1H), 6.80 (d, 1H), 6.89 (d, 2H), 7.20 (d, 2H), 7.75 (bs, 1H), 7.82 (bs, 2H).

Example 149

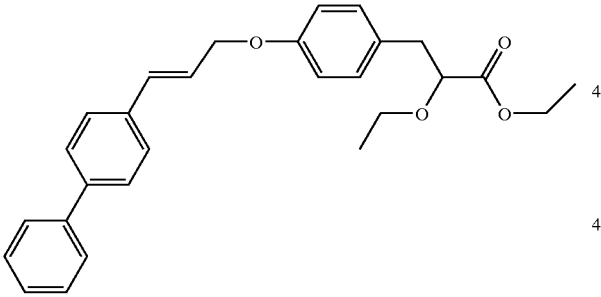

(E)-(R,S)-3-[4-(3-Biphenyl-4-yl-allyloxy)-phenyl]-2-ethoxy-propionic acid ethyl ester The title compound was prepared from 3-biphenyl-4-yl-prop-2-en-1-ol (0.25 g, 0.001 mol) by a procedure analogous to that described in example 3c yielding 0.050 g of (E)-(R,S)-3-[4-(3-biphenyl-4-yl-allyloxy)-phenyl]-2-ethoxy-propionic acid ethyl ester.

$^1$H NMR (200 MHz, CDCl$_3$) δ: 1.1–1.26 (6H, m), 2.97 (2H, d), 3.3–3.4 (1H, m), 3.52–3.7 (1H, m), 4.0 (1H, t), 4.15 (2H, q), 4.75 (2H, dd), 6.35–6.5 (1H, dt), 6.75 (1H, d), 6.87 (2H, d), 7.15 (2H, d), 7.4–7.7 (9H, m).

Example 150

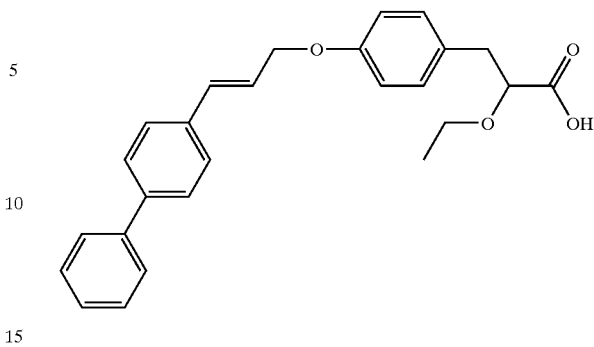

(E)-(R,S)-3-[4-(3-Biphenyl-4-yl-allyloxy)-phenyl]-2-ethoxy-propionic acid

The title compound was prepared from (E)-(S)-3-[4-(3-biphenyl-4-yl-allyloxy)-phenyl]-2-ethoxy-propionic acid ethyl ester (example 149) (0.040 g) by a procedure analogous to that described in example 2 yielding 0.0045 g of (E)-(R,S)-3-[4-(3-biphenyl-4-yl-allyloxy)-phenyl]-2-ethoxy-propionic acid.

$^1$H NMR (300 MHz, CDCl$_3$) δ: 1.14 (3H, t), 2.85 (1H, dd), 3.1 (1H, dd) 3.42–3.57 (2H, m), 3.84–3.96 (2H, m), 4.1 (1H, dd), 4.7 (2H, d), 6.3–6.5 (1H, dt), 6.78 (1H, d), 6.88 (2H, d), 7.15 (2H, d) 7.4–7.6 (9H, m).

Example 151

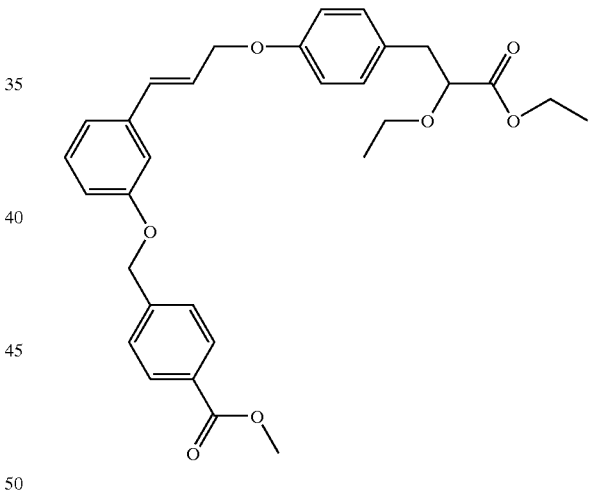

(E)-(S)-4-(3-{3-[4-(2-Ethoxy-2-ethoxycarbonyl-ethyl)-phenoxy]-propenyl}-phenoxymethyl)-benzoic acid methyl ester a)
(E)-3-(3-Hydroxy-propenyl)-phenol was prepared from 3-hydroxybenzaldehyde (6.0 g, 0.049 mol) by a procedure analogous to that described in example 1a–b yielding 1.5 g $^1$H NMR (300 MHz, CDCl$_3$) δ: 1.4 (1H, t), 4.27 (2H, m), 4.88 (1H, s), 6.35 (1H, dt), 6.57 (1H, d), 6.68 (1H, dd), 6.87 (1H, s), 6.96 (1H, d), 7.19 (1H, dd).

b)
A mixture of (E)-3-(3-Hydroxy-propenyl)-phenol (0.5 g, 3.33 mmol), methyl 4-(bromomethyl) benzoate (763 mg, 3.33 mmol) and potassium carbonate (1.8 g, 13.3 mmol) in acetone (40 ml) was stirred at room temperature over night. The reaction mixtyre was added water (30 ml) and acidified with 1N HCl and extracted with ethyl acetate (90 ml). The organic phase was washed with water, brine and dried with sodium sulphate and evaporated and dried in vacuo yielding 954 mg (96%) (E)-4-[3-(3-Hydroxy-propenyl)-phenoxymethyl]-benzoic acid methyl ester.

$^1$H NMR (300 MHz, CDCl$_3$) δ: 3.8 (3H, s), 4.24 (2H, d), 5.15 (2H, s), 6.3 (1H, dt), 6.57 (1H, d), 7.0 (2H, d), 7.2 (1H, d), 7.51 (2H, d), 8.08 (2H, d).

c)

The title compound was prepared from (E)-4-[3-(3-Hydroxy-propenyl)-phenoxymethyl]-benzoic acid methyl ester (0.298 g, 1.0 mmol) by a procedure analogous to that described in example 3c yielding 0.184 g (35%) of (E)-(S)-4-(3-{3-[4-(2-Ethoxy-2-ethoxycarbonyl-ethyl)-phenoxy]-propenyl}-phenoxymethyl)-benzoic acid methyl ester.

$^1$H NMR (300 MHz, CDCl$_3$) δ: 1.15–1.35 (6H, m), 2.9 (2H, d) 3.3–3.45 (1H, m), 3.53–3.68 (1H, m), 3.89 (3H, s), 3.97 (1H, t), 4.13 (2H, q), 4.68 (2H, dd), 5.15 (2H, s), 6.35 (1H, dt), 6.62 (1H, d), 6.87 (3H, d), 7.05 (2H, d), 7.13–7.3 (3H, m), 7.5 (2H, d), 8.10 (2H, d).

Example 152

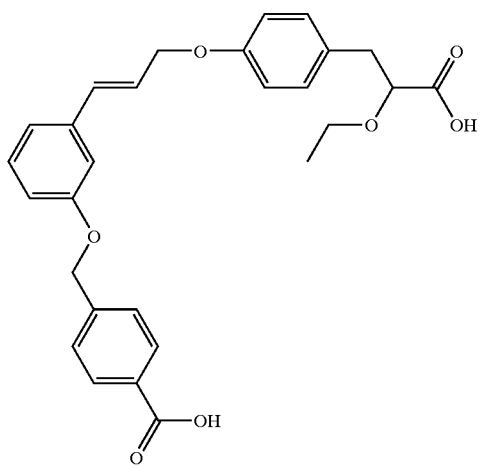

(E)-(S)-4-(3-{3-[4-(2-Carboxy-2-ethoxy-ethyl)-phenoxy]-propenyl}-phenoxymethyl)-benzoic acid The title compound was prepared from (E)-(S)-4-(3-{3-[4-(2-ethoxy-2-ethoxycarbonyl-ethyl)-phenoxy]-propenyl}-phenoxymethyl)-benzoic acid methyl ester (example 151) (0.220 g) by a procedure analogous to that described in example 2 yielding 0.160 g (77%) (E)-(S)-4-(3-{3-[4-(2-carboxy-2-ethoxy-ethyl)-phenoxy]-propenyl}-phenoxymethyl)-benzoic acid.

$^1$H NMR (300 MHz, CDCl$_3$) δ: δ: 1.17 (3H, t), 2.9–3.15 (2H, m) 3.3–3.68 (2H, m), 4.1 (2H, q), 4.67 (2H, d), 5.17 (2H, s), 6.35 (1H, dt), 6.68 (1H, d), 6.86 (3H, d), 7.05 (2H, d), 7.12–7.32 (3H, m), 7.52 (2H, d), 8.12 (2H, d).

Example 153

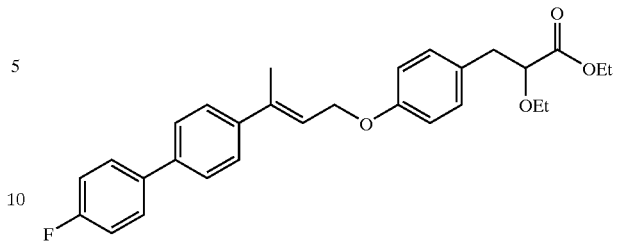

(E)-(S)-Ethyl 2-Ethoxy-3-{4-[3-(4'-fluoro-biphenyl-4-yl)-but-2-enyloxy]-phenyl}-propionate a)

The colourless solid (E)-ethyl 3-(4'-fluoro-biphenyl-4-yl)-but-2-enoate was prepared from (E)-ethyl 3-(4-iodophenyl)-but-2-enoate (example 91 a) and 4-fluorobenzene boronic acid by a procedure analogous to that described in example 52a.

Mpt. 63.5–64.5° C. $^1$H NMR (300 MHz, CDCl$_3$) δ: 1.33 (3H, t), 2.61 (3H, d), 4.23 (2H, q), 6.20 (1H, m), 7.14 (2H, dd), 7.52–7.62 (6H, m). MS: 284 (100%, M$^+$), 255, 239, 212, 196. Microanalysis Calculated % C, 76.04; H, 6.03. found C, 76.10; H, 6.17.

b)

The colourless solid (E)-3-(4'-fluoro-biphenyl-4-yl)-but-2-en-1-ol was prepared by DIBAL-H reduction of (E)-ethyl 3-(4'-fluoro-biphenyl-4-yl)-but-2-enoate as described for example 52b.

Mpt. 120.5–122° C. (n-heptane). $^1$H NMR (300 MHz, CDCl$_3$) δ: 1.39 (1H, br s), 2.12 (3H, d), 4.40 (2H, d), 6.05 (1H, tm), 7.12 (2H, dd), 7.42–7.60 (6H, m). MS: 242 (100%, M$^+$), 227 (M-Me), 224 (M–H$_2$O), 203, 199. Microanalysis Calculated % C, 79.32; H, 6.24. found C, 79.34; H, 6.37.

c)

The title compound (849 mg, 89%) was prepared as a colourless gum from (E)-3-(4'-fluorobiphenyl-4-yl)-but-2-en-1-ol (500 mg, 2.06 mmol) and (S)-ethyl 2-ethoxy-3-(4-hydroxyphenyl)-propionate (516 mg, 2.17 mmol) by a procedure analogous to that described in example 52c.

$^1$H NMR (200 MHz, CDCl$_3$) δ: 1.17 (3H, t), 1.23 (3H, t), 2.17 (3H, d), 2.97 (2H, d), 3.27–3.44 (1H, m), 3.52–3.69 (1H, m), 3.98 (1H, t), 4.17 (2H, q), 4.75 (2H, d), 6.12 (1H, tm), 6.88 (2H, dm), 7.05–7.22 (4H, m), 7.44–7.62 (6H, m). LCMS: 687 (M+225), 641 (687-EtOH), 485 (M+Na), 480 (M+NH$_4$), 225 (100%).

Example 154

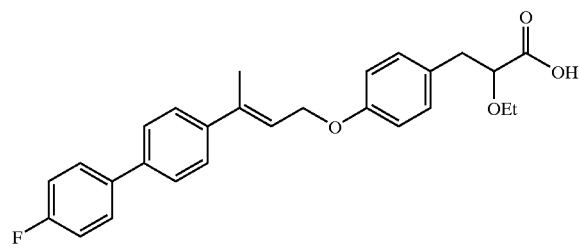

(E)-(S)-2-Ethoxy-3-{4-[3-(4'-fluoro-biphenyl-4-yl)-but-2-enyloxy]-phenyl}-propionic acid The title compound was prepared from (E)-(S)-ethyl 2-ethoxy-3-{4-[3-(4'-fluoro-biphenyl-4-yl)-but-2-enyloxy]- phenyl}-propionate (example 153) (463 mg, 1.0 mmol) and sodium hydroxide (1M, 1.5 ml, 1.5 mmol) by a procedure analogous to that described in example 51, yielding (E)-(S)-2-ethoxy-3-{4-[3-(4'-fluoro-biphenyl-4-yl)-but-2-enyloxy]-phenyl}-propionic acid (229 mg, 53%) as a colourless solid containing a trace of water.

$^1$H NMR (300 MHz, CDCl$_3$) δ: 1.19 (3H, t), 2.16 (3H, d), 2.97 (1H, dd), 3.09 (1H, dd), 3.42–3.65 (2H, m), 4.07 (1H, dd), 4.75 (2H, d), 6.11 (1H, tm), 6.90 (2H, dm), 7.07–7.20 (4H, m), 7.45–7.60 (6H, m), carboxylic acid proton not observed. LCMS: 457 (M+Na), 225 (100%). Microanalysis for C$_{27}$H$_{27}$FO$_4$·0.05H$_2$O Calculated % C, 74.48; H, 6.27; H$_2$O 0.21. found C, 74.25; H, 6.39; H$_2$O, 0.21.

Example 155

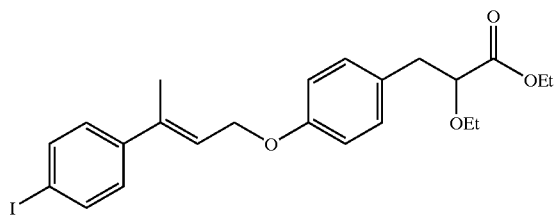

(E)-(S)-Ethyl 2-Ethoxy-3-{4-[3-(4-Iodophenyl)-but-2-enyloxy]-phenyl}-propionate

The title compound (398 mg, 80%) was prepared as a colourless gum, from (E)-3-(4-iodophenyl)-but-2-en-1-ol (example 107a) (275 mg, 1.0 mmol) and (S)-ethyl 2-ethoxy-3-(4-hydroxyphenyl)-propionate (256 mg, 1.07 mmol) by a procedure analogous to that described in example 52c.

$^1$H NMR (300 MHz, CDCl$_3$) δ: 1.17 (3H, t), 2.10 (3H, d), 2.96 (2H, d), 3.30–3.40 (1H, m), 3.55–3.65 (1H, m), 3.97 (1H, t), 4.16 (2H, q), 4.70 (2H, d), 6.04 (1H, tm), 6.86 (2H, dm), 7.13–7.20 (4H, m), 7.64 (2H, dm). LCMS: 751 (M+257), 705 (751-EtOH), 517 (100%, M+Na), 512 (M+NH$_4$), 449 (M+H-EtOH), 257, 130.

What is claimed is:

1. A compound of formula (I)

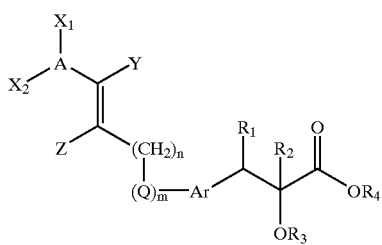

wherein A is heteroaryl, a 5–10 membered ring system containing from 1–4 heteroatoms selected from O, N, and S, and wherein A is optionally substituted with one or more substituents selected from hydroxy, halogen, perhalomethyl, perhalomethoxy, acyl, cyano, amino, C$_{1-6}$-alkylamino, C$_{1-6}$-dialkylamino, methylenedioxy, aralkenyl, aralkynyl, heteroaryloxy, heteroaralkoxy, aralkyl, heteroaralkyl, a straight or branched saturated carbon chain containing from 1–6 carbons substituted with 1 heteroaryl group, arylamino, or A is optionally substituted with C$_{1-6}$-alkyl, C$_{2-6}$-alkenyl or C$_{2-6}$-alkynyl each of which is optionally substituted with one or more substituents selected from C$_{1-6}$-alkoxycarbonyl or carboxy, or A is optionally substituted with C$_{1-6}$-alkoxy, C$_{1-6}$-alkylthio or C$_{2-6}$-alkenyloxy each of which is optionally substituted with one or more halogens, or A is optionally substituted with aryloxy, arylthio or aralkoxy each of which is optionally substituted with one or more substituents selected from C$_{1-6}$-alkoxy, nitro, carboxy or C$_{1-6}$-alkoxycarbonyl; and X$_1$ and X$_2$ independently are hydrogen, aryl or heteroaryl, a 5–10 membered ring system containing from 1–4 heteroatoms selected from O, N, and S, each of which is optionally substituted with one or more substituents selected from hydroxy, aryloxy, arylthio, aralkoxy, heteroaryloxy, aralkoxy, C$_{1-6}$-alkoxy, C$_{1-6}$-alkylthio, halogen, perhalomethyl, perhalomethoxy, acyl, aryl, heteroaryl, aralkyl, heteroaralkyl, a straight or branched saturated carbon chain containing from 1–6 carbons substituted with 1 heteroaryl group, cyano, amino, C$_{1-6}$-alkylamino, C$_{1-6}$-dialkylamino, arylamino or methylenedioxy, or aryl or heteroaryl each of which is optionally substituted with one or more substituents selected from C$_{1-6}$-alkyl, C$_{2-6}$-alkenyl or C$_{2-6}$-alkynyl each of which is optionally substituted with hydroxy; and Y is hydrogen, or Y is C$_{1-12}$-alkyl, C$_{2-12}$-alkenyl, C$_{2-12}$-alkynyl, C$_{4-12}$-alkenynyl, aralkyl or heteroaralkyl each of which is optionally substituted with one or more substituents selected from halogen, C$_{1-6}$-alkyl, perhalomethyl, hydroxy, aryl, heteroaryl, a 5–10 membered ring system containing from 1–4 heteroatoms selected from O, N, and S, carboxy or amino; and Z is hydrogen, halogen, hydroxy, or Z is C$_{1-6}$-alkyl or C$_{1-6}$-alkoxy each of which is optionally substituted with one or more substituents selected from halogen, hydroxy, carboxy, amino, cyano or C$_{1-6}$-alkoxy; and Q is O, S or NR$_6$, wherein R$_6$ is hydrogen, C$_{1-6}$-alkyl, C$_{2-6}$-alkenyl, C$_{2-6}$-alkynyl, C$_{4-6}$-alkenynyl, aralkyl, heteroaralkyl and wherein R$_6$ is optionally substituted with one or more substituents selected from halogen, hydroxy, C$_{1-6}$-alkoxy, amino or carboxy; and Ar is arylene, which can be optionally substituted with one or more substituents selected from C$_{1-6}$-alkyl, aryl or C$_{1-6}$-alkoxy each of which can be optionally substituted with halogen, hydroxy, carboxy, cyano or heterocyclyl; and R$_1$ is hydrogen, hydroxy or halogen; or R$_1$ forms a bond together with R$_2$; and R$_2$ is hydrogen or C$_{1-6}$-alkyl; or R$_2$ forms a bond together with R$_1$; and R$_3$ is hydrogen, or R$_3$ is C$_{1-6}$-alkyl, C$_{2-6}$-alkenyl, C$_{2-6}$-alkynyl, C$_{4-6}$-alkenynyl, aryl, aralkyl, C$_{1-6}$-alkoxyC$_{1-6}$-alkyl, acyl, heterocyclyl, a 5–10 membered ring system containing from 1–4 heteroatoms selected from O, N, and S, heteroaryl, a 5–10 membered ring system containing from 1–4 heteroatoms selected from O, N, and S, or heteroaralkyl, a straight or branched saturated carbon chain containing from 1–6 carbons substituted with 1 heteroaryl group, each of which is optionally substituted with one or more substituents selected from halogen, perhalomethyl, hydroxy or cyano; and R$_4$ is hydrogen, C$_{1-6}$-alkyl, C$_{2-6}$-alkenyl, C$_{2-6}$-alkynyl, C$_{4-6}$-alkenynyl or aryl; and n is an integer ranging from 0 to 3; and m is an integer ranging from 0 to 1;

or a pharmaceutically acceptable salt thereof, or a pharmaceutically acceptable solvate thereof, or any tautomeric forms, stereoisomers, mixture of stereoisomers, or a racemic mixture.

2. A compound according to claim 1 of formula (I)

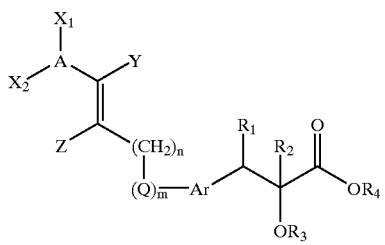
(I)

wherein A is aryl or heteroaryl and wherein A is optionally substituted with one or more substituents selected from hydroxy, halogen, perhalomethyl, perhalomethoxy, acyl, cyano, amino, $C_{1-6}$-alkylamino, $C_{1-6}$-dialkylamino, methylenedioxy, aralkenyl, aralkynyl, heteroaryloxy, heteroaralkoxy, aralkyl, heteroaralkyl, arylamino, or A is optionally substituted with $C_{1-6}$-alkyl, $C_{2-6}$-alkenyl or $C_{2-6}$-alkynyl each of which is optionally substituted with one or more substituents selected from $C_{1-6}$-alkoxycarbonyl or carboxy, or A is optionally substituted with $C_{1-6}$-alkoxy, $C_{1-6}$-alkylthio or $C_{2-6}$-alkenyloxy each of which is optionally substituted with one or more halogens, or A is optionally substituted with aryloxy, arylthio or aralkoxy each of which is optionally substituted with one or more substituents selected from $C_{1-6}$-alkoxy, nitro, carboxy or $C_{1-6}$-alkoxycarbonyl; and $X_1$ and $X_2$ independently are hydrogen, aryl or heteroaryl each of which is optionally substituted with one or more substituents selected from hydroxy, aryloxy, arylthio, aralkoxy, heteroaryloxy, aralkoxy, $C_{1-6}$-alkoxy, $C_{1-6}$-alkylthio, halogen, perhalomethyl, perhalomethoxy, acyl, aryl, heteroaryl, aralkyl, heteroaralkyl, cyano, amino, $C_{1-6}$-alkylamino, $C_{1-6}$-dialkylamino, arylamino or methylenedioxy, or aryl or heteroaryl each of which is optionally substituted with one or more substituents selected from $C_{1-6}$-alkyl, $C_{2-6}$-alkenyl or $C_{2-6}$-alkynyl each of which is optionally substituted with hydroxy; and Y is hydrogen, or Y is $C_{1-12}$-alkyl, $C_{2-12}$-alkenyl, $C_{2-12}$-alkynyl, $C_{4-12}$-alkenynyl, aralkyl or heteroaralkyl each of which is optionally substituted with one or more substituents selected from halogen, $C_{1-6}$-alkyl, perhalomethyl, hydroxy, aryl, heteroaryl, carboxy or amino; and Z is hydrogen, halogen, hydroxy, or Z is $C_{1-6}$-alkyl or $C_{1-6}$-alkoxy each of which is optionally substituted with one or more substituents selected from halogen, hydroxy, carboxy, amino, cyano or $C_{1-6}$-alkoxy; and Q is O, S or $NR_6$, wherein $R_6$ is hydrogen, $C_{1-6}$-alkyl, $C_{2-6}$-alkenyl, $C_{2-6}$-alkynyl, $C_{4-6}$-alkenynyl, aralkyl, heteroaralkyl and wherein $R_6$ is optionally substituted with one or more substituents selected from halogen, hydroxy, $C_{1-6}$-alkoxy, amino or carboxy; and Ar is arylene, which can be optionally substituted with one or more substituents selected from $C_{1-6}$-alkyl, aryl or $C_{1-6}$-alkoxy each of which can be optionally substituted with halogen, hydroxy, carboxy, cyano or heterocyclyl; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, or $R_3$ is $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl each of which is optionally substituted with one or more substituents selected from halogen, perhalomethyl, hydroxy or cyano; and $R_4$ is hydrogen, $C_{1-6}$-alkyl, $C_{2-6}$-alkenyl, $C_{2-6}$-alkynyl, $C_{4-6}$-alkenynyl or aryl; and n is an integer ranging from 1 to 3; and m is 1;

or a pharmaceutically acceptable salt thereof, or a pharmaceutically acceptable solvate thereof, or any tautomeric forms, stereoisomers, mixture of stereoisomers, or a racemic mixture.

3. A compound according to claim 1 of formula (I)

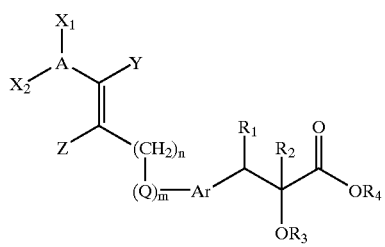
(I)

wherein A is heteroaryl and wherein A is optionally substituted with one or more substituents selected from $C_{1-6}$-alkyl, $C_{2-6}$-alkenyl, $C_{2-6}$-alkynyl, hydroxy, aryloxy, arylthio, aralkoxy, $C_{1-6}$-alkoxy, $C_{1-6}$-alkylthio, heteroaryloxy, heteroaralkoxy, halogen, perhalomethyl, perhalomethoxy, acyl, aralkyl, heteroaralkyl, cyano, amino, $C_{1-6}$-alkylamino, $C_{1-6}$-dialkylamino, arylamino or methylenedioxy; and $X_1$ and $X_2$ independently are hydrogen, aryl or heteroaryl optionally substituted with one or more substituents selected from $C_{1-6}$-alkyl, $C_{2-6}$-alkenyl, $C_{2-6}$-alkynyl, hydroxy, aryloxy, arylthio, aralkoxy, heteroaryloxy, aralkoxy, $C_{1-6}$-alkoxy, $C_{1-6}$-alkylthio, halogen, perhalomethyl, perhalomethoxy, acyl, aryl, heteroaryl, aralkyl, heteroaralkyl, cyano, amino, $C_{1-6}$-alkylamino, $C_{1-6}$-dialkylamino, arylamino or methylenedioxy;

Y is hydrogen, $C_{1-12}$-alkyl, $C_{2-12}$-alkenyl, $C_{2-12}$-alkynyl, $C_{4-12}$-alkenynyl, aralkyl or heteroaralkyl optionally substituted with one or more substituents selected from halogen, $C_{1-6}$-alkyl, perhalomethyl, hydroxy, aryl, heteroaryl, carboxy or amino; and Z is hydrogen, halogen, hydroxy, $C_{1-6}$-alkyl or $C_{1-6}$-alkoxy optionally substituted with one or more substituents selected from halogen, hydroxy, carboxy, amino, cyano or $C_{1-6}$-alkoxy; and Q is O, S or $NR_6$, wherein $R_6$ is hydrogen, $C_{1-6}$-alkyl, $C_{2-6}$-alkenyl, $C_{2-6}$-alkynyl, $C_{4-6}$-alkenynyl, aralkyl, heteroaralkyl and wherein $R_6$ is optionally substituted with one or more substituents selected from halogen, hydroxy, $C_{1-6}$-alkoxy, amino or carboxy; and Ar is arylene, which can be optionally substituted with one or more substituents selected from $C_{1-6}$-alkyl, aryl or $C_{1-6}$-alkoxy each of which can be optionally substituted with halogen, hydroxy, carboxy, cyano or heterocyclyl; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl groups optionally substituted with one or more substituents selected from halogen, perhalomethyl, hydroxy or cyano; and $R_4$ is hydrogen, $C_{1-6}$-alkyl, $C_{2-6}$-alkenyl, $C_{2-6}$-alkynyl, $C_{4-6}$-alkenynyl or aryl; and n is an integer ranging from 0 to 3; and m is an integer ranging from 0 to 1;

or a pharmaceutically acceptable salt thereof, or a pharmaceutically acceptable solvate thereof, or any tautomeric forms, stereoisomers, mixture of stereoisomers, or a racemic mixture.

4. A compound according to claim 1 of formula (I)

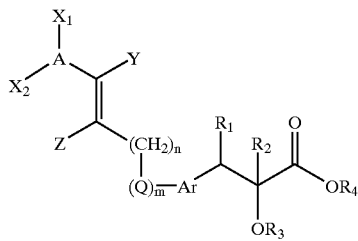

wherein A is heteroaryl and wherein A is optionally substituted with one or more substituents selected from $C_{1-6}$-alkyl, $C_{2-6}$-alkenyl, $C_{2-6}$-alkynyl, hydroxy, aryloxy, arylthio, aralkoxy, $C_{1-6}$-alkoxy, $C_{1-6}$-alkylthio, heteroaryloxy, heteroaralkoxy, halogen, perhalomethyl, perhalomethoxy, acyl, aralkyl, heteroaralkyl, cyano, amino, $C_{1-6}$-alkylamino, $C_{1-6}$-dialkylamino, arylamino or methylenedioxy; and $X_1$ and $X_2$ independently are hydrogen, aryl or heteroaryl optionally substituted with one or more substituents selected from $C_{1-6}$-alkyl, $C_{2-6}$-alkenyl, $C_{2-6}$-alkynyl, hydroxy, aryloxy, arylthio, aralkoxy, heteroaryloxy, aralkoxy, $C_{1-6}$-alkoxy, $C_{1-6}$-alkylthio, halogen, perhalomethyl, perhalomethoxy, acyl, aryl, heteroaryl, aralkyl, heteroaralkyl, cyano, amino, $C_{1-6}$-alkylamino, $C_{1-6}$-dialkylamino, arylamino or methylenedioxy; and Y is hydrogen, $C_{1-12}$-alkyl, $C_{2-12}$-alkenyl, $C_{2-12}$-alkynyl, $C_{4-12}$-alkenynyl, aralkyl or heteroaralkyl optionally substituted with one or more substituents selected from halogen, $C_{1-6}$-alkyl, perhalomethyl, hydroxy, aryl, heteroaryl, carboxy or amino; and Z is hydrogen, halogen, hydroxy, $C_{1-6}$-alkyl or $C_{1-6}$-alkoxy optionally substituted with one or more substituents selected from halogen, hydroxy, carboxy, amino, cyano or $C_{1-6}$-alkoxy; and Q is O, S or $NR_6$, wherein $R_6$ is hydrogen, $C_{1-6}$-alkyl, $C_{2-6}$-alkenyl, $C_{2-6}$-alkynyl, $C_{4-6}$-alkenynyl, aralkyl, heteroaralkyl and wherein $R_6$ is optionally substituted with one or more substituents selected from halogen, hydroxy, $C_{1-6}$-alkoxy, amino or carboxy; and Ar is arylene, of which can be optionally substituted with one or more substituents selected from $C_{1-6}$-alkyl, aryl or $C_{1-6}$-alkoxy each of which can be optionally substituted with halogen, hydroxy, carboxy, cyano or heterocyclyl; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl groups optionally substituted with one or more substituents selected from halogen, perhalomethyl, hydroxy or cyano; and $R_4$ is hydrogen, $C_{1-6}$-alkyl, $C_{2-6}$-alkenyl, $C_{2-6}$-alkynyl, $C_{4-6}$-alkenynyl or aryl; and n is an integer ranging from 0 to 3; and m is an integer ranging from 0 to 1;

or a pharmaceutically acceptable salt thereof, or a pharmaceutically acceptable solvate thereof, or any tautomeric forms, stereoisomers, mixture of stereoisomers, or a racemic mixture.

5. A compound according to claim 1, wherein A is heteroaryl optionally substituted with one or more substituents selected from from $C_{1-6}$-alkyl, $C_{2-6}$-alkenyl each of which is optionally substituted with one or more substituents selected from $C_{1-6}$-alkoxycarbonyl or carboxy, or A is optionally substituted with aryloxy optionally substituted with one or more $C_{1-6}$-alkoxy, or A is optionally substituted with aralkoxy optionally substituted with one or more substituents selected from $C_{1-6}$-alkoxy, nitro, carboxy or $C_{1-6}$-alkoxycarbonyl, or A is optionally substituted with $C_{1-6}$-alkoxy optionally substituted with one or more halogens, or A is optionally substituted with aralkenyl, $C_{2-6}$-alkenyloxy, aralkynyl, halogen, perhalomethyl, perhalomethoxy, acyl, aralkyl or methylenedioxy.

6. A compound according to claim 1, wherein A is heteroaryl optionally substituted with one or more substituents selected from aryloxy, arylthio, aralkoxy, $C_{1-6}$-alkoxy, $C_{1-6}$-alkylthio, halogen, perhalomethyl, aralkyl, heteroaralkyl, heteroaryloxy or heteroaralkoxy.

7. A compound according to claim 1, wherein A is heteroaryl optionally substituted with one or more substituents selected from aryloxy, arylthio, aralkoxy, $C_{1-6}$-alkoxy, $C_{1-6}$-alkylthio, halogen, perhalomethyl, aralkyl, heteroaralkyl, heteroaryloxy or heteroaralkoxy.

8. A compound according to claim 1, wherein A is heteroaryl.

9. A compound according to claim 1, wherein $X_1$ and $X_2$ independently are hydrogen, aryl or heteroaryl optionally substituted with one or more substituents selected from aryloxy, arylthio, aralkoxy, halogen, perhalomethyl, aryl, heteroaryl, aralkyl, heteroaralkyl, heteroaryloxy or heteroaralkoxy.

10. A compound according to claim 9, wherein $X_1$ and $X_2$ independently are hydrogen, aryl or heteroaryl optionally substituted with one or more substituents selected from halogen, acyl, aryl, or aryl or heteroaryl optionally substituted with one or more substituents selected from $C_{1-6}$-alkyl, $C_{2-6}$-alkynyl each of which is optionally substituted with hydroxy.

11. A compound according to claim 1, wherein Y is hydrogen or $C_{1-12}$-alkyl.

12. A compound according to claim 1, wherein Z is hydrogen or $C_{1-6}$-alkoxy.

13. A compound according to claim 1, wherein Q is O.

14. A compound according to claim 1, wherein Ar is arylene optionally substituted with one or more substituents selected from $C_{1-6}$-alkyl or $C_{1-6}$-alkoxy each of which can be optionally substituted with carboxy.

15. A compound according to claim 1, wherein $R_1$ is hydrogen or $R_1$ forms a bond together with $R_2$.

16. A compound according to claim 1, wherein $R_2$ is hydrogen.

17. A compound according to claim 1, wherein $R_3$ is $C_{1-6}$-alkyl or aralkyl.

18. A compound according to claim 1, wherein $R_4$ is hydrogen, or $C_{1-3}$-alkyl.

19. A compound according to claim 1, wherein alkyl is methyl, ethyl, n-propyl, iso-propyl, butyl, tert-butyl, pentyl, hexyl, cyclopropyl or cyclopentyl.

20. A compound according to claim 1, wherein alkenyl is vinyl or 1-propenyl.

21. A compound according to claim 1, wherein alkynyl is ethynyl, 1-propynyl and 2-propynyl.

22. A compound according to claim 1, wherein alkoxy is methoxy, ethoxy, propoxy, butoxy, pentoxy, hexoxy, isopropoxy or cyclopentyloxy.

23. A compound according to claim 1, wherein alkylthio is methylthio, ethylthio, propylthio or cyclopentylthio.

24. A compound according to claim 1, wherein aryl is phenyl optionally substituted with halogen.

25. A compound according to claim 1, wherein arylene is phenylene optionally substituted with halogen.

26. A compound according to claim 1, wherein halogen is fluorine or chlorine.

27. A compound according to claim 1, wherein perhalomethyl is trifluoromethyl.

28. A compound according to claim 1, wherein acyl is acetyl.

29. A compound according to claim 1, wherein heteroaryl is furan, thiophene, pyrrole, imidazole, pyrazole, pyridine, quinoline, isoquinoline, quinazoline, quinoxaline, indole, benzimidazole or benzofuran.

30. A compound according to claim 1, wherein aralkyl is benzyl or phenethyl.

31. A compound according to claim 1, wherein aryloxy is phenoxy.

32. A compound according to claim 1, wherein aralkoxy is benzyloxy.

33. A compound according to claim 1, wherein n is an integer ranging from 1 to 3 and m is 1.

34. A compound according to claim 1, wherein the substituents Z and Y are arranged in a trans-configuration.

35. A compound according to claim 1, wherein the substituents Z and Y are arranged in a cis-configuration.

36. The compound according to claim 1, which is:
(E)-(S)-2-Ethoxy-3-[4-(3-pyridin-2-yl-but-2-enyloxy)-phenyl]-propionic acid ethyl ester,
(E)-(S)-2-Ethoxy-3-[4-(3-pyridin-2-yl-but-2-enyloxy)-phenyl]-propionic acid,
(S)-3-[4-(2-Benzofuran-3-yl-allyloxy)-phenyl]-2-ethoxy-propionic acid ethyl ester,
(S)-3-[4-(2-Benzofuran-3-yl-allyloxy)-phenyl]-2-ethoxy-propionic acid;
or a pharmaceutically acceptable salt thereof.

37. The compound according to claim 4 which is:
(E)-(S)-2-Ethoxy-3-[4-(3-pyridin-2-yl-but-2-enyloxy)-phenyl]-propionic acid ethyl ester,
(E)-(S)-2-Ethoxy-3-[4-(3-pyridin-2-yl-but-2-enyloxy)-phenyl]-propionic acid,
(S)-3-[4-(2-Benzofuran-3-yl-allyloxy)-phenyl]-2-ethoxy-propionic acid ethyl ester,
(S)-3-[4-(2-Benzofuran-3-yl-allyloxy)-phenyl]-2-ethoxy-propionic acid;
or a pharmaceutically acceptable salt thereof.

38. The compound according to claim 1, which is:
(E)-(S)-3-[4-(3-Benzo[1,3]dioxol-5-yl-allyloxy)-phenyl]-2-ethoxy-propionic acid ethyl ester,
(E)-(S)-3-[4-(3-Benzo[1,3]dioxol-5-yl-allyloxy)-phenyl]-2-ethoxy-propionic acid,
(E)-(S)-3-[4-(3-Benzofuran-7-yl-allyloxy)-phenyl]-2-ethoxy-propionic acid ethyl ester,
(E)-(S)-3-[4-(3-Benzofuran-7-yl-allyloxy)-phenyl]-2-ethoxy-propionic acid,
(S)-2-Ethoxy-3-[4-(3-quinolin-2-yl-allyloxy)-phenyl]-propionic acid ethyl ester,
(S)-2-Ethoxy-3-[4-(3-quinolin-2-yl-allyloxy)-phenyl]-propionic acid,
or a pharmaceutically acceptable salt thereof.

39. The compound according to claim 4 which is:
(E)-(S)-3-[4-(3-Benzofuran-7-yl-allyloxy)-phenyl]-2-ethoxy-propionic acid ethyl ester,
(E)-(S)-3-[4-(3-Benzofuran-7-yl-allyloxy)-phenyl]-2-ethoxy-propionic acid,
(S)-2-Ethoxy-3-[4-(3-quinolin-2-yl-allyloxy)-phenyl]-propionic acid ethyl ester,
(S)-2-Ethoxy-3-[4-(3-quinolin-2-yl-allyloxy)-phenyl]-propionic acid,
or a pharmaceutically acceptable salt thereof.

40. The compound according to claim 1, which is:
(E)-(S)-Ethyl 2-Ethoxy-3-{4-[3-(4-furan-2-yl-phenyl)-but-2-enyloxy]-phenyl}-propionate.

41. A composition comprising, as an active ingredient, a compound according to claim 1, or a pharmaceutically acceptable salt thereof together with a pharmaceutically acceptable carrier or diluent.

42. A composition according to claim 41 in unit dosage form, comprising from about 0.05 to about 100 mg of the compound or a pharmaceutically acceptable salt thereof.

43. A composition according to claim 41 for oral, nasal, transdermal, pulmonal, or parenteral administration.

44. A method for the treatment of diabetes and/or obesity, the method comprising administering to a subject in need thereof an effective amount of a composition according to claim 41.

45. The method according to claim 44, wherein the effective amount of the compound in said composition is in the range of from about 0.05 to about 100 mg per day.

46. A composition suitable for treating type I diabetes, type II diabetes, impaired glucose tolerance, insulin resistance or obesity comprising a compound according to claim 1 or a pharmaceutically acceptable salt thereof, or a pharmaceutically acceptable solvate thereof, or any tautomeric forms, stereoisomers, mixture of stereoisomers, or racemic mixture together with one or more pharmaceutically acceptable carriers or diluents and an ACE (angiotensin converting enzyme) inhibitor.

47. A method of treating type I diabetes, type II diabetes, impaired glucose tolerance, insulin resistance or obesity comprising administering to a subject in need thereof an effective amount of a compound according to claim 1 or a pharmaceutically acceptable salt thereof, or a pharmaceutically acceptable solvate thereof, or any tautomeric forms, stereoisomers, mixture of stereoisomers, or racemic mixture, together with one or more pharmaceutically acceptable carriers or diluents and an ACE (angiotensin converting enzyme) inhibitor to said subject.

48. A composition suitable for treating type I diabetes, type II diabetes, impaired glucose tolerance, insulin resistance or obesity comprising a compound according to claim 1 or a pharmaceutically acceptable salt thereof, or a pharmaceutically acceptable solvate thereof, or any tautomeric forms, stereoisomers, mixture of stereoisomers, or racemic mixture together with one or more pharmaceutically acceptable carriers or diluents and an agent stimulating insulin release from β cells such as a meglitinide, like repaglinide or senaglinide.

49. A method of treating type I diabetes, type II diabetes, impaired glucose tolerance, insulin resistance or obesity comprising administering to a subject in need thereof an effective amount of a compound according to claim 1 and an agent stimulating insulin release from β cells such as a meglitinide, like repaglinide or senaglinide, to said subject.

50. A composition suitable for treating type I diabetes, type II diabetes, impaired glucose tolerance, insulin resistance or obesity comprising a compound according to claim 1 or a pharmaceutically acceptable salt thereof, or a pharmaceutically acceptable solvate thereof, or any tautomeric forms, stereoisomers, mixture of stereoisomers, or racemic mixture together with one or more pharmaceutically acceptable carriers or diluents and a biguanide like metformin.

51. A method of treating type I diabetes, type II diabetes, impaired glucose tolerance, insulin resistance or obesity comprising administering to a subject in need thereof an effective amount of a compound according to claim 1 or a pharmaceutically acceptable salt thereof, or a pharmaceutically acceptable solvate thereof, or any tautomeric forms, stereoisomers, mixture of stereoisomers, or racemic mixture together with one or more pharmaceutically acceptable carriers or diluents and a biguanide, like metformin, to said subject.

52. A composition suitable for treating type I diabetes, type II diabetes, impaired glucose tolerance, insulin resistance or obesity comprising a compound according to claim 1 or a pharmaceutically acceptable salt thereof, or a pharmaceutically acceptable solvate thereof, or any tautomeric forms, stereoisomers, mixture of stereoisomers, or racemic mixture together with one or more pharmaceutically acceptable carriers or diluents and a HMG CoA inhibitor.

53. A method of treating type I diabetes, type II diabetes, impaired glucose tolerance, insulin resistance or obesity comprising administering to a subject in need thereof an effective amount of a compound according to claim 1 or a pharmaceutically acceptable salt thereof, or a pharmaceutically acceptable solvate thereof, or any tautomeric forms, stereoisomers, mixture of stereoisomers, or racemic mixture together with one or more pharmaceutically acceptable carriers or diluents and a HMG CoA inhibitor to said subject.

* * * * *

UNITED STATES PATENT AND TRADEMARK OFFICE
CERTIFICATE OF CORRECTION

PATENT NO. : 6,867,218 B2
APPLICATION NO. : 10/370856
DATED : March 15, 2005
INVENTOR(S) : Mogensen et al.

It is certified that error appears in the above-identified patent and that said Letters Patent is hereby corrected as shown below:

Column 126, line 57, claim 1:
Delete "a 5-10 membered ring" and insert --a 5-6 membered ring--.
Column 132, line 44, claim 44:
Delete "diabetes and/or obesity" and insert --conditions mediated by the Peroxisome Proliferator-Activated Receptors (PPAR)--.

Signed and Sealed this

Twentieth Day of November, 2007

JON W. DUDAS
*Director of the United States Patent and Trademark Office*